(12) United States Patent
Drukker et al.

(10) Patent No.: US 10,870,879 B2
(45) Date of Patent: Dec. 22, 2020

(54) METHOD FOR THE PREPARATION OF BAR-CODED PRIMER SETS

(71) Applicant: HELMHOLTZ ZENTRUM MÜNCHEN—DEUTSCHES FORSCHUNGSZENTRUM FÜR GESUNDHEIT UND UMWELT (GMBH), Neuherberg (DE)

(72) Inventors: Micha Drukker, Munich (DE); Florian Opperer, Munich (DE); Christian Krendl, Munich (DE); Can Sönmezer, Heidelberg (DE)

(73) Assignee: HELMHOLTZ ZENTRUM MÜNCHENDEUTSCHES FORSCHUNGSZENTRUM FÜR GESUNDHEIT UND UMWELT, Neuherberg (DE)

( * ) Notice: Subject to any disclaimer, the term of this patent is extended or adjusted under 35 U.S.C. 154(b) by 0 days.

(21) Appl. No.: 15/765,742

(22) PCT Filed: Oct. 5, 2016

(86) PCT No.: PCT/EP2016/073816
§ 371 (c)(1),
(2) Date: Apr. 4, 2018

(87) PCT Pub. No.: WO2017/060316
PCT Pub. Date: Apr. 13, 2017

(65) Prior Publication Data
US 2019/0002953 A1 Jan. 3, 2019

(30) Foreign Application Priority Data
Oct. 5, 2015 (EP) .................................. 15188404

(51) Int. Cl.
*C12Q 1/6806* (2018.01)
*C12N 15/10* (2006.01)
*C12Q 1/6874* (2018.01)

(52) U.S. Cl.
CPC ....... *C12Q 1/6806* (2013.01); *C12N 15/1065* (2013.01); *C12N 15/1096* (2013.01);
(Continued)

(58) Field of Classification Search
CPC ............... C12Q 1/6806; C12Q 1/6874; C12Q 2525/155; C12Q 2525/161; C12N 15/1065
See application file for complete search history.

(56) References Cited

U.S. PATENT DOCUMENTS
2009/0203085 A1  8/2009  Kurn et al.

FOREIGN PATENT DOCUMENTS
WO  2010/029520 A1  3/2010
WO  2012/112804 A1  8/2012

OTHER PUBLICATIONS

Tu et al. (BMC Genomics 2012, 13:43, 31 pages including supplemental material).*

(Continued)

*Primary Examiner* — Robert H Havlin
(74) *Attorney, Agent, or Firm* — Riverside Law LLP

(57) ABSTRACT

The present invention relates to a method of producing a set of primers suitable for the reverse transcription and/or amplification of a plurality (N) of nucleic acid molecules of interest, wherein for each nucleic acid molecule of interest at least one primer is produced and wherein the primers carry a bar-code, the method comprising the steps of: (a)(i) combining (1) a first oligonucleotide, wherein said first oligonucleotide comprises a first bar-code nucleic acid sequence linked at its 3' end to a first adapter nucleic acid sequence with (2) a plurality (N) of second oligonucleotides, wherein each second oligonucleotide comprises the reverse complementary sequence of a forward primer specific for a nucleic acid molecule of interest, wherein said reverse complementary sequence of the forward primer is linked at its 3' end to the reverse complementary sequence of the first adapter nucleic acid sequence; and/or (a)(ii) combining (1) a third oligonucleotide, wherein said third oligonucleotide comprises a second bar-code nucleic acid sequence linked at its 3' end to a second adapter nucleic acid sequence with (2) a plurality (N) of fourth oligonucleotides, wherein each fourth oligonucleotide comprises the reverse complementary sequence of a reverse primer specific for said nucleic acid molecule of interest, wherein said reverse complementary sequence of the reverse primer is linked at its 3' end to the reverse complementary sequence of the second adapter nucleic acid sequence; wherein steps (a)(i) and (a)(ii) are carried out under conditions that enable the annealing of the first and second adapter nucleic acid sequences to the respective reverse complementary sequences thereof; (b) extending the oligonucleotides of (a)(i) and (a)(ii) by polymerase-mediated oligonucleotide synthesis; and (c) optionally, removing the second and fourth oligonucleotides. The present invention further relates to methods of producing a plurality (M) of nucleic acid amplification products of interest carrying at least one sample-specific bar-code as well as to a method for multiplex sequencing of a plurality (M) of nucleic acid amplification products of interest from a plurality (X) of samples in a single reaction chamber and identifying the individual sample from which each nucleic acid amplification product is derived. Furthermore, the present invention relates to a target-unspecific bar-code-adapter panel, its use in the methods of the invention as well as a kit comprising same.

Figure 1:
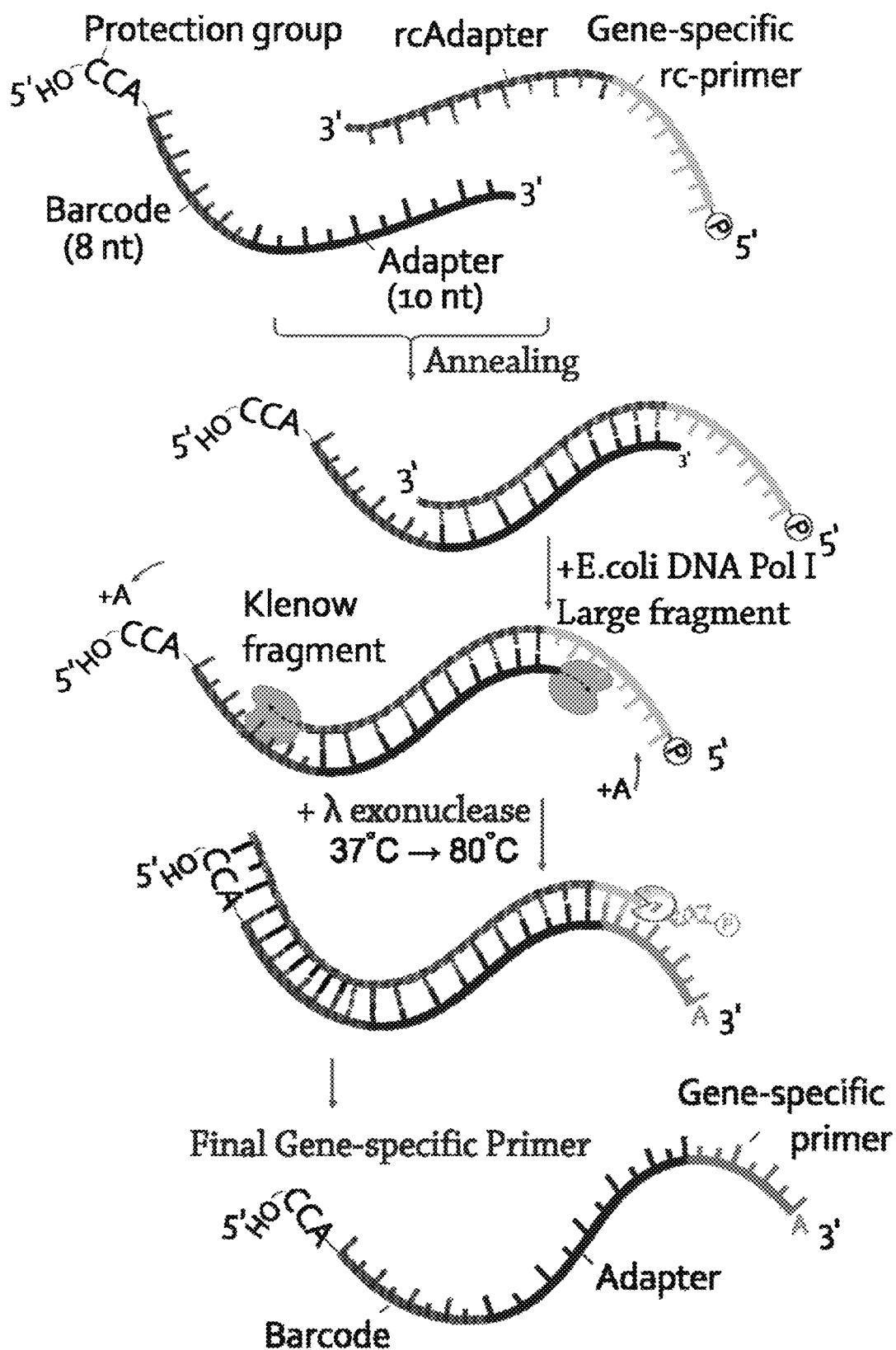

6 Claims, 22 Drawing Sheets
Specification includes a Sequence Listing.

(52) U.S. Cl.
CPC ..... *C12Q 1/6874* (2013.01); *C12Q 2525/155* (2013.01); *C12Q 2525/161* (2013.01)

(56) References Cited

OTHER PUBLICATIONS

Peng et al., "Reducing amplification artifacts in high multiplex amplicon sequencing by using molecular barcodes," BMC Genomics, 2015, 16:589, pp. 1-12.

Tu et a., "Pair-barcode high-throughput sequencing for large-scale multiplexed sample analysis," BMC Genomics, 2012, 13:43, pp. 1-10.

\* cited by examiner

SEQUENCE LISTING

<160> NUMBER OF SEQ ID NOS: 198

<210> SEQ ID NO 1
<211> LENGTH: 21
<212> TYPE: DNA
<213> ORGANISM: Artificial Sequence
<220> FEATURE:
<223> OTHER INFORMATION: unassigned DNA -- Barcode L01 -- F Adapter
      (Table 1)

<400> SEQUENCE: 1
ccatcctcag gtagcgacga g                                             21

<210> SEQ ID NO 2
<211> LENGTH: 21
<212> TYPE: DNA
<213> ORGANISM: Artificial Sequence
<220> FEATURE:
<223> OTHER INFORMATION: unassigned DNA -- Barcode L02 -- F Adapter
      (Table 1)

<400> SEQUENCE: 2
ccaccgaaca ctagcgacga g                                             21

<210> SEQ ID NO 3
<211> LENGTH: 21
<212> TYPE: DNA
<213> ORGANISM: Artificial Sequence
<220> FEATURE:

```
<223> OTHER INFORMATION: unassigned DNA -- Barcode L03 -- F Adapter
      (Table 1)

<400> SEQUENCE: 3
ccaactgagg ctagcgacga g                                              21

<210> SEQ ID NO 4
<211> LENGTH: 21
<212> TYPE: DNA
<213> ORGANISM: Artificial Sequence
<220> FEATURE:
<223> OTHER INFORMATION: unassigned DNA -- Barcode L04 -- F Adapter
      (Table 1)

<400> SEQUENCE: 4
ccacacctag gtagcgacga g                                              21

<210> SEQ ID NO 5
<211> LENGTH: 21
<212> TYPE: DNA
<213> ORGANISM: Artificial Sequence
<220> FEATURE:
<223> OTHER INFORMATION: unassigned DNA -- Barcode L05 -- F Adapter
      (Table 1)

<400> SEQUENCE: 5
ccacacacct ctagcgacga g                                              21

<210> SEQ ID NO 6
<211> LENGTH: 21
<212> TYPE: DNA
<213> ORGANISM: Artificial Sequence
<220> FEATURE:
<223> OTHER INFORMATION: unassigned DNA -- Barcode L06 -- F Adapter
 (Table 1)

<400> SEQUENCE: 6
ccatacggca ctagcgacga g                                              21

<210> SEQ ID NO 7
<211> LENGTH: 21
<212> TYPE: DNA
<213> ORGANISM: Artificial Sequence
<220> FEATURE:
<223> OTHER INFORMATION: unassigned DNA -- Barcode L07 -- F Adapter
      (Table 1)

<400> SEQUENCE: 7
ccagatccag gtagcgacga g                                              21

<210> SEQ ID NO 8
<211> LENGTH: 21
<212> TYPE: DNA
<213> ORGANISM: Artificial Sequence
<220> FEATURE:
<223> OTHER INFORMATION: unassigned DNA -- Barcode L08 -- F Adapter
      (Table 1)

<400> SEQUENCE: 8
ccaccagacg atagcgacga g                                              21

<210> SEQ ID NO 9
<211> LENGTH: 21
<212> TYPE: DNA
<213> ORGANISM: Artificial Sequence
<220> FEATURE:
<223> OTHER INFORMATION: unassigned DNA -- Barcode R01 -- R Adapter
```

-continued

```
      (Table 1)

<400> SEQUENCE: 9
ccaacgcgct accatacgac g                                           21

<210> SEQ ID NO 10
<211> LENGTH: 21
<212> TYPE: DNA
<213> ORGANISM: Artificial Sequence
<220> FEATURE:
<223> OTHER INFORMATION: unassigned DNA -- Barcode R02 -- R Adapter
      (Table 1)

<400> SEQUENCE: 10
ccaacgctag cccatacgac g                                           21

<210> SEQ ID NO 11
<211> LENGTH: 21
<212> TYPE: DNA
<213> ORGANISM: Artificial Sequence
<220> FEATURE:
<223> OTHER INFORMATION: unassigned DNA -- Barcode R03 -- R Adapter
      (Table 1)

<400> SEQUENCE: 11
ccaactcctc cccatacgac g                                           21

<210> SEQ ID NO 12
<211> LENGTH: 21
<212> TYPE: DNA
<213> ORGANISM: Artificial Sequence
<220> FEATURE:
<223> OTHER INFORMATION: unassigned DNA -- Barcode R04 -- R Adapter
      (Table 1)

<400> SEQUENCE: 12
ccagcgcatc tccatacgac g                                           21

<210> SEQ ID NO 13
<211> LENGTH: 21
<212> TYPE: DNA
<213> ORGANISM: Artificial Sequence
<220> FEATURE:
<223> OTHER INFORMATION: unassigned DNA -- Barcode R05 -- R Adapter
      (Table 1)

<400> SEQUENCE: 13
ccacggacaa gccatacgac g                                           21

<210> SEQ ID NO 14
<211> LENGTH: 21
<212> TYPE: DNA
<213> ORGANISM: Artificial Sequence
<220> FEATURE:
<223> OTHER INFORMATION: unassigned DNA -- Barcode R06 -- R Adapter
      (Table 1)

<400> SEQUENCE: 14
ccacggtcca accatacgac g                                           21

<210> SEQ ID NO 15
<211> LENGTH: 21
<212> TYPE: DNA
<213> ORGANISM: Artificial Sequence
<220> FEATURE:
<223> OTHER INFORMATION: unassigned DNA -- Barcode R07 -- R Adapter
      (Table 1)
```

```
<400> SEQUENCE: 15
ccaggacgca accatacgac g                                              21

<210> SEQ ID NO 16
<211> LENGTH: 21
<212> TYPE: DNA
<213> ORGANISM: Artificial Sequence
<220> FEATURE:
<223> OTHER INFORMATION: unassigned DNA -- Barcode R08 -- R Adapter
      (Table 1)

<400> SEQUENCE: 16
ccagaccttc cccatacgac g                                              21

<210> SEQ ID NO 17
<211> LENGTH: 21
<212> TYPE: DNA
<213> ORGANISM: Artificial Sequence
<220> FEATURE:
<223> OTHER INFORMATION: unassigned DNA -- Barcode R09 -- R Adapter
      (Table 1)

<400> SEQUENCE: 17
ccaaggagag cccatacgac g                                              21

<210> SEQ ID NO 18
<211> LENGTH: 21
<212> TYPE: DNA
<213> ORGANISM: Artificial Sequence
<220> FEATURE:
<223> OTHER INFORMATION: unassigned DNA -- Barcode R10 -- R Adapter
      (Table 1)

<400> SEQUENCE: 18
ccaccatcac gccatacgac g                                              21

<210> SEQ ID NO 19
<211> LENGTH: 21
<212> TYPE: DNA
<213> ORGANISM: Artificial Sequence
<220> FEATURE:
<223> OTHER INFORMATION: unassigned DNA -- Barcode R11 -- R Adapter
      (Table 1)

<400> SEQUENCE: 19
ccacggcaac accatacgac g                                              21

<210> SEQ ID NO 20
<211> LENGTH: 21
<212> TYPE: DNA
<213> ORGANISM: Artificial Sequence
<220> FEATURE:
<223> OTHER INFORMATION: unassigned DNA -- Barcode R12 -- R Adapter
      (Table 1)

<400> SEQUENCE: 20
ccacggaatg cccatacgac g                                              21

<210> SEQ ID NO 21
<211> LENGTH: 33
<212> TYPE: DNA
<213> ORGANISM: Artificial Sequence
<220> FEATURE:
<223> OTHER INFORMATION: unassigned DNA -- rcF Primer 185delAG -- rcF
      Adapter (Table 1)
```

<400> SEQUENCE: 21
gacattttgt acttcttcaa cgcctcgtcg cta                              33

<210> SEQ ID NO 22
<211> LENGTH: 31
<212> TYPE: DNA
<213> ORGANISM: Artificial Sequence
<220> FEATURE:
<223> OTHER INFORMATION: unassigned DNA -- rcR Primer 185delAG -- rcR
      Adapter (Table 1)

<400> SEQUENCE: 22
ctcctatgca aatgaacaga acgtcgtatg g                                31

<210> SEQ ID NO 23
<211> LENGTH: 29
<212> TYPE: DNA
<213> ORGANISM: Artificial Sequence
<220> FEATURE:
<223> OTHER INFORMATION: unassigned DNA -- rcF Primer 5382insC -- rcF
      Adapter (Table 1)

<400> SEQUENCE: 23
cttgctcgct ttggaccttc tcgtcgcta                                   29

<210> SEQ ID NO 24
<211> LENGTH: 29
<212> TYPE: DNA
<213> ORGANISM: Artificial Sequence
<220> FEATURE:
<223> OTHER INFORMATION: unassigned DNA --rcR Primer 5382insC -- rcR
      Adapter (Table 1)

<400> SEQUENCE: 24
cactcttcca tcccaaccac gtcgtatgg                                   29

<210> SEQ ID NO 25
<211> LENGTH: 35
<212> TYPE: DNA
<213> ORGANISM: Artificial Sequence
<220> FEATURE:
<223> OTHER INFORMATION: unassigned DNA -- rcF Primer p.Y978* - rcF
      Adapter (Table 1)

<400> SEQUENCE: 25
atttggagta atgagtccag tttcgctcgt cgcta                            35

<210> SEQ ID NO 26
<211> LENGTH: 33
<212> TYPE: DNA
<213> ORGANISM: Artificial Sequence
<220> FEATURE:
<223> OTHER INFORMATION: unassigned DNA -- rcR Primer p.Y978* - rcR
      Adapter (Table 1)

<400> SEQUENCE: 26
gagaacattc caagtacagt gagcgtcgta tgg                              33

<210> SEQ ID NO 27
<211> LENGTH: 30
<212> TYPE: DNA
<213> ORGANISM: Artificial Sequence
<220> FEATURE:
<223> OTHER INFORMATION: unassigned DNA -- rcF Primer p.A1708E - rcF
      Adapter (Table 1)

<400> SEQUENCE: 27
gtccgttcac acacaaactc ctcgtcgcta                                30

<210> SEQ ID NO 28
<211> LENGTH: 29
<212> TYPE: DNA
<213> ORGANISM: Artificial Sequence
<220> FEATURE:
<223> OTHER INFORMATION: unassigned DNA -- rcR Primer p.A1708E -- rcR
      Adapter (Table 1)

<400> SEQUENCE: 28
cccctcctcc ctttaacacc gtcgtatgg                                 29

<210> SEQ ID NO 29
<211> LENGTH: 29
<212> TYPE: DNA
<213> ORGANISM: Artificial Sequence
<220> FEATURE:
<223> OTHER INFORMATION: unassigned DNA -- rcF Primer 981delAT -- rcF
      Adapter (Table 1)

<400> SEQUENCE: 29
ccttacttcc agcccatctc tcgtcgcta                                 29

<210> SEQ ID NO 30
<211> LENGTH: 29
<212> TYPE: DNA
<213> ORGANISM: Artificial Sequence
<220> FEATURE:
<223> OTHER INFORMATION: unassigned DNA -- rcR Primer 981delAT -- rcR
      Adapter (Table 1)

<400> SEQUENCE: 30
gccatgctca gagaatcctc gtcgtatgg                                 29

<210> SEQ ID NO 31
<211> LENGTH: 33
<212> TYPE: DNA
<213> ORGANISM: Artificial Sequence
<220> FEATURE:
<223> OTHER INFORMATION: unassigned DNA -- rcF Primer c.6174delT -- rcF
      Adapter (Table )

<400> SEQUENCE: 31
gacttatgaa gcttccctat actctcgtcg cta                            33

<210> SEQ ID NO 32
<211> LENGTH: 29
<212> TYPE: DNA
<213> ORGANISM: Artificial Sequence
<220> FEATURE:
<223> OTHER INFORMATION: unassigned DNA -- rcR Primer c.6174delT -- rcR
      Adapter (Table 1)

<400> SEQUENCE: 32
ccaggtatca gatgcttcac gtcgtatgg                                 29

<210> SEQ ID NO 33
<211> LENGTH: 35
<212> TYPE: DNA
<213> ORGANISM: Artificial Sequence
<220> FEATURE:
<223> OTHER INFORMATION: unassigned DNA -- rcF Primer 8765delAG -- rcF
      Adapter (Table 1)

<400> SEQUENCE: 33

```
cattgcgaaa tatgtataat ccagactcgt cgcta                                    35

<210> SEQ ID NO 34
<211> LENGTH: 36
<212> TYPE: DNA
<213> ORGANISM: Artificial Sequence
<220> FEATURE:
<223> OTHER INFORMATION: unassigned DNA -- rcR Primer 8765delAG -- rcR
      Adapter (Table 1)

<400> SEQUENCE: 34
ggtacacatt gttatttcta atatgacgtc gtatgg                                   36

<210> SEQ ID NO 35
<211> LENGTH: 31
<212> TYPE: DNA
<213> ORGANISM: Artificial Sequence
<220> FEATURE:
<223> OTHER INFORMATION: unassigned DNA -- rcF Primer IVS2+1G>A -- rcF
      Adapter (Table 1)

<400> SEQUENCE: 35
acgatattcc tccaatgctt gctcgtcgct a                                        31

<210> SEQ ID NO 36
<211> LENGTH: 33
<212> TYPE: DNA
<213> ORGANISM: Artificial Sequence
<220> FEATURE:
<223> OTHER INFORMATION: unassigned DNA -- rcR Primer IVS2+1G>A -- rcR
      Adapter (Table 1)

<400> SEQUENCE: 36
ccagttaaca acataatcat cgtcgtcgta tgg                                      33

<210> SEQ ID NO 37
<211> LENGTH: 29
<212> TYPE: DNA
<213> ORGANISM: Artificial Sequence
<220> FEATURE:
<223> OTHER INFORMATION: unassigned DNA -- rcF Primer p.R2336P -- rcF
      Adapter (Table 1)

<400> SEQUENCE: 37
acacaggtaa tcggctctac tcgtcgcta                                           29

<210> SEQ ID NO 38
<211> LENGTH: 34
<212> TYPE: DNA
<213> ORGANISM: Artificial Sequence
<220> FEATURE:
<223> OTHER INFORMATION: unassigned DNA -- rcR Primer p.R2336P - rcR
      Adapter (Table 1)

<400> SEQUENCE: 38
ggtagtattt tatagtgctg ttcacgtcgt atgg                                     34

<210> SEQ ID NO 39
<211> LENGTH: 31
<212> TYPE: DNA
<213> ORGANISM: Artificial Sequence
<220> FEATURE:
<223> OTHER INFORMATION: unassigned DNA -- rcF Primer p.P1812A -- rcF
      Adapter (Table 1)

<400> SEQUENCE: 39
aggactactg gaactgtcac tctcgtcgct a                                        31
```

<210> SEQ ID NO 40
<211> LENGTH: 29
<212> TYPE: DNA
<213> ORGANISM: Artificial Sequence
<220> FEATURE:
<223> OTHER INFORMATION: unassigned DNA -- rcR Primer p.P1812A -- rcR
      Adapter (Table 1)

<400> SEQUENCE: 40
ggtaaggtgc ctgcatgtac gtcgtatgg                                            29

<210> SEQ ID NO 41
<211> LENGTH: 21
<212> TYPE: DNA
<213> ORGANISM: Artificial Sequence
<220> FEATURE:
<223> OTHER INFORMATION: unassigned DNA -- Barcode R01 - R Adapter
      (Table 7)

<400> SEQUENCE: 41
ccagccacct tagcgtaacc t                                                    21

<210> SEQ ID NO 42
<211> LENGTH: 21
<212> TYPE: DNA
<213> ORGANISM: Artificial Sequence
<220> FEATURE:
<223> OTHER INFORMATION: unassigned DNA -- Barcode R02 - R Adapter
      (Table 7)

<400> SEQUENCE: 42
ccagaaccac gagcgtaacc t                                                    21

<210> SEQ ID NO 43
<211> LENGTH: 21
<212> TYPE: DNA
<213> ORGANISM: Artificial Sequence
<220> FEATURE:
<223> OTHER INFORMATION: unassigned DNA -- Barcode R03 - R Adapter
      (Table 7)

<400> SEQUENCE: 43
ccactcaggc aagcgtaacc t                                                    21

<210> SEQ ID NO 44
<211> LENGTH: 21
<212> TYPE: DNA
<213> ORGANISM: Artificial Sequence
<220> FEATURE:
<223> OTHER INFORMATION: unassigned DNA -- Barcode R04 - R Adapter
      (Table 7)

<400> SEQUENCE: 44
ccagtacagc gagcgtaacc t                                                    21

<210> SEQ ID NO 45
<211> LENGTH: 21
<212> TYPE: DNA
<213> ORGANISM: Artificial Sequence
<220> FEATURE:
<223> OTHER INFORMATION: unassigned DNA -- Barcode R05 - R Adapter
      (Table 7)

<400> SEQUENCE: 45
ccactcgagc tagcgtaacc t                                                    21

<210> SEQ ID NO 46
<211> LENGTH: 21
<212> TYPE: DNA
<213> ORGANISM: Artificial Sequence
<220> FEATURE:
<223> OTHER INFORMATION: unassigned DNA -- Barcode R06 - R Adapter
      (Table 7)

<400> SEQUENCE: 46
ccagcgacac aagcgtaacc t                                          21

<210> SEQ ID NO 47
<211> LENGTH: 21
<212> TYPE: DNA
<213> ORGANISM: Artificial Sequence
<220> FEATURE:
<223> OTHER INFORMATION: unassigned DNA -- Barcode R07 - R Adapter
      (Table 7)

<400> SEQUENCE: 47
ccagtcatcg gagcgtaacc t                                          21

<210> SEQ ID NO 48
<211> LENGTH: 21
<212> TYPE: DNA
<213> ORGANISM: Artificial Sequence
<220> FEATURE:
<223> OTHER INFORMATION: unassigned DNA -- Barcode R08 - R Adapter
      (Table 7)

<400> SEQUENCE: 48
ccatgcctcc aagcgtaacc t                                          21

<210> SEQ ID NO 49
<211> LENGTH: 21
<212> TYPE: DNA
<213> ORGANISM: Artificial Sequence
<220> FEATURE:
<223> OTHER INFORMATION: unassigned DNA -- Barcode R09 - R Adapter
      (Table 7)

<400> SEQUENCE: 49
ccaccgattc cagcgtaacc t                                          21

<210> SEQ ID NO 50
<211> LENGTH: 21
<212> TYPE: DNA
<213> ORGANISM: Artificial Sequence
<220> FEATURE:
<223> OTHER INFORMATION: unassigned DNA -- Barcode R10 - R Adapter
      (Table 7)

<400> SEQUENCE: 50
ccagcatagg cagcgtaacc t                                          21

<210> SEQ ID NO 51
<211> LENGTH: 21
<212> TYPE: DNA
<213> ORGANISM: Artificial Sequence
<220> FEATURE:
<223> OTHER INFORMATION: unassigned DNA -- Barcode R11 - R Adapter
      (Table 7)

<400> SEQUENCE: 51
ccagacagag gagcgtaacc t                                          21

```
<210> SEQ ID NO 52
<211> LENGTH: 21
<212> TYPE: DNA
<213> ORGANISM: Artificial Sequence
<220> FEATURE:
<223> OTHER INFORMATION: unassigned DNA -- Barcode R12 - R Adapter
      (Table 7)

<400> SEQUENCE: 52
ccacaccggt aagcgtaacc t                                                 21

<210> SEQ ID NO 53
<211> LENGTH: 21
<212> TYPE: DNA
<213> ORGANISM: Artificial Sequence
<220> FEATURE:
<223> OTHER INFORMATION: unassigned DNA -- Barcode R13 - R Adapter
      (Table 7)

<400> SEQUENCE: 53
ccagtggaag gagcgtaacc t                                                 21

<210> SEQ ID NO 54
<211> LENGTH: 21
<212> TYPE: DNA
<213> ORGANISM: Artificial Sequence
<220> FEATURE:
<223> OTHER INFORMATION: unassigned DNA -- Barcode R14 - R Adapter
      (Table 7)

<400> SEQUENCE: 54
ccaggatcct cagcgtaacc t                                                 21

<210> SEQ ID NO 55
<211> LENGTH: 21
<212> TYPE: DNA
<213> ORGANISM: Artificial Sequence
<220> FEATURE:
<223> OTHER INFORMATION: unassigned DNA -- Barcode R15 - R Adapter
      (Table 7)

<400> SEQUENCE: 55
ccaggacagt gagcgtaacc t                                                 21

<210> SEQ ID NO 56
<211> LENGTH: 21
<212> TYPE: DNA
<213> ORGANISM: Artificial Sequence
<220> FEATURE:
<223> OTHER INFORMATION: unassigned DNA -- Barcode R16 - R Adapter
      (Table 7)

<400> SEQUENCE: 56
ccatgtggcg tagcgtaacc t                                                 21

<210> SEQ ID NO 57
<211> LENGTH: 21
<212> TYPE: DNA
<213> ORGANISM: Artificial Sequence
<220> FEATURE:
<223> OTHER INFORMATION: unassigned DNA -- Barcode R17 - R Adapter
      (Table 7)

<400> SEQUENCE: 57
ccagcgatca gagcgtaacc t                                                 21

<210> SEQ ID NO 58
```

```
<211> LENGTH: 21
<212> TYPE: DNA
<213> ORGANISM: Artificial Sequence
<220> FEATURE:
<223> OTHER INFORMATION: unassigned DNA -- Barcode R18 - R Adapter
      (Table 7)

<400> SEQUENCE: 58
ccaacaaggc cagcgtaacc t                                              21

<210> SEQ ID NO 59
<211> LENGTH: 21
<212> TYPE: DNA
<213> ORGANISM: Artificial Sequence
<220> FEATURE:
<223> OTHER INFORMATION: unassigned DNA -- Barcode R19 - R Adapter
      (Table 7)

<400> SEQUENCE: 59
ccactcggag aagcgtaacc t                                              21

<210> SEQ ID NO 60
<211> LENGTH: 21
<212> TYPE: DNA
<213> ORGANISM: Artificial Sequence
<220> FEATURE:
<223> OTHER INFORMATION: unassigned DNA -- Barcode R20 - R Adapter
      (Table 7)

<400> SEQUENCE: 60
ccacaagctg cagcgtaacc t                                              21

<210> SEQ ID NO 61
<211> LENGTH: 21
<212> TYPE: DNA
<213> ORGANISM: Artificial Sequence
<220> FEATURE:
<223> OTHER INFORMATION: unassigned DNA -- Barcode R21 - R Adapter
      (Table 7)

<400> SEQUENCE: 61
ccagtccacc aagcgtaacc t                                              21

<210> SEQ ID NO 62
<211> LENGTH: 21
<212> TYPE: DNA
<213> ORGANISM: Artificial Sequence
<220> FEATURE:
<223> OTHER INFORMATION: unassigned DNA -- Barcode R22 - R Adapter
      (Table 7)

<400> SEQUENCE: 62
ccatcgagga cagcgtaacc t                                              21

<210> SEQ ID NO 63
<211> LENGTH: 21
<212> TYPE: DNA
<213> ORGANISM: Artificial Sequence
<220> FEATURE:
<223> OTHER INFORMATION: unassigned DNA -- Barcode R23 - R Adapter
      (Table 7)

<400> SEQUENCE: 63
ccatccggca aagcgtaacc t                                              21

<210> SEQ ID NO 64
<211> LENGTH: 21
```

```
<212> TYPE: DNA
<213> ORGANISM: Artificial Sequence
<220> FEATURE:
<223> OTHER INFORMATION: unassigned DNA -- Barcode R24 - R Adapter
      (Table 7)

<400> SEQUENCE: 64
ccagtctcac gagcgtaacc t                                           21

<210> SEQ ID NO 65
<211> LENGTH: 21
<212> TYPE: DNA
<213> ORGANISM: Artificial Sequence
<220> FEATURE:
<223> OTHER INFORMATION: unassigned DNA -- Barcode L01 - F Adapter
      (Table 7)

<400> SEQUENCE: 65
ccaccttctc gatgcgcatt c                                           21

<210> SEQ ID NO 66
<211> LENGTH: 21
<212> TYPE: DNA
<213> ORGANISM: Artificial Sequence
<220> FEATURE:
<223> OTHER INFORMATION: unassigned DNA -- Barcode L02 - F Adapter
      (Table 7)

<400> SEQUENCE: 66
ccaccagtag catgcgcatt c                                           21

<210> SEQ ID NO 67
<211> LENGTH: 21
<212> TYPE: DNA
<213> ORGANISM: Artificial Sequence
<220> FEATURE:
<223> OTHER INFORMATION: unassigned DNA -- Barcode L03 - F Adapter
      (Table 7)

<400> SEQUENCE: 67
ccacctaacg catgcgcatt c                                           21

<210> SEQ ID NO 68
<211> LENGTH: 21
<212> TYPE: DNA
<213> ORGANISM: Artificial Sequence
<220> FEATURE:
<223> OTHER INFORMATION: unassigned DNA -- Barcode L04 - F Adapter
      (Table 7)

<400> SEQUENCE: 68
ccaggccgat tatgcgcatt c                                           21

<210> SEQ ID NO 69
<211> LENGTH: 21
<212> TYPE: DNA
<213> ORGANISM: Artificial Sequence
<220> FEATURE:
<223> OTHER INFORMATION: unassigned DNA -- Barcode L05 - F Adapter
      (Table 7)

<400> SEQUENCE: 69
ccacgttcgt catgcgcatt c                                           21

<210> SEQ ID NO 70
<211> LENGTH: 21
<212> TYPE: DNA
```

<213> ORGANISM: Artificial Sequence
<220> FEATURE:
<223> OTHER INFORMATION: unassigned DNA -- Barcode L06 - F Adapter
      (Table 7)

<400> SEQUENCE: 70
ccagcctggt aatgcgcatt c                                            21

<210> SEQ ID NO 71
<211> LENGTH: 21
<212> TYPE: DNA
<213> ORGANISM: Artificial Sequence
<220> FEATURE:
<223> OTHER INFORMATION: unassigned DNA -- Barcode L07 - F Adapter
      (Table 7)

<400> SEQUENCE: 71
ccaccagacg aatgcgcatt c                                            21

<210> SEQ ID NO 72
<211> LENGTH: 21
<212> TYPE: DNA
<213> ORGANISM: Artificial Sequence
<220> FEATURE:
<223> OTHER INFORMATION: unassigned DNA -- Barcode L08 - F Adapter
      (Table 7)

<400> SEQUENCE: 72
ccaacgacac catgcgcatt c                                            21

<210> SEQ ID NO 73
<211> LENGTH: 21
<212> TYPE: DNA
<213> ORGANISM: Artificial Sequence
<220> FEATURE:
<223> OTHER INFORMATION: unassigned DNA -- Barcode L09 - F Adapter
      (Table 7)

<400> SEQUENCE: 73
ccagcctctt gatgcgcatt c                                            21

<210> SEQ ID NO 74
<211> LENGTH: 21
<212> TYPE: DNA
<213> ORGANISM: Artificial Sequence
<220> FEATURE:
<223> OTHER INFORMATION: unassigned DNA -- Barcode L10 - F Adapter
      (Table 7)

<400> SEQUENCE: 74
ccatacggca catgcgcatt c                                            21

<210> SEQ ID NO 75
<211> LENGTH: 21
<212> TYPE: DNA
<213> ORGANISM: Artificial Sequence
<220> FEATURE:
<223> OTHER INFORMATION: unassigned DNA -- Barcode L11 - F Adapter
      (Table 7)

<400> SEQUENCE: 75
ccactccagt catgcgcatt c                                            21

<210> SEQ ID NO 76
<211> LENGTH: 21
<212> TYPE: DNA
<213> ORGANISM: Artificial Sequence
<220> FEATURE:
<223> OTHER INFORMATION: unassigned DNA -- Barcode L12 - F Adapter
      (Table 7)

<400> SEQUENCE: 76
ccaaacgtcg gatgcgcatt c                                             21

<210> SEQ ID NO 77
<211> LENGTH: 21
<212> TYPE: DNA
<213> ORGANISM: Artificial Sequence
<220> FEATURE:
<223> OTHER INFORMATION: unassigned DNA -- Barcode L13 - F Adapter
      (Table 7)

<400> SEQUENCE: 77
ccagttggag catgcgcatt c                                             21

<210> SEQ ID NO 78
<211> LENGTH: 21
<212> TYPE: DNA
<213> ORGANISM: Artificial Sequence
<220> FEATURE:
<223> OTHER INFORMATION: unassigned DNA -- Barcode L14 - F Adapter
      (Table 7)

<400> SEQUENCE: 78
ccaacgagcc tatgcgcatt c                                             21

<210> SEQ ID NO 79
<211> LENGTH: 21
<212> TYPE: DNA
<213> ORGANISM: Artificial Sequence
<220> FEATURE:
<223> OTHER INFORMATION: unassigned DNA -- Barcode L15 - F Adapter
      (Table 7)

<400> SEQUENCE: 79
ccagatccag gatgcgcatt c                                             21

<210> SEQ ID NO 80
<211> LENGTH: 21
<212> TYPE: DNA
<213> ORGANISM: Artificial Sequence
<220> FEATURE:
<223> OTHER INFORMATION: unassigned DNA -- Barcode L16 - F Adapter
      (Table 7)

<400> SEQUENCE: 80
ccatcctggc tatgcgcatt c                                             21

<210> SEQ ID NO 81
<211> LENGTH: 28
<212> TYPE: DNA
<213> ORGANISM: Artificial Sequence
<220> FEATURE:
<223> OTHER INFORMATION: unassigned DNA - rcF Primer GAPDH - rcF Adapter
      (Table 7)

<400> SEQUENCE: 81
gatggcatgg actgtggtga atgcgcat                                      28

<210> SEQ ID NO 82
<211> LENGTH: 28
<212> TYPE: DNA
<213> ORGANISM: Artificial Sequence
<220> FEATURE:

<223> OTHER INFORMATION: unassigned DNA - rcR Primer GAPDH - rcR Adapter
(Table 7)

<400> SEQUENCE: 82
gaacgggaag ctcactggag gttacgct                28

<210> SEQ ID NO 83
<211> LENGTH: 27
<212> TYPE: DNA
<213> ORGANISM: Artificial Sequence
<220> FEATURE:
<223> OTHER INFORMATION: unassigned DNA - rcF Primer B2M - rcF Adapter
(Table 7)

<400> SEQUENCE: 83
aaggccacgg agcgagagaa tgcgcat                27

<210> SEQ ID NO 84
<211> LENGTH: 29
<212> TYPE: DNA
<213> ORGANISM: Artificial Sequence
<220> FEATURE:
<223> OTHER INFORMATION: unassigned DNA - rcR Primer B2M - rcR Adapter
(Table 7)

<400> SEQUENCE: 84
cacgtcatcc agcagagaaa ggttacgct                29

<210> SEQ ID NO 85
<211> LENGTH: 29
<212> TYPE: DNA
<213> ORGANISM: Artificial Sequence
<220> FEATURE:
<223> OTHER INFORMATION: unassigned DNA - rcF Primer POU5F1 - rcF
Adapter (Table 7)

<400> SEQUENCE: 85
gagaaaggag acccagcagg aatgcgcat                29

<210> SEQ ID NO 86
<211> LENGTH: 29
<212> TYPE: DNA
<213> ORGANISM: Artificial Sequence
<220> FEATURE:
<223> OTHER INFORMATION: unassigned DNA - rcR Primer POU5F1 - rcR
Adapter (Table 7)

<400> SEQUENCE: 86
cactgcactg tactcctcga ggttacgct                29

<210> SEQ ID NO 87
<211> LENGTH: 29
<212> TYPE: DNA
<213> ORGANISM: Artificial Sequence
<220> FEATURE:
<223> OTHER INFORMATION: unassigned DNA - rcF Primer NANOG - rcF Adapter
(Table 7)

<400> SEQUENCE: 87
ggtggaagaa tcagggctgg aatgcgcat                29

<210> SEQ ID NO 88
<211> LENGTH: 30
<212> TYPE: DNA
<213> ORGANISM: Artificial Sequence
<220> FEATURE:
<223> OTHER INFORMATION: unassigned DNA - rcR Primer NANOG - rcR Adapter (Table 7)

<400> SEQUENCE: 88
cccggtcaag aaacagaaga aggttacgct                                    30

<210> SEQ ID NO 89
<211> LENGTH: 29
<212> TYPE: DNA
<213> ORGANISM: Artificial Sequence
<220> FEATURE:
<223> OTHER INFORMATION: unassigned DNA - rcF Primer SOX2 - rcF Adapter
      (Table 7)

<400> SEQUENCE: 89
ggagtgggag gaagaggtag aatgcgcat                                     29

<210> SEQ ID NO 90
<211> LENGTH: 28
<212> TYPE: DNA
<213> ORGANISM: Artificial Sequence
<220> FEATURE:
<223> OTHER INFORMATION: unassigned DNA - rcR Primer SOX2 - rcR Adapter
      (Table 7)

<400> SEQUENCE: 90
gtcccagcac taccagagag gttacgct                                      28

<210> SEQ ID NO 91
<211> LENGTH: 29
<212> TYPE: DNA
<213> ORGANISM: Artificial Sequence
<220> FEATURE:
<223> OTHER INFORMATION: unassigned DNA - rcF Primer LIN28A - rcF
      Adapter (Table 7)

<400> SEQUENCE: 91
catggacagg aagccgaacg aatgcgcat                                     29

<210> SEQ ID NO 92
<211> LENGTH: 29
<212> TYPE: DNA
<213> ORGANISM: Artificial Sequence
<220> FEATURE:
<223> OTHER INFORMATION: unassigned DNA - rcR Primer LIN28A - rcR
      Adapter (Table 7)

<400> SEQUENCE: 92
aagctgcaca tggaagggta ggttacgct                                     29

<210> SEQ ID NO 93
<211> LENGTH: 29
<212> TYPE: DNA
<213> ORGANISM: Artificial Sequence
<220> FEATURE:
<223> OTHER INFORMATION: unassigned DNA - rcF Primer RNA 1 (EC2) - rcF
      Adapter (Table 7)

<400> SEQUENCE: 93
tgcatggcct ttggtgatgg aatgcgcat                                     29

<210> SEQ ID NO 94
<211> LENGTH: 29
<212> TYPE: DNA
<213> ORGANISM: Artificial Sequence
<220> FEATURE:
<223> OTHER INFORMATION: unassigned DNA - rcR Primer RNA 1 (EC2) - rcR
      Adapter (Table 7)

<210> SEQ ID NO 95
<211> LENGTH: 28
<212> TYPE: DNA
<213> ORGANISM: Artificial Sequence
<220> FEATURE:
<223> OTHER INFORMATION: unassigned DNA - rcF Primer RNA 2 (EC12) - rcF
      Adapter (Table 7)

<400> SEQUENCE: 94
gcaagcgtgt aagatcgtca ggttacgct                                    29

<210> SEQ ID NO 95
<211> LENGTH: 28
<212> TYPE: DNA
<213> ORGANISM: Artificial Sequence
<220> FEATURE:
<223> OTHER INFORMATION: unassigned DNA - rcF Primer RNA 2 (EC12) - rcF
      Adapter (Table 7)

<400> SEQUENCE: 95
acggcgatag aggcgatcga atgcgcat                                     28

<210> SEQ ID NO 96
<211> LENGTH: 29
<212> TYPE: DNA
<213> ORGANISM: Artificial Sequence
<220> FEATURE:
<223> OTHER INFORMATION: unassigned DNA - rcR Primer RNA 2 (EC12) - rcR
      Adapter (Table 7)

<400> SEQUENCE: 96
tgaacaggca gcggaaaaga ggttacgct                                    29

<210> SEQ ID NO 97
<211> LENGTH: 29
<212> TYPE: DNA
<213> ORGANISM: Artificial Sequence
<220> FEATURE:
<223> OTHER INFORMATION: unassigned DNA - rcF Primer RNA 6 (EC13) - rcF
      Adapter (Table 7)

<400> SEQUENCE: 97
cgatgtgtta gatgcgctgg aatgcgcat                                    29

<210> SEQ ID NO 98
<211> LENGTH: 29
<212> TYPE: DNA
<213> ORGANISM: Artificial Sequence
<220> FEATURE:
<223> OTHER INFORMATION: unassigned DNA - rcR Primer RNA 6 (EC13) - rcR
      Adapter (Table 7)

<400> SEQUENCE: 98
gttgcggatg atattggcga ggttacgct                                    29

<210> SEQ ID NO 99
<211> LENGTH: 29
<212> TYPE: DNA
<213> ORGANISM: Artificial Sequence
<220> FEATURE:
<223> OTHER INFORMATION: unassigned DNA - rcF Primer RNA 8 (EC5) - rcF
      Adapter (Table 7)

<400> SEQUENCE: 99
gtcggcaggt aacttcaacg aatgcgcat                                    29

<210> SEQ ID NO 100
<211> LENGTH: 29
<212> TYPE: DNA
<213> ORGANISM: Artificial Sequence
<220> FEATURE:
<223> OTHER INFORMATION: unassigned DNA - rcR Primer RNA 8 (EC5) - rcR
      Adapter (Table 7)

```
<400> SEQUENCE: 100
gcgtagtcat aagcgtccta ggttacgct                                        29

<210> SEQ ID NO 101
<211> LENGTH: 21
<212> TYPE: DNA
<213> ORGANISM: Artificial Sequence
<220> FEATURE:
<223> OTHER INFORMATION: unassigned DNA - Barcode L01 - F Adapter

<400> SEQUENCE: 101
ccaccttctc gatgcgcatt c                                                21

<210> SEQ ID NO 102
<211> LENGTH: 21
<212> TYPE: DNA
<213> ORGANISM: Artificial Sequence
<220> FEATURE:
<223> OTHER INFORMATION: unassigned DNA - Barcode L02 - F Adapter

<400> SEQUENCE: 102
ccaccagtag catgcgcatt c                                                21

<210> SEQ ID NO 103
<211> LENGTH: 21
<212> TYPE: DNA
<213> ORGANISM: Artificial Sequence
<220> FEATURE:
<223> OTHER INFORMATION: unassigned DNA  - Barcode L03 - F Adapter

<400> SEQUENCE: 103
ccacctaacg catgcgcatt c                                                21

<210> SEQ ID NO 104
<211> LENGTH: 21
<212> TYPE: DNA
<213> ORGANISM: Artificial Sequence
<220> FEATURE:
<223> OTHER INFORMATION: unassigned DNA - Barcode L04 - F Adapter

<400> SEQUENCE: 104
ccaggccgat tatgcgcatt c                                                21

<210> SEQ ID NO 105
<211> LENGTH: 21
<212> TYPE: DNA
<213> ORGANISM: Artificial Sequence
<220> FEATURE:
<223> OTHER INFORMATION: unassigned DNA - Barcode L05 - F Adapter

<400> SEQUENCE: 105
ccacgttcgt catgcgcatt c                                                21

<210> SEQ ID NO 106
<211> LENGTH: 21
<212> TYPE: DNA
<213> ORGANISM: Artificial Sequence
<220> FEATURE:
<223> OTHER INFORMATION: unassigned DNA - Barcode L06 - F Adapter

<400> SEQUENCE: 106
ccagcctggt aatgcgcatt c                                                21

<210> SEQ ID NO 107
<211> LENGTH: 21
```

```
<212> TYPE: DNA
<213> ORGANISM: Artificial Sequence
<220> FEATURE:
<223> OTHER INFORMATION: unassigned DNA - Barcode L08 - F Adapter

<400> SEQUENCE: 107
ccaacgacac catgcgcatt c                                         21

<210> SEQ ID NO 108
<211> LENGTH: 21
<212> TYPE: DNA
<213> ORGANISM: Artificial Sequence
<220> FEATURE:
<223> OTHER INFORMATION: unassigned DNA - Barcode L09 - F Adapter

<400> SEQUENCE: 108
ccagcctctt gatgcgcatt c                                         21

<210> SEQ ID NO 109
<211> LENGTH: 21
<212> TYPE: DNA
<213> ORGANISM: Artificial Sequence
<220> FEATURE:
<223> OTHER INFORMATION: unassigned DNA -- Barcode R01 - R Adapter

<400> SEQUENCE: 109
ccagccacct tagcgtaacc t                                         21

<210> SEQ ID NO 110
<211> LENGTH: 21
<212> TYPE: DNA
<213> ORGANISM: Artificial Sequence
<220> FEATURE:
<223> OTHER INFORMATION: unassigned DNA -- Barcode R02 - R Adapter

<400> SEQUENCE: 110
ccagaaccac gagcgtaacc t                                         21

<210> SEQ ID NO 111
<211> LENGTH: 21
<212> TYPE: DNA
<213> ORGANISM: Artificial Sequence
<220> FEATURE:
<223> OTHER INFORMATION: unassigned DNA -- Barcode R03 - R Adapter

<400> SEQUENCE: 111
ccactcaggc aagcgtaacc t                                         21

<210> SEQ ID NO 112
<211> LENGTH: 21
<212> TYPE: DNA
<213> ORGANISM: Artificial Sequence
<220> FEATURE:
<223> OTHER INFORMATION: unassigned DNA -- Barcode R04 - R Adapter

<400> SEQUENCE: 112
ccagtacagc gagcgtaacc t                                         21

<210> SEQ ID NO 113
<211> LENGTH: 21
<212> TYPE: DNA
<213> ORGANISM: Artificial Sequence
<220> FEATURE:
<223> OTHER INFORMATION: unassigned DNA -- Barcode R05 - R Adapter

<400> SEQUENCE: 113
```
ccactcgagc tagcgtaacc t                                              21

<210> SEQ ID NO 114
<211> LENGTH: 21
<212> TYPE: DNA
<213> ORGANISM: Artificial Sequence
<220> FEATURE:
<223> OTHER INFORMATION: unassigned DNA -- Barcode R06 - R Adapter

<400> SEQUENCE: 114
ccagcgacac aagcgtaacc t                                              21

<210> SEQ ID NO 115
<211> LENGTH: 21
<212> TYPE: DNA
<213> ORGANISM: Artificial Sequence
<220> FEATURE:
<223> OTHER INFORMATION: unassigned DNA -- Barcode R07 - R Adapter

<400> SEQUENCE: 115
ccagtcatcg gagcgtaacc t                                              21

<210> SEQ ID NO 116
<211> LENGTH: 21
<212> TYPE: DNA
<213> ORGANISM: Artificial Sequence
<220> FEATURE:
<223> OTHER INFORMATION: unassigned DNA -- Barcode R08 - R Adapter

<400> SEQUENCE: 116
ccatgcctcc aagcgtaacc t                                              21

<210> SEQ ID NO 117
<211> LENGTH: 21
<212> TYPE: DNA
<213> ORGANISM: Artificial Sequence
<220> FEATURE:
<223> OTHER INFORMATION: unassigned DNA -- Barcode R09 - R Adapter

<400> SEQUENCE: 117
ccaccgattc cagcgtaacc t                                              21

<210> SEQ ID NO 118
<211> LENGTH: 21
<212> TYPE: DNA
<213> ORGANISM: Artificial Sequence
<220> FEATURE:
<223> OTHER INFORMATION: unassigned DNA -- Barcode R11 - R Adapter

<400> SEQUENCE: 118
ccagacagag gagcgtaacc t                                              21

<210> SEQ ID NO 119
<211> LENGTH: 30
<212> TYPE: DNA
<213> ORGANISM: Artificial Sequence
<220> FEATURE:
<223> OTHER INFORMATION: unassigned DNA - rcF Primer EGFR_1 -- rcF
      Adapter

<400> SEQUENCE: 119
tcgcatgaag aggccgatcc gaatgcgcat                                     30

<210> SEQ ID NO 120
<211> LENGTH: 28
<212> TYPE: DNA

```
<213> ORGANISM: Artificial Sequence
<220> FEATURE:
<223> OTHER INFORMATION: unassigned DNA -- rcR Primer EGFR_1 -- rcR
      Adapter

<400> SEQUENCE: 120
ctgcctcacc tccaccgtag gttacgct                                        28

<210> SEQ ID NO 121
<211> LENGTH: 29
<212> TYPE: DNA
<213> ORGANISM: Artificial Sequence
<220> FEATURE:
<223> OTHER INFORMATION: unassigned DNA -- rcF Primer EGFR_2 -- rcF
      Adapter

<400> SEQUENCE: 121
gatgagctgc acggtggagg aatgcgcat                                       29

<210> SEQ ID NO 122
<211> LENGTH: 30
<212> TYPE: DNA
<213> ORGANISM: Artificial Sequence
<220> FEATURE:
<223> OTHER INFORMATION: unassigned DNA -- rcR Primer EGFR_2 -- rcR
      Adapter

<400> SEQUENCE: 122
gatgtctgga gctacggggt aggttacgct                                      30

<210> SEQ ID NO 123
<211> LENGTH: 27
<212> TYPE: DNA
<213> ORGANISM: Artificial Sequence
<220> FEATURE:
<223> OTHER INFORMATION: unassigned DNA - rcF Primer KRAS - rcF Adapter

<400> SEQUENCE: 123
ctctcccgca cctgggagaa tgcgcat                                         27

<210> SEQ ID NO 124
<211> LENGTH: 30
<212> TYPE: DNA
<213> ORGANISM: Artificial Sequence
<220> FEATURE:
<223> OTHER INFORMATION: unassigned DNA - rcR Primer KRAS - rcR Adapter

<400> SEQUENCE: 124
ggggagggct ttctttgtgt aggttacgct                                      30

<210> SEQ ID NO 125
<211> LENGTH: 30
<212> TYPE: DNA
<213> ORGANISM: Artificial Sequence
<220> FEATURE:
<223> OTHER INFORMATION: unassigned DNA - rcF Primer RNA 2 (EC12) - rcF
      Adapter

<400> SEQUENCE: 125
aagcggctga acggtgagt gaatgcgcat                                       30

<210> SEQ ID NO 126
<211> LENGTH: 30
<212> TYPE: DNA
<213> ORGANISM: Artificial Sequence
<220> FEATURE:
<223> OTHER INFORMATION: unassigned DNA - rcR Primer RNA 2 (EC12) - rcR
```

```
                                      Adapter

<400> SEQUENCE: 126
tgaacaggca gcggaaaagc aggttacgct                                           30

<210> SEQ ID NO 127
<211> LENGTH: 30
<212> TYPE: DNA
<213> ORGANISM: Artificial Sequence
<220> FEATURE:
<223> OTHER INFORMATION: unassigned DNA - rcF Primer RNA 8 (EC5) - rcF
      Adapter

<400> SEQUENCE: 127
cgatgaagtg atggacgcgt gaatgcgcat                                           30

<210> SEQ ID NO 128
<211> LENGTH: 30
<212> TYPE: DNA
<213> ORGANISM: Artificial Sequence
<220> FEATURE:
<223> OTHER INFORMATION: unassigned DNA - rcR Primer RNA 8 (EC5) - rcR
      Adapter

<400> SEQUENCE: 128
ggtaacgcac gctgaggtta aggttacgct                                           30

<210> SEQ ID NO 129
<211> LENGTH: 21
<212> TYPE: DNA
<213> ORGANISM: Artificial Sequence
<220> FEATURE:
<223> OTHER INFORMATION: unassigned DNA  -- Barcode R01 - R Adapter

<400> SEQUENCE: 129
ccagccacct tagcgtaacc t                                                    21

<210> SEQ ID NO 130
<211> LENGTH: 21
<212> TYPE: DNA
<213> ORGANISM: Artificial Sequence
<220> FEATURE:
<223> OTHER INFORMATION: unassigned DNA  -- Barcode R02 - R Adapter

<400> SEQUENCE: 130
ccagaaccac gagcgtaacc t                                                    21

<210> SEQ ID NO 131
<211> LENGTH: 21
<212> TYPE: DNA
<213> ORGANISM: Artificial Sequence
<220> FEATURE:
<223> OTHER INFORMATION: unassigned DNA  -- Barcode R03 - R Adapter

<400> SEQUENCE: 131
ccactcaggc aagcgtaacc t                                                    21

<210> SEQ ID NO 132
<211> LENGTH: 21
<212> TYPE: DNA
<213> ORGANISM: Artificial Sequence
<220> FEATURE:
<223> OTHER INFORMATION: unassigned DNA  -- Barcode R04 - R Adapter

<400> SEQUENCE: 132
ccagtacagc gagcgtaacc t                                                    21
```

<210> SEQ ID NO 133
<211> LENGTH: 21
<212> TYPE: DNA
<213> ORGANISM: Artificial Sequence
<220> FEATURE:
<223> OTHER INFORMATION: unassigned DNA -- Barcode R05 - R Adapter

<400> SEQUENCE: 133
ccactcgagc tagcgtaacc t                                              21

<210> SEQ ID NO 134
<211> LENGTH: 21
<212> TYPE: DNA
<213> ORGANISM: Artificial Sequence
<220> FEATURE:
<223> OTHER INFORMATION: unassigned DNA -- Barcode R06 - R Adapter

<400> SEQUENCE: 134
ccagcgacac aagcgtaacc t                                              21

<210> SEQ ID NO 135
<211> LENGTH: 21
<212> TYPE: DNA
<213> ORGANISM: Artificial Sequence
<220> FEATURE:
<223> OTHER INFORMATION: unassigned DNA -- Barcode R07 - R Adapter

<400> SEQUENCE: 135
ccagtcatcg gagcgtaacc t                                              21

<210> SEQ ID NO 136
<211> LENGTH: 21
<212> TYPE: DNA
<213> ORGANISM: Artificial Sequence
<220> FEATURE:
<223> OTHER INFORMATION: unassigned DNA -- Barcode R08 - R Adapter

<400> SEQUENCE: 136
ccatgcctcc aagcgtaacc t                                              21

<210> SEQ ID NO 137
<211> LENGTH: 21
<212> TYPE: DNA
<213> ORGANISM: Artificial Sequence
<220> FEATURE:
<223> OTHER INFORMATION: unassigned DNA -- Barcode R09 - R Adapter

<400> SEQUENCE: 137
ccaccgattc cagcgtaacc t                                              21

<210> SEQ ID NO 138
<211> LENGTH: 21
<212> TYPE: DNA
<213> ORGANISM: Artificial Sequence
<220> FEATURE:
<223> OTHER INFORMATION: unassigned DNA -- Barcode R10 - R Adapter

<400> SEQUENCE: 138
ccagcatagg cagcgtaacc t                                              21

<210> SEQ ID NO 139
<211> LENGTH: 21
<212> TYPE: DNA
<213> ORGANISM: Artificial Sequence
<220> FEATURE:

<223> OTHER INFORMATION: unassigned DNA -- Barcode R11 - R Adapter

<400> SEQUENCE: 139
ccagacagag gagcgtaacc t                    21

<210> SEQ ID NO 140
<211> LENGTH: 21
<212> TYPE: DNA
<213> ORGANISM: Artificial Sequence
<220> FEATURE:
<223> OTHER INFORMATION: unassigned DNA -- Barcode R12 - R Adapter

<400> SEQUENCE: 140
ccacaccggt aagcgtaacc t                    21

<210> SEQ ID NO 141
<211> LENGTH: 21
<212> TYPE: DNA
<213> ORGANISM: Artificial Sequence
<220> FEATURE:
<223> OTHER INFORMATION: unassigned DNA -- Barcode R13 - R Adapter

<400> SEQUENCE: 141
ccagtggaag gagcgtaacc t                    21

<210> SEQ ID NO 142
<211> LENGTH: 21
<212> TYPE: DNA
<213> ORGANISM: Artificial Sequence
<220> FEATURE:
<223> OTHER INFORMATION: unassigned DNA -- Barcode R14 - R Adapter

<400> SEQUENCE: 142
ccaggatcct cagcgtaacc t                    21

<210> SEQ ID NO 143
<211> LENGTH: 21
<212> TYPE: DNA
<213> ORGANISM: Artificial Sequence
<220> FEATURE:
<223> OTHER INFORMATION: unassigned DNA -- Barcode R15 - R Adapter

<400> SEQUENCE: 143
ccaggacagt gagcgtaacc t                    21

<210> SEQ ID NO 144
<211> LENGTH: 21
<212> TYPE: DNA
<213> ORGANISM: Artificial Sequence
<220> FEATURE:
<223> OTHER INFORMATION: unassigned DNA -- Barcode R16 - R Adapter

<400> SEQUENCE: 144
ccatgtggcg tagcgtaacc t                    21

<210> SEQ ID NO 145
<211> LENGTH: 21
<212> TYPE: DNA
<213> ORGANISM: Artificial Sequence
<220> FEATURE:
<223> OTHER INFORMATION: unassigned DNA -- Barcode R17 - R Adapter

<400> SEQUENCE: 145
ccagcgatca gagcgtaacc t                    21

```
<210> SEQ ID NO 146
<211> LENGTH: 21
<212> TYPE: DNA
<213> ORGANISM: Artificial Sequence
<220> FEATURE:
<223> OTHER INFORMATION: unassigned DNA  -- Barcode R18 - R Adapter

<400> SEQUENCE: 146
ccaacaaggc cagcgtaacc t                                           21

<210> SEQ ID NO 147
<211> LENGTH: 21
<212> TYPE: DNA
<213> ORGANISM: Artificial Sequence
<220> FEATURE:
<223> OTHER INFORMATION: unassigned DNA  -- Barcode R19 - R Adapter

<400> SEQUENCE: 147
ccactcggag aagcgtaacc t                                           21

<210> SEQ ID NO 148
<211> LENGTH: 21
<212> TYPE: DNA
<213> ORGANISM: Artificial Sequence
<220> FEATURE:
<223> OTHER INFORMATION: unassigned DNA  -- Barcode R21 - R Adapter

<400> SEQUENCE: 148
ccagtccacc aagcgtaacc t                                           21

<210> SEQ ID NO 149
<211> LENGTH: 21
<212> TYPE: DNA
<213> ORGANISM: Artificial Sequence
<220> FEATURE:
<223> OTHER INFORMATION: unassigned DNA  -- Barcode R22 - R Adapter

<400> SEQUENCE: 149
ccatcgagga cagcgtaacc t                                           21

<210> SEQ ID NO 150
<211> LENGTH: 21
<212> TYPE: DNA
<213> ORGANISM: Artificial Sequence
<220> FEATURE:
<223> OTHER INFORMATION: unassigned DNA  -- Barcode R23 - R Adapter

<400> SEQUENCE: 150
ccatccggca aagcgtaacc t                                           21

<210> SEQ ID NO 151
<211> LENGTH: 21
<212> TYPE: DNA
<213> ORGANISM: Artificial Sequence
<220> FEATURE:
<223> OTHER INFORMATION: unassigned DNA  -- Barcode R24 - R Adapter

<400> SEQUENCE: 151
ccagtctcac gagcgtaacc t                                           21

<210> SEQ ID NO 152
<211> LENGTH: 21
<212> TYPE: DNA
<213> ORGANISM: Artificial Sequence
<220> FEATURE:
<223> OTHER INFORMATION: unassigned DNA  -- Barcode R25 - R Adapter
```

```
<400> SEQUENCE: 152
ccagatcggc tagcgtaacc t                                              21

<210> SEQ ID NO 153
<211> LENGTH: 21
<212> TYPE: DNA
<213> ORGANISM: Artificial Sequence
<220> FEATURE:
<223> OTHER INFORMATION: unassigned DNA -- Barcode L01 - F Adapter

<400> SEQUENCE: 153
ccaccttctc gatgcgcatt c                                              21

<210> SEQ ID NO 154
<211> LENGTH: 21
<212> TYPE: DNA
<213> ORGANISM: Artificial Sequence
<220> FEATURE:
<223> OTHER INFORMATION: unassigned DNA -- Barcode L02 - F Adapter

<400> SEQUENCE: 154
ccaccagtag catgcgcatt c                                              21

<210> SEQ ID NO 155
<211> LENGTH: 21
<212> TYPE: DNA
<213> ORGANISM: Artificial Sequence
<220> FEATURE:
<223> OTHER INFORMATION: unassigned DNA -- Barcode L03 - F Adapter

<400> SEQUENCE: 155
ccacctaacg catgcgcatt c                                              21

<210> SEQ ID NO 156
<211> LENGTH: 21
<212> TYPE: DNA
<213> ORGANISM: Artificial Sequence
<220> FEATURE:
<223> OTHER INFORMATION: unassigned DNA -- Barcode L04 - F Adapter

<400> SEQUENCE: 156
ccaggccgat tatgcgcatt c                                              21

<210> SEQ ID NO 157
<211> LENGTH: 21
<212> TYPE: DNA
<213> ORGANISM: Artificial Sequence
<220> FEATURE:
<223> OTHER INFORMATION: unassigned DNA -- Barcode L05 - F Adapter

<400> SEQUENCE: 157
ccacgttcgt catgcgcatt c                                              21

<210> SEQ ID NO 158
<211> LENGTH: 21
<212> TYPE: DNA
<213> ORGANISM: Artificial Sequence
<220> FEATURE:
<223> OTHER INFORMATION: unassigned DNA -- Barcode L06 - F Adapter

<400> SEQUENCE: 158
ccagcctggt aatgcgcatt c                                              21

<210> SEQ ID NO 159
<211> LENGTH: 21
```

```
<212> TYPE: DNA
<213> ORGANISM: Artificial Sequence
<220> FEATURE:
<223> OTHER INFORMATION: unassigned DNA -- Barcode L08 - F Adapter

<400> SEQUENCE: 159
ccaacgacac catgcgcatt c                                              21

<210> SEQ ID NO 160
<211> LENGTH: 21
<212> TYPE: DNA
<213> ORGANISM: Artificial Sequence
<220> FEATURE:
<223> OTHER INFORMATION: unassigned DNA -- Barcode L09 - F Adapter

<400> SEQUENCE: 160
ccagcctctt gatgcgcatt c                                              21

<210> SEQ ID NO 161
<211> LENGTH: 21
<212> TYPE: DNA
<213> ORGANISM: Artificial Sequence
<220> FEATURE:
<223> OTHER INFORMATION: unassigned DNA -- Barcode L10 - F Adapter

<400> SEQUENCE: 161
ccatacggca catgcgcatt c                                              21

<210> SEQ ID NO 162
<211> LENGTH: 21
<212> TYPE: DNA
<213> ORGANISM: Artificial Sequence
<220> FEATURE:
<223> OTHER INFORMATION: unassigned DNA -- Barcode L11 - F Adapter

<400> SEQUENCE: 162
ccactccagt catgcgcatt c                                              21

<210> SEQ ID NO 163
<211> LENGTH: 21
<212> TYPE: DNA
<213> ORGANISM: Artificial Sequence
<220> FEATURE:
<223> OTHER INFORMATION: unassigned DNA -- Barcode L12 - F Adapter

<400> SEQUENCE: 163
ccaaacgtcg gatgcgcatt c                                              21

<210> SEQ ID NO 164
<211> LENGTH: 21
<212> TYPE: DNA
<213> ORGANISM: Artificial Sequence
<220> FEATURE:
<223> OTHER INFORMATION: unassigned DNA -- Barcode L13 - F Adapter

<400> SEQUENCE: 164
ccagttggag catgcgcatt c                                              21

<210> SEQ ID NO 165
<211> LENGTH: 21
<212> TYPE: DNA
<213> ORGANISM: Artificial Sequence
<220> FEATURE:
<223> OTHER INFORMATION: unassigned DNA -- Barcode L14 - F Adapter

<400> SEQUENCE: 165
```
ccaacgagcc tatgcgcatt c                                         21

<210> SEQ ID NO 166
<211> LENGTH: 21
<212> TYPE: DNA
<213> ORGANISM: Artificial Sequence
<220> FEATURE:
<223> OTHER INFORMATION: unassigned DNA -- Barcode L15 - F Adapter

<400> SEQUENCE: 166
ccagatccag gatgcgcatt c                                         21

<210> SEQ ID NO 167
<211> LENGTH: 21
<212> TYPE: DNA
<213> ORGANISM: Artificial Sequence
<220> FEATURE:
<223> OTHER INFORMATION: unassigned DNA -- Barcode L16 - F Adapter

<400> SEQUENCE: 167
ccatcctggc tatgcgcatt c                                         21

<210> SEQ ID NO 168
<211> LENGTH: 21
<212> TYPE: DNA
<213> ORGANISM: Artificial Sequence
<220> FEATURE:
<223> OTHER INFORMATION: unassigned DNA -- Barcode L17 - F Adapter

<400> SEQUENCE: 168
ccaggtccat gatgcgcatt c                                         21

<210> SEQ ID NO 169
<211> LENGTH: 29
<212> TYPE: DNA
<213> ORGANISM: Artificial Sequence
<220> FEATURE:
<223> OTHER INFORMATION: unassigned DNA - rcF Primer GAPDH - rcF Adapter

<400> SEQUENCE: 169
ccgaccttca ccttccccag aatgcgcat                                 29

<210> SEQ ID NO 170
<211> LENGTH: 30
<212> TYPE: DNA
<213> ORGANISM: Artificial Sequence
<220> FEATURE:
<223> OTHER INFORMATION: unassigned DNA - rcR Primer GAPDH - rcR Adapter

<400> SEQUENCE: 170
caaggctgag aacgggaagc aggttacgct                                30

<210> SEQ ID NO 171
<211> LENGTH: 29
<212> TYPE: DNA
<213> ORGANISM: Artificial Sequence
<220> FEATURE:
<223> OTHER INFORMATION: unassigned DNA - rcF Primer B2M - rcF Adapter

<400> SEQUENCE: 171
cacatggttc acacggcagg aatgcgcat                                 29

<210> SEQ ID NO 172
<211> LENGTH: 31
<212> TYPE: DNA
<213> ORGANISM: Artificial Sequence
<220> FEATURE:
<223> OTHER INFORMATION: unassigned DNA - rcR Primer B2M - rcR Adapter

<400> SEQUENCE: 172
catggaggtt tgaagatgcc gaggttacgc t                                31

<210> SEQ ID NO 173
<211> LENGTH: 29
<212> TYPE: DNA
<213> ORGANISM: Artificial Sequence
<220> FEATURE:
<223> OTHER INFORMATION: unassigned DNA - rcF Primer POU5F1 - rcF
      Adapter

<400> SEQUENCE: 173
gggtggagga agctgacaag aatgcgcat                                  29

<210> SEQ ID NO 174
<211> LENGTH: 29
<212> TYPE: DNA
<213> ORGANISM: Artificial Sequence
<220> FEATURE:
<223> OTHER INFORMATION: unassigned DNA - rcR Primer POU5F1 - rcR
      Adapter

<400> SEQUENCE: 174
caaagcggca gatggtcgta ggttacgct                                  29

<210> SEQ ID NO 175
<211> LENGTH: 29
<212> TYPE: DNA
<213> ORGANISM: Artificial Sequence
<220> FEATURE:
<223> OTHER INFORMATION: unassigned DNA - rcF Primer NANOG - rcF Adapter

<400> SEQUENCE: 175
gtcttttcta ggcagggcgg aatgcgcat                                  29

<210> SEQ ID NO 176
<211> LENGTH: 31
<212> TYPE: DNA
<213> ORGANISM: Artificial Sequence
<220> FEATURE:
<223> OTHER INFORMATION: unassigned DNA - rcR Primer NANOG - rcR Adapter

<400> SEQUENCE: 176
gtttgggatt gggaggcttt gaggttacgc t                               31

<210> SEQ ID NO 177
<211> LENGTH: 29
<212> TYPE: DNA
<213> ORGANISM: Artificial Sequence
<220> FEATURE:
<223> OTHER INFORMATION: unassigned DNA - rcF Primer SOX2 - rcF Adapter

<400> SEQUENCE: 177
cctgcaaagc tcctaccgtg aatgcgcat                                  29

<210> SEQ ID NO 178
<211> LENGTH: 36
<212> TYPE: DNA
<213> ORGANISM: Artificial Sequence
<220> FEATURE:
<223> OTHER INFORMATION: unassigned DNA - rcR Primer SOX2 - rcR Adapter

<400> SEQUENCE: 178

-continued cgagataaac atggcaatca aaatgtaggt tacgct                          36

<210> SEQ ID NO 179
<211> LENGTH: 30
<212> TYPE: DNA
<213> ORGANISM: Artificial Sequence
<220> FEATURE:
<223> OTHER INFORMATION: unassigned DNA - rcF Primer LIN28A - rcF
      Adapter

<400> SEQUENCE: 179
ccctttcttg gcctcctgac gaatgcgcat                                 30

<210> SEQ ID NO 180
<211> LENGTH: 34
<212> TYPE: DNA
<213> ORGANISM: Artificial Sequence
<220> FEATURE:
<223> OTHER INFORMATION: unassigned DNA - rcR Primer LIN28A - rcR
      Adapter

<400> SEQUENCE: 180
tatgtcaaag tggccacaag attgaggtta cgct                            34

<210> SEQ ID NO 181
<211> LENGTH: 29
<212> TYPE: DNA
<213> ORGANISM: Artificial Sequence
<220> FEATURE:
<223> OTHER INFORMATION: unassigned DNA - rcF Primer CCND1 - rcF Adapter

<400> SEQUENCE: 181
gaacctggac gtgagctggg aatgcgcat                                  29

<210> SEQ ID NO 182
<211> LENGTH: 29
<212> TYPE: DNA
<213> ORGANISM: Artificial Sequence
<220> FEATURE:
<223> OTHER INFORMATION: unassigned DNA - rcR Primer CCND1 - rcR Adapter

<400> SEQUENCE: 182
gttgtgtgtg cagggaggga ggttacgct                                  29

<210> SEQ ID NO 183
<211> LENGTH: 29
<212> TYPE: DNA
<213> ORGANISM: Artificial Sequence
<220> FEATURE:
<223> OTHER INFORMATION: unassigned DNA - rcF Primer CCNE1 - rcF Adapter

<400> SEQUENCE: 183
tggctgcaga agagggtgtg aatgcgcat                                  29

<210> SEQ ID NO 184
<211> LENGTH: 30
<212> TYPE: DNA
<213> ORGANISM: Artificial Sequence
<220> FEATURE:
<223> OTHER INFORMATION: unassigned DNA - rcR Primer CCNE1 - rcR Adapter

<400> SEQUENCE: 184
gaccggtata tggcgacaca aggttacgct                                 30

<210> SEQ ID NO 185
<211> LENGTH: 30

```
<212> TYPE: DNA
<213> ORGANISM: Artificial Sequence
<220> FEATURE:
<223> OTHER INFORMATION: unassigned DNA - rcF Primer CER1 - rcF Adapter

<400> SEQUENCE: 185
agtctggctg aagggcactg gaatgcgcat                                    30

<210> SEQ ID NO 186
<211> LENGTH: 29
<212> TYPE: DNA
<213> ORGANISM: Artificial Sequence
<220> FEATURE:
<223> OTHER INFORMATION: unassigned DNA - rcR Primer CER1 - rcR Adapter

<400> SEQUENCE: 186
tgcctgccaa gttcaccaca ggttacgct                                     29

<210> SEQ ID NO 187
<211> LENGTH: 29
<212> TYPE: DNA
<213> ORGANISM: Artificial Sequence
<220> FEATURE:
<223> OTHER INFORMATION: unassigned DNA - rcF Primer DNMT3B - rcF
      Adapter

<400> SEQUENCE: 187
cccggcatgt ctgacagagg aatgcgcat                                     29

<210> SEQ ID NO 188
<211> LENGTH: 29
<212> TYPE: DNA
<213> ORGANISM: Artificial Sequence
<220> FEATURE:
<223> OTHER INFORMATION: unassigned DNA - rcR Primer DNMT3B - rcR
      Adapter

<400> SEQUENCE: 188
gccggtgttt ctgtgtggaa ggttacgct                                     29

<210> SEQ ID NO 189
<211> LENGTH: 35
<212> TYPE: DNA
<213> ORGANISM: Artificial Sequence
<220> FEATURE:
<223> OTHER INFORMATION: unassigned DNA - rcF Primer ZFP42 - rcF Adapter

<400> SEQUENCE: 189
agctaagttt aaacatgttg tggggaatg cgcat                               35

<210> SEQ ID NO 190
<211> LENGTH: 31
<212> TYPE: DNA
<213> ORGANISM: Artificial Sequence
<220> FEATURE:
<223> OTHER INFORMATION: unassigned DNA - rcR Primer ZFP42 - rcR Adapter

<400> SEQUENCE: 190
gaagcaggag gatagcttga gaggttacgc t                                  31

<210> SEQ ID NO 191
<211> LENGTH: 29
<212> TYPE: DNA
<213> ORGANISM: Artificial Sequence
<220> FEATURE:
<223> OTHER INFORMATION: unassigned DNA - rcF Primer RNA 1 (EC2) - rcF
      Adapter
```

```
<400> SEQUENCE: 191
gcagcatatt ctcggggcgg aatgcgcat                                            29

<210> SEQ ID NO 192
<211> LENGTH: 29
<212> TYPE: DNA
<213> ORGANISM: Artificial Sequence
<220> FEATURE:
<223> OTHER INFORMATION: unassigned DNA - rcR Primer RNA 1 (EC2) - rcR
      Adapter

<400> SEQUENCE: 192
cgcgccaaag tagagaggga ggttacgct                                            29

<210> SEQ ID NO 193
<211> LENGTH: 29
<212> TYPE: DNA
<213> ORGANISM: Artificial Sequence
<220> FEATURE:
<223> OTHER INFORMATION: unassigned DNA - rcF Primer RNA 2 (EC12) - rcF
      Adapter

<400> SEQUENCE: 193
atcatcggag gggctacggg aatgcgcat                                            29

<210> SEQ ID NO 194
<211> LENGTH: 29
<212> TYPE: DNA
<213> ORGANISM: Artificial Sequence
<220> FEATURE:
<223> OTHER INFORMATION: unassigned DNA - rcR Primer RNA 2 (EC12) - rcR
      Adapter

<400> SEQUENCE: 194
gatgcaatgg tggtacgcga ggttacgct                                            29

<210> SEQ ID NO 195
<211> LENGTH: 29
<212> TYPE: DNA
<213> ORGANISM: Artificial Sequence
<220> FEATURE:
<223> OTHER INFORMATION: unassigned DNA - rcF Primer RNA 6 (EC13) - rcF
      Adapter

<400> SEQUENCE: 195
ggccgaaatc atccctggg aatgcgcat                                             29

<210> SEQ ID NO 196
<211> LENGTH: 28
<212> TYPE: DNA
<213> ORGANISM: Artificial Sequence
<220> FEATURE:
<223> OTHER INFORMATION: unassigned DNA - rcR Primer RNA 6 (EC13) - rcR
      Adapter

<400> SEQUENCE: 196
gatcgtggca ccagagcgag gttacgct                                             28

<210> SEQ ID NO 197
<211> LENGTH: 29
<212> TYPE: DNA
<213> ORGANISM: Artificial Sequence
<220> FEATURE:
<223> OTHER INFORMATION: unassigned DNA - rcF Primer RNA 8 (EC5) - rcF
      Adapter
```

```
<400> SEQUENCE: 197
gctggctgaa actgctggag aatgcgcat                                    29

<210> SEQ ID NO 198
<211> LENGTH: 29
<212> TYPE: DNA
<213> ORGANISM: Artificial Sequence
<220> FEATURE:
<223> OTHER INFORMATION: unassigned DNA - rcR Primer RNA 8 (EC5) - rcR
      Adapter

<400> SEQUENCE: 198
aacacagttg cagcgcctga ggttacgct                                    29
```

METHOD FOR THE PREPARATION OF BAR-CODED PRIMER SETS

CROSS-REFERENCE TO RELATED APPLICATIONS

This application is a U.S. national phase application filed under 35 U.S.C. § 371 claiming benefit to International Patent Application No. PCT/EP2016/073816, filed Oct. 5, 2016, which is entitled to priority to European Application No. 15188404.6, filed Oct. 5, 2015, each of which is hereby incorporated herein by reference in its entirety.

The present invention relates to a method of producing a set of primers suitable for the reverse transcription and/or amplification of a plurality (N) of nucleic acid molecules of interest, wherein for each nucleic acid molecule of interest at least one primer is produced and wherein the primers carry a bar-code, the method comprising the steps of: (a)(i) combining (1) a first oligonucleotide, wherein said first oligonucleotide comprises a first bar-code nucleic acid sequence linked at its 3' end to a first adapter nucleic acid sequence with (2) a plurality (N) of second oligonucleotides, wherein each second oligonucleotide comprises the reverse complementary sequence of a forward primer specific for a nucleic acid molecule of interest, wherein said reverse complementary sequence of the forward primer is linked at its 3' end to the reverse complementary sequence of the first adapter nucleic acid sequence; and/or (a)(ii) combining (1) a third oligonucleotide, wherein said third oligonucleotide comprises a second bar-code nucleic acid sequence linked at its 3' end to a second adapter nucleic acid sequence with (2) a plurality (N) of fourth oligonucleotides, wherein each fourth oligonucleotide comprises the reverse complementary sequence of a reverse primer specific for said nucleic acid molecule of interest, wherein said reverse complementary sequence of the reverse primer is linked at its 3' end to the reverse complementary sequence of the second adapter nucleic acid sequence; wherein steps (a)(i) and (a)(ii) are carried out under conditions that enable the annealing of the first and second adapter nucleic acid sequences to the respective reverse complementary sequences thereof; (b) extending the oligonucleotides of (a)(i) and (a)(ii) by polymerase-mediated oligonucleotide synthesis; and (c) optionally, removing the second and fourth oligonucleotides. The present invention further relates to methods of producing a plurality (M) of nucleic acid amplification products of interest carrying at least one sample-specific bar-code as well as to a method for multiplex sequencing of a plurality (M) of nucleic acid amplification products of interest from a plurality (X) of samples in a single reaction chamber and identifying the individual sample from which each nucleic acid amplification product is derived. Furthermore, the present invention relates to a target-unspecific bar-code-adapter panel, its use in the methods of the invention as well as a kit comprising same.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Next-generation sequencing (NGS) is a term which is used to describe a number of different modern high throughput sequencing technologies. These sequencing technologies allow the sequencing of DNA and RNA in a high throughput manner (also known as deep sequencing) and are much quicker and cheaper than previously used Sanger sequencing techniques. Presently the most effective NGS platforms provide up to 600 billion base pair (bp) coverage per run at 98% accuracy for a maximum amplicon read length of up to 500 bp, and at a cost of several thousands of dollars. Genomic studies focusing on human health, disease and environment have been transformed though the introduction of NGS over the last decade. The impact of NGS on these fields and others, including environmental health and agriculture, is very likely to further increase alongside developments of NGS technologies that provide greater read length, higher converge (number of individual molecules sequenced), and superior sample multiplexing techniques.

Multiplex sequencing is an application of NGS used for simultaneously measuring multiple DNA or RNA analytes (two or more) that correspond to distinct samples in a single run/cycle of the instrument. Multiplex sequencing is the primary approach used for reducing the per-sample cost of NGS for a variety of applications, including molecular diagnostics (Tu et al., "Pair-barcode high-throughput sequencing for large-scale multiplexed sample analysis", BMC Genomics, 13: 43 (2012)). Multiplex sequencing is almost entirely based on DNA bar-codes, i.e. short unique sequences that are synthesized in vitro, and later individually incorporated into the DNA fragments of the respective samples to be multiplexed. Thus, the DNA bar-codes serve as molecular identifiers (also known as indexes) for the origin of the individual samples. Indexing distinct samples with known DNA bar-codes is often known as directional bar-coding, as opposed to random bar-coding that is used mostly for indexing libraries of cells or molecules. The majority of the protocols developed for incorporating DNA bar-codes as indexes employ either i) ligation enzymes for joining bar-codes and templates (Shiroguchi et al., "Digital RNA sequencing minimizes sequence-dependent bias and amplification noise with optimized single-molecule bar-codes", Proceedings of the National Academy of Sciences, 109: 1347-1352 (2012)), or ii) pre-synthesized bar-coded primers (primers containing bar-codes) for amplifying certain sequences or libraries, and thereby generating bar-coded amplicons (PCR products) for sequencing (Hashimshony et al., "CEL-Seq: Single-Cell RNA-Seq by Multiplexed Linear Amplification", Cell Reports, 2: 666-673 (2012)). A variation of the above methods is ligation of adapter sequences followed by PCR employing primers that are specific to the adapter sequences linked 5' to bar-code sequences (Kozarewa and Turner, "96-Plex Molecular Barcoding for the Illumina Genome Analyzer", Methods in Molecular Biology, 733: 279-298 (2011)). These DNA bar-coding methods provide solutions for multiplexing genomic libraries consisting of, for example, transcriptomes or genomic DNA of the human and the mouse, and require typically several millions and up to dozens of millions of NGS reads per sample for characterizing the repertoire of molecules in these libraries.

Targeted sequencing is an approach enabling sequencing of only specific desired regions of interest (not whole genomes), and is often combined into multiplex sequencing for increasing the cost-effectiveness (per sample cost) of sequencing studies. Moreover, targeted sequencing often considerably reduces the complexity of bioinformatics analysis compared with whole genome sequencing, and thereby reduces cost and improves accuracy of the analysis. One example of targeted sequencing application is Exome sequencing, a technique for sequencing all the protein-coding genes in a genome (known as the exome). The method incorporates i) selection of only the DNA subsets that encode proteins (known as exons), and ii) subsequent sequencing of the selected molecules (Bamshad et al., "Exome sequencing as a tool for Mendelian disease gene discovery", Nat Rev Genet, 12: 745-755 (2011)). Focusing on the exome (constituting about 1% of the total human genome) allows researchers to use DNA bar-codes for multiplexing several whole exomes from different patients/sources for a single NGS run.

The majority of protocols for DNA bar-coding employs ligation by enzymes and/or pre-synthesized bar-coded primers and adapters for multiplexing up to several dozens of samples, and in some infrequent cases up to hundreds of samples (Jaitin et al., "Massively Parallel Single-Cell RNA-Seq for Marker-Free Decomposition of Tissues into Cell Types", Science, 343: 776-779 (2014)). These protocols are often used for generating combinations of bar-codes, typically employing distinct forward and reverse bar-codes (at the respective ends of the DNA molecules). The purpose of using combinations of bar-codes is to simplify the experiment by reducing the number of bar-code batches, and for decreasing costs by avoiding synthesis of large panels of bar-codes. For example, 12 forward and 8 reverse bar-codes suffice for bar-coding 96 samples utilizing combinations of forward and reverse bar-codes (Kircher et al., "Double indexing overcomes inaccuracies in multiplex sequencing on the Illumina platform", Nucleic Acids Research, 40 (2012)).

State of-the-art bar-coding and targeted NGS methods are optimised for deep sequencing of small numbers of multiplexed samples, for example, for generating millions of sequence reads in up to several dozens of samples (whole genome approaches). However, it is unfeasible to utilize these methods for multiplex sequencing of very large collections of samples by targeting only a small number of specific genomic regions of interest. This means that the state-of-the-art techniques for multiplexing and targeted sequencing of several dozens of specific regions or less (e.g. in the range of 1-50 specific loci) have significant disadvantages, i.e. the currently available technologies do not technically allow retrieval of specific genetic information from whole genome sequences and/or numerous pooled samples in a cost- and time-efficient manner. These disadvantages presently prevent a broad application for diagnostic purposes of these technologies, in particular personalised diagnostics that are based on genotyping and transcriptional analysis of single cells. As a result, despite the fact that there is a huge demand by millions of patients (in particular cancer patients) around the globe, there is currently no affordable method for NGS-based personalised diagnostics that is based on high-throughput single cell sequencing. Accordingly, there is still a need for developing novel and optimise existing NGS methods and reagents for the analysis of panels of disease-associated genes in highly multiplexed NGS samples.

In particular, there is an immanent and immediate need for a sample multiplexing method that i) enables very high bar-coding efficiency, ii) enables targeted sequencing, iii) does not dependent on ligation or nested PCR, iv) enables the quantitative measurements of gene expression, also for single cells, v) enables the usage of bar-codes in combinations without nested PCR, vi) is applicable and feasible for high throughput bar-coding involving e.g. >$10^4$ samples, and vii) enables linking the individual samples to individual sequences, i.e. providing the option of directional multiplex sequencing.

This need is addressed by the provision of the embodiments characterised in the claims.

Accordingly, the present invention relates to a method of producing a set of primers suitable for the reverse transcription and/or amplification of a plurality (N) of nucleic acid molecules of interest, wherein for each nucleic acid molecule of interest at least one primer is produced and wherein the primers carry a bar-code, the method comprising the steps of: (a)(i) combining (1) a first oligonucleotide, wherein said first oligonucleotide comprises a first bar-code nucleic acid sequence linked at its 3' end to a first adapter nucleic acid sequence with (2) a plurality (N) of second oligonucleotides, wherein each second oligonucleotide comprises the reverse complementary sequence of a forward primer specific for a nucleic acid molecule of interest, wherein said reverse complementary sequence of the forward primer is linked at its 3' end to the reverse complementary sequence of the first adapter nucleic acid sequence; and/or (a)(ii) combining (1) a third oligonucleotide, wherein said third oligonucleotide comprises a second bar-code nucleic acid sequence linked at its 3' end to a second adapter nucleic acid sequence with (2) a plurality (N) of fourth oligonucleotides, wherein each fourth oligonucleotide comprises the reverse complementary sequence of a reverse primer specific for said nucleic acid molecule of interest wherein said reverse complementary sequence of the reverse primer is linked at its 3' end to the reverse complementary sequence of the second adapter nucleic acid sequence; wherein steps (a)(i) and (a)(ii) are carried out under conditions that enable the annealing of the first and second adapter nucleic acid sequences to the respective reverse complementary sequences thereof; (b) extending the oligonucleotides of (a)(i) and (a)(ii) by polymerase-mediated oligonucleotide synthesis; and (c) optionally, removing the second and fourth oligonucleotides.

The term "set of primers", as used herein, relates to a collection of bar-coded primers (also referred to herein as "bar-coded primers"), i.e. a collection of more than one molecular species of primer oligonucleotides carrying specific barcodes. Accordingly, at least two different primer oligonucleotides are produced in accordance with the method of the present invention. It will be appreciated that the set of primers in accordance with the invention may contain one primer for each nucleic acid of interest, but may also contain more than one primer for each nucleic acid of interest, such as e.g. two primers (e.g. one forward and one reverse primer). In its broadest sense, the term "set" does not require the presence of any other compounds, vials, containers, manuals and the like. In those cases where the nucleic acid molecule of interest is specific gene, the primers of the present invention are also referred to herein as "gene-specific primers".

The term "at least", as used herein, refers to the specifically recited amount or number but also to more than the specifically recited amount or number. For example, the term "at least two" encompasses also at least 3, at least 4, at least 5, at least 6, at least 7, at least 8, at least 9, at least 10, such as at least 20, at least 30, at least 40, at least 50 and so on. Furthermore, this term also encompasses exactly 2, exactly 3, exactly 4, exactly 5, exactly 6, exactly 7, exactly 8, exactly 9, exactly 10, exactly 20, exactly 30, exactly 40, exactly 50 and so on.

In accordance with the method of the present invention, the primers have to be "suitable" for the reverse transcription and/or amplification of nucleic acid molecules of interest. To that end, the bar-coded primers produced are primers that bind to their respective target nucleic acid molecule of interest and serve as a starting point for DNA synthesis, using the strand of the nucleic acid molecule of interest to which they are bound as the template. In accordance with the method of the present invention, the primers are specific for their respective target nucleic acid molecule of interest, i.e. they anneal under stringent hybridisation conditions to their target nucleic acid molecule of interest, but not or not significantly to non-target nucleic acids. It is well known in the art how to design primers that bind specifically to their target nucleic acid.

In accordance with the present invention, the term "reverse transcription and/or amplification of a nucleic acid molecule of interest" does not require the reverse transcription/amplification of the entire nucleic acid molecule, e.g. an entire gene or chromosomal sequence, but also encompasses the reverse transcription/amplification of parts thereof that are of relevance, such as for example parts that carry a mutation or marker to be analysed. In a preferred embodiment, the reverse transcription and/or amplification of a nucleic acid molecule of interest relates to the transcription/amplification of parts of (a) gene or chromosomal sequence(s).

Moreover, in accordance with the method of the present invention, primers are produced that can be employed in the simultaneous reverse transcription and/or amplification of a "plurality (N) of nucleic acid molecules of interest". In other words, for a certain number of different nucleic acid molecules of interest—N—the same (or higher) number (N) of bar-coded primers is produced, wherein for each nucleic acid molecule of interest at least one primer is produced. More preferably, at least one forward and one reverse primer are produced for each nucleic acid molecule of interest.

Also encompassed by the method of the present invention is the production of more than one or two primers for one nucleic acid molecule of interest, such as e.g. three, four, five, six, seven, eight etc. different primers. In that case, it is preferred that said primers specifically bind to—and allow the reverse transcription and/or amplification of—different parts of the nucleic acid molecule of interest, in order to avoid competitive binding of the primers to the target. Such an approach is for example advantageous in those cases where different regions of a nucleic acid molecule of interest need to be investigated, e.g. where a gene associated with a disease carries several different disease-associated polymorphisms.

The term "a plurality (N) of nucleic acid molecules of interest" refers to an integral number of at least 2 different nucleic acid molecules of interest, such as at least 3, at least 4, at least 5, at least 6, at least 7, at least 8, at least 9, at least 10 different nucleic acid molecules of interest. Preferably, (N) is an integral number in the range between 10 and 500, such as e.g. between 20 and 250, more preferably between 30 and 150 and most preferably between 50 and 100 different nucleic acid molecules of interest. It will be appreciated that these preferred ranges include all other combinations of upper and lower limits, such as e.g. between 20 and 500, between 20 and 150, between 20 and 100 etc.

In accordance with the present invention, the nucleic acid molecules to be amplified include DNA, such as for example genomic DNA, fragmented genomic DNA, complementary DNA (cDNA), modified/synthetic DNA (e.g. eDNA, ANA, FANA, TNA, LNA, CeNA, HNA) as well as RNA. The term RNA includes all forms of RNA such as e.g. mRNA, rRNA, SRP RNA, tRNA and tmRNA, polyadenylated and uridinilated RNA); RNAs involved in post-transcriptional modification or DNA replication (e.g. snRNA, snoRNA, SmY, scaRNA, gRNA, RNase P, RNase MRP, Y RNA, Telomerase RNA and spliced leader RNA); regulatory RNAs (e.g. antisense RNA, cis-natural antisense transcript, crRNA, long ncRNA, miRNA, siRNA, lncRNA, tasiRNA, rasiRNA and 7SK RNA), parasitic RNAs (e.g. retrotransposons, viral genomes, viroids and satellite RNAs) as well as modified/synthetic RNA. Preferably, embodiments reciting "RNA" are directed to polyadenylated mRNA. In a preferred embodiment the nucleic acid molecule(s) of the invention is/are DNA. Even more preferably, the nucleic acid molecule is a gene of interest.

A bar-code is a detectable representation of data containing information about the object the bar-code is associated with. In accordance with the present invention, the bar-code is a pre-determined, i.e. known, nucleic acid sequence consisting of nucleotides in a particular order. By using different combinations and/or different amounts of nucleotides, different bar-codes can be generated. Preferably, bar-codes are employed that differ only the combination of nucleotides, but have the same length. Also preferably, the bar-codes are designed such that they differ significantly enough to ensure that they can be differentiated post sequencing. For example, different bar-codes can be designed such that they differ by at least 2 nucleotides, more preferably by at least 3 nucleotides from each other. It will further be appreciated that the bar-codes are designed such that they can be differentiated from naturally occurring nucleic acid sequences, as well as from the primer and adapter nucleic acid sequence(s) employed in accordance with the present invention. Methods to ensure a sufficiently large difference between these sequences are well known in the art. The length of the bar-codes in accordance with the present invention is not particularly limited.

In accordance with the method of the present invention, such a bar-code is incorporated into each of the bar-coded primers produced in accordance with the present invention. For the unequivocal identification of amplification products prepared from one particular sample, the primers for amplification of the nucleic acid molecules of interest carry the same sample-specific bar-code or sample-specific combination of bar-codes. This means that each of the plurality (N) of amplicons obtained from one sample carry the same bar-code(s).

In other words, where the set of primers for a plurality of nucleic acid molecules of interest from one particular sample comprises only bar-coded forward or only bar-coded reverse primers, all primers in this set of primers carry the same bar-code.

It is also envisaged that all primers in the set of primers for the particular sample carry the same bar-code even when the set of primers comprises both bar-coded forward and bar-coded reverse primers. It is more preferred, however, that where the set of primers for a particular sample comprises primer pairs of bar-coded forward and bar-coded reverse primers, all the forward primers for amplification of nucleic acid molecules of interest from said sample carry the same bar-code, while all the reverse primers for amplification of nucleic acid molecules of interest from said sample carry a bar-code that is (i) the same for all reverse primers for amplification of nucleic acid molecules of interest from said sample but (ii) is different from the bar-code carried by the respective forward primers, thereby providing a unique bar-code combination for amplification products obtained from said sample.

The pre-determined bar-codes described above may optionally contain an additional nucleic acid sequence representing a random bar-code sequence. The random bar-code is preferably present at the 5' end of the pre-determined bar-codes, but can also be present 3' to the pre-determined bar-code (i.e. between the pre-determined bar-code and the adapter). Such a bar-code assembly consisting of pre-determined sequences and random sequences can e.g. be used to analyse biases introduced by reverse transcriptase reactions. Random bar-codes are thereby incorporated into individual cDNA molecules and, following amplification by PCR and sequencing, it is possible to quantify the number of molecules containing the same random bar-code, and to calculate how many of the respective molecules were in the initial sample (Kivioja et al., "Counting absolute numbers of molecules using unique molecular identifiers", Nat Meth, 9: 72-74 (2012)).

The method of the present invention comprises a first step (a), in which a bar-code-adapter oligonucleotide is combined with a plurality (N) of oligonucleotides comprising the reverse complementary sequence of the adapter nucleic acid sequence and the reverse complementary sequence of a primer.

The term "comprising", as used herein, denotes that further steps and/or components can be included in addition to the specifically recited steps and/or components. However, this term also encompasses that the claimed subject-matter consists of exactly the recited steps and/or components.

The term "combining", as used herein, relates to the in contact-bringing of the recited compounds. There is no particular restriction to the way in which the compounds are brought in contact with each other, i.e. they may simply be added to the same vessel or they may be actively mixed, for example by pipetting the sample up and down or by swiveling the vessel gently around. Suitable methods of combining compounds are well known in the art.

The "bar-code-adapter oligonucleotides" in accordance with the present invention are oligonucleotides that comprise at their 5' end a bar-code as defined herein above. Linked to the 3' end of said bar-code nucleic acid sequences is an adapter nucleic acid sequence. The nature of the adapter nucleic acid sequence is not particularly limited, as long as it is capable of specifically annealing to its reverse complementary sequence, i.e. without annealing to other sequences that are not complementary to the adapter nucleic acid sequence. The skilled person is aware of how to design such adapter sequences by choosing appropriate lengths and nucleotide combinations to ensure this specificity. Such methods have been described in the art, and are used for a variety of molecular biology techniques including oligonucleotide ends annealing for ligation of DNA molecules (e.g. Sambrook and Russell, "Molecular Cloning: A Laboratory Manual", Third Edition, Cold Spring Harbor, N.Y. (2001). Where different adapters are to be employed, it is preferred that these adapters differ by at least 2 nucleotides, more preferably by at least 3 nucleotides from each other. Generally, the differing nucleotides between the adapters may be located anywhere in the sequence of the adapters. Preferably, the different nucleotides are located towards the 3' end of the adapters. The length of the adapters in accordance with the present invention is not particularly limited.

The term "oligonucleotide", as used herein, refers to DNA or RNA nucleic acid sequences, i.e. sequences composed of 2'-deoxyribonucleotides, of ribonucleotides, or of mixtures thereof, as well as to nucleic acid mimicking molecules known in the art such as synthetic or semi-synthetic derivatives of DNA or RNA and mixed polymers. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA) and locked nucleic acid (LNA) (Braasch and Corey, "Locked nucleic acid (LNA): fine-tuning the recognition of DNA and RNA", Chemistry & Biology, 8: 1-7 (2001)). LNA is an RNA derivative in which the ribose ring is constrained by a methylene linkage between the 2'-oxygen and the 4'-carbon. They may contain additional non-natural or derivatised nucleotide bases, as will be readily appreciated by those skilled in the art. The length of the oligonucleotides in accordance with the present invention is not particularly limited, but preferably the oligonucleotides of the present invention have a length of less than 200 nucleotides, more preferably less than 150 nucleotides, even more preferably less than 100 nucleotides and most preferably less than 50 nucleotides. It is particularly preferred that oligonucleotides comprising the bar-code and adapter sequences as well as oligonucleotides comprising the reverse complementary adapter sequence and reverse complementary primary sequence have a length between 18 to 21 bp.

Means and methods of preparing oligonucleotides are well known in the art and any method may be employed in accordance with the present invention. Preferably, the oligonucleotides to be used in the present invention are chemically synthesized using conventional methods that use, for example, appropriately protected (deoxy)-ribonucleoside phosphoramidites and a conventional DNA/RNA synthesizer. These methods are well known in the art. Exemplary suppliers of DNA/RNA synthesis reagents are Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). More conveniently, oligonucleotides can be obtained from commercial oligo synthesis suppliers, which sell products of different quality and costs. In general, the oligonucleotides applicable in the present invention are conventionally synthesized and are readily provided in high quality.

In those embodiments where an oligonucleotide comprises (rather than consists of) the recited sequences, additional nucleotides can be included between the recited sequences or can extend over the specific sequence either on the 5' end or the 3' end or both. Preferably, the oligonucleotides of the present invention comprise less than 100 such additional nucleotides, such as e.g. less than 50, less than 40, less than 30, more preferably less than 20, even more preferably less than 10 and most preferably less than 5 additional nucleotides other than the specifically recited sequences. Additional nucleotides may form, for example, linker nucleic acid sequences, e.g. in particular when located between the recited sequences, adapter nucleic acid sequences for next generation sequencing as well as nucleic acid sequences that serve as tags for e.g. purification, protection of oligonucleotides from digestion or as additional bar-codes. Adapter (sometimes also referred to as adaptor) nucleic acid sequences for next generation sequencing are well known in the art and have been described e.g. in Kivioja et al., "Counting absolute numbers of molecules using unique molecular identifiers", Nat Meth, 9: 72-74 (2012). Non-limiting examples of tags suitable for purification purposes include polyA stretches, polyT stretches, polyG stretches etc, as well as DNA methylation tags, His-tag as well as biotin tags and aptamers. A non-limiting example of a tag suitable for protection from digestion is a tag comprising or consisting of phosphorothioated sequences (Nikiforov et al., "The use of phosphorothioate primers and exonuclease hydrolysis for the preparation of single-stranded PCR products and their detection by solid-phase hybridization", Genome Research, 3: 285-291 (1994); Civit et al., "Evaluation of techniques for generation of single-stranded DNA for quantitative detection", Analytical Biochemistry, 431: 132-138 (2012)), or specific sequences that lead to lambda exonuclease pausing such as GGCGAT-TCT (Perkins et al., "Sequence-Dependent Pausing of Single Lambda Exonuclease Molecules", Science, 301: 1914-1918 (2003)). Tags for use as additional bar-codes include, amongst others, tags that are not sequence based, such as e.g. tags having a particular DNA methylation pattern.

The bar-code-adapter oligonucleotides of the present invention are then combined, i.e. brought into contact, with a plurality (N) of oligonucleotides comprising the reverse complementary sequence of the adapter nucleic acid sequence and the reverse complementary sequence of a primer. It will be appreciated that the plurality (N) of oligonucleotides refers to a plurality of different oligonucleotides that differ at least in the reverse complementary sequence of a primer comprises therein.

Each of the plurality of oligonucleotides comprises as one sequence the reverse complementary sequence of the adapter nucleic acid sequence comprised in the oligonucleotide with which it is combined. In other words, where a first oligonucleotide comprises an adapter A, then this oligonucleotide is brought into contact with a plurality of oligonucleotides that comprise the reverse complementary sequence of adapter A. This reverse complementary sequence of an adapter is also referred to herein as "rcAdapter". As used herein, the term "reverse complementary" refers to a sequence that represents the counterpart to a particular sequence, thereby ensuring that both sequences anneal to each other when brought into contact with each other under conditions that allow for nucleotide annealing. For example, if the sequence of interest, e.g. the adapter nucleic acid sequence, contains a "G" at position 1 red from the 5' to the 3' end, then the "reverse complementary sequence of the adapter nucleic acid sequence" contains a "C" at the last position when red from the 5' to the 3' end. It is particularly preferred that said reverse complementary sequences have the identical length as their respective template sequence.

Linked to the 5' end of the rcAdapter is a second sequence, namely a reverse complementary sequence of a primer to be employed in a later nucleic acid amplification sequence. This reverse complementary primer sequence is also referred to herein as "rcPrimer". For a plurality (N) of nucleic acid molecules of interest, at least (N) different forward and/or different reverse rcPrimers are employed, in order to generate at least one primer carrying a bar-code for each nucleic acid molecule of interest, in accordance with the present invention. The term "linked", as used herein, refers to the covalent connection of two sequences, either directly via a phosphodiester linkage or via an intermediate linker, such as an additional nucleic acid sequence.

By combining a bar-code-adapter oligonucleotide with an oligonucleotide comprising the reverse complementary sequence of the respective adapter nucleic acid sequence under suitable conditions, the adapter sequence comprised in the one oligonucleotide anneals with the rcAdapter of the other oligonucleotide.

In accordance with the present invention, the oligonucleotides are combined in step (a) under conditions that enable the annealing of the adapter nucleic acid sequences with their respective reverse complementary sequences. The term "annealing", as used herein, refers to the pairing of a nucleic acid sequence to a reverse complementary strand of this nucleic acid sequence, which thereby form a hybrid/double-stranded molecule over the length of the complementary region.

Conditions that affect the annealing of nucleic acid sequences to each other are well known in the art. These conditions are sequence-dependent and will be different in different circumstances. For example, changes in the strength of annealing can be accomplished through the manipulation of salt condition, temperature, pyrimidine/purine ratio, sequence composition of the oligonucleotide, viscosity of the solution and solvents. The person skilled in the art knows which conditions he/she has to use to achieve a successful annealing in accordance with the invention. The establishment of suitable annealing conditions is referred to in standard text books such as Sambrook and Russell, "Molecular Cloning: A Laboratory Manual", Third Edition, Cold Spring Harbor, N.Y. (2001); Ausubel, "Current Protocols in Molecular Biology", Green Publishing Associates and Wiley Interscience, N.Y. (1989) or Higgins and Hames (Eds.), "Nucleic acid hybridization, a practical approach", IRL Press Oxford, Washington D.C. (1985).

In accordance with the present invention, the annealing conditions are such that the nucleic acid sequences anneal only to each other (i.e. the adapter to the rcAdapter) but not to other sequences.

Upon annealing of a bar-code-adapter oligonucleotide with one of the oligonucleotides comprising the rcAdapter and an rcPrimer, a partially double-stranded nucleic acid molecule is generated. This molecule is double-stranded in those parts that correspond to the adapter/rcAdapter sequence and is single-stranded in those parts that are linked to the 5' end of the adapter/rcAdapter sequence, i.e. the bar-code nucleic acid sequence and the rcPrimer, respectively (see FIG. 1).

In accordance with the present invention, for each nucleic acid molecule of interest at least one oligonucleotide comprising an rcAdapter and an rcPrimer that is specific for said nucleic acid molecule of interest is provided. For example, where a set of bar-coded forward primers for 20 different nucleic acid molecules of interest is to be produced, the method of the invention encompasses the combination (and annealing) of a first oligonucleotide comprising a first bar-code nucleic acid sequence (e.g. BC1) linked at its 3' end to a first adapter nucleic acid sequence (e.g. A1) with at least 20 different second oligonucleotides, wherein each second oligonucleotide comprises the reverse complementary sequence of one primer (rcP1 to rcP20) specific for one of the nucleic acid molecules of interest linked at its 3' end to the reverse complementary sequence of A1 (e.g. rcA1). Thus, 20 different annealing products would result, i.e. BC1-A1 with rcA1-rcP1, BC1-A1 with rcA1-rcP2, BC1-A1 with rcA1-rcP3, BC1-A1 with rcA1-rcP4 and so on, up to BC1-A1 with rcA1-rcP20.

It will be appreciated that the term "a [first/second/third/fourth] oligonucleotide" does not refer to the total number of molecules, but to the number of different types of molecules, i.e. the term "a [first/second/third/fourth] oligonucleotide" refers to one type of molecule, whereas the number of this molecule present may in fact be any number, such as e.g. 100, 1000 or even 10.000. Similarly, the term "20 different second oligonucleotides" refers to 20 molecularly distinct oligonucleotides, whereas the number of each of said oligonucleotides is not particularly limited and may be any number, such as e.g. 100, 1000, 10.000 etc. It will be appreciated that the terms "a first oligonucleotide", "a second oligonucleotide", "a third oligonucleotide" and "a fourth oligonucleotide" relate to different oligonucleotides that can be distinguished from each other by their respective nucleic acid sequence.

In accordance with the present invention, the method may comprise either step (a)(i), thereby providing annealing products for the generation of bar-coded forward primers for the nucleic acid molecules of interest; or the method comprises step (a)(ii), thereby providing annealing products for the generation of bar-coded reverse primers for the nucleic acid molecules of interest; or the method comprises both step (a)(i) and (a)(ii), thereby providing annealing products for the generation of bar-coded primer pairs for the nucleic acid molecules of interest comprising bar-coded forward and bar-coded reverse primers. In those cases where both step (a)(i) and (a)(ii) are included in the method of the invention, it is preferred that two different adapter sequences and two different bar-code sequences are employed.

In accordance with the present invention, it is preferred that both step (a)(i) and (a)(ii) are carried out. It is further preferred that the steps (a)(i) and (a)(ii) are carried out in separate reaction vessels, such as e.g. two separate reaction tubes.

In accordance with this preferred embodiment, primer pairs specific for the nucleic acid molecules of interest are provided that carry two different bar-codes. This approach enables a combinatorial use of the thus bar-coded, i.e. labelled, sets of forward and reverse primers. For example, if 100 samples are to be differently labelled, only 10 differently bar-coded forward and 10 differently bar-coded reverse primers are needed as opposed to 100 different forward/reverse primers when using only one single label per nucleic acid molecule of interest.

In accordance with the present invention, the forward and reverse primers have to be designed to enable the amplification of the nucleic acid molecule of interest based on the usage of these two primers. The primer sequence may be any primer sequence suitable for nucleic acid amplification and/or reverse transcription, including gene-specific primer sequences as well as primer sequences for the PolyA tail of eukaryotic mRNAs (applicable for reverse primers, i.e. the fourth oligonucleotide according to (a)(ii)(2)). Means and methods for designing suitable primers and primer pairs, as well as specific considerations that have to be kept in mind, such as ensuring an optimum annealing temperature etc., are well known in the art. Moreover, it has to be ensured that the length of the amplification product is chosen such that it encompasses the relevant sequence to be investigated (e.g. a polymorphism of interest) and is suitable in length for subsequent sequencing. Suitable sequence lengths for sequencing are well known in the art. Preferably, the primer pairs are designed such that the resulting amplification product has a length of less than 40.000 bp, such as e.g. less than 30.000 bp, more preferably less than 20.000 bp, such as e.g. less than 10.000 bp, even more preferably less than 5.000 bp, such as e.g. less than 2.500 bp, more preferably less than 1.000 bp, such as e.g. less than 750 bp, such as less than 500 bp, even more preferably less than 250 bp, such as less than 200 bp, such as less than 150 bp, and most preferably less than 100 bp. It is further preferred that the amplicon has a length of at least 35 bp. In addition, it is further preferred that for one experiment, primer and primer pairs are chosen that generate amplicons of approximately the same length. Preferably, this amplicon length is in the range of 100 to 250 bp.

As detailed herein above, the method of the present invention also encompasses the option that only forward or only reverse bar-coded primers are produced. In that case, these primers may subsequently be used in a linear amplification reaction or, more preferably, they are used as primer pairs in combination with the corresponding non-bar-coded reverse or forward primers, respectively, thereby enabling an exponential amplification. The same considerations with regard to primer pair design as outlined above apply mutatis mutandis also in this case.

Furthermore, the bar-coded primers produced in accordance with the present invention can also be employed for reverse transcription (RT) and RT-PCR. To this end, a bar-coded primer is generated that consists of an adapter and bar-code as well as a primer sequence that anneals to a specific RNA sequence or to a plurality of different RNAs. In the first case, a sequence-specific primer is employed that specifically binds to the RNA sequence of interest. In the latter case, a primer such as a poly T primer is employed, that is capable to bind to the polyA tail of eukaryotic mRNA. Upon reverse transcription with such a bar-coded primer, a cDNA with one bar-code is produced. For subsequent amplification by PCR or linear amplification, either a non-bar-coded forward primer or a bar-coded forward primer can be used.

After annealing of the bar-code-adapter oligonucleotides with the oligonucleotides comprising the rcAdapter and an rcPrimer has been carried out in step (a) of the method of the invention, the 3' ends of the oligonucleotides are extended in step (b) by polymerase-mediated oligonucleotide synthesis.

To this end, a polymerase as well as nucleotides and a reaction buffer are added to the annealed oligonucleotides obtained in step (a) and oligonucleotide synthesis is carried out. Suitable conditions for oligonucleotide synthesis are well known in the art and have been described, e.g. in Nolan and Bustin (Eds.), "PCR Technology: Current Innovations", Third Edition, CRC Press (2013) or Sambrook and Russell, "Molecular Cloning: A Laboratory Manual", Third Edition, Cold Spring Harbor, N.Y. (2001).

Preferably, the polymerase is a DNA polymerase. The overhanging 5' end of the one strand serves as template for the DNA synthesis of the other strand. In other words, the reverse complementary primer nucleic acid sequence of the second (and/or fourth) oligonucleotide serves as a template to incorporate the primer nucleic acid sequence (i.e. the actual primer) into the first (and/or third) oligonucleotide that already comprises the bar-code. At the same time, the second (and/or fourth) oligonucleotide is extended using the first (and/or third) oligonucleotide as the template, thus resulting in an extended second (and/or fourth) oligonucleotide. Preferably, extension of the employed second (and/or fourth) oligonucleotides should be avoided through the use of a 3' nucleotide that can not be used for DNA extension (Atkinson et al., "Enzymic synthesis of deoxyribonucleic acid. XXXIV. Termination of chain growth by a 2',3'-dideoxyribonucleotide", Biochemistry, 8: 4897-4904 (1969)). Most preferably, the polymerase is a DNA polymerase which shows optimal activity between 10-30° C., in order to minimise the denaturation of partially double stranded DNA molecules formed during step (a)(i) and (a)(ii). Such DNA polymerases are well known in the art and include, but are not limited to Klenow DNA polymerase and T4 DNA polymerase.

After the oligonucleotide synthesis step (b), double stranded nucleic acid molecules are provided that comprise a strand that comprises a bar-code, an adapter and a primer nucleic acid sequence (in 5' to 3' direction) and a complementary strand, comprising the reverse complementary sequence of the bar-code, the reverse complementary sequence of the adapter and the reverse complementary sequence of the primer (in 3' to 5' direction).

In a further, optional, step (step (c)), the second and fourth oligonucleotides are removed.

Any method of removing a particular set of oligonucleotides from mixed samples known in the art may be employed in accordance with the present invention. For example, methods can be employed that allow for the direct removal of the second and fourth oligonucleotides from the mixture (herein also referred to as positive selection). Alternatively, or additionally, methods for enriching the first and third oligonucleotides can be employed, thereby indirectly leading to the removal of the second and fourth oligonucleotides (also referred to herein as negative selection).

Exemplary methods for removing the second and fourth oligonucleotides in step (c) include: (i) exonuclease digestion; (ii) affinity separation; and/or (iii) uracil N-glycosylase treatment.

In accordance with the first option, the second and fourth oligonucleotides are removed by digestion with an exonuclease. One possibility of achieving this is that a bar-code-adapter oligonucleotide (i.e. a first and/or third oligonucleotide) is employed that comprises phosphorothioates instead of phosphate residues in the bases of the 5' nucleotides of the bar-code nucleic acid sequence. Preferably, at least the last four bases at the 5' end of the bar-code are modified in this way, more preferably between the last four and the last six bases at the 5' end of the bar-code are modified in this way. The incorporation of phosphothioates instead of phosphate residues protects the 5' end of oligonucleotides from the activity of some 5'→3' exonucleases, as e.g. described in U.S. Pat. No. 5,518,900. Accordingly, when a 5'→3' exonuclease is added after the step of oligonucleotide synthesis in accordance with step (b) of the method of the invention, only the unprotected oligonucleotides are digested by said exonuclease, i.e. the second and fourth oligonucleotides.

Alternatively, the second and fourth oligonucleotides can be removed by employing an exonuclease having a strong preference for initiating degradation on dsDNA containing a 5' phosphate, such as e.g. lambda exonuclease (Mitsis and Kwagh, "Characterization of the interaction of lambda exonuclease with the ends of DNA", Nucleic Acids Research, 27: 3057-3063 (1999)). In that case, it has to be ensured that a bar-code-adapter oligonucleotide (i.e. a first and/or third oligonucleotide) is employed that carries hydroxyl groups at its 5' end, while second and fourth oligonucleotides are used that are modified at the 5' end with phosphate, rather than a hydroxyl group.

In accordance with step (c) of the invention, second and/fourth oligonucleotides are removed by said exonuclease that selectively begins degradation at the phosphorylated ends of double stranded DNA molecules. Subsequently, the exonuclease employed for the removal of the second and fourth oligonucleotides is inactivated, for example by heat denaturation, e.g. by an incubation at 80° C.:

In addition to the above, a combination approach of protecting the first and/or third oligonucleotide and enzymatically degrading the second and/or fourth oligonucleotide can be employed. To this end, a bar-code-adapter oligonucleotide (i.e. a first and/or third oligonucleotide) is employed that comprises specific exonuclease pausing sequences linked 5' to the barcode sequence. A known example in the art is the '5GGCGATTCT3' sequence that inhibits lambda exonuclease (Perkins et al., "Sequence-Dependent Pausing of Single Lambda Exonuclease Molecules", Science, 301: 1914-1918 (2003)). It is particularly preferred to use a '5CCA3' sequence that is presumed to act via counteracting the initial binding of lambda exonuclease. This approach has been successfully employed herein, see e.g. Table 4, FIG. 4 and FIG. 5 below. In addition, second and fourth oligonucleotides are used that are modified at the 5' end with phosphate, rather than a hydroxyl group. As detailed above, lambda exonuclease has a strong preference for initiating degradation on dsDNA containing a 5' phosphate. Thus, its addition after the step of oligonucleotide synthesis in accordance with step (b) of the method of the invention, results in the digestion of the unprotected oligonucleotides, i.e. the second and fourth oligonucleotides, while the first and/or third oligonucleotide are additionally protected from exonuclease digestion. Subsequently, lambda exonuclease is inactivated by heat denaturation, e.g. by an incubation at 80° C.

Another method for the removal of second and/or fourth oligonucleotides by exonuclease degradation employs tagged second and fourth oligonucleotides and a tag-dependant exonuclease. Such tags and tag-dependant enzymatic activity of exonucleases have been described e.g. by Symmons et al. in "Running rings around RNA: a superfamily of phosphate-dependent RNases", Trends Biochem Sci, 27: 11-18 (2002).

Suitable 5'→3' exonucleases are well known in the art and include, without being limiting, T7 exonuclease and lambda exonuclease, both of which can degrade a single specific strand of a double stranded DNA molecule, starting from its 5' end. Use of such exonucleases to digest oligonucleotides is well known in the art and has been described, e.g. in Avci-Adali et al., "Upgrading SELEX Technology by Using Lambda Exonuclease Digestion for Single-Stranded DNA Generation", Molecules, 15: 1 (2009); Higuchi and Ochman, "Production of single-stranded DNA templates by exonuclease digestion following the polymerase chain reaction", Nucleic Acids Research, 17: 5865 (1989). It will be appreciated that the choice of exonuclease depends on the overall experimental design, e.g. the choices made when designing the oligonucleotides, as discussed above with regard to the presence of inhibitory effects, including, without being limiting, the effect of phosphorothioates or other protective sequences such as 5GGCGATTCT3', as well as the presence of 5' phosphates that promote degradation by specific exonucleases; but also the ability to denature the enzyme after the exonuclease reaction.

A downstream purification of the processed oligonucleotides is possible but not necessary, as exonucleases break down the second and fourth oligonucleotides into mononucleotides that are not interfering with subsequent reactions such as PCR amplification. Moreover, and as discussed above, it is preferred that prior to the subsequent use of the bar-coded primers, the exonuclease is denatured, e.g. by heat denaturation. Preferably, the enzyme is denatured by heating it at e.g. 95 C.° for 10 minutes. Upon heat denaturation, the enzyme molecules lose their activity. Also for this reason a purification of the extended first and third oligonucleotides is not necessary.

Alternatively (or additionally), the second and fourth oligonucleotides may be removed by affinity separation. It will be appreciated that this encompasses on the one hand that the second and fourth oligonucleotides are bound via affinity-binding and are removed from the mixture, thus leaving the first and third oligonucleotides in the mix. On the other hand, this option encompasses that the first and third oligonucleotides are bound via affinity-binding and the remainder of the mixtures is washed off, leaving only the bound first and third oligonucleotides. Any known method of affinity separation may be employed in accordance with the present invention.

Such methods can for example involve the inclusion of an affinity tag in the oligonucleotide to be separated. In accordance with the present invention, affinity tags can be for example magnetic beads or protein-/peptide-/oligonucleotide-/or aptamer-tags. The presence of the affinity tag in the oligonucleotides enables their separation based on the binding of said tag to an interacting moiety, such as a magnetic matrix for interaction with magnetic beads or a natural (e.g. streptavidin) or artificial (such as e.g. specific antibodies) interaction partner for interaction with protein or peptide tags.

Non-limiting examples of protein or peptide tags include biotin, Strep-tags, chitin binding proteins (CBP), maltose binding proteins (MBP), glutathione-S-transferase (GST), FLAG-tags, HA-tags, Myc-tags, poly(His)-tags as well as derivatives thereof. All these affinity tags as well as derivatives thereof are well known in the art and have been described, e.g. in Lichty et al., "Comparison of affinity tags for protein purification", Protein Expression and Purification, 41: 98-105 (2005); Diamandis and Christopoulos, "The biotin-(strept)avidin system: principles and applications in biotechnology", Clinical Chemistry, 37: 625-636 (1991); Berensmeier, "Magnetic particles for the separation and purification of nucleic acids", Applied Microbiology and Biotechnology, 73: 495-504 (2006).

Biotin binds to streptavidin-coated matrices and the binding of biotin to streptavidin is one of the strongest non-covalent interactions known in nature. The Strep-tag family of tags, for example, is separated using streptavidin or strep-tactin tetrameric protein complexes (Schmidt and Skerra, "The Strep-tag system for one-step purification and high-affinity detection or capturing of proteins", Nat. Protocols, 2: 1528-1535 (2007)). Chitin binding proteins (CBP) allow native purification via chitin as the binding partner-matrix (offered for example by NEB). Maltose binding proteins bind to amylase-coated matrices. Glutathione-S-transferase (GST) as a tag binds to glutathione labelled matrices. FLAG, MYC and HA tags bind to respective monoclonal antibodies coupled to a matrix. His-tags form complexes with nickel or cobalt ions also bound by the purification matrix.

Alternatively, affinity separation includes the addition of magnetic beads to the oligonucleotides to be separated and subsequent immobilisation of these oligonucleotides via said magnetic beads. To this end, the oligonucleotide to be separated needs to be provided initially with an amine at its 5' end. After DNA synthesis according to step (b), the mixture is brought into contact with magnet beads to which carboxyl groups are attached, thus reacting the amine groups of the oligonucleotides with the carboxyl groups of the magnetic beads, leading to the formation of a covalent bond between the magnetic beads and the respective oligonucleotides. Subsequently, the magnetic beads are immobilised and the mixture is heated to denature the DNA duplexes and the supernatant comprising the not immobilised oligonucleotides is removed.

It will be appreciated that it is possible to either use the oligonucleotides comprised in the supernatant or the oligonucleotides immobilised via the magnetic beads. In the first case, only those oligonucleotides are removed from the mixture that are not required or that need to be absent to avoid interference with subsequent approaches. In the second case, those oligonucleotides that are required for the subsequent methods, i.e. in the present case the first and third oligonucleotides, are removed from the mixture and subsequently cleaved off the magnetic beads and used in the subsequent procedures.

In a further alternative, affinity separation may be carried out by addition of biotin to the oligonucleotides to be separated and subsequent immobilisation of these oligonucleotides via magnetic beads coated with streptavidin. In yet another alternative, affinity separation includes the addition of digoxigenin (DIG) to the oligonucleotides to be separated and subsequent immobilisation of these oligonucleotides via magnetic beads coated with antibodies specific for DIG. The definitions provided herein above with regard to the addition of magnetic beads to the oligonucleotides to be separated and subsequent immobilisation of these oligonucleotides via magnetic beads apply mutatis mutandis also to this alternative.

Such magnetic bead systems are commercially available, e.g. from Roche Diagnostics GmbH.

It will be appreciated that depending on the method employed for removing the second and fourth oligonucleotides, it may be necessary to denature the nucleic acid strands into single-strand oligonucleotides prior to removal of the second and fourth oligonucleotides. In particular, where the method is affinity separation, it is preferred that the oligonucleotide strands are denatured, for example by heat denaturation as is well known in the art, in order to enable removal of only the second and fourth oligonucleotides while the first and third oligonucleotides remain available for further applications.

Alternatively, in accordance with the third option, the second and fourth oligonucleotides may be removed by uracil N-glycosylase treatment. To this end, uridine is incorporated into the rcAdapter sequence instead of thymidine. Preferably, at least four uridine nucleotides are incorporated. After oligonucleotide synthesis in accordance with step (b), the enzyme uracil N-glycosylase (UNG) is employed to hydrolyse the strand containing the uridines, leading to the degradation of the second and fourth oligonucleotides.

In a preferred embodiment of the method of the invention, said removing the second and fourth oligonucleotides in step (c) is effected by exonuclease digestion.

As is shown in Table 5 below, the method of the invention can also be carried out without the removal step according to (c). Preferably, however, step (c) is included in the method as described herein above.

In accordance with optional step (c) of the method of the invention, any second and fourth oligonucleotides are removed, both extended second and fourth oligonucleotides, as well as non-extended oligonucleotides, in case such oligonucleotides are present in the mixture after step (b).

The term "and" in steps (b) and (c) means that in those cases in which both steps (a)(i) and (a)(ii) were carried out, then the oligonucleotides obtained from both steps need to be processed as described i.e. the first, second, third and fourth oligonucleotides are extended and, optionally, the second and fourth oligonucleotides are removed. In those cases in which only (a)(i) was carried out, only the first and the second oligonucleotides are extended and only the second oligonucleotides are removed and, mutatis mutandis, in those cases in which only (a)(ii) was carried out, only the third and the fourth oligonucleotides are extended and only the fourth oligonucleotides are removed.

In those cases where the sets of primers are produced in order to generate amplification products for subsequent sequencing, such as next generation sequencing, a suitable primer binding site is preferably additionally incorporated into the bar-coded primers in order to enable binding of a sequencing primer. The design and general considerations regarding sequencing primers are well known in the art and have been described, e.g. in Quail et at. Improved Protocols for Illumina Sequencing Curr Protoc Hum Genet. 2009. In short, the binding site for the sequencing primer is ideally incorporated into the bar-coded primers produced in accordance with the present invention such that the sequencing primer is located 5' of the bar-codes in the final bar-coded primer produced by the method of the present invention.

The length of the bar-coded primers produced by the method of the invention is not particularly limited. Preferably, the overall length of the bar-coded primers produced by the method of the invention is between up 34 and 50 bp, more preferably it is between 36 and 42 bp.

In accordance with the present invention, a method is provided for the cost- and time-efficient production of bar-coded sets of multiple primers or primer pairs. Such primers are of pivotal importance in the multiplexed analysis of multiple nucleic acid molecules of interest in a large number of different samples in parallel, for example for targeted sequencing and next generation sequencing (NGS).

The current state-of-the-art for DNA bar-coding methods is mainly based on the individual chemical synthesis of a bar-code sequence combined with the primer sequence. This individually designed oligonucleotide primer is then introduced to DNA or cDNA by use of PCR amplification. However, for a whole NGS run, chemical synthesis of individually bar-coded primers would be far too expensive to be considered for directional multiplexing of templates from thousands of samples. This is demonstrated by the following example: analysis of 50 gene regions in 1000 patient samples currently requires purchasing of 50×1000 bar-coded primers, for an estimate cost of €250,000.

Alternative methods utilise a separate synthesis of sequence specific primers and bar-codes, which are subsequently ligated, as e.g. described in WO2012112804. Employing this method enables the generation of a large pool of different barcodes (several millions) but requires the ligation of the two oligonucleotide sequences. Similarly, amplicon samples (following PCR) may be directly ligated to distinct barcodes. However, ligation of 1000 amplicon samples (following PCR with 50 primer sets) will cost more than €5000.

Moreover, although these procedures are more cost effective than direct synthesis of bar-coded primers, they do not represent a sufficiently reliable solution for targeted sequencing of hundreds to hundreds of thousands of samples, especially when targeted sequencing is used for quantifying template amounts, e.g. RNAs. This is because several steps of DNA end processing and purification are necessary for preparing the fragments for ligation, and the ligation reaction itself is prone to fluctuations. These inconsistencies in ligation efficiencies between samples generate non- or partially (e.g. containing only a single barcode, instead of two)-bar-coded templates, and hence reduce the usability of the sequencing data for quantitative analysis of transcript (gene) expression levels. Moreover, in the case of preparation of samples for ligation of bar-codes to oligonucleotides, handling over a thousand of samples is cumbersome and requires sample purification steps, thus leading to an amount of time and associated costs that are too high for situations requiring multiplexing with over a thousand templates, and can be performed only using highly specialized equipment and professional personnel. Furthermore, although the technology discussed in e.g. WO2012112804 offers the possibility of carrying out thousands of reactions in parallel in micro-droplets, it suffers from the additional limitation that individual samples, such as individual patient samples, will need to be processed sequentially, as a correlation between the micro-droplets and the origin of an amplicon from one particular sample out of a plurality of samples is not possible (as reviewed in e.g. Meldrum et al., "Next-Generation Sequencing for Cancer Diagnostics: a Practical Perspective", The Clinical Biochemist Reviews, 32: 177-195 (2011)). The loss of individualized sample information in multiplexed reactions consisting of thousands of samples is a central caveat not only for diagnostic purposes, but also for research purposes such as single cell transcriptional profiling and genotyping, since it is impossible to correlate expressed genes/mutations with other cellular parameters such as cell surface protein expression or with clone identity. Thus, the advantage associated with multiplexing many genes of interest in a large number of samples is lost in such approaches.

The random sequencing data produced by NGS and the costs of producing bar-coded oligonucleotides for directional multiplexing, as well as the disadvantages of primer/amplicon-bar-code ligation, are critical bottlenecks for numerous NGS applications which cannot be solved by current sample preparation and multiplexing technologies for NGS.

With the aid of the method of the present invention, customised DNA bar-coded primer panels are produced at costs up to one order of magnitude lower compared to currently available procedures. The method of the present invention provides a targeted approach that relies on unique bar-code identifiers that are generated completely unrelated to a specific sequence of the nucleic acid molecule of interest. Via an adapter sequence comprised in the bar-code containing oligonucleotide, a bar-code of choice can be linked to a set of several different primers to be used for the amplification of nucleic acid molecules of interest from the same sample. As a prerequisite, no conventional primers are provided, but a reverse complement of the primer sequences is provided, linked to the reverse complement of the adapter sequence. The reverse complement of the adapter sequence binds to the oligonucleotide comprising the adapter sequence by physico-chemical means, i.e. via annealing of the complementary DNA strands. The subsequent fill-in reaction for extension of the oligonucleotides is a more efficient and less error-prone method as compared to the enzymatic ligation and solid-phase synthesis methods employed in the art, as discussed above. Thus, the present method offers a fast reliable and cost-efficient approach of bar-coding several primers in one reaction with one predetermined bar-code (see FIG. 1 for an overview of all steps).

Thus, to refer to the examples provided above, for the production of 50 bar-coded primers only one reaction is necessary, in which one sample-specific bar-code is introduced into each of the 50 primers. Alternatively, where 50 primer pairs are to be bar-coded, again only one reaction each is necessary, in which one bar-code is introduced into each of the 50 forward primers and a second bar-code is introduced into each of the 50 reverse primers. Amplification of nucleic acid molecules of interest with this primer pair results in amplification products that carry a sample-specific bar-code combination.

In order to amplify nucleic acid molecules of interest from 10,000 different samples, this procedure is carried out in 200 reactions in parallel (100 forward and 100 reverse), thus providing reagents for 10,000 bar-code reactions. Generating the combinations and amplification by PCR can be performed using high throughput technologies and at costs significantly reduced as compared to the above discussed prior art methods. After amplification from the 10,000 samples, the thus obtained amplicons can be pooled into one sample and sequenced using NGS.

Most importantly, as compared to the above discussed ligation techniques, the method of the present invention provides a set of primers in which each and every primer is in fact bar-coded. This is because of the initial use of a complementary primer sequence, which is only changed into the correct primer via extension of the bar-code-adapter oligonucleotide. Thus, errors in quantitative amplification methods as previously observed using primers or amplicons that have been bar-coded via ligation can be excluded when employing primers produced in accordance with the method of the present invention.

Examples where the bar-coded primers prepared in accordance with the present invention remove significant bottlenecks for molecular diagnostics, research and commercial applications include, without being limiting, genetic diagnosis, transcriptional profiling, genotyping or quality control for food and hygiene industries, and high-throughput screening of compounds for drug discovery and validation:

As regards genetic diagnosis, current applications requiring the analysis of only several founder mutations (e.g. BRCA1 analysis for founder mutations leading to breast cancer) or the expression of several genes (e.g. in the range of 1 to 10) typically involve inexpensive but laborious testing by Sanger sequencing and/or quantitative PCR, respectively. Deep sequencing (NGS) and/or DNA hybridization microarrays, on the other hand, are used for genetic diagnosis that requires the analysis of dozens or more loci and de novo mutations. The costs of the latter tests are in the range of hundreds to over ten thousands of Euros per sample. Multiplexing hundreds/thousands of patient samples for a single NGS reaction when target genes are known would lead to a dramatic reduction of per-patient-costs, and thereby accelerate the development of novel assays and drugs for more ailments, including multi-factorial diseases, such as diabetes, metabolic syndrome or cardiovascular diseases, as well as cancer.

Of particular relevance is genetic diagnostics of cancer. Cancer is a genetic disease, and tumor behaviour (e.g. growth, metastasis, remission, response to therapy) depends on cohorts of mutation present in single cells. Currently, there is no cost effective method to analyse cohorts of mutations in thousands and up to tens of thousands of single tumor cells, and to define the landscape of mutation cohorts and the levels of expressed genes in massive numbers of single cell preparations (e.g. >10,000 single cells). As a result and although potential patient benefit is high, cancer diagnostics does not involve single cell genotyping and transcriptional profiling. Furthermore, current diagnostic techniques typically do not allow linking genetic information of single cells (mutations/transcripts) with additional molecular parameters of single cells, such as levels of receptors involved in cell transformation, e.g the oestrogen receptor in breast cancer patients. The expected impact of high throughput single tumor cell genetic diagnostics is a considerable improvement in the success rate of targeted therapy. Potentially, linking genetic information with levels of certain proteins, such as receptors, can provide even more accurate prognosis.

Transcriptional profiling of single cells is another important field, as the cohorts of transcripts expressed by a given cell determine its function. Transcriptional heterogeneity has been recognized as a pivotal phenomenon in tissues consisting of seemingly identical cells. Analysing transcriptional heterogeneity in tissues remains a significant challenge due to the lack of methods enabling inexpensive analysis of tens of thousands of cells.

Genotyping several loci and analysing expression of several genes, in dozens and up to tens of thousands of samples obtained from humans, animals (including laboratory animals, pets and livestock), plants and other eukaryotes for research purposes is one of the most frequent analytics conducted in research labs. Conducting these experiments is highly tedious due to the lack of a massive sample multiplexing method. Applications include discovering mutations/polymorphisms and expressed genes in patient cells and cell lines for drug screening purposes, for human genetic and biochemical studies, and for genotyping cell samples, tissues and animals following genome editing procedures, using, for example, Crispr Cas and TALEN systems. The genomes of some species of eukaryotes, primarily plants, exhibit polyploidy of up to 10 sets, and in special cases even more, of chromosomes. Some of the most important agricultural plants, including bread wheat, and yeast strains used for fermentation are polyploid. Since it is very difficult to analyse mutations/polymorphisms in polyploid organisms by Sanger sequencing, and polyploid plants are intensely investigated for derivation of strains with certain properties, a method that enables multiplexing of massive sample pools for analysing multiple chromosomes simultaneously by NGS is highly desired.

Analysing the compositions of products containing meat (and fish) and dairy is of a major importance for public health and safety. Many cases have been reported in recent years where products contained unreported meat ingredients. Tests for the presence of foreign species of meat/fish/diary typically involve quantification of protein, or PCR and Sanger sequencing, or NGS of pooled samples. The costs of such tests can be considerably lowered by a method enabling massive multiplexing of thousands and up to tens of thousands of samples in a single NGS reaction. Also with regard to such quality control methods for food and hygiene industries it is desired that the multiplexing method enables the linking of sequence information to the individual samples to quickly identify contaminated batches of products.

Finally, diverse areas of biological sciences employ high-throughput screening (HTS) for testing of large numbers of chemical substances for specific activities. Screens conducted in the pharmaceutical industry frequently span $10^5$ to $10^6$ compounds. The biological responses to compounds in HTS typically rely on biochemical assays, such as assays that indicate activation of a signalling pathway, and enzymatic readouts, such as colorimetric readouts. However, transcriptional measurements are very rarely utilized as readouts in HTS assays since it is highly costly to conduct industrial-scale RT-PCR analysis. Also, as mentioned above, current sample multiplexing techniques for NGS are limited to dozens or hundreds of samples, and involve extensive bioinformatics, making NGS an expensive assay end point readout. Therefore, a method that enables measuring the expression of a plurality of transcripts in tens of thousands of multiplexed samples by NGS as a readout in HTS screening is highly desired by the pharmaceutical and biomedical industries and by academia alike.

Thus, the present invention addresses the technical limitations for sequencing specific nucleic acid molecules and for quantifying amounts of specific nucleic acid transcripts in massive pools of samples. The present invention i) enables multiplex sequencing of a vast number of samples, for example in the range of hundreds to tens of thousands of distinct samples in a single multiplexed pool, ii) it enables targeted sequencing of very few loci, even as few as a singe locus, iii) it reaches bar-coding efficiently of nearly 100% even when combinations of barcodes are used, iv) it allows to link (track back) each bar-coded sequence with the specific sequence of each individual sample in highly multiplexed sample pools, and thus v) it enables to quantify the amounts (expression levels) of transcripts by targeted sequencing in highly multiplexed sample pools, consisting of hundreds to tens of thousands of distinct samples or even more.

In a preferred embodiment of the method of the invention, the bar-code nucleic acid sequence is at least 3 nucleotides in length. Means and methods to ensure that such a 3-nucleotide sequence is not present in the sample of interest (e.g. a human sample) adjacent to the primer-binding site of the nucleic acid sequences of interest are well known in the art.

As is known in the art, the length of the bar-code affects the coding capacity of an individual bar-code, i.e. it influences how many different samples can be differentially labelled. This capacity can be increased by the combination of two bar-codes, e.g. by using one bar-coded forward primer in combination with a differently bar-coded reverse primer. For example, in order to differently label 100 samples, either 100 different bar-codes are required when only one bar-coded primer is employed in the method of the invention or 10 different bar-codes are required for the forward primer and 10 different bar-codes for the reverse primer, i.e. a total of only 20 different bar-codes is required.

The upper limit of length of a bar-code nucleic acid sequence is determined by the capabilities of the sequencing method to be employed. Currently, sequencing platforms that provide the highest numbers of reads per reaction (Illumina) are limited to a maximum of 250 nucleotides. Consequently, short DNA bar-codes are preferred in order to not unduly limit the amplicon size of the nucleic acid molecule of interest.

Accordingly, bar-code nucleic acid sequences of a length of at least 3 nucleotides, such as e.g. at least 4 nucleotides, such as at least 5 nucleotides, such as at least 6 nucleotides, more preferably at least 7 nucleotides, such as at least 8 nucleotides etc. can be employed in accordance with the present invention. Preferably, the bar-code nucleic acid sequence is between 3 and 20 nucleotides in length, more preferably between 3 and 15 nucleotides, even more preferably between 3 and 12 nucleotides, and most preferably between 8 and 12 nucleotides, such as 8, 9, 10, 11 or 12 nucleotides.

In another preferred embodiment of the method of the invention, the adapter nucleic acid sequence is at least 4 nucleotides in length.

As detailed above with regard to the bar-code nucleic acid sequence, non-amplicon sequences should be kept at a minimal length due to the restrictions presently imposed on sequencing read lengths. In addition, longer sequences are also more likely to interfere with multiplex PCR: Thus, short adapter nucleic acid sequences are preferred in order to not unduly limit the amplicon size of the nucleic acid molecule of interest.

Accordingly, adapter nucleic acid sequences of a length of at least 4 nucleotides, such as e.g. at least 5 nucleotides, such as at least 6 nucleotides, more preferably at least 7 nucleotides, such as at least 8 nucleotides etc. can be employed in accordance with the present invention. Preferably, the adapter nucleic acid sequence is between 4 and 20 nucleotides in length, more preferably between 6 and 15 nucleotides and even more preferably between 8 and 12 nucleotides, such as e.g. 8, 9, 10, 11 or 12 nucleotides. Most preferably, the adapter nucleic acid sequence is 10 nucleotides in length.

In a further preferred embodiment of the method of the invention, the primer length is at least 10 nucleotides in length.

As discussed herein above, means and methods as well as the necessary considerations for the design of suitable primers are well known in the art. Accordingly, it is within the skills of the skilled person to choose the appropriate primer length to ensure specific binding to the nucleic acid molecule of interest from a sample of a particular species. In accordance with the present invention, primers with a length of at least 10 nucleotides, such as e.g. at least 12 nucleotides, at least 15 nucleotides or at least 17 nucleotides can be employed. Preferably, the primer length is between 10 and 30 nucleotides, more preferably between 15 and 25 nucleotides and even more preferably between 17 and 20 nucleotides. Most preferably, the primers are 20 nucleotides in length for specific amplification of a nucleic acid molecule of interest from a sample obtained from a human.

In another preferred embodiment of the method of the invention, the polymerase is a DNA polymerase. More preferably, the DNA polymerase is selected from the group consisting of Klenow DNA polymerase and T4 polymerase. Klenow DNA polymerase and T4 polymerase are all well known in the art.

The term "Klenow DNA polymerase", also used interchangeably in the art with "Klenow fragment", refers to the large protein fragment produced when DNA polymerase I from *E. coli* is enzymatically cleaved by the protease subtilisin. This fragment retains the 5'→3' polymerase activity as well as the 3'→5' exonuclease activity, but loses its 5'→3' exonuclease activity.

T4 DNA Polymerase also catalyzes the synthesis of DNA in the 5'→3' direction in the presence of template and primer. This enzyme has a more active 3'→5' exonuclease activity than that found in DNA polymerase I (*E. coli*) and naturally does not have a 5'→3' exonuclease function.

The Klenow DNA polymerase and T4 polymerase can be obtained commercially from e.g. Invitrogen, New England Biolabs or Qiagen and are used in accordance with manufacturer's instructions or as discussed in the appended examples.

In an even more preferred embodiment of the method of the invention, the DNA polymerase is Klenow DNA polymerase.

Klenow DNA polymerase has significantly lower exonuclease activity compared with DNA Polymerase (Gupta et al., "The effect of the 3',5' thiophosphoryl linkage on the exonuclease activities of T4 polymerase and the Klenow fragment", Nucleic Acids Research, 12: 5897-5911 (1984)), decreasing the probability of oligonucleotide degradation during bar-code-adapter-primer preparation. Exonuclease activities of both Klenow fragment and T4 DNA Polymerase increase with higher temperatures, such as 60° C. During the inactivation process, where the enzymes are denatured by heat, the reaction mixture is heated up, leading to a transient increase in the exonuclease activity until the enzymes are denatured which can result in lower primer yields due to oligonucleotide degradation. Thus, use of Klenow Polymerase with less exonuclease activity is preferred.

In a further preferred embodiment of the method of the invention, the nucleic acid molecules of interest are selected from the group consisting of genes, polymorphic nucleic acid sequences, species-specific nucleic acid sequences, in particular species-specific nucleic acid sequences that are epigenetically modified, such as e.g. nucleic acid sequences that include 5'methylcytosine and 5-hydroxymethylcytosine.

In accordance with the method of the present invention, sets of bar-coded primers are produced that are suitable for the amplification of a variety of nucleic acid molecules of interest.

For example, the sets of bar-coded primers may be suitable for the amplification of particular genes of interest, for example disease-associated genes, such as cancer-associated genes. Non-limiting examples include alleles (i.e. disease markers) that are only present or absent once the disease has manifested, such that detection of the presence or absence of these alleles provides diagnostic information about the health status of the subject of which the sample analysed has been obtained. In addition, determination of the amount of a particular gene transcript of interest present in a sample may be of a diagnostic value, e.g. in those cases where the change in the amount of gene expression is associated with a particular disease.

The sets of bar-coded primers may further be suitable for the amplification of polymorphic nucleic acid sequences of interest. A number of genetic polymorphisms have been identified in the art that are associated (being either causative or merely indicative) with an increased risk for developing certain diseases, such as e.g. cancer, diabetes, coronary artery disease, rheumatoid arthritis, and other common diseases. In accordance with the present invention, polymorphic nucleic acid sequences are nucleic acid sequences carrying one or more mutations at a given location on a chromosome. Typically, when the occurrence of a particular nucleotide exchange is an infrequent event, it is referred to as a mutation while more frequent events (i.e. occurring with at least 1% prevalence in a population of individuals) are referred to as polymorphisms. Nonetheless, both terms are often used interchangeably in the art and, accordingly, are used interchangeably herein.

In accordance with the present invention, the term "polymorphic nucleic acid sequences" embraces polymorphisms in exons, introns and regulatory regions such as promoters. Polymorphisms in exons may be determined or analysed using genomic DNA or cDNA (or equivalently mRNA), while polymorphisms in introns or regulatory regions such as promoters may be determined or analysed using genomic DNA.

Furthermore, the sets of bar-coded primers produced in accordance with the present invention may also be suitable to determine which species a particular probe is derived from. This may be of particular importance when analysing e.g. food samples.

The identification of food species has received great attention for various reasons: food allergies, medical requirements, religious practices, ethic and economic reasons. Food adulteration has been shown to be an important problem in the food industry. Some of the products most frequently related with food fraud are meat products, especially when provided as meat mixtures. Species identification according to the methods of the present invention is a fast, easily feasible and cheap way for disclosure and prevention of food fraud.

In addition, the sets of primers produced in accordance with the present invention may also be used to determine the genotypes of cell clones following modification by gene editing techniques such as Crispr-CAS9 and TALEN. In eukaryotes, this procedure produces thousands of clones that are difficult and cumbersome to genotype by traditional sequencing (Sanger method). This is because multiple sites are often modified simultaneously and because one allele or more can be modified in a variety of ways (i.e. to produce different genotypes). Massive sample multiplexing for NGS in accordance with the present invention can be used to maintain clone information during NGS and analyse two or more alleles simultaneously.

Epigenetic modifications that influence the transcription level of nucleic acids can also be analysed using the primer sets of the present invention. Known modifications of nucleic acids include methylation and hydroxymethylation of cytosine, produced by cytosine replacement with 5'methylcytosine and 5-hydroxymethylcytosine, respectively. Methods for detecting positions of 5'methylcytosine and 5-hydroxymethylcytosine in DNA molecules include, without being limiting, bisulfite treatment or detection with specific antibodies.

Treatment of the DNA with bisulfite leads to the conversion of cytosine, but not 5'methylcytosine or 5-hydroxymethylcytosine, to uracil. Uracil bases pair with adenines, thus DNA polymerization leads to replacement of cytosine with thymine following bisulfite treatment and PCR and sequencing. The sites of 5'methylcytosine and 5-hydroxymethylcytosine are identified by comparing sequencing data of bisulfite-treated with untreated samples. The sets of bar coded primers of the present invention can be applied to bisulfite-treated and non-treated DNA samples, and hence to detect by NGS sites where the DNA bears 5'methylcytosine or 5-hydroxymethylcytosine epigenetic markers, which will be protected from conversion to uracil by bisulfite. In the same manner that the present invention enables genotyping of massive sets of amplicons from thousands of samples by assembling barcodes to primer panels and NGS, the present invention enables the detection of the positions of 5'methylcytosine and 5-hydroxymethylcytosine residues in DNA fragments within massive pools of samples.

Alternatively, specific antibodies for 5'methylcytosine and 5-hydroxymethylcytosine can be used to bind the respective regions where these modifications exist across genomes, and in conjunction with immunoprecipitation and sequencing the regions that harbour 5'methylcytosine and 5-hydroxymethylcytosine can be detected. Moreover, novel approaches enable to specifically detect 5-hydroxymethylcytosine on single nucleotide resolution, and in combination with bisulfite single nucleotide detection of 5'methylcytosine and 5-hydroxymethylcytosine, sequence information can be used to resolve, individually, 5'methylcytosine and 5-hydroxymethylcytosine modified nucleotide sequences. The sets of bar coded primers of the present invention can be applied to the antibody-mediated approach for detecting 5'methylcytosine or 5-hydroxymethylcytosine, and hence for detecting by NGS sites where the DNA bears 5'methylcytosine or 5-hydroxymethylcytosine epigenetic markers.

In another preferred embodiment of the method of the invention, the first and/or third oligonucleotide further comprises a protecting group at its 5'-end to ensure protection from degradation of said oligonucleotides. Suitable protection groups include, without being limiting, the above described '5GGCGATTCT3' sequence that inhibits lambda exonuclease as well as the '5CCA3' sequence employed in the appended examples, see e.g. Table 4, FIG. 4 and FIG. 5 below.

The present invention further relates to a method of producing a plurality (M) of nucleic acid amplification products and/or reverse transcription products of interest carrying at least one sample-specific bar-code, the method comprising (i) producing a set of bar-coded primers in accordance with the method of the invention; and (ii) amplifying and/or reverse transcribing a plurality (M) of nucleic acid molecules of interest from a sample using the set of primers produced in (i).

The term "a plurality (M) of nucleic acid amplification products and/or reverse transcription products of interest" refers to an integral number of at least 2, such as at least 3, at least 4, at least 5, at least 6, at least 7, at least 8, at least 9, at least 10. Preferably, (N) is an integral number in the range between 1 and 500, such as e.g. between 2 and 250, more preferably between 3 and 150 and most preferably between 5 and 100. It will be appreciated that these preferred ranges include all other combinations of upper and lower limits, such as e.g. between 10 and 500, between 10 and 150, between 10 and 100 etc.

Preferably, the number of the plurality (M) of nucleic acid amplification products and/or reverse transcription products of interest is identical to the number of the plurality (N) of nucleic acid molecules of interest.

In accordance with this method of the invention, nucleic acid molecules of interest are reverse transcribed and/or amplified from a sample while at the same time a label specific for said sample is incorporated into said reverse transcription products and/or amplification products, wherein the label is in form of a bar-code or a combination of bar-codes.

In a first step, a set of bar-coded primers is prepared in accordance with the method of the invention of producing primer sets, as described herein above. Where for example a plurality (M) of 20 nucleic acid molecules of interest are to be reverse transcribed/amplified, a set of primers suitable for the reverse transcription/amplification of said 20 nucleic acid molecules of interest is provided carrying a bar-code specific for the sample. To this end, either at least 20 forward primers, or at least 20 reverse primers, or at least 20 primer pairs (forward and reverse primers) are provided. Where only forward primers are prepared by the method of the invention, all forward primers carry the same bar-code. The same applies where only reverse primers are prepared by the method of the invention. In both cases, linear amplification may be carried out with these single primers or, preferably, exponential amplification is achieved by additionally employing the corresponding non-bar-coded reverse or forward primers. For reverse transcription, bar-coded reverse primers are prepared by the method of the invention and optionally combined with bar-coded or non-bar-coded forward primers for further amplification.

Where bar-coded primer pairs are prepared, all primers may carry the same bar-code or, preferably, all forward primers carry one (identical) bar-code while all reverse primers carry one (identical) bar-code, wherein the bar-code of the reverse primer is different from the bar-code of the forward primer.

The term "at least one sample-specific bar-code", as used herein, encompasses both the option that the sample-specific bar-code consists of only one bar-code (i.e. where only one bar-coded primer is employed) as well as the option that the sample-specific bar-code consists of a "combination of bar-codes", i.e. where a primer pair with two different bar-codes is employed, thus resulting in an amplification production having a bar-code at the 5' end and a different bar-code at the 3' end, i.e. a combination of two bar-codes.

In a second step of this method of the invention, these primers are employed in an amplification and/or reverse transcription method to produce amplification products and/or reverse transcription products from the nucleic acid molecules of interest from a sample.

As used herein, the term "amplification" or "amplify" refers to an increase in copy number. Methods to amplify nucleic acid molecules are well known in the art and include both linear as well as exponential amplification methods. For example, polymerase chain reaction (PCR) can be employed for exponential amplification. For linear amplification, only one primer is employed, such as e.g. only a forward or only a reverse primer.

A non-limiting example for reverse transcription represents the so-called RT-IVT-RT method, described e.g. by Hashimshony et al., "CEL-Seq: Single-Cell RNA-Seq by Multiplexed Linear Amplification", Cell Reports, 2: 666-673 (2012). When applied in accordance with the present invention, first and/or third oligonucleotides are employed that carry an additional viral promoter sequence, such as a T4 or T7 promoter, 5' to the barcode sequence. These oligonucleotides are then combined via their adapter regions with a second/fourth oligonucleotide, harbouring a 3' rcAdapter sequence and a 5' oligo-adenine stretch, e.g. 18 adenine nucleotides in a row, and are extended with a DNA polymerase. Depletion of the second/fourth oligonucleotide results in bar-coded oligo-dT primers with a 5' viral promoter.

Subsequently, these primers can anneal to the Poly-A tail of eukaryotic mRNAs and initiate reverse transcription reaction, where mRNAs from samples can be transcribed into complementary DNA (cDNA) by a reverse transcriptase. The resulting cDNA molecules carry the initial bar-code sequence as well as the viral promoter sequence on their 5' ends. In vitro transcription (IVT), in-tube enzymatic generation of RNA from a DNA template, can be utilized to linearly amplify the cDNA with a viral RNA-polymerase, targeting its specific promoter site on the 5'. A single cDNA molecule can yield many RNA copies, which can undergo another round of reverse transcription, giving rise to a pool of bar-coded and amplified cDNA molecules. Such pools can be generated for different samples, with different bar-codes and combined together for a sequencing library.

Preferably, amplification is accomplished by using polymerase chain reaction (PCR). PCR consists of several repetitions of a cycle which consists of: (a) a denaturation step, which melts both strands of a nucleic acid molecule; (b) an annealing step, which is aimed at allowing the primers to anneal specifically to the single strands of the DNA molecule; and (c) an extension step, which adds nucleotides to the primers complementary to those of the strand of DNA to which the primers are annealed.

The concentrations of primers, nucleotidetriphosphates, enzyme and buffers are well known in the art and can be chosen and adjusted, where necessary, by the skilled person without further ado. To give a non-limiting example, PCR can be performed for example in a 50 µl reaction mixture containing 5 µl of 10×PCR buffer with 1.5 mM $MgCl_2$, 200 µM of each deoxynucleoside triphosphate, 0.5 µl of each primer (10 µM), 0.5 µl (30 ng) of template DNA and 2.5 Units of Taq Polymerase. DNA amplification can be performed, e.g., with a model 2400 thermal cycler (Applied Biosystems, Foster City, Calif.): 2 min at 94° C., followed by 35 cycles consisting of annealing (30 s at 50° C.), extension (1 min at 72° C.), denaturation (10 s at 94° C.) and a final annealing step at 55° C. for 1 min as well as a final extension step at 72° C. for 5 min.

It is well known in the art how to optimize these conditions for the amplification of specific nucleic acid molecules (see for example Sambrook and Russell, "Molecular Cloning: A Laboratory Manual", Third Edition, Cold Spring Harbor, N.Y. (2001)).

A further method of nucleic acid amplification is the "reverse transcriptase polymerase chain reaction" (RT- PCR). This method is used when the nucleic acid to be amplified consists of RNA. The term "reverse transcriptase" refers to an enzyme that catalyzes the polymerisation of deoxyribonucleoside triphosphates to form primer extension products that are complementary to a ribonucleic acid template. The enzyme initiates synthesis at the 3'-end of the primer and proceeds toward the 5'-end of the template until synthesis terminates. Examples of suitable polymerizing agents that convert the RNA target sequence into a complementary, copy-DNA (cDNA) sequence are avian myeloblastosis virus reverse transcriptase and *Thermus thermophilus* DNA polymerase, a thermostable DNA polymerase with reverse transcriptase activity marketed by Perkin Elmer. Typically, the genomic RNA/cDNA duplex template is heat denatured during the first denaturation step after the initial reverse transcription step leaving the DNA strand available as an amplification template. Suitable polymerases for use with a DNA template include, for example, *E. coli* DNA polymerase I or its Klenow fragment, T.sub.4 DNA polymerase, Tth polymerase, and Taq polymerase, a heat-stable DNA polymerase isolated from *Thermus aquaticus* and developed and manufactured by Hoffmann-La Roche and commercially available from Perkin Elmer. The latter enzyme is widely used in the amplification and sequencing of nucleic acids. The reaction conditions for using Taq polymerase are known in the art and are described, e.g. in Erlich, "PCR Technology: Principles and Applications for DNA Amplification", Stockton Press, New York (1989) or Innis et al. (Eds.), "PCR Protocols: A Guide to Methods and Applications", Academic Press, San Diego, Calif. (1990).

High-temperature RT provides greater primer specificity and improved efficiency. U.S. patent application Ser. No. 07/746,121, filed Aug. 15, 1991, describes a "homogeneous RT-PCR" in which the same primers and polymerase suffice for both the reverse transcription and the PCR amplification steps, and the reaction conditions are optimized so that both reactions occur without a change of reagents. *Thermus thermophilus* DNA polymerase, a thermostable DNA polymerase that can function as a reverse transcriptase, can be used for all primer extension steps, regardless of template. Both processes can be done without having to open the tube to change or add reagents; only the temperature profile is adjusted between the first cycle (RNA template) and the rest of the amplification cycles (DNA template). The RT Reaction can be performed, for example, in a 20 µl reaction mix containing: 4 µl of 5×AMV-RT buffer 4 µl, 2 µl of Oligo dT (100 µg/ml), 2 µl of 10 mM dNTPs, 1 µl total RNA, 10 Units of AMV reverse transcriptase and H2O to 20 µl final volume. The reaction may be, for example, performed by using the following conditions: The reaction is held at 70 C.° for 15 minutes to allow for reverse transcription. The reaction temperature is then raised to 95 C.° for 1 minute to denature the RNA-cDNA duplex. Next, the reaction temperature undergoes two cycles of 95° C. for 15 seconds and 60 C.° for 20 seconds followed by 38 cycles of 90 C.° for 15 seconds and 60 C.° for 20 seconds. Finally, the reaction temperature is held at 60 C.° for 4 minutes for the final extension step, cooled to 15 C.°, and held at that temperature until further processing of the amplified sample.

The sample may be any sample comprising nucleic acid molecules, such as e.g. blood, serum, plasma, lymph nodes, bone marrow, faeces, fetal tissue, saliva, urine, mucosal tissue, mucus, vaginal tissue, skin, hair, hair follicle or other tissue. The sample can be a freshly isolate sample or a preserved sample, such as e.g. paraffin-embedded tissues or frozen tissues. Moreover, the sample may be obtained from any organism of interest. For example, the organism may be selected from humans, companion animals such as cats, dogs or rabbits, farm animals such as horses, cows, pigs, deer, fish, chicken or other poultry, animals kept for example in zoological gardens such as e.g. primates and monkeys, wild cats, canines, elephants, bears, giraffes, marsupials etc. Moreover, the sample may be a sample obtained from or comprising bacteria, viruses, yeast, plants, artificial organisms/sequences including ribozymes and organisms comprising or consisting of novel/engineered forms of nucleic acids.

Preferably, the subject is a human subject.

In a preferred embodiment, the method of the invention of producing a plurality (M) of nucleic acid amplification products and/or reverse transcription products further comprises: (iii) producing at least a second set of bar-coded primers in accordance with the method of the invention, wherein said at least one second set of bar-coded primers differs in its bar-code nucleic acid sequence from the first set of primers of (i); and (iv) amplifying and/or reverse transcribing said plurality (M) of nucleic acid molecules of interest from a second sample by PCR using the second set of primers produced in (iii).

In accordance with this preferred embodiment, a second set of bar-coded primers is prepared, wherein the primers can be identical to the primers of the first set of primers, with the exception of the bar-code nucleic acid sequence(s) they carry. By using a differently bar-coded set of primers, a second sample such as e.g. a sample from a different subject may be employed for the amplification and/or reverse transcription of nucleic acid molecules of interest. Because these nucleic acid amplification products and/or reverse transcription products of the second sample carry a different bar-code, the bar-coded amplification products and/or reverse transcription products obtained from the two different samples can subsequently be mixed (i.e. pooled) together and be analysed in a single reaction, such as e.g. in next generation sequencing methods. Although it is encompassed herein that the second set of bar-coded primers are different in their specific primer sequence, it is preferred that the specific primer sequences of the second set of bar-coded primers is the same as in the first set of bar-coded primers, such that the same nucleic acid molecules of interest are amplified and/or reverse transcribed by use of said bar-coded primers.

It will be appreciated that the second sample is not restricted to a sample from another subject. Instead, the second sample may also be a different sample from the same subject. For example, where the first sample is derived from cancerous tissue from a patient, a second sample may be obtained from healthy tissue of the same patient. Alternatively, the second sample may be derived from the same origin (e.g. same tissue) as the first sample, but may serve as a repeat control.

In a more preferred embodiment of the method of the invention of producing a plurality (M) of nucleic acid amplification products and/or reverse transcription products, the steps (iii) and (iv) are repeated for a plurality (X) of samples, wherein each set of bar-coded primers produced in (iii) differs in their bar-code nucleic acid sequences from each of the other sets of primers; thereby producing from each sample a plurality (M) of nucleic acid amplification products and/or reverse transcription products of interest carrying at least one sample-specific bar-code.

In accordance with the preferred embodiment, nucleic acid molecules of interest are amplified and/or reverse transcribed from further samples, such as e.g. a third sample, a fourth sample, a fifth sample and so on, by using sets of primers that carry specific bar-codes for each sample, i.e. a third set of bar-coded primers, a fourth set of bar-coded primers, a fifth set of bar-coded primers and so on. Accordingly, amplification products and/or reverse transcription products from a plurality (M) of nucleic acid molecules of interest, such as e.g. 20 different amplification products and/or reverse transcription products, can be obtained from a plurality (X) of samples, such as e.g. 100 to 10.000 different samples.

It will be appreciated that the steps (iii) and (iv) are repeated individually, i.e. in separate reaction vessels. In this way, amplification products and/or reverse transcription products are individually produced that differ in their bar-code. As it is known which bar-code was incorporated into which set of primers/which sample, it is now possible to mix (pool) all amplification products and/or reverse transcription products into one reaction vessel for further processing, such as e.g. for sequencing while the sequencing results can unambiguously be allocated to the respective sample.

In accordance with the method of producing a plurality (M) of nucleic acid amplification products and/or reverse transcription products of the invention, amplification and/or reverse transcription of nucleic acid molecules from a first sample is carried out, comprising steps (i) and (ii). In accordance with the preferred embodiment, amplification and/or reverse transcription of nucleic acid molecules from a second sample, comprising the steps (iii) and (iv), is then carried out. Thus, in accordance with this preferred embodiment, the method enables the amplification and/or reverse transcription of nucleic acid molecules from two samples. In accordance with the even more preferred embodiment, the method further enables the production of nucleic acid amplification products and/or reverse transcription products from a plurality of samples, i.e. in addition to the second sample, further samples are amplified and/or reverse transcribed by a method comprising the steps (iii) and (iv). Accordingly, wherein the second sample already represents one sample from which nucleic acid molecules are amplified using steps (iii) and (iv), a third sample may employed (in which case the plurality (X) of samples would be 2), a fourth sample may be employed (in which case the plurality (X) of samples would be 3) and so on. In accordance with the present invention, the number of the plurality (X) of samples is not particularly restricted. Preferably, X represents an integral number of at least two, such as e.g. at least three, at least four, at least five, at least six, at least seven, at least eight, at least nine, at least ten, at least 15, at least 20, at least 30, at least 50, at least 100 and so on. More preferably, X represents an integral number of at least 200, such as at least 500, at least 1000, at least 2000, at least 5000, at least 6000, at least 7000, at least 8000, at least 9000 and most preferably at least 10000.

The present invention further relates to a method for multiplex sequencing of a plurality (M) of nucleic acid amplification products and/or reverse transcription products of interest from different samples and identifying the individual sample from which each nucleic acid amplification product and/or reverse transcription products is derived, the method comprising: (a) producing a plurality (M) of nucleic acid amplification products and/or reverse transcription products of interest for each individual sample in accordance with the method of the invention of producing a plurality (M) of nucleic acid amplification products and/or reverse transcription products from different samples; (b) combining the nucleic acid amplification products and/or reverse transcription products produced in (a) from all samples; (c) sequencing the combined nucleic acid amplification products and/or reverse transcription products of (b); and (d) identifying the individual sample from which each nucleic acid amplification product and/or reverse transcription products is derived based on the sample-specific bar-code associated with the nucleic acid amplification product and/or reverse transcription products.

In a more preferred embodiment, the present invention relates to a method for multiplex sequencing of a plurality (M) of nucleic acid amplification products and/or reverse transcription products of interest from a plurality (X) of samples and identifying the individual sample from which each nucleic acid amplification product and/or reverse transcription products is derived, the method comprising: (a) producing a plurality (M) of nucleic acid amplification products and/or reverse transcription products of interest for each individual sample of the plurality (X) of samples in accordance with the method of the invention of producing a plurality (M) of nucleic acid amplification products and/or reverse transcription products from a plurality (x) of samples; (b) combining the nucleic acid amplification products and/or reverse transcription products produced in (a) from all samples; (c) sequencing the combined nucleic acid amplification products and/or reverse transcription products of (b); and (d) identifying the individual sample from which each nucleic acid amplification product and/or reverse transcription products is derived based on the sample-specific bar-code associated with the nucleic acid amplification product and/or reverse transcription products.

Preferably, these methods of multiplex sequencing of a plurality (M) of nucleic acid amplification products and/or reverse transcription products are carried out in a single reaction vessel. In other words, these methods are for the simultaneous multiplex sequencing of a plurality (M) of nucleic acid amplification products and/or reverse transcription products.

As detailed herein above, and as further discussed in the appended examples, the amplification products and/or reverse transcription products obtained by amplification and/or reverse transcription with differently bar-coded primer sets can be combined in one reaction vessel, due to the presence of a sample-specific bar-code in said amplification products. These combined samples can then be analysed by multiplex sequencing, such as for example next generation sequencing, in situ sequencing (Lee et al., "Highly multiplexed subcellular RNA sequencing in situ", Science, 343: 1360-1363 (2014)) or nanopore sequencing. Such sequencing methods are well known in the art and have been described, for example, in Meldrum et al., "Next-Generation Sequencing for Cancer Diagnostics: a Practical Perspective", The Clinical Biochemist Reviews, 32: 177-195 (2011).

When sequencing the amplification products and/or reverse transcription products, the bar-codes encompassed therein are also sequenced. Because for each sample a predetermined, i.e. known bar-code (or bar-code combination) is employed, this information can now be used to allocate a sequence to a particular sample. In other words, it is possible to identify the individual sample from which each nucleic acid amplification product is derived based on the sample-specific bar-code associated with the nucleic acid amplification product.

The bar-coding method of the present invention overcomes the current technical limitations encountered in the art with regard to large-scale sample analysis by targeted sequencing in an affordable manner. As compared to whole genome sequencing, the present method offers the directional identification of e.g. disease-associated genes in a large pool of patient samples. Ultimately, these assays can be adjusted for analyzing the molecular signatures in transcriptional programs, mutation cohorts, or epigenetic modifications of interest in thousands of individual samples that can be single cells or bulk cell preparations.

This includes for example patient biopsies or single cells from patient biopsies (e.g. tumor cells) for providing the most accurate diagnosis concerning the co-existence of oncogenic mutations in single cells and expression cohorts of genes related to cancer in single cells. This is of particular relevance for the treatment of tumor metastasis, relapse, response to therapies, resistance to therapies, etc.

This also includes, for example, the bulk or single cell analysis of normal and malignant cells of the immune system for providing diagnostic information, for example concerning cohorts of mutations in single tumor cells and cohorts of mutations and transcripts that serve as markers for haematological disorders such as anaemia, allergy, auto immunity, etc. Cell types suitable for use include, without being limiting, T cells, regulatory T cells, helper T cells, naïve T cells, cytotoxic T cells, NK cells, NKT cells, B cells, plasma cells, megakaryocytes, platelets, neutrophils, basophils or esenophils.

Further included are, for example, the bulk or single cell analysis of normal and malignant cells of the central and peripheral nervous system that consists of neurons, glial cells, oligodendrocytes, radial glial cells, Schwan cells etc. for providing diagnostic information concerning mutations in single tumor cells and cohorts of mutations and transcripts that serve as markers for neurological disorders such as dementia, Parkinson's disease, Alzheimer etc. Furthermore, also included are, for example, the bulk or single cell analysis of normal and malignant cells of all other physiological systems in the body, including the lungs, heart, liver, pancreas, muscles, eyes, kidneys, skin, gut etc. for providing diagnostic information concerning mutations in single tumor cells and cohorts of mutations and transcripts that serve as markers for diseases and disorders affecting embryos, fetuses, new-borns, juvenile, the adult and aged individuals including cancer, pathogen borne diseases etc.

The present invention further relates to a target-unspecific bar-code-adapter panel, comprising a plurality of single-stranded oligonucleotides, wherein each single-stranded oligonucleotide comprises a bar-code nucleic acid sequence linked at its 3' end to an adapter nucleic acid sequence; wherein (i) the bar-code nucleic acid sequence differs between the single-stranded oligonucleotides comprised in the panel; and (ii) the adapter nucleic acid sequence is the same in all single-stranded oligonucleotides comprised in the panel.

The term "bar-code-adapter panel", as used herein, relates to a collection of individual bar-code-adapter oligonucleotides. Within the panel, several different bar-code-adapter oligonucleotides are present in distinct compartments, such as e.g. different vials or tubes. In other words, in one compartment, only one molecular type of bar-code-adapter oligonucleotide is present, although the number of bar-code-adapter molecules is not particularly limited, i.e. several tens, hundreds or even thousands of copies of a particular bar-code-adapter oligonucleotide can be present in one compartment. For each compartment of the panel, the information about the bar-code-adapter oligonucleotide sequence comprised in said compartment is known and recorded to enable the directed use of individual bar-code-adapter oligonucleotides. This information enables the linking of sequence information obtained after sequencing to the samples for which (a) particular barcode(s) has/have been used. Hence, genotypes, transcripts and DNA methylation sequences can be allocated to specific samples.

In accordance with the present invention, the bar-code-adapter oligonucleotides of the panel are "target-unspecific", i.e. they do not specifically bind to target nucleic acid molecules of interest. Instead, the adapter nucleic acid sequence is capable of binding to a reverse complementary sequence of this adapter, in order to enable hybridisation and oligonucleotide extension as described in accordance with the method of the invention.

Preferably, these oligonucleotides are designed to not bind to any of the nucleic acid molecule(s) derived from a sample to be investigated. Means and methods for designing oligonucleotides such that they do not bind to nucleic acid molecules from a particular sample are well known in the art and have been described, e.g. in Apte and Daniel, "PCR Primer Design", Cold Spring Harbor Protocols, N.Y. (2009). Additionally, bioinformatic tools such as BLAST and in silico PCR can be utilised to avoid possible interactions between nucleic acid sequences, such as the adapter or bar-code sequences to the genome or to assess whether given bar-code-adapter oligonucleotides would generate amplification artefacts when combined with the genome or the transcriptome. (Described e.g. in Ye et al., "Primer-BLAST: A tool to design target-specific primers for polymerase chain reaction", BMC Bioinformatics, 13: 134 (2012). Preferably, only those bar-code-adapter oligonucleotides are employed which are found to be completely target-unspecific by bioinformatic analyses.

The panel of the present invention comprises "a plurality of single-stranded oligonucleotides". As mentioned above, this refers to the fact that the panel comprises several different bar-code-adapter oligonucleotides in distinct compartments. In accordance with the present invention, the panel comprises at least 2 different single-stranded oligonucleotides. The term "at least" has been defined herein above. Accordingly, the panel of the present invention may e.g. comprise at least three, at least four, at least five, at least six, at least seven, at least eight, at least nine, at least ten, at least 15, at least 20, at least 30, at least 50, at least 100 different single-stranded oligonucleotides and so on. More preferably, the panel of the present invention may comprise at least 200, such as at least 500, at least 1000, at least 2000, at least 5000, at least 6000, at least 7000, at least 8000, at least 9000 and most preferably at least 10000 different single-stranded oligonucleotides.

In accordance with the present invention, the bar-code-adapter oligonucleotides are single-stranded.

The term "bar-code-adapter", as used herein, refers to an oligonucleotide comprising a bar-code and an adapter as defined herein above with regard to the method of the invention. Said bar-code-adapter comprises the bar-code nucleic acid sequence linked at its 3' end to an adapter nucleic acid sequence.

The bar-code nucleic acid sequence differs between the individual single-stranded oligonucleotides comprised in the different compartments of the panel, while the adapter nucleic acid sequence is the same in all single-stranded oligonucleotides comprised in the panel.

The definitions as well as the preferred embodiments provided herein above with regard to the methods of the invention apply mutatis mutandis also to the embodiments relating to the panel of the present invention. For example, preferred embodiments of the design and the preparation of oligonucleotides have their counterparts in preferred embodiments of the above defined panel.

The provision of the target-unspecific bar-code-adapter panel of the present invention provides the simple and quick use of such a panel in bar-coding sequence-specific primers with a desired, known bar-code, for example by employing the method of producing primers or primer sets in accordance with the present invention. One type of bar-code-adapter oligonucleotide (i.e. one single-stranded bar-code-adapter oligonucleotide comprised in one of the compartments of the panel) can be used for bar-coding a primer or primer set (e.g. non-bar-coded primer or primer set (i)) with this one type of bar-code (e.g. bar-code A), suitable for the amplification and bar-coding of nucleic acid molecules of one individual sample (e.g. sample 1). For a second sample (e.g. sample 2), the same primer or primer set (e.g. non-bar-coded primer or primer set (i)) can be labelled with a second type of bar-code-adapter oligonucleotide (i.e. from a second, different compartment of the panel, wherein the bar-code-adapter oligonucleotide comprises e.g. bar-code B)), which is subsequently employed in the amplification and bar-coding of nucleic acid molecules of said second individual sample. For a third sample (e.g. sample 3), again the same primer or primer set (e.g. non-bar-coded primer or primer set (i)) can be labelled with a third type of bar-code-adapter oligonucleotide (i.e. from a third, again different compartment of the panel, wherein the bar-code-adapter oligonucleotide comprises e.g. bar-code C)), which is subsequently employed in the amplification and bar-coding of nucleic acid molecules of said third individual sample, and so on.

The present invention further relates to the use of the target-unspecific bar-code-adapter panel of the invention in any of the methods of the invention.

The present invention further relates to a kit comprising: (a-i) a first target-unspecific bar-code-adapter panel according to the present invention; and (a-ii) a first plurality (Z) of oligonucleotides, wherein each oligonucleotide comprises the reverse complementary sequence of a forward primer specific for a nucleic acid molecule of interest linked at its 3' end to the reverse complementary sequence of the adapter nucleic acid sequence of the first target-unspecific bar-code-adapter panel; and/or (b-i) a second target-unspecific bar-code-adapter panel according to the present invention; and (b-ii) a second plurality (Z) of oligonucleotides, wherein each oligonucleotide comprises the reverse complementary sequence of a reverse primer specific for said nucleic acid molecule of interest linked at its 3' end to the reverse complementary sequence of the adapter nucleic acid sequence of the second target-unspecific bar-code-adapter panel; wherein the single-stranded oligonucleotides of the first bar-code-adapter panel are different from the single-stranded oligonucleotides of the second bar-code-adapter panel.

The term "comprising" in the context of the kit of the invention denotes that further components can be present in the kit. Non-limiting examples of such further components include preservatives, buffers for storage, enzymes etc. In addition, the kit may comprise additional nucleic acid molecules that are not intended to be bar-coded, such as e.g. non-bar-coded primers, either reverse or forward, depending on which primer is the bar-coded primer. In that case, it is preferred that the same number (Z) of such non-bar-coded primers is comprised in the kit of the invention as are oligonucleotides for bar-coding. Preferably, the kit consists of the recited components.

The various components of the kit may be present in isolation or combination. For example, the components of the kit may be packaged in one or more containers such as one or more vials, optionally with instructions for use.

The definitions as well as the preferred embodiments provided herein above with regard to the methods and the panel of the invention apply mutatis mutandis also to the embodiments relating to the kit of the present invention. For example, preferred embodiments of the oligonucleotides or the panel have their counterparts in preferred embodiments of the above defined kit.

In accordance with one embodiment of the kit of the invention, the kit comprises all of (a-i), (a-ii), (b-i) and (b-ii) recited above and the single-stranded oligonucleotides of the first bar-code-adapter panel (i.e. of (a-i)) are different from the single-stranded oligonucleotides of the second bar-code-adapter panel (i.e. of (a-ii)). This embodiment is the preferred embodiment.

In accordance with another embodiment of the kit of the invention, the kit comprises (a-i) a target-unspecific bar-code-adapter panel according to the present invention; and (a-ii) a first plurality (Z) of oligonucleotides, wherein each oligonucleotide comprises the reverse complementary sequence of a forward primer specific for a nucleic acid molecule of interest linked at its 3' end to the reverse complementary sequence of the adapter nucleic acid sequence of the first target-unspecific bar-code-adapter panel.

In accordance with another embodiment of the kit of the invention, the kit comprises (b-i) a target-unspecific bar-code-adapter panel according to the present invention; and (b-ii) a plurality (Z) of oligonucleotides, wherein each oligonucleotide comprises the reverse complementary sequence of a reverse primer specific for said nucleic acid molecule of interest linked at its 3' end to the reverse complementary sequence of the adapter nucleic acid sequence of the second target-unspecific bar-code-adapter panel.

The term "a plurality (Z) of oligonucleotides" refers to an integral number of at least 2, such as at least 3, at least 4, at least 5, at least 6, at least 7, at least 8, at least 9, at least 10. Preferably, (Z) is an integral number in the range between 10 and 500, such as e.g. between 20 and 250, more preferably between 30 and 150 and most preferably between 50 and 100. It will be appreciated that these preferred ranges include all other combinations of upper and lower limits, such as e.g. between 20 and 500, between 20 and 150, between 20 and 100 etc. Preferably, the number of the plurality (Z) of oligonucleotides is identical to the number of the plurality (N) of nucleic acid molecules of interest.

The kit of the present invention provides the bar-code-adapter panel and the rcAdapter-rcPrimer oligonucleotides required for carrying out the method of the present invention.

In accordance with the present invention, in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed and also the combination of the subject-matter of claims 3, 2 and 1 is clearly and unambiguously disclosed. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The figures show:

FIG. 1: Schematic overview of the barcode assembly principle. Oligonucleotides consisting of (i) barcode-adapter and (ii) a reverse complementary sequence of gene specific primer and adapter (rcAdapter and rcPrimer, respectively) are combined into one solution; Partial dsDNA duplexes are generated by heating and cooling, and complementary strands are synthesized by DNA polymerase, which is subsequently inactivated by heating. The polymerase frequently adds Adenine 5' to the template, leaving a 5' "A" overhang. Next, as an optional step, the reverse complementary barcode-adapter-primer strands are specifically degraded, here shown by the use of Lambda exonuclease. This last step can be achieved by using a hydroxylated nucleotide and a "protection group" consisting of a CCA stretch 5' to the bar-code (own data), and a phosphate 5' to the rcPrimer sequence. Lambda exonuclease preferably initiates DNA degradation of 5' phosphorylated nucleotides. Finally, the Lambda exonuclease is inactivated (denaturated) by heating.

Figure 2:
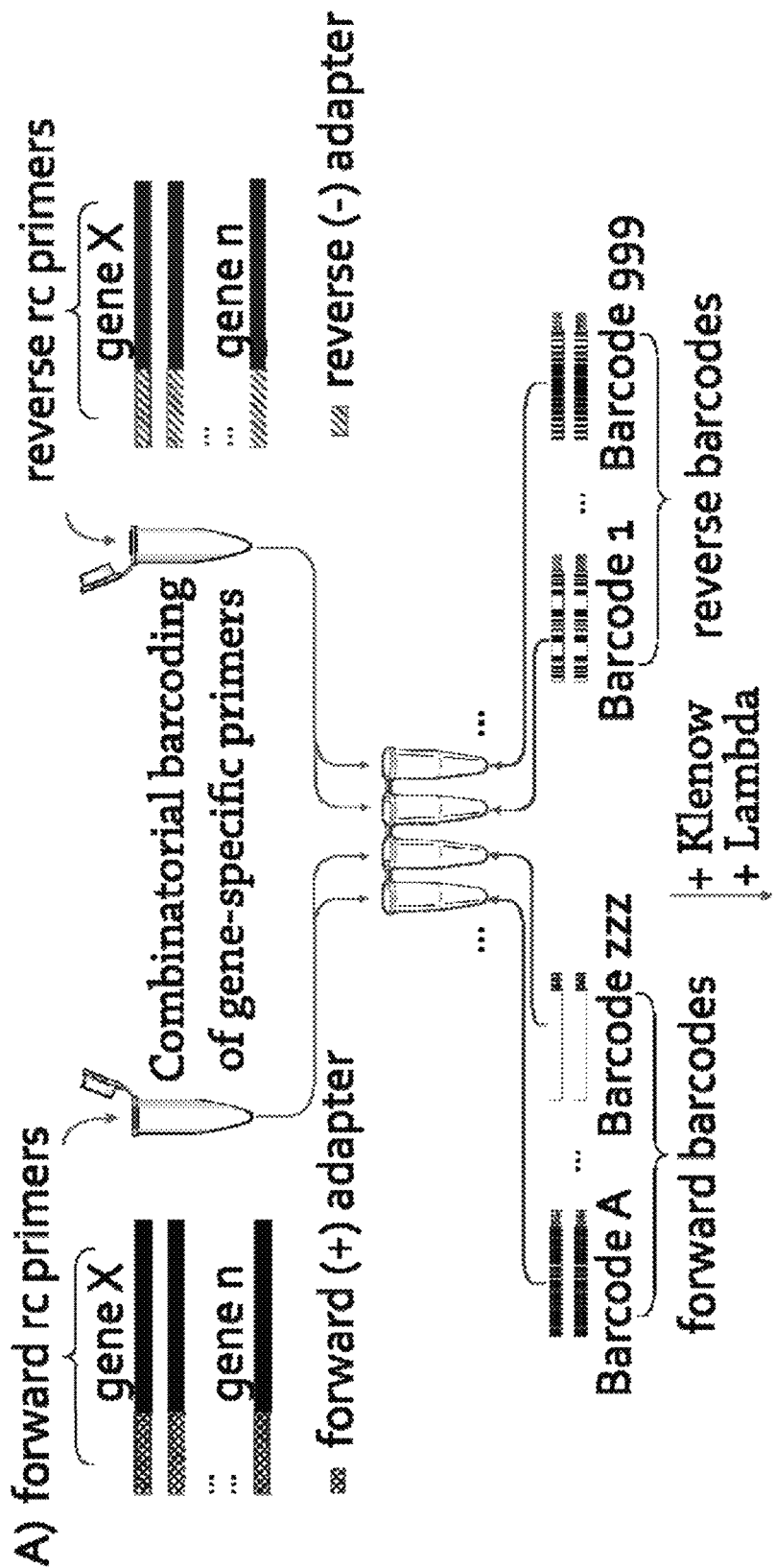
Figure 2:
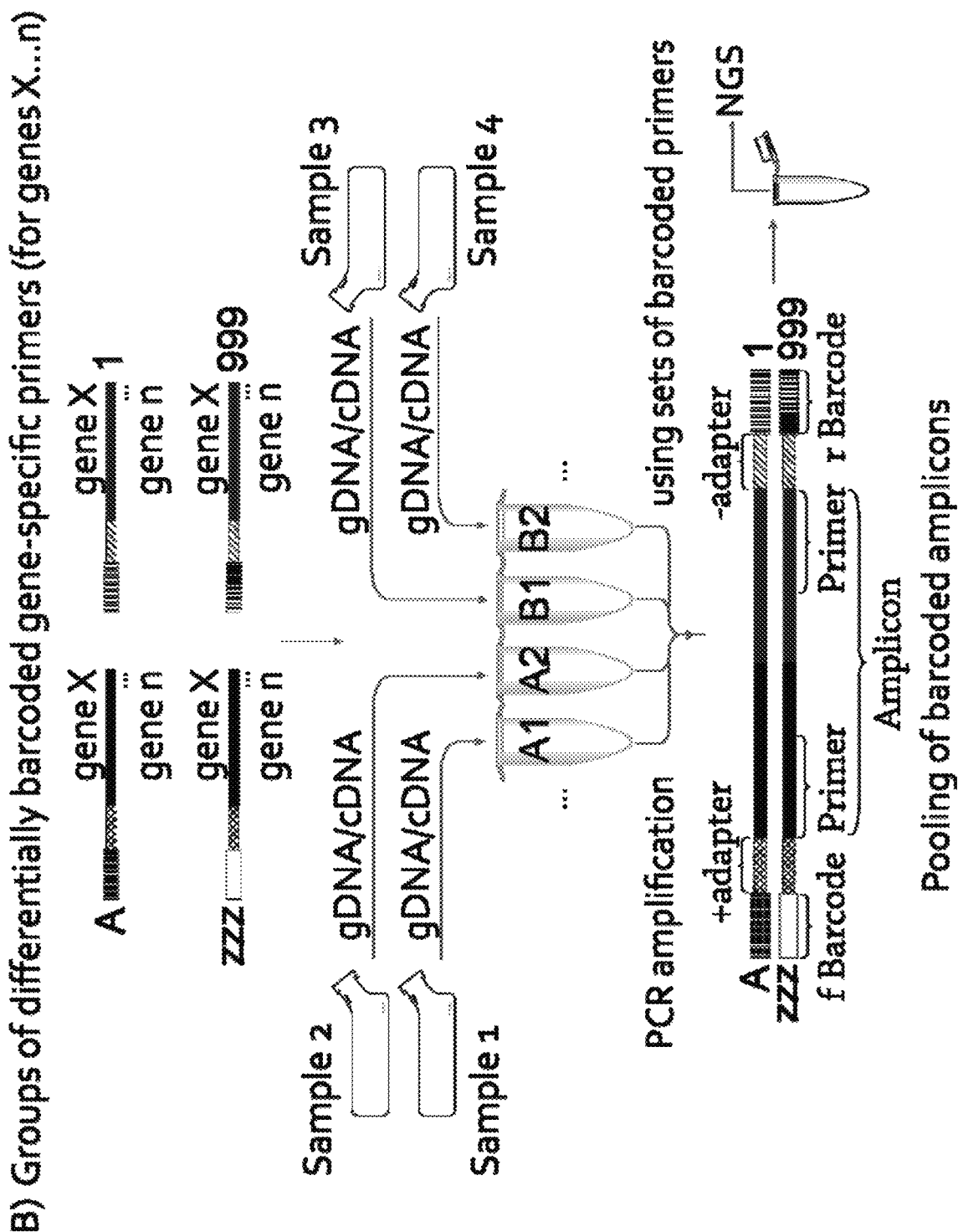

FIG. 2: Principle of directional multiplexing of amplicons.

A) A first bar-code-adapter panel comprising a plurality of single-stranded oligonucleotides each comprising a bar-code nucleic acid sequence (bar-codes A, B, ZZZ) linked to the sequence of an adapter ("+adapter") is combined with a first set of different oligonucleotides specific for a panel of e.g. various transcripts, genes, loci, or DNA methylated regions. Each oligonucleotide of the first set comprises the reverse complementary sequence of the respective adapter and the reverse complementary sequence of a forward (+)primer. A second bar-code-adapter panel comprising a plurality of single-stranded oligonucleotides each comprising a bar-code nucleic acid sequence (bar-codes 1, 2, . . . 999) linked to the sequence of an adapter ("− adapter") is combined with a second set of different oligonucleotides that is also specific for the panel of e.g. various transcripts, genes, loci, or DNA methylated regions. Each oligonucleotide of the second set comprises the reverse complementary sequence of the respective adapter and the reverse complementary sequence of a reverse (−)primer.

B) The + and − adapters are distinct. Barcode assembly protocol is performed as shown in FIG. 1. Next, a matrix of forward and reverse bar-coded primer sets are generated by combining A with 1, A with 2, A with 3 and so on till A with 999, and combining B with 1, B with 2, B with 3 and so on till B with 999, and till ZZZ is combined with 999. Each bar-coded primer set is then combined with template DNA (cDNA, modified DNA, artificial DNA), and amplified by PCR. At the final stage, all samples are pooled (ZZZx999 samples), amplicons are purified, and prepared for sequencing (library preparation for NGS).

Figure 3:
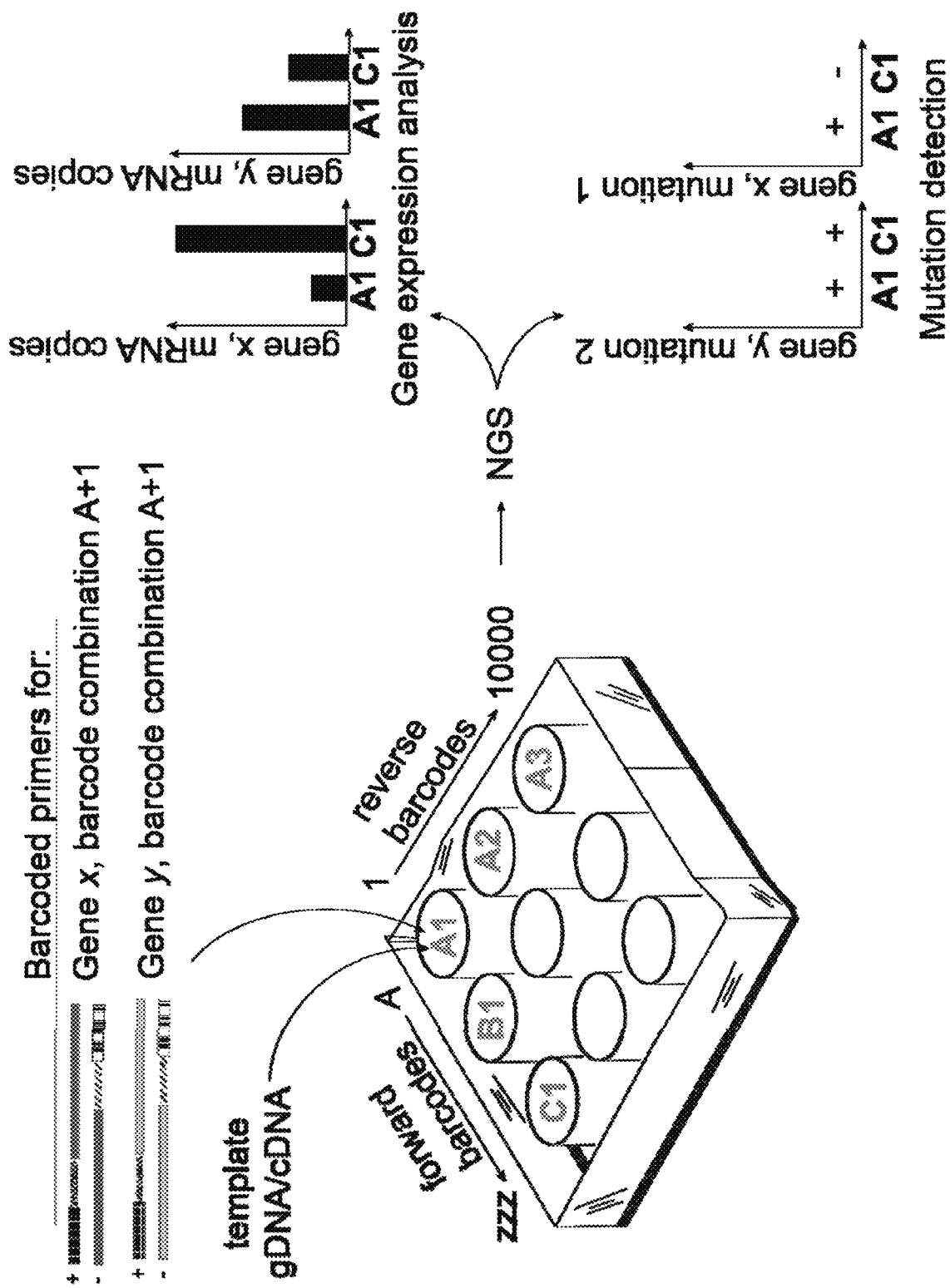

FIG. 3: Hypothetical set-up of the method of the invention for characterizing mutation cohorts of interest (left histogram panel) and for analysis of transcriptional cohorts of interest (right histogram panel). Details for bar-code assembly are provided in Example 2. Forward barcode panel comprising of barcodes A, B, ZZZ, and reverse barcode panel comprising of barcodes 1, 2, . . . 999, in accordance to barcode panels outlined in FIGS. 2 A and B.

Figure 4:
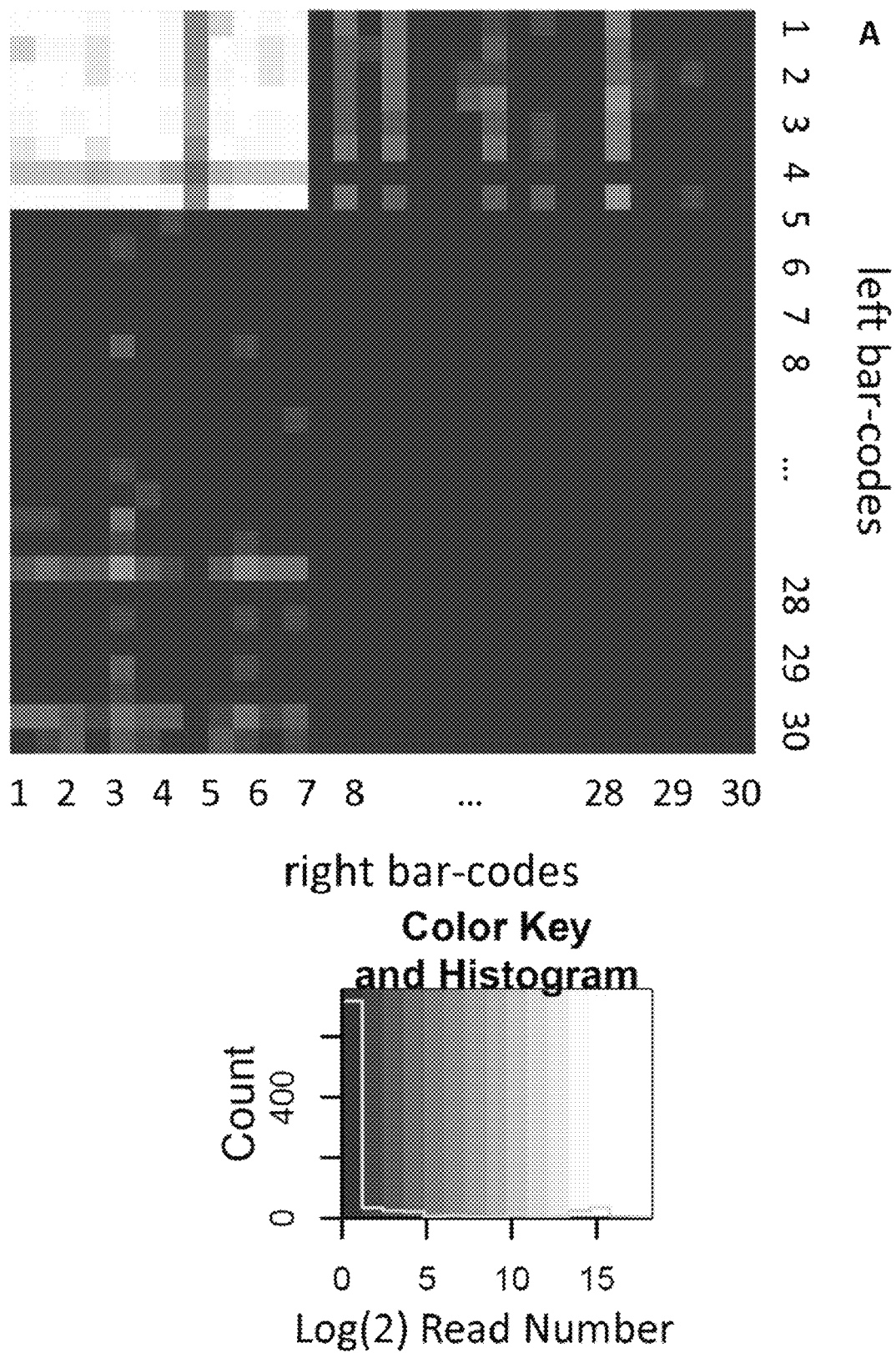
Figure 4:
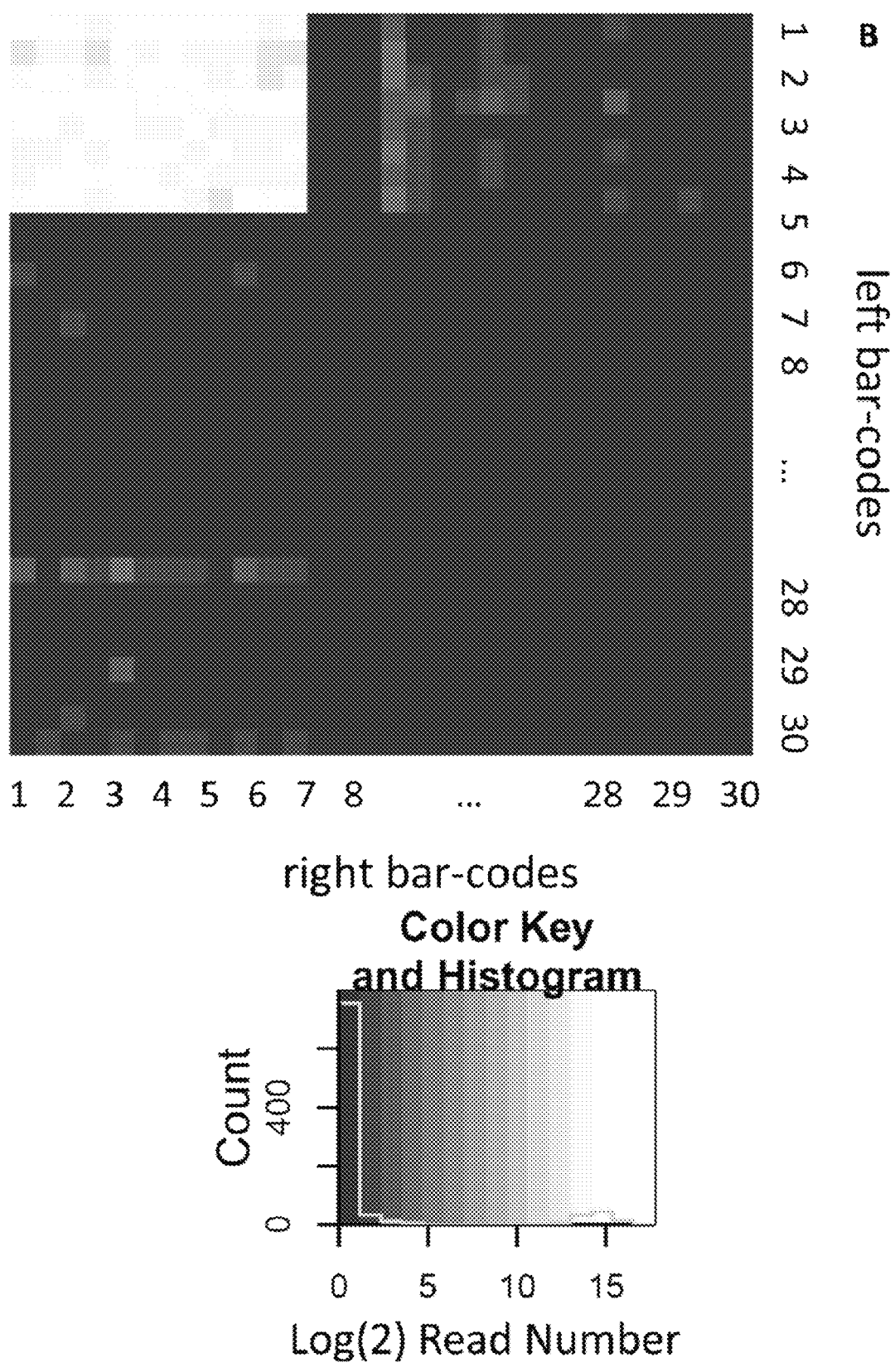

FIG. 4: Heat maps representing read number distribution of the 96 patient samples. Bar-code assembly was performed using 8 forward/left and 12 reverse/right bar-codes, as outlined in Table 2, with 5' CCA protection (B) and without 5' CCA protection (A) of bar-codes. Intensity range light to dark corresponds to high to low read numbers, respectively. 30 forward and 30 reverse barcode sequences were plotted to exemplify proper bar-code sorting. Comparison of heat maps A to B demonstrates that the use of 5' protected bar-codes employing the CCA sequence during the bar-code assembly step yields more equal distribution of reads compared to usage of unprotected bar-codes.

Figure 5:
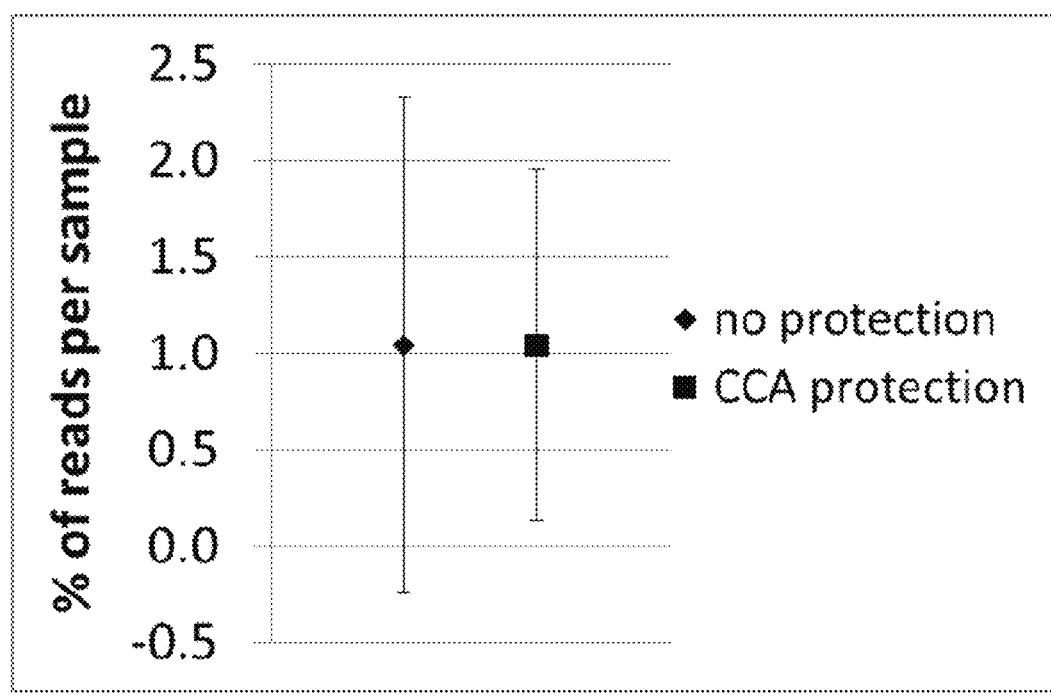

FIG. 5: comparison of variation in read number average between 96 samples performed with and without 5' CCA protection of bar-codes. This further demonstrates that inclusion of 5'CCA3' protection group reduces variation of read numbers between differentially bar-coded (different bar-code combinations) samples.

Figure 6:
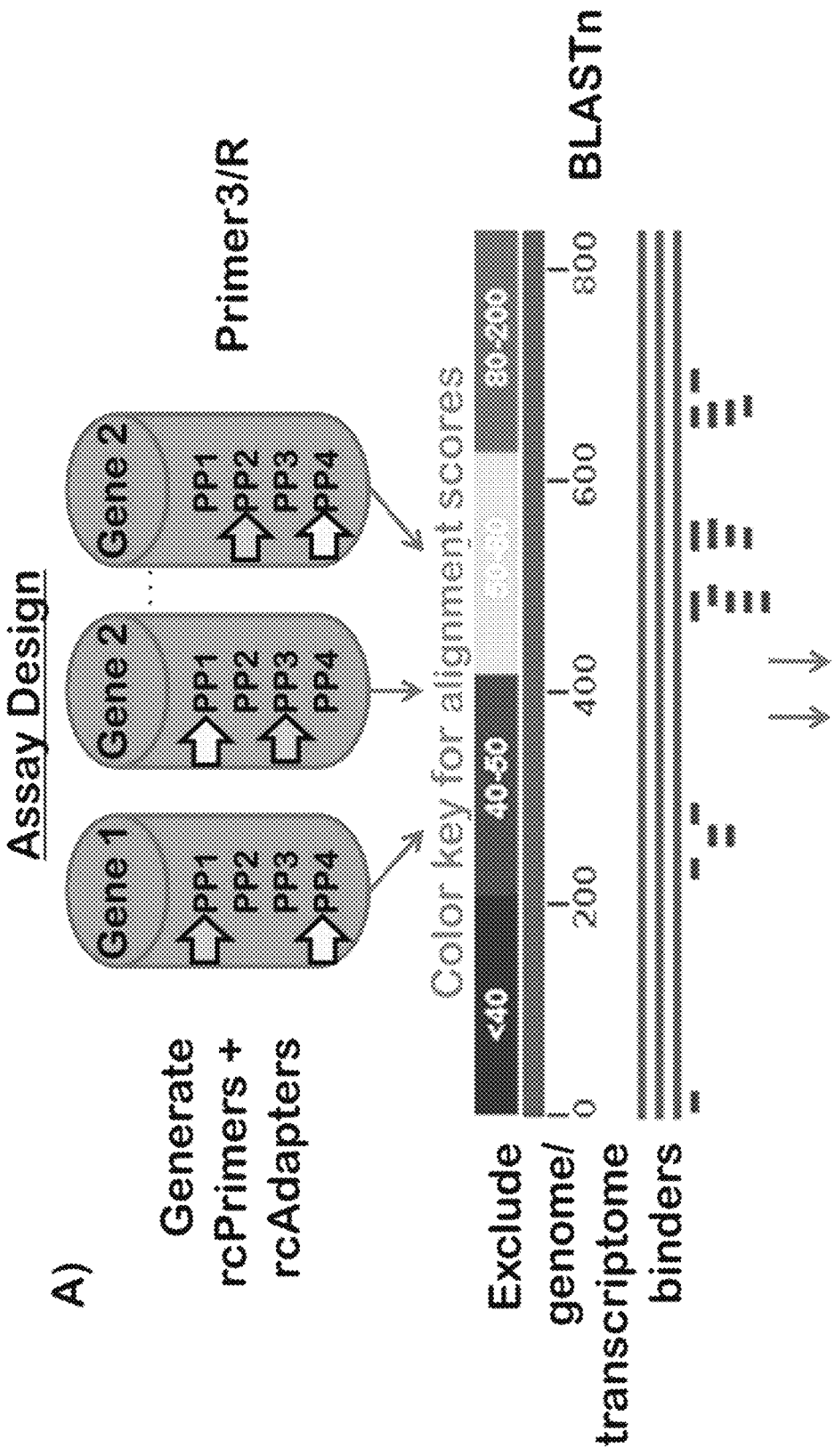
Figure 6:
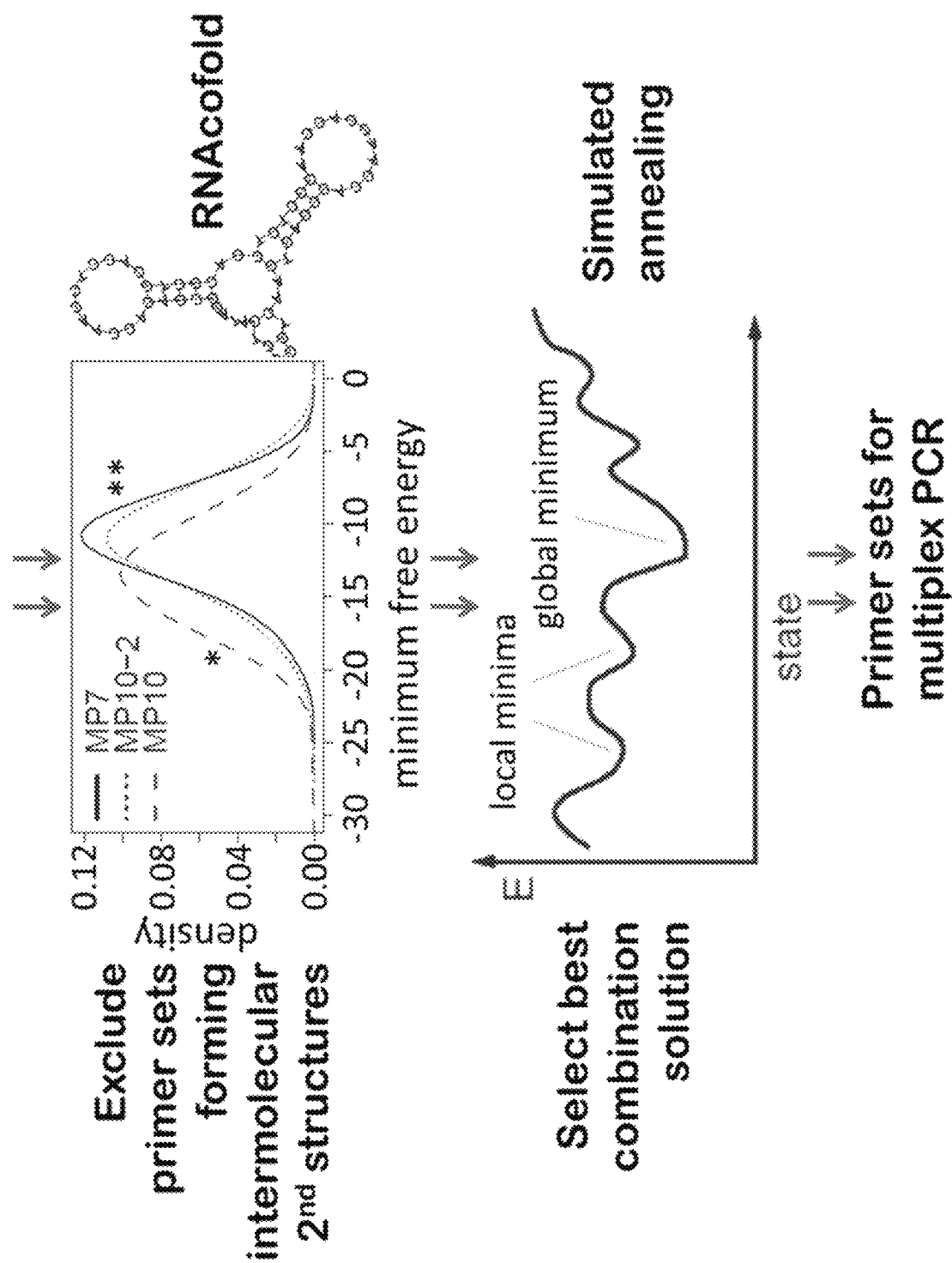
Figure 6:
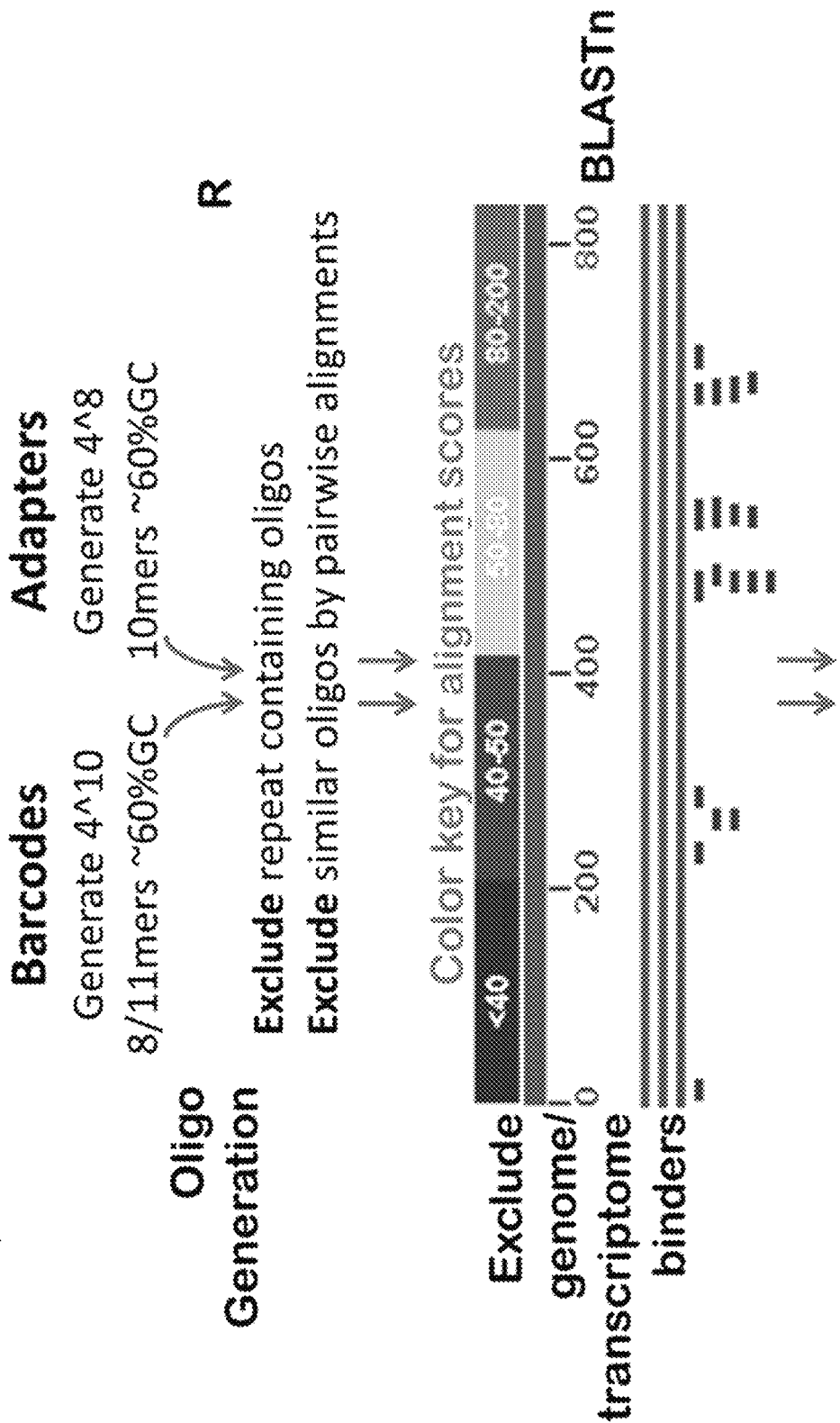
Figure 6:
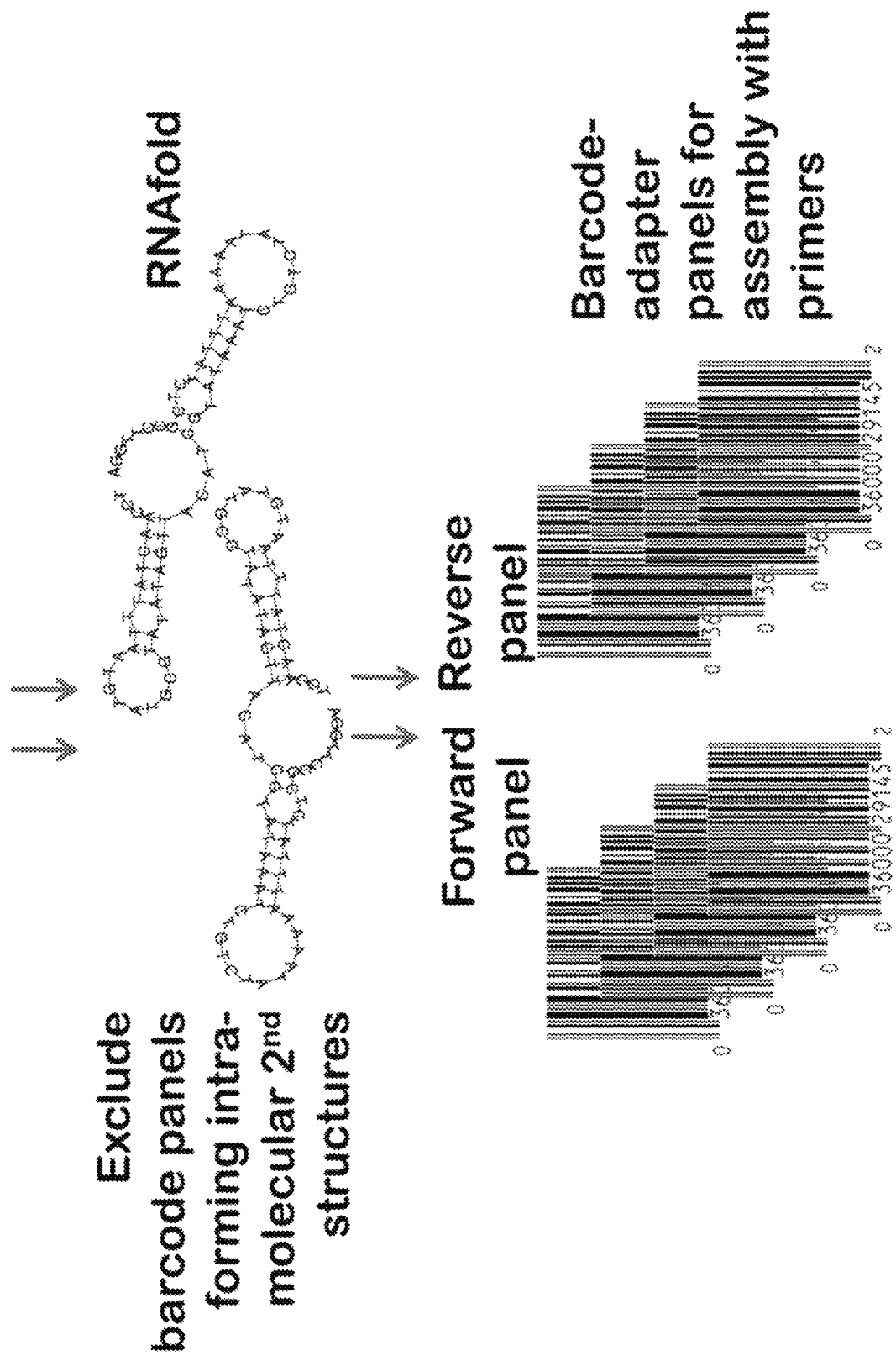

FIG. 6: Illustration of the informatics workflow used for generation of primers and barcodes. The RNAcofold minimum free energy diagram exemplifies two assay sets (MP7 and MP10-2) predicted to multiplex with high and low probability score (** and *, respectively); these scores correlated with experimental data, demonstrating that the calculation of minimum free energy facilities selection of suitable multiplexed primer sets.

Figure 7:
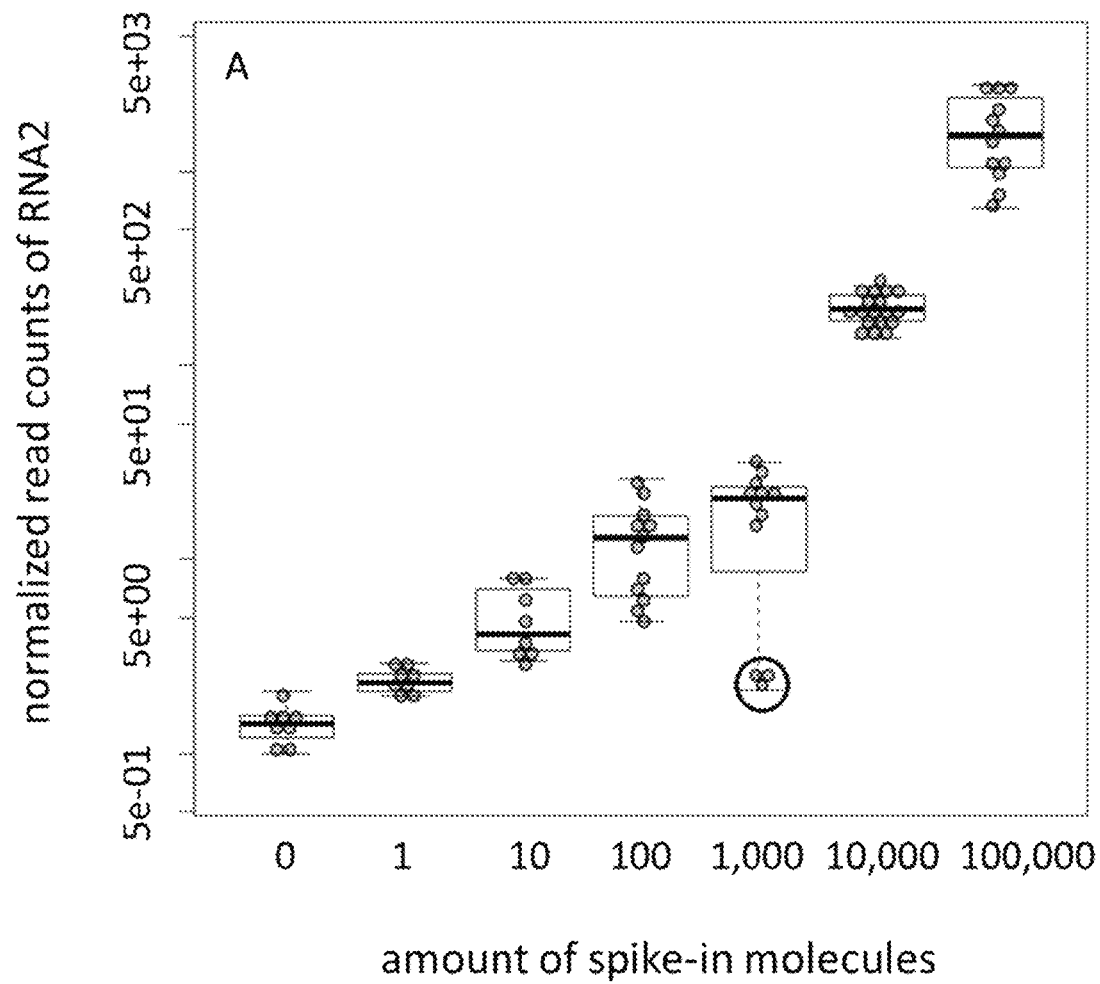
Figure 7:
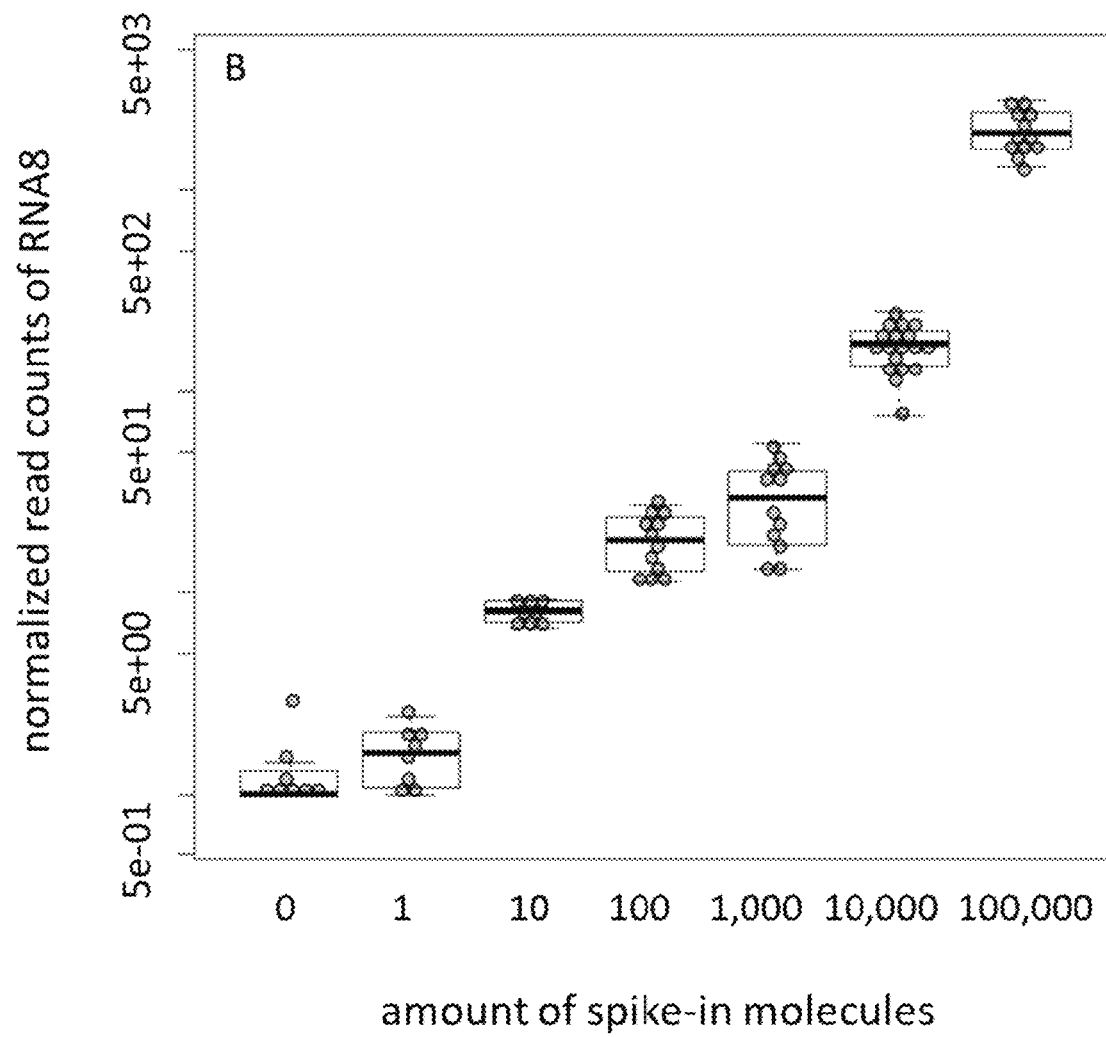
Figure 8:
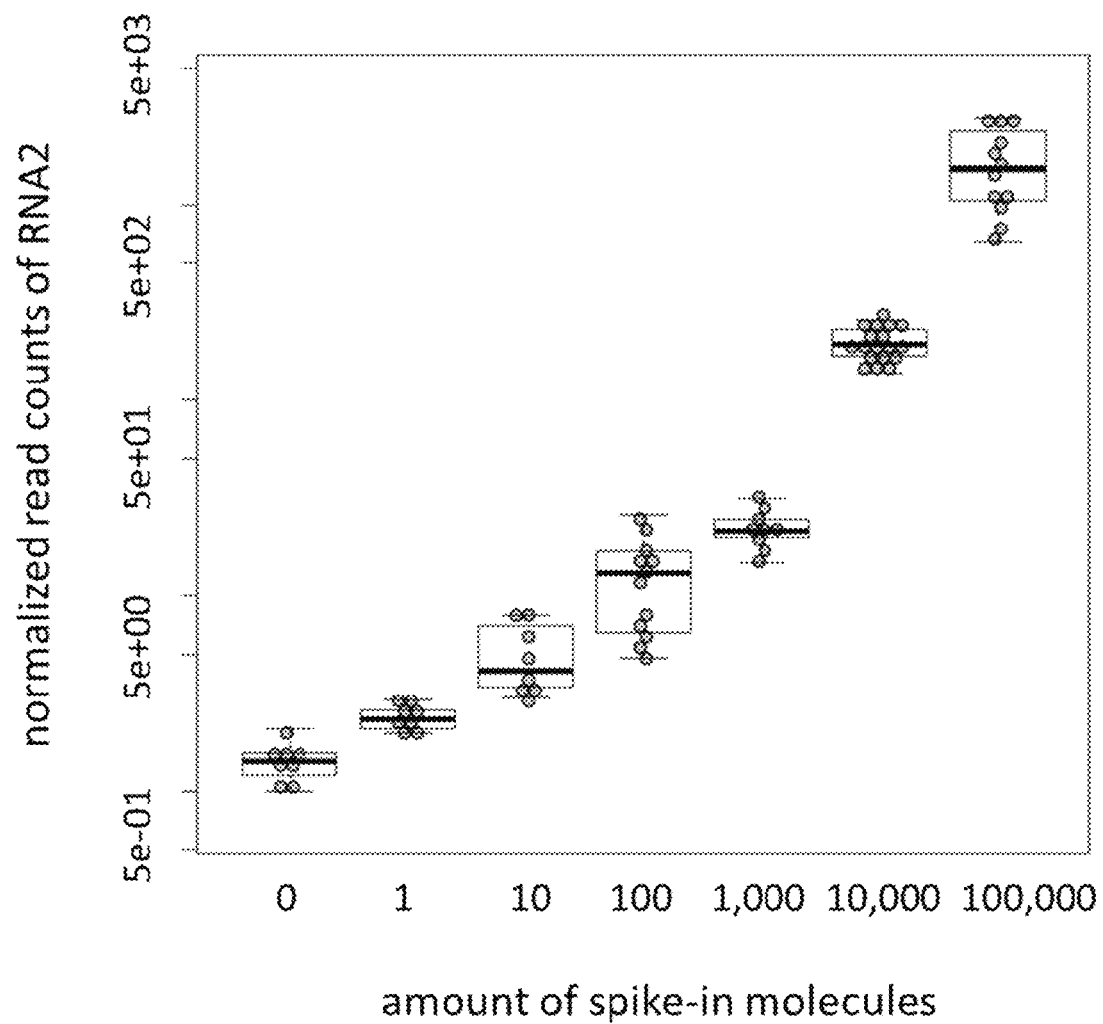

FIG. 7: Weighted correlation plots of spike RNAs 2 and 8 to normalized sequence read counts. Individual barcode combinations and template amounts are represented by the individual dots. The plot demonstrates correlation ($R^2$=0.88 for RNA2, $R^2$=0.93 for RNA8) to the amount of spike-in molecules. Bar-code R10 exhibited overall poor performance, primarily with respect to detection of RNA2 (indicated by circle in top panel). A correlation plot of spike RNA2 in which wells bar-coded by R10 are excluded is shown in FIG. 8. Normalization of the spike-in reads was performed by dividing the read number by the geometric mean of read numbers of genes. This was carried out for each well and each spike-in individually. Validation of barcode performances by qPCR is outlined in FIG. 9, below.

FIG. 8: Weighted correlation plot of spike RNA2 to normalized sequence read counts. Individual barcode combinations and template amounts are represented by the individual dots. Due to overall poor performance of bar-code R10 (see FIG. 7A), wells containing this bar-code were excluded from this plot. This results in higher correlation ($R^2$=0.94) to the amount of spike-in molecules compared to FIG. 7A ($R^2$=0.88). Normalization of the spike-in reads was performed by dividing the read number by the geometric mean of read numbers of genes. This was carried out for each well and each spike-in individually.

Figure 9:
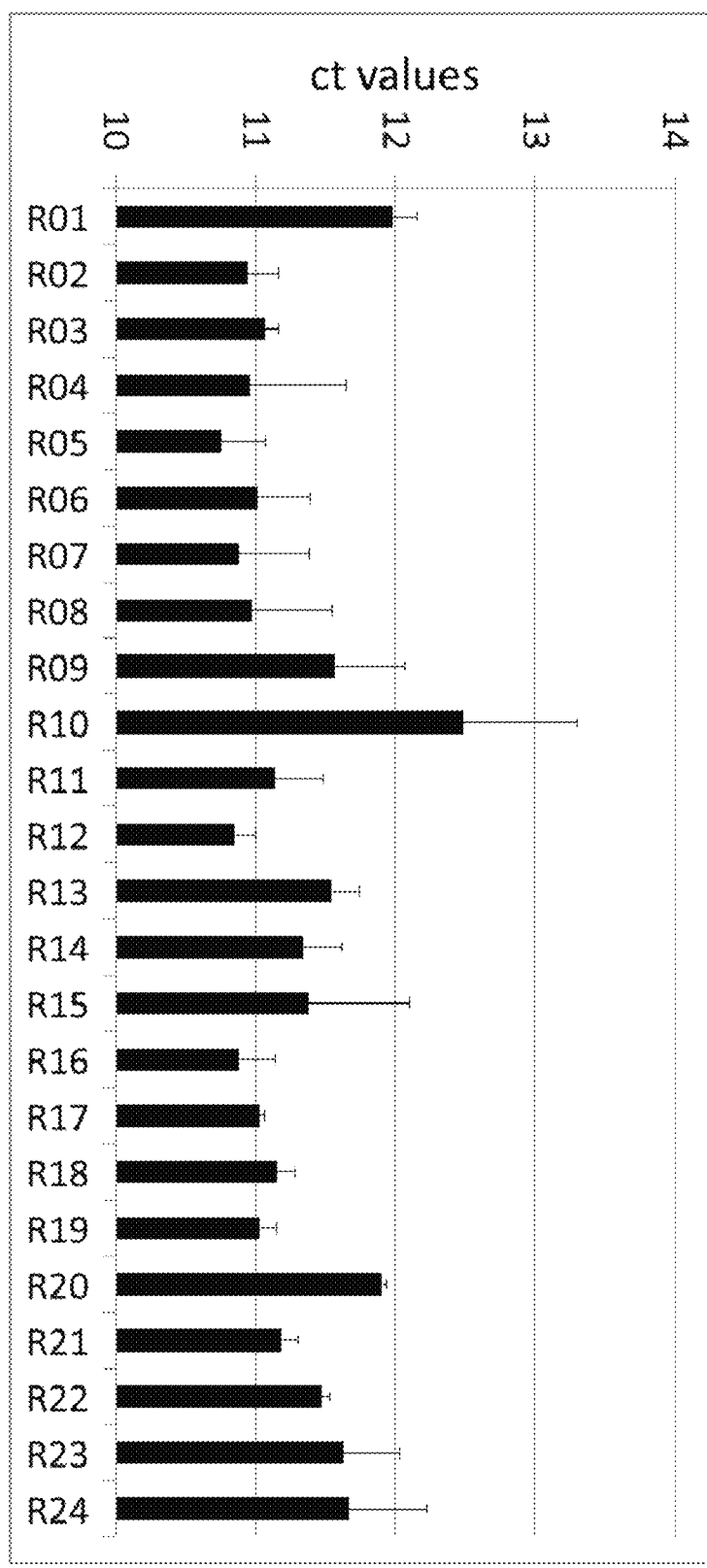

FIG. 9: Validation of barcode performance by qPCR. This plot shows ct values of a qPCR experiment performed with 24 barcodes. Bar-code R10 exhibited lowest efficacy (highest Ct), data that correspond to the results obtained by NGS (compare, FIG. 7A). This exemplifies that qPCR can be used to evaluate barcodes quality before usage in NGS experiments.

Figure 10:
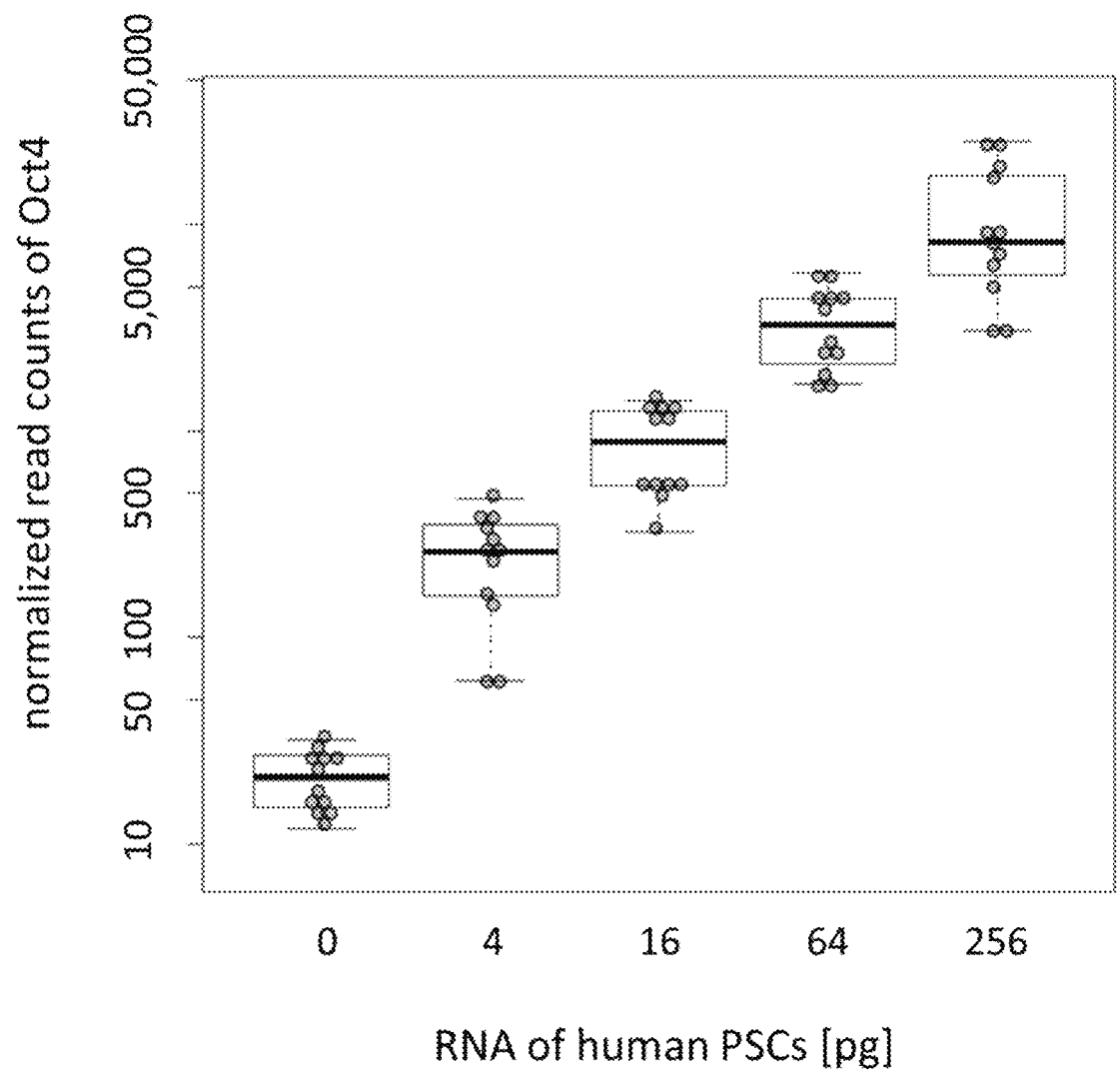

FIG. 10: Weighted correlation plot of normalized sequence read counts of the pluripotency gene Oct4 (POU5F1) analyzed for bulk RNA samples. Individual barcode combinations and template amounts are represented by every dot. The plot demonstrates nearly linear correlation to the amount of bulk RNA (R2=0.94). Read numbers per gene/well were normalized with respect to the geometric mean of read numbers of all four spike-ins.

Figure 11:
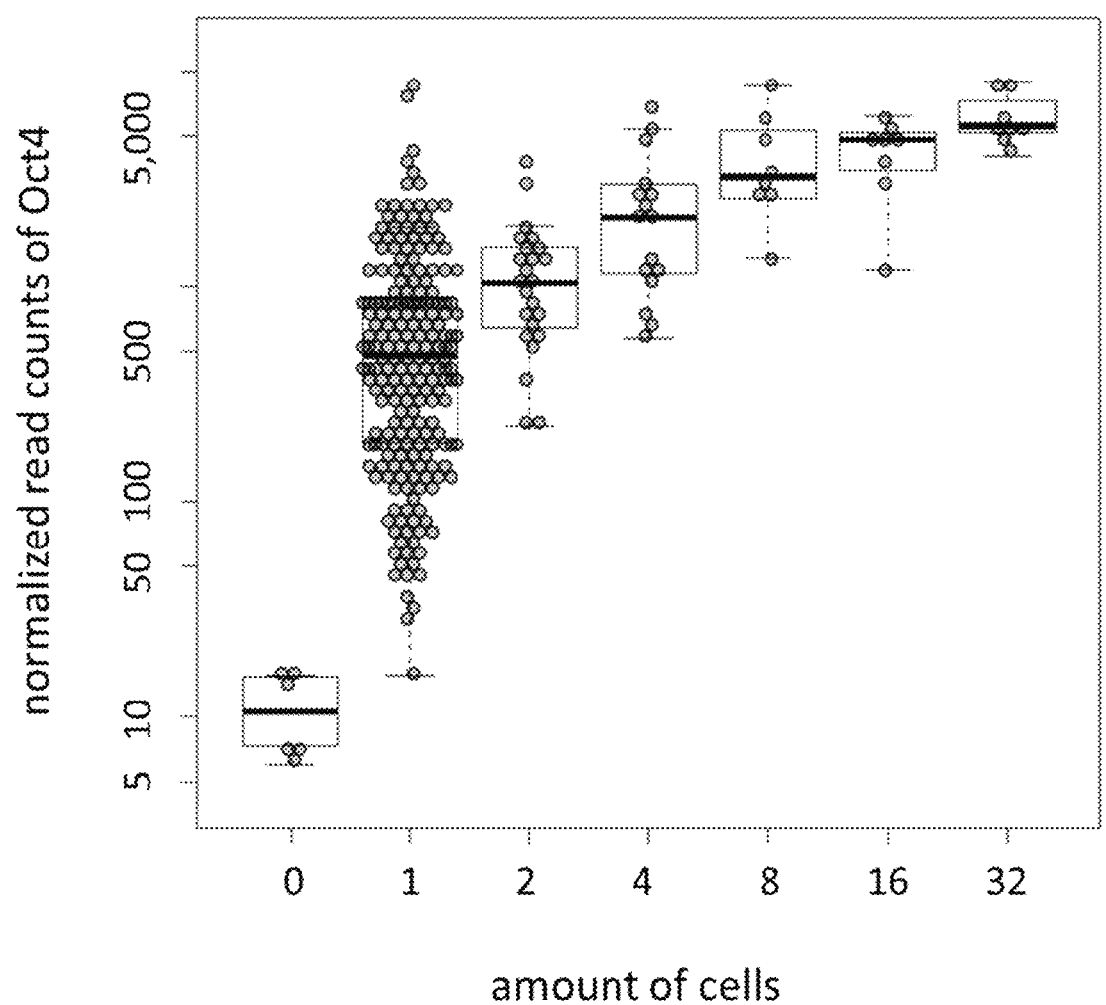

FIG. 11: Weighted correlation plot of normalized sequence read counts of the pluripotency gene Oct4 (POU5F1) analyzed for single and bulk cell templates. Individual barcode combinations and template amounts are represented by every dot. Read numbers per gene/well were normalized with respect to the geometric mean of read numbers of all four spike-ins. Wells were filtered out if they didn't match an expression value criterion, calculated by analyzing the expression levels of individual genes with respect to the average in the same group of samples (containing the same number of cells). This exemplifies heterogeneity of Oct 4 expression in single cells.

Figure 12:
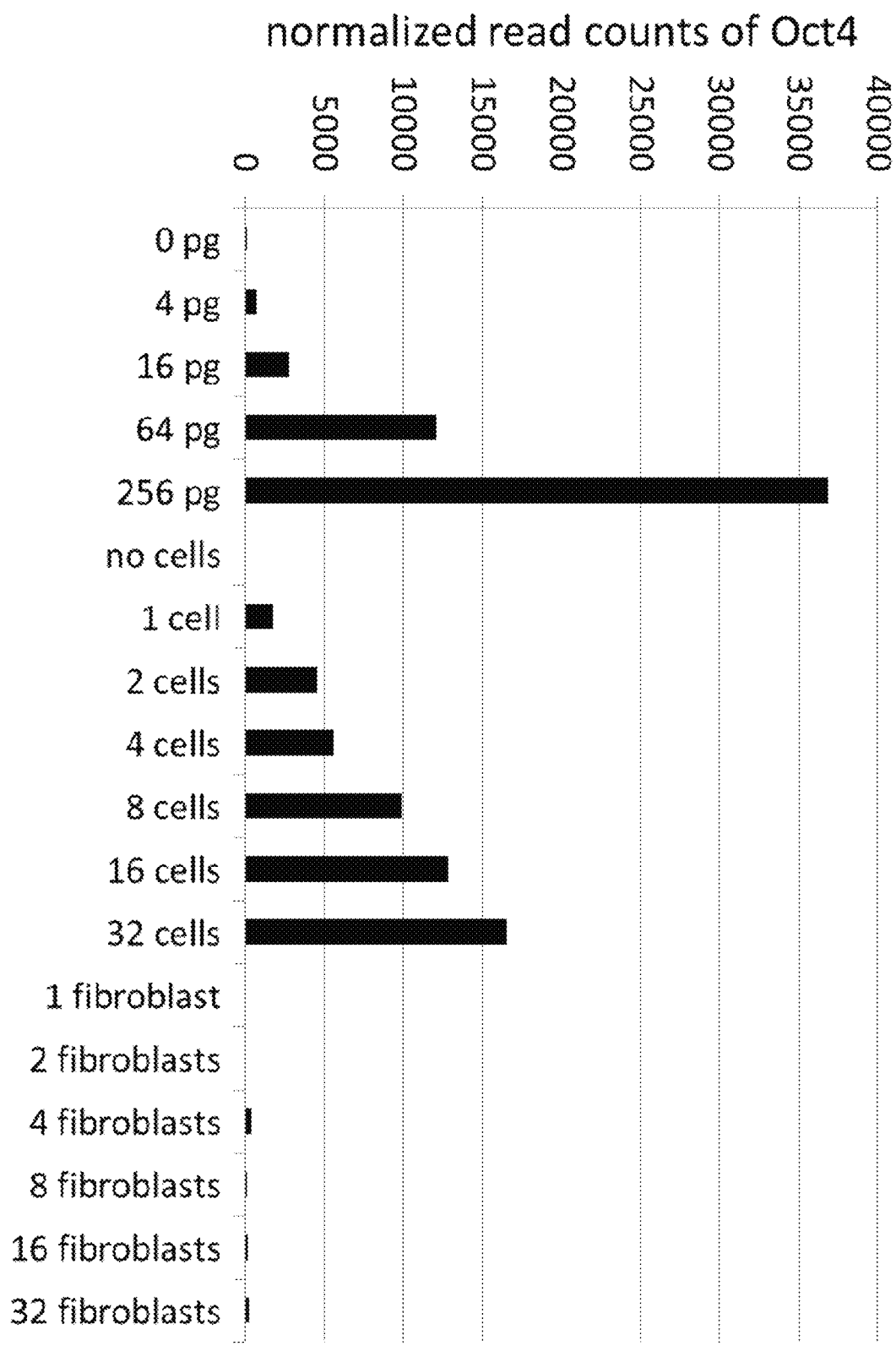

FIG. 12: Averaged expression of pluripotency gene Oct4 (POU5F1) in bulk RNA of hPSCs, in single and bulk hPSCs and single and bulk human fibroblasts (negative control). The following amounts of independent bar-code combinations (i.e. wells) were used for the different data points: 12 wells for 0 pg, 4 pg, 16 pg, 64 pg and 256 pg each; 10 wells for no cells; 208 wells for 1 cell; 24 wells for 2 cells; 16 wells for 4 cells; 8 wells for 8 cells, 16 cells and 32 cells, each; 18 wells for 1 fibroblast; 9 wells for 2 fibroblasts; 6 wells for 4 fibroblasts; and 3 wells for 8 fibroblasts, 16 fibroblasts and 32 fibroblasts, each. For example, well H3 contains 16 pg bulk RNA, well 016 contains one hPSC (see FIG. 13). Read numbers per gene/well were normalized with respect to the geometric mean of read numbers of all four spike-ins. The plot demonstrates nearly linear correlation ($R^2$=0.99) to the amount of input bulk RNA and the number of sorted hPSCs ($R^2$=0.98). Oct4 was not detected in fibroblasts.

Figure 13:
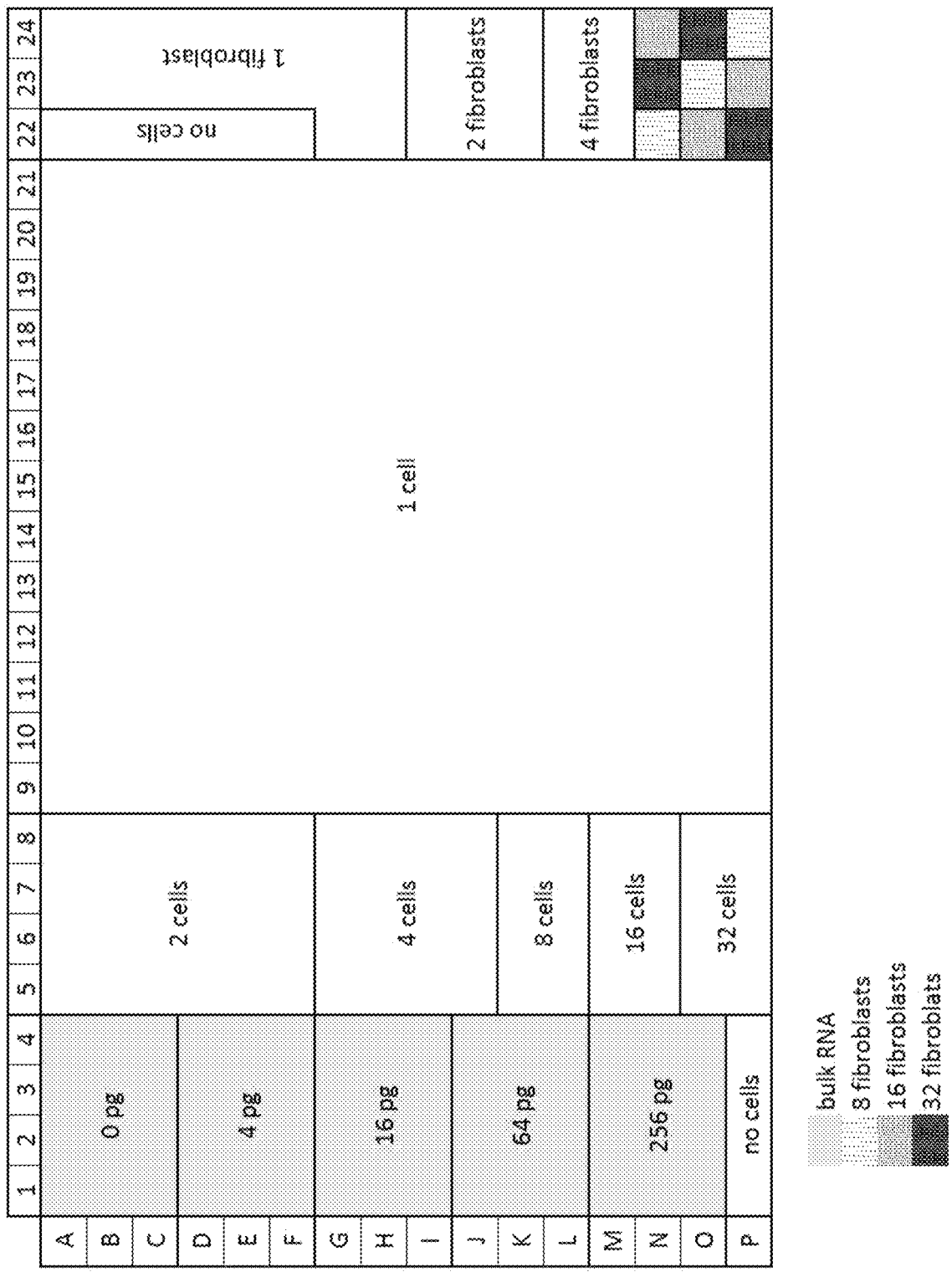

FIG. 13: Map of bulk RNA and single/bulk cell distribution in 384 well plate. Wells containing the same type and amount of template RNA or cells were clustered together. Bulk RNA-containing wells are shown in solid gray, the respective amount of bulk RNA is indicated. Cell-containing wells (and negative controls) are shown in white or gray, with the respective amount of cells indicated. For example, well H3 contains 16 pg bulk RNA, well 016 contains one hPSC.

Figure 14:
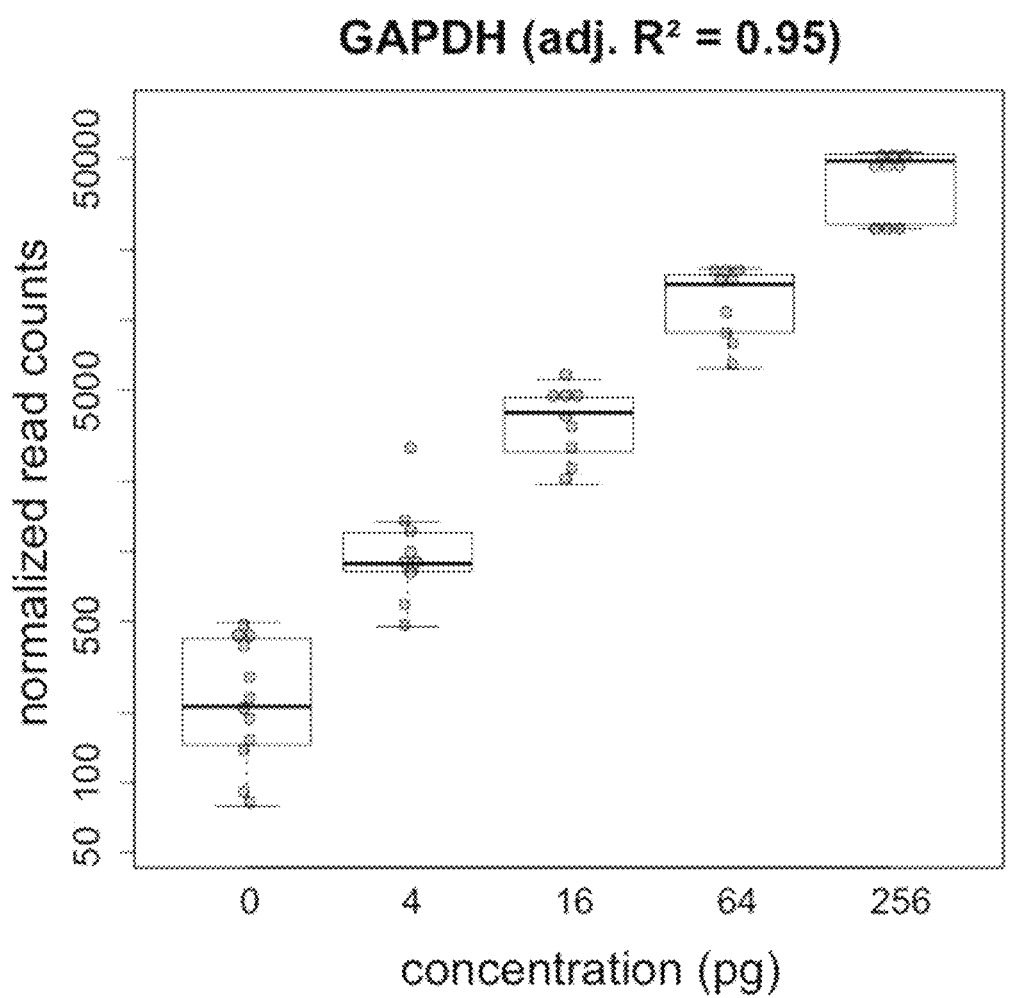

FIG. 14: A weighted correlation plot of normalized sequence read counts of the gene GAPDH in bulk titrated RNA samples. Individual dots correspond to distinct bar-code combinations and template concentrations. The plot shows nearly linear correlation of the read number to the amount of bulk RNA (R2=0.95). Read numbers per gene/well were normalized with respect to the geometric mean of the read numbers of all four spike-in molecules.

Figure 15:
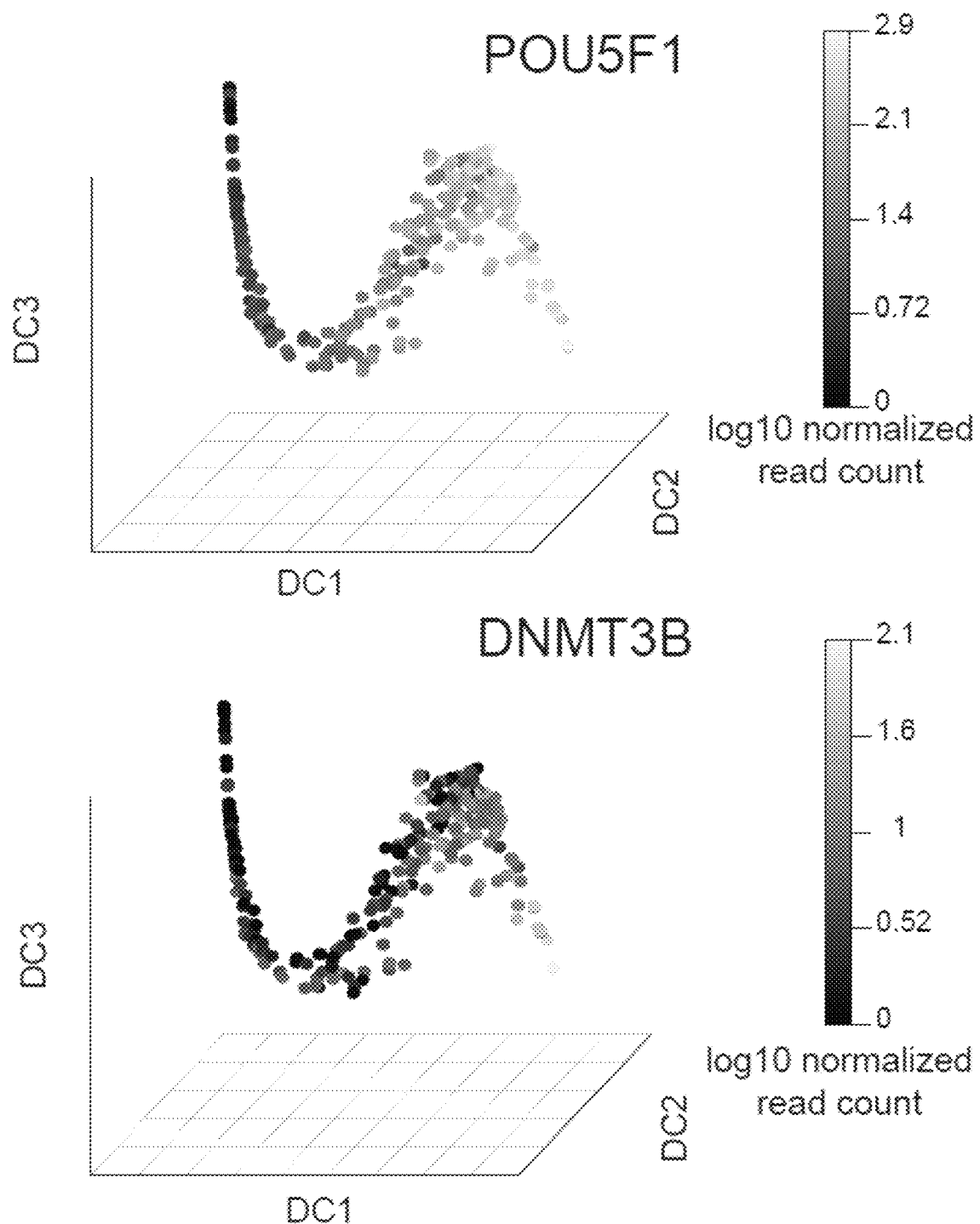

FIG. 15: A diffusion map exhibiting ~100 single cells clustered according to transcript cohorts. The different levels of POU5F1 (OCT4) and DNMT3B reveal different states of pluripotent cell subpopulations.

Figure 16:
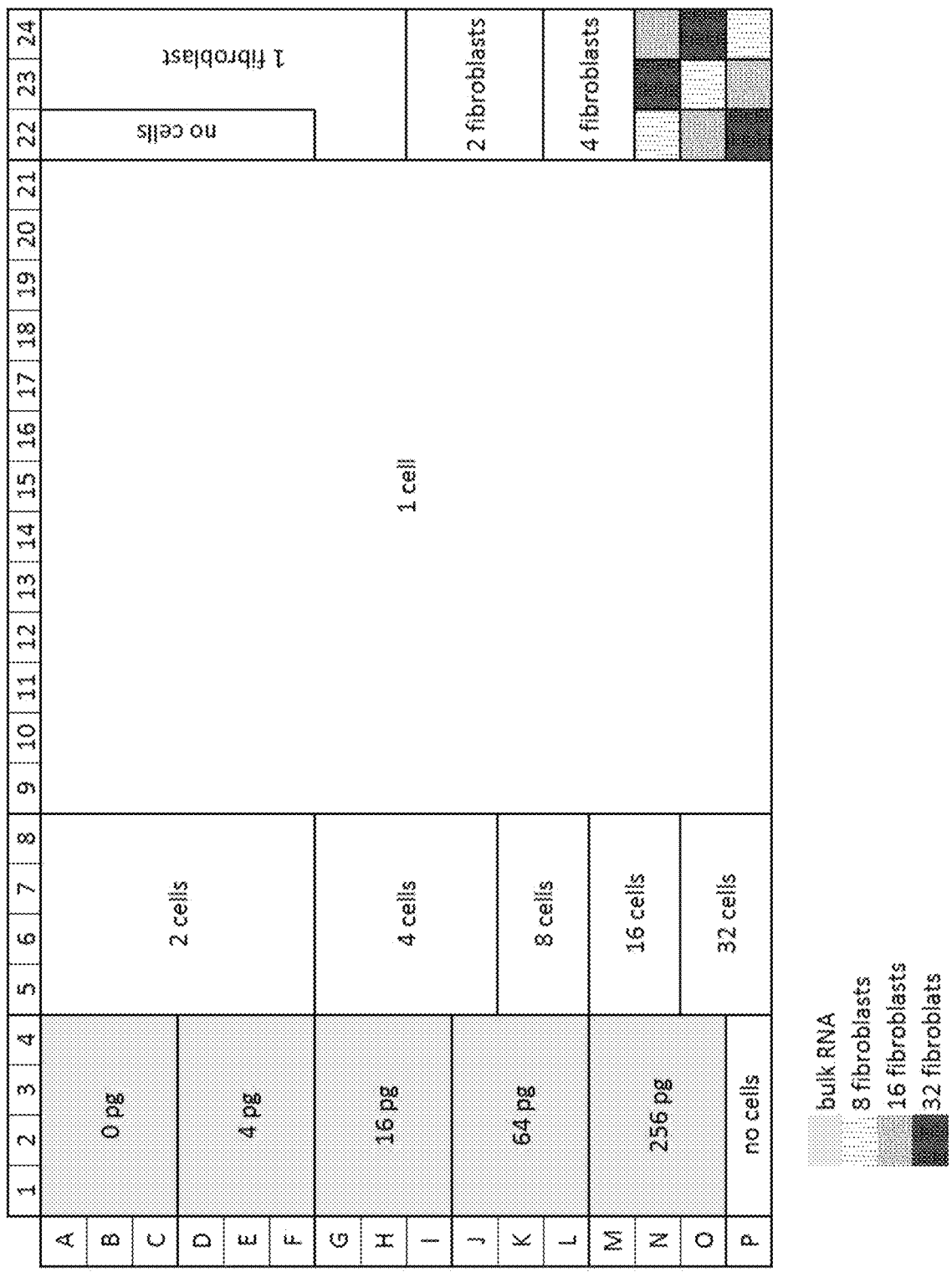

FIG. 16: A map of bulk RNA and single/bulk cell distribution in 384 well plate. Wells containing the same type and amount of template RNA or cells were clustered together. Bulk RNA-containing wells are shown in solid gray; the respective amounts of bulk RNA is indicated. Wells containing sorted cells (and negative controls) are shown in white or gray, with the respective amount of cells indicated. For example, well H3 contains 16 pg bulk RNA, well 016 contains one hPSC.

The examples below illustrate the invention.

EXAMPLE 1: VERIFICATION OF THE METHOD OF THE INVENTION AND ESTABLISHMENT OF A DIAGNOSTIC ASSAY FOR FOUNDER MUTATIONS LEADING TO BREAST CANCER

We designed 10 assays to span 10 human mutations correlated with early onset of breast cancer including: 185delAG, 5382insC, p.Y978*, p.A1708E, 981delAT, c.6174delT, 8765delAG, IVS2+1G>A, p.R2336P and p.P1812A. We analysed 96 patient samples pre-diagnosed (including non-affected controls) by Sanger sequencing as carriers of founder mutations that predispose women to breast cancer.

Barcodes, Adapters, Primers, rcBarcodes, rcAdapters and rcPrimers (Table 1 and Table 2) were designed by the bioinformatics approach outlined in FIG. 6. Two versions of oligonucleotides were used: 1) bearing CCA protection at the 5' ends of the bar-codes listed in Table 1, and 2) bar-codes lacking the 5' CCA protection (not listed). The results in FIG. 4 exemplify that inclusion of a protection group improves genotyping. A third analysis was conducted, skipping the lambda digestion (steps 6-7); exemplifying that lambda step is beneficial (but not necessary) for the method of invention.

Barcode Assembly

1. Bar-code-adapter and rcAdapter-rcPrimer oligonucleotides were obtained from a manufacturer, and reconstituted in water to 100 μM. 25 μM working solutions of bar-code-adapter and rcAdapter-rcPrimer oligonucleotides were prepared by diluting stock solutions in water, and stored at −20° C. DNase and RNase-free water were used for all steps of this protocol.
2. All forward and reverse rcAdapter-rcPrimers were combined separately in two tubes (i.e. all forward in one tube and all reverse in the second tube) at a final concentration of 25 μM; equimolar amounts of all rcAdapter-rcPrimers. For analysing the above mentioned founder mutations in 96 patients, 2×36 μl pools of forward and reverse rcAdapter-rcPrimers were prepared by combining 8 forward rcAdapter-rcPrimers, 4.5 μl of 25 μM each, and 12 reverse rcAdapter-rcPrimers, 3 μl of 25 μM each, respectively.
3. Equal volumes of forward and reverse bar-code-adapter and forward and reverse rcAdapter-rcPrimer were combined, respectively (all 25 μM). For the experimental outline below, consisting of a matrix of 8 forward bar-codes and 12 reverse barcodes, the forward rcAdapter-rcPrimer pool was aliquoted into 8 tubes by pipetting 3 μl into each tub, and the reverse rcAdapter-rcPrimer pool was aliquoted into 12 tubes by pipetting 3 μl into each tube (total of 20 tubes, 8 containing forward rcAdapter-rcPrimer mix, and 12 containing reverse rcAdapter-rcPrimer mix). 3 μl aliquots of individual forward bar-code-adapters were added to each forward 3 μl rcAdapter-rcPrimer mix, and 3 μl aliquots of individual reverse bar-code-adapters were added to each reverse 3 μl rcAdapter-rcPrimer mix.
4. A 480 μl master mix for 20 bar-coding reactions each consisting of 30 μl total volume was prepared, by combining 60 μl Klenow fragment reaction buffer (10×REact 2 Buffer), 16 μl 10 mM dNTP mix (to a final concentration of 267 μM), 1.67 μl (6 units/μl, 0.5 units/reaction) E. coli DNA Polymerase I Klenow fragment (diluted in 18.37 μl Klenow Dilution Buffer to 0.5 units/μl) and 384 μl water to a final volume of 480 μl. 24 μl aliquots of the master mix were combined with each of the bar-code-adapter and rcAdapter-rcPrimer (6 μl) mix to reach a final volume of 30 μl (total of 20 reactions, 8 forward and 12 reverse). The 8 forward bar-codes were labelled by L01 through L08, and the 12 reverse bar-codes were labelled by R01 through R12 as outlined in Table 1.
5. Samples were incubated at 25° C. for 60 minutes for the fill-in reaction, and subsequently at 80° C. for 10 mins for denaturing (inactivating) the Klenow fragment polymerase.
6. A master mix for 20 lambda exonuclease reactions, each consisting of 15 μl total volume reactions, was prepared by combining 30 µl lambda exonuclease reaction buffer, 20 µl (5 units/µl) lambda exonuclease (NEB) and 50 µl of water to a final volume of 100 µl. 5 µl aliquots were transferred into new PCR tubes, and combined with 10 µl Klenow product (obtained in step 5) to reach a final volume of 15 µl per reaction. In parallel, one set was processed omitting the lambda digestion (steps 6-7); instead 5 µl nuclease-free water was added to 10 µl of each Klenow product obtained in step 5 in order to provide comparable concentrations for reactions in step 8.

7. For lambda exonuclease digestion of rcprimer-adapter-bar-code strands that harbour 5' phosphate and lack CCA sequence (that is present 5' to primer-adapter-bar-code sequence), samples were incubated at 37° C. for 30 mins, and subsequently at 80° C. for 10 mins to inactivate the enzyme.

8. Next, the matrix of 96 bar-code combinations was generated employing the products of 20 barcode assembly reactions, 8 forward and 12 reverse, as outlined in Table 1 and Table 2. For each of the 96 reactions, equal volumes of forward and reverse bar-coded primer solutions were combined. In this case, 6 µl of forward and reverse primer solutions (3 µl each) were combined with 5 µl of Platinum Multiplex PCR Master Mix (Life Technologies), 3.6 µl of 25 µM magnesium chloride, 1 µl of template patient DNA (concentration range 1 ng/ml to 40 ng/ml) and 4.4 µl of nuclease-free water to a total volume of 20 µl. The patient sample map in Table 4 exhibits the genotypes as determined by Sanger sequencing. PCR stripes were placed in a thermocycler and incubated in the following cycling conditions:
  i) 5 minutes at 95 degrees: HotStart DNA Polymerase Activation
  ii) 18 cycles: 30 seconds at 95 degrees; 3 minutes at 60 degrees; 1 minute at 72 degrees
  iii) 10 minutes at 68 degrees.

Library Preparation for Next Generation Sequencing
  i. All samples were pooled following PCR; a total volume of 1920 µl for the given example.
  ii. For precipitating the amplicons, 192 µl NaAc pH 5.3 was added and 2 volumes of 100% EtOH, 4000 µl. The sample was incubated at −20° C. over night, and subsequently centrifuged for 30 min at 4700 g and 4° C. The supernatant was removed, pellet was washed with 70% EtOH, air-dried for 5 min and re-suspended in 200 µl nuclease-free water.
  iii. PCR product size selection using double-sided bead approach: two different ratios of AMPure beads were used for the clean-up and amplicon selection procedure. Negative selection: 0.5×AMPure beads were used to bind fragments longer than 300 bps, and supernatant discarded. Positive selection: 1×AMPure beads were used to bind fragments longer than 100 bp. After washing and drying according to the AMPure manufacturer's protocol, the amplicons were eluted from the beads in 40 µl of nuclease-free water.
  iv. An amplicon library with NEBNext ChIP-Seq Library Prep kit was prepared according to manufacturers protocol by ligating the purified amplicons to sequencing adapters (for Illumina Inc instruments), employing 15 cycles of PCR enrichment.
  v. The amplicons containing the barcodes and adapters were sequenced on a next generation sequencing (NGS) instrument (Illumina MiSeq), using a 2×150 bp paired-end kit.
  vi. Bioinformatics was used to align paired-end reads (analysed from the forward and reverse direction) filtering out sequences that do not align from the two ends (less then 5%). Additionally, reads with an alignment score below a certain threshold at the 5' end of barcodes were discarded in order to guarantee an unambiguous identification of bar-codes. Haplotype maps were analysed by BLAST, and sorting the reads according to the bar-code map (Table 2).

9. Finally, the sorted map of barcodes and genotypes was compared to patient genotypes (analysed by Sanger sequencing, exemplifying correct genotyping success rate of >98%, and false positive discovery rate was 0%. In addition, of all samples that were genotypes correctly ($^{95}/_{96}$), the analysis was 100% accurate in genotyping the two alleles e.g. false positive discovery rate of 0%. The results are summarized in Table 4.

EXAMPLE 2: TRANSCRIPTIONAL ANALYSIS IN BULK AND SINGLE HUMAN PLURIPOTENT STEM CELLS (PSCS)

In this experiment we aimed to analyse pluripotency transcript amounts in bulk undifferentiated human pluripotent stem cells (hPSCs) and single cells. Titration of spike-in RNA molecules (input molecules at know concentrations) was used to validate the quantitative performance of the method. 10 assays were designed to span 6 genes and 4 spike-in RNAs including, B2M, GAPDH, LIN28A, NANOG, POU5F1, SOX2, and RNA Spike 1 (EC2), RNA Spike 2 (EC12), RNA Spike 6 (EC13) and RNA Spike 8 (EC5), respectively. The 4 spike-in molecules were purchased as ArrayControl RNA Spikes (Life Technologies).

Barcodes, Adapters, Primers, rcAdapters and rcPrimers are outlined in Table 7; designed by the bioinformatics approach outlined in FIG. 6.

RNA Isolation
1. 10 cm dish containing hPSCs was washed with 10 ml PBS, and cells were treated with 4 ml trypsin (0.25%); incubated at 37° C. for 2 minutes.
2. Trypsin was inactivated, and cells were transferred to a 15 ml tube and centrifuged.
3. The pellet was resuspended in 3 ml of PBS.4. RNA isolation was performed with RNeasy Mini Kit (Qiagen) according to manufacturer's protocol. Concentration was measured by Qubit RNA HS Assay Kit, RNA integrity was determined by Agilent RNA 6000 Pico kit. RNA was stored at −80° C.

Template Preparation by Reverse Transcription of hPSC RNA and Control (Spike-in) RNAs
1. A matrix of 96 samples derived from bulk hPSC RNA and spiked-in RNAs was prepared according the sample map outlined in Table 6, hPSC RNA was aliquoted in evenly all wells at a concentration of 512 pg/µl. Unless indicated otherwise, the wells contained 4 spike-in molecules; T stands for thousands. Wells aliquoted with individual spiked-ins, e.g. RNA1, RNA2, etc, are indicated in the table; each containing 10T molecules. The spiked-in molecules contained a Poly A tract, enabling to reverse transcribe these molecules using Oligo(dT)$_{18}$ primers targeting cellular mRNA (step 2).
2. cDNA synthesis: preparation of reverse transcription master mix, consisting of 25 µl Oligo(dT)$_{18}$ (100 µM), 50 µl dNTPs (10 mM), 200 µl RT Buffer (5×), 100 µl DTT (0.1M), 50 µl RNaseOUT (40U/µl), 12.5 µl Superscript III RT (200 U/µl) and 62.5 µl nuclease-free water. Next, 5 µl master mix was combined with 5 µl hPSC spike-in RNA mixture. The content of the entire well plate was then reverse transcribed according to manufacturer's protocol, and stored at −20° C.

Barcode Assembly

1. Bar-code-adapter and rcAdapter-rcPrimer oligonucleotides were obtained from a manufacturer, and reconstituted in water to 100 μM. 25 μM working solutions of bar-code-adapter and rcAdapter-rcPrimer oligonucleotides were prepared by diluting stock solutions in water, and stored at −20° C. DNase and RNase-free water was used for all steps of this protocol.
2. All forward and reverse rcAdapter-rcPrimers were combined separately in two tubes (i.e. all forward in one tube and all reverse in the second tube) at a final concentration of 25 μM; equimolar amounts of all rcAdapter-rcPrimers. 2×36 μl pools of forward and reverse rcAdapter-rcPrimers were prepared by combining 8 forward rcAdapter-rcPrimers, 4.5 μl of 25 μM each, and 12 reverse rcAdapter-rcPrimers, 3 μl of 25 μM each, respectively.
3. Equal volumes of forward and reverse bar-code-adapter and forward and reverse rcAdapter-rcPrimer were combined, respectively (all 25 μM). The experimental outline consisted of a matrix of 8 forward barcodes and 12 reverse barcodes, the forward rcAdapter-rcPrimer pool was aliquoted into 8 tubes by pipetting 3 μl into each tub, and the reverse rcAdapter-rcPrimer pool was aliquoted into 12 tubes by pipetting 3 μl into each tube (total of 20 tubes, 8 containing forward rcAdapter-rcPrimer mix, and 12 containing reverse rcAdapter-rcPrimer mix). 3 μl aliquots of individual forward bar-code-adapters were added to each forward 3 μl rcAdapter-rcPrimer mix, and 3 μl aliquots of individual reverse bar-code-adapters were added to each reverse 3 μl rcAdapter-rcPrimer mix.
4. A 480 μl master mix for 20 bar-coding reactions each consisting of 30 μl total volume was prepared by combining 60 μl Klenow fragment reaction buffer (10×REact 2 Buffer), 16 μl 10 mM dNTP mix (to a final concentration of 267 μM), 1.67 μl (6 units/μl, 0.5 units/reaction) E. coli DNA Polymerase I Klenow fragment (diluted in 18.37 μl Klenow Dilution Buffer to 0.5 units/μl) and 384 μl water to a final volume of 480 μl. 24 μl aliquots of the master mix were combined with each of the bar-code-adapter and rcAdapter-rcPrimer (6 μl) mix to reach a final volume of 30 μl (total of 20 reactions, 8 forward and 12 reverse). The 8 forward bar-codes were labelled by L01 through L08, and the 12 reverse bar-codes were labelled by R01 through R12 as outlined in Table 8.
5. Samples were incubated at 25° C. for 60 minutes for the fill-in reaction, and subsequently at 80° C. for 10 mins for denaturating (inactivating) the Klenow fragment polymerase.
6. A master mix for 20 lambda exonuclease reactions, each consisting of 15 μl total volume reactions, was prepared by combining 30 μl lambda exonuclease reaction buffer, 20 μl (5 units/μl) lambda exonuclease (NEB) and 50 μl of water to a final volume of 100 μl. 5 μl aliquots were transferred into new PCR tubes, and combined with 10 μl Klenow product (obtained in step 5) to reach a final volume of 15 μl per reaction.
7. For lambda exonuclease digestion of rcprimer-adapter-bar-code strands that harbour 5' phosphate and lack CCA sequence (that is present 5' to primer-adapter-bar-code sequence), samples were incubated at 37° C. for 30 mins, and subsequently at 80° C. for 10 mins to inactivate the enzyme.
8. Next, the matrix of 96 bar-code combinations was generated employing the products of 20 barcode assembly reactions, 8 forward and 12 reverse, as outlined in Table 6 and Table 8. For each of the 96 reactions, equal volumes of forward and reverse bar-coded primer solutions were combined. In this case, 6 μl of forward and reverse primer solutions (3 μl each) were combined with 5 μl of Platinum Multiplex PCR Master Mix (Life Technologies), 3.6 μl of 25 μM magnesium chloride, 4 μl of cDNA (from undifferentiated hPSCs as described above; concentration 512 pg/μl) and 1.4 μl of nuclease-free water to a total volume of 20 μl. Table 6 illustrates the amount of spike-ins control molecules in each well.

PCR stripes were placed in a thermocycler and incubated in the following cycling conditions:
i) 5 minutes at 95 degrees: HotStart DNA Polymerase Activation
ii) 18 cycles: 30 seconds at 95 degrees; 3 minutes at 60 degrees; 1 minute at 72 degrees
iii) 10 minutes at 68 degrees.

Library Preparation for Next Generation Sequencing

1. All samples were pooled following PCR, to a total volume of 1920 μl for the given example.
2. Amplicons were precipitated by adding 192 μl NaAc pH 5.3 and 2 volumes of 100% EtOH, 4000 μl. The sample was incubated at −20° C. over night, and subsequently centrifuged for 30 min at 4700 g and 4° C. The supernatant was then removed, pellet washed with 70% EtOH, air-dried for 5 min and re-suspended in 200 μl nuclease-free water.
3. Amplicon (100-250 bps) size selection was performed using double-sided bead approach employing two different ratios of AMPure beads (Beckman Coulter). Negative selection: incubation with 0.5×AMPure beads, fragments longer than 300 bp were removed by discarding the beads. Positive selection: incubation with 1×AMPure beads, fragments longer than 100 bp were retained. After washing and drying the beads according to the AMPure manufacturer's protocol, the amplicons were eluted from the beads in 40 μl of nuclease-free water.
4. Amplicon library was prepared using NEBNext ChIP-Seq Library Prep kit according to manufacturer's protocol by ligating purified amplicons to sequencing adapters (for Illumina Inc instruments) and utilizing PCR enrichment for 15 cycles.
5. Amplicons were sequenced using next generation sequencing (NGS) instrument, Illumina MiSeq instrument, employing 2×150 bp paired-end kit.
6. Bioinformatics was used to align paired-end reads (analysed from the forward and reverse direction) filtering out opposing sequences that do not align from the two ends (<5%). Additionally, reads with an alignment score below a certain threshold at the 5' end of bar-codes were discarded in order to guarantee an unambiguous identification of bar-codes. Read sequences were identified using BLAST, and sorted according to the bar-code combinations linked to the amplicons.
7. Finally, the sorted map of barcodes and amplicons was compared to the map of spike in amounts (Table 8), resulting in the plots outlined below, demonstrating quantitative detection of the transcripts using the method of invention.

EXAMPLE 2-CONTINUED; TRANSCRIPTIONAL ANALYSIS OF SINGLE HPSCS WITH RESPECT TO A PANEL OF PLURIPOTENCY TRANSCRIPTS AND SPIKED-IN RNAS

Single and bulk hPSCs and fibroblasts (negative control) were sorted into individual wells of a 384 well plate aliquoted with reverse transcription master mix and spiked-in controls. Transcript assays and barcodes were identical to the abovementioned. Transcript levels in single cells were analysed by counting the number of amplicons with the respective barcodes (principle shown in FIG. 3B, right histogram).

RNA Isolation
1. 10 cm dish containing hPSCs was washed with 10 ml PBS, and cells were treated with 4 ml trypsin (0.25%); incubated at 37° C. for 2 minutes.
2. Trypsin was inactivated, and cells were transferred to a 15 ml tube and centrifuged.
3. The pellet was resuspended in 3 ml of PBS.
4. RNA isolation was performed with RNeasy Mini Kit (Qiagen) according to manufacturer's protocol. Concentration was measured by Qubit RNA HS Assay Kit, RNA integrity was determined by Agilent RNA 6000 Pico kit. RNA was stored at −80° C.

Reverse Transcription Master Mix
1. A master mix of 20 µl Oligo(dT)$_{18}$ (100 µM), 40 µl dNTPs (10 mM), 160 µl RT Buffer (5×), 80 µl DTT (0.1M), 40 µl RNaseOUT (40U/µl), 10 µl Superscript III RT (200 U/µl) and 50 µl nuclease-free water to a total volume of 400 µl was prepared. Additionally, isolated RNA (described above) was diluted to 512, 128, 32, and 8 pg/µl to give final RNA amounts of 256, 64, 16, and 4 pg RNA per well for bulk RNA reverse transcription. For each well of a 384 well plate, 1 µl of master mix was combined with 0.5 µl of a spike-in master mix containing 10,000 molecules of RNA Spike 1, 2, 6, and 8. To each well containing bulk RNA (shown in Table 9 in solid gray), 0.5 µl of the respective diluted RNA was added. To each of the remaining wells, 0.5 µl nuclease-free water was added.

FACS-mediated purification of individual cells
1. 10 cm dishes of hPSCs and of fibroblasts were washed with 10 ml PBS, and treated with 4 ml trypsin (0.25%), and incubated at 37° C. for 2 minutes.
2. Trypsin was inactivated DMEM/F-12 medium with serum, and centrifuged for 2 minutes at 100 g.
3. Pellet was washed in 3 ml PBS and resuspended in 800 µl Flow Cytometry Staining Buffer. 3.5 µl propidium iodide (PI) was added for live/dead discrimination of cells and cells kept on ice until cell sorting.
4. Size gated and PI− cells where sorted into a 384 well plate according to the scheme depicted in FIG. 13.
5. The plate was shortly spun down and immediately put on dry ice for 5 min to lyse cell membranes.

Reverse Transcription
1. The content of the 384 well plate was reverse transcribed according to manufacturer's protocol of SuperScript III First-Strand Synthesis System (Life Technologies), and stored at −20° C. until further use.

Barcode Assembly
1. Bar-code-adapter and rcAdapter-rcPrimer oligonucleotides were obtained from a manufacturer, and reconstituted in water to 100 µM concentration. 25 µM working solutions of bar-code-adapter and rcAdapter-rcPrimer oligonucleotides were prepared by diluting stock solutions in water, and stored at −20° C. DNase and RNase-free water were used for all steps of this protocol.
2. All forward and reverse rcAdapter-rcPrimers were combined separately in two tubes (i.e. all forward in one tube and all reverse in the second tube) at a final concentration of 25 µM; equimolar amounts of all rcAdapter-rcPrimers. 2×48 µl pools of forward and reverse rcAdapter-rcPrimers were prepared by combining 16 forward rcAdapter-rcPrimers, 3 µl of 25 µM each, and 24 reverse rcAdapter-rcPrimers, 2 µl of 25 µM each, respectively.
3. Equal volumes of forward and reverse bar-code-adapter and forward and reverse rcAdapter-rcPrimer were combined, respectively (all 25 µM). For the experimental outline below, consisting of a matrix of 16 forward barcodes and 24 reverse barcodes, the forward rcAdapter-rcPrimer pool was aliquoted into 16 tubes by pipetting 3 µl into each tub, and the reverse rcAdapter-rcPrimer pool was aliquoted into 24 tubes by pipetting 3 µl into each tube (total of 40 tubes, 16 containing forward rcAdapter-rcPrimer mix, and 24 containing reverse rcAdapter-rcPrimer mix). 3 µl aliquots of individual forward bar-code-adapters were added to each forward 3 µl rcAdapter-rcPrimer mix, and 3 µl aliquots of individual reverse bar-code-adapters were added to each reverse 3 µl rcAdapter-rcPrimer mix.
4. A 1008 µl master mix for 40 bar-coding reactions each consisting of 30 µl total volume was prepared, by combining 126 µl Klenow fragment reaction buffer (10×REact 2 Buffer), 33.6 µl 10 mM dNTP mix (to a final concentration of 267 µM), 3.5 µl (6 units/µl, 0.5 units/reaction) E. coli DNA Polymerase I Klenow fragment (diluted in 38.5 µl Klenow Dilution Buffer to 0.5 units/µl) and 806.4 µl water to a final volume of 1008 µl. 241 aliquots of the master mix were combined with each of the bar-code-adapter and rcAdapter-rcPrimer (6 µl) mix to reach a final volume of 30 µl (total of 40 reactions, 16 forward and 24 reverse). The 16 forward bar-codes were labelled by L01 through L16, and the 24 reverse bar-codes were labelled by R01 through R24 as outlined in Table 7 and Table 9.
5. Samples were incubated at 25° C. for 60 minutes for the fill-in reaction, and subsequently at 80° C. for 10 mins for denaturating (inactivating) the Klenow fragment polymerase.
6. A master mix for 40 lambda exonuclease reactions, each consisting of 15 µl total volume reactions, was prepared by combining 67.5 µl lambda exonuclease reaction buffer, 45 µl (5 units/µl) lambda exonuclease (NEB) and 113 µl of water to a final volume of 225 µl. 5 µl aliquots were transferred into new PCR tubes, and combined with 10 µl Klenow product (obtained in step 5) to reach a final volume of 15 µl per reaction.
7. For lambda exonuclease digestion of rcprimer-adapter-bar-code strands that harbour 5' phosphate and lack CCA sequence (that is present 5' to primer-adapter-bar-code sequence), samples were incubated at 37° C. for 30 mins, and subsequently at 80° C. for 10 mins to inactivate the enzyme.
8. Next, the matrix of 384 bar-code combinations was generated employing the products of 40 barcode assembly reactions, 16 forward and 24 reverse, as outlined in Table 6 and FIG. 13. For each of the 384 reactions, equal volumes of forward and reverse bar-coded primer solutions were combined. In this case, 3 µl of forward and reverse primer solutions (1.5 µl each) were combined with 2.5 µl of Platinum Multiplex PCR Master Mix (Life Technologies), 1.8 µl of 25 µM magnesium chloride and 0.7 µl of nuclease-free water were added to the respective well of the 384 well plate containing 2 µl cDNA which has been produced as described above to a total volume of 10 µl. Table 9 illustrates the amount of bulk RNA and cells in each well, respectively.

PCR stripes were placed in a thermocycler and incubated in the following cycling conditions:
i) 5 minutes at 95 degrees: HotStart DNA Polymerase Activation ii) 18 cycles: 30 seconds at 95 degrees; 3 minutes at 60 degrees; 1 minute at 72 degrees
iii) 10 minutes at 68 degrees.

Library Preparation for Next Generation Sequencing

1. All samples were pooled into one tube following PCR, a total volume of 3840 µl for the given example.
2. Amplicons were precipitated by adding 384 µl NaAc pH 5.3 and 2 volumes of 100% EtOH, 8000 µl. The sample was incubated at −20° C. over night, and subsequently centrifuged for 30 min at 4700g and 4° C. The supernatant was then removed, pellet was washed with 70% EtOH, air-dried for 5 min and re-suspended in 200 µl nuclease-free water.
3. Amplicon (100-250 bps) size selection was performed using double-sided bead approach employing two different ratios of AMPure beads (Beckman Coulter). Negative selection: incubation with 0.5×AMPure beads, fragments longer than 300 bp were removed by discarding the beads. Positive selection: incubation with 1×AMPure beads, fragments longer than 100 bp were retained. After washing and drying the beads according to the AMPure manufacturer's protocol, the amplicons were eluted from the beads in 40 µl of nuclease-free water.
4. Amplicon library was prepared using NEBNext ChIP-Seq Library Prep kit according to manufacturer's protocol by ligating purified amplicons to sequencing adapters (for Illumina Inc instruments) and utilizing 15 cycles of PCR enrichment.
5. Amplicons were sequenced using next generation sequencing (NGS) instrument, Illumina MiSeq instrument, employing 2×150 bp paired-end kit.
6. Bioinformatics was used to align paired-end reads (analysed from the forward and reverse direction) filtering out sequences that do not align from the two ends (<5%). Additionally, reads with an alignment score below a certain threshold at the 5' end of bar-codes were discarded in order to guarantee an unambiguous identification of bar-codes. Read sequences were identified using BLAST, and sorted according to the bar-code combinations linked to the amplicons.
7. Finally, the sorted map of barcodes and amplicons was compared to the map of bulk RNA and single/bulk cell distribution plan (FIG. 13), resulting in the plots outlined below, demonstrating quantitative detection of the transcripts using the method of invention.

EXAMPLE 3: ESTABLISHMENT OF A DIAGNOSTIC ASSAY FOR HOT-SPOT MUTATIONS CORRELATED WITH LUNG CANCER 5 assays were designed to span 2 spike-in RNAs (RNA Spike-in 2 (EC12) and RNA Spike-in 8 (EC5); Table 10) and 2 mutation hot-spot regions of EGFR (2 assays) and KRAS covering at least 26 known human mutations that are correlated with lung cancer (Table 12). The 2 spike-in molecules were purchased as ArrayControl RNA Spikes (Life Technologies). We analysed 18 patient samples (16 obtained from tumor tissue, 2 non-affected tissue) with unkown mutation status, 6 lung cancer cell lines with known mutation status (2 of which were used for dilution series of 2048 ng, 1024 ng, 512 ng, 256 ng, 128 ng, 64 ng) and 6 negative controls. All samples were run in duplicates.

Barcodes, Adapters, Primers, rcBarcodes, rcAdapters and rcPrimers (Table 10 and Table 11) were designed by the bioinformatics approach outlined in FIG. 6.

Template Preparation by Reverse Transcription of Patient Sample Tissue RNA, Lung Cancer Cell Line RNA, HEK293 RNA and Control (Spike-in) RNAs 1. For each RNA sample separately, a reverse transcription reaction was performed according to manufacturers protocol of SuperScript III First-Strand Synthesis System (Life Technologies), and stored at −20° C. until further use.

Barcode Assembly

1. Bar-code-adapter and rcAdapter-rcPrimer oligonucleotides were obtained from a manufacturer, and reconstituted in water to 100 µM. 25 µM working solutions of bar-code-adapter and rcAdapter-rcPrimer oligonucleotides were prepared by diluting stock solutions in water, and stored at −20° C. DNase and RNase-free water were used for all steps of this protocol.
2. All forward and reverse rcAdapter-rcPrimers were combined separately in two tubes (i.e. all forward in one tube and all reverse in the second tube) at a final concentration of 25 µM; equimolar amounts of all rcAdapter-rcPrimers. For analysing the above mentioned mutations in 80 samples, 2×36 µl pools of forward and reverse rcAdapter-rcPrimers were prepared by combining 8 forward rcAdapter-rcPrimers, 4.5 µl of 25 µM each, and 10 reverse rcAdapter-rcPrimers, 3 µl of 25 µM each, respectively.
3. Equal volumes of forward and reverse bar-code-adapter and forward and reverse rcAdapter-rcPrimer were combined, respectively (all 25 µM). For the experimental outline below, consisting of a matrix of 8 forward barcodes and 10 reverse barcodes, the forward rcAdapter-rcPrimer pool was aliquoted into 8 tubes by pipetting 3 µl into each tub, and the reverse rcAdapter-rcPrimer pool was aliquoted into 10 tubes by pipetting 3 µl into each tube (total of 18 tubes, 8 containing forward rcAdapter-rcPrimer mix, and 10 containing reverse rcAdapter-rcPrimer mix). 3 µl aliquots of individual forward bar-code-adapters were added to each forward 3 µl rcAdapter-rcPrimer mix, and 3 µl aliquots of individual reverse bar-code-adapters were added to each reverse 3 µl rcAdapter-rcPrimer mix.
4. A 432 µl master mix for 18 bar-coding reactions each consisting of 30 µl total volume was prepared, by combining 54 µl Klenow fragment reaction buffer (10×REact 2 Buffer), 14.4 µl 10 mM dNTP mix (to a final concentration of 267 µM), 1.5 µl (6 units/µl, 0.5 units/reaction) *E. coli* DNA Polymerase I Klenow fragment (diluted in 16.5 µl Klenow Dilution Buffer to 0.5 units/µl) and 345.6 µl water to a final volume of 432 µl. 24 µl aliquots of the master mix were combined with each of the bar-code-adapter and rcAdapter-rcPrimer (6 µl) mix to reach a final volume of 30 µl (total of 18 reactions, 8 forward and 10 reverse). The 8 forward bar-codes were labelled by L01 to L06, L08 and L09, and the 10 reverse bar-codes were labelled by R01 to R09, and R11 as outlined in Table 11.
5. Samples were incubated at 25° C. for 60 minutes for the fill-in reaction, and subsequently at 80° C. for 10 mins for denaturating (inactivating) the Klenow fragment polymerase.
6. A master mix for 18 lambda exonuclease reactions, each consisting of 15 µl total volume reactions, was prepared by combining 27 µl lambda exonuclease reaction buffer, 18 µl (5 units/µl) lambda exonuclease (NEB) and 45 µl of water to a final volume of 90 µl. 5 µl aliquots were transferred into new PCR tubes, and combined with 10 µl Klenow product (obtained in step 5) to reach a final volume of 15 µl per reaction.

7. For lambda exonuclease digestion of reverse complement primer-adapter-bar-code strands that harbour 5' phosphate and lack CCA sequence (that is present 5' to primer-adapter-bar-code sequence), samples were incubated at 37° C. for 30 mins, and subsequently at 80° C. for 10 mins to inactivate the enzyme.
8. Next, the matrix of 80 bar-code combinations was generated employing the products of 18 barcode assembly reactions, 8 forward and 10 reverse, as outlined in Table 10 and Table 11. For each of the 80 reactions, equal volumes of forward and reverse bar-coded primer solutions were combined. In this case, 6 µl of forward and reverse primer solutions (3 µl each) were combined with 5 µl of Platinum Multiplex PCR Master Mix (Life Technologies), 3.6 µl of 25 µM magnesium chloride, 1 µl of template cDNA (concentration 5 ng/ul, for the serial dilutions from 32 ng/ul (HEK293) and 64 ng/ul (A549) to 2,048 ng/ul, respectively), 1 ul of a spike-in cDNA mix (containing 200 molecules cDNA of spike-in RNA2 and 2,000 molecules cDNA of spike-in RNA8) and 3.4 µl of nuclease-free water to a total volume of 20 µl. The sample map in Table 13 exhibits the comparison of genotyping results obtained by BART-seq to expected mutations: PCR stripes were placed in a thermocycler and incubated in the following cycling conditions:
  i) 5 minutes at 95° C.: HotStart DNA Polymerase Activation
  ii) 18 cycles: 30 seconds at 95° C.; 3 minutes at 60° C.; 1 minute at ° C.
  iii) 10 minutes at 68° C.

Library Preparation for Next Generation Sequencing
  i. All samples were pooled following PCR; a total volume of 1920 µl for the given example.
  ii. For precipitating the amplicons, 192 µl NaAc pH 5.3 was added and 2 volumes of 100% EtOH, 4000 µl. The sample was incubated at −20° C. over night, and subsequently centrifuged for 30 min at 4700g and 4° C. The supernatant was removed, pellet was washed with 70% EtOH, air-dried for 5 min and re-suspended in 200 µl nuclease-free water.
  iii. PCR product size selection using double-sided bead approach: two different ratios of AMPure beads were used for the clean-up and amplicon selection procedure. Negative selection: 0.45×AMPure beads were used to bind fragments longer than 500 bp, and supernatant discarded. Positive selection: 1.05×AMPure beads were used to bind fragments longer than 100 bp. After washing and drying according to the AMPure manufacturers protocol, the amplicons were eluted from the beads in 40 µl of nuclease-free water.
  iv. An amplicon library with NEBNext ChIP-Seq Library Prep kit was prepared according to manufacturer's protocol by ligating the purified amplicons to sequencing adapters (for Illumina Inc instruments), employing 15 cycles of PCR enrichment.
  v. The amplicons containing the barcodes and adapters were sequenced on a next generation sequencing (NGS) instrument (Illumina MiSeq), using a 2×250 bp paired-end kit.
  vi. Bioinformatics was used to align paired-end reads (analysed from the forward and reverse direction) filtering out sequences that do not align from the two ends (less then 5%). Additionally, reads with an alignment score below a certain threshold at the 5' end of bar-codes were discarded in order to guarantee an unambiguous identification of bar-codes. Haplotype maps were analysed by BLAST, and sorting the reads according to the bar-code map (Table 11).
9. Finally, the sorted map of barcodes and genotypes was compared to known genotypes from lung cancer cell lines and negative controls. For those samples with known mutations status, a correct genotyping success rate of 95.8% (23 out of 24 samples) was achieved. Only one sample was not identified correctly (G>A instead of expected G>T). However, the BART-seq result for this sample is statistically significant so it is likely that this mutation has been previously misclassified. If so, the BART-seq analysis would yield 100% accuracy of the method. The results are summarized in Table 13.

EXAMPLE 4: TRANSCRIPTIONAL ANALYSIS IN BULK AND SINGLE HUMAN PLURIPOTENT STEM CELLS (PSCS)

The aim of this experiment was to analyse pluripotency transcript amounts in bulk undifferentiated human pluripotent stem cells (hPSCs) and single cells. Titration of spike-in RNA molecules (input molecules at known concentrations) was used to validate the quantitative performance of the method. 15 assays were designed to span 11 genes and 4 spike-in RNAs including B2M, GAPDH, LIN28A, NANOG, POU5F1, SOX2, CCND1, CCNE1, CER1, DNMT3B, ZFP42, and RNA Spike 1 (EC2), RNA Spike 2 (EC12), RNA Spike 6 (EC13) and RNA Spike 8 (EC5), respectively. The 4 spike-in molecules were purchased as ArrayControl RNA Spikes (Life Technologies).

Barcodes, Adapters, Primers, rcAdapters and rcPrimers are outlined in Table 15; designed by the bioinformatics approach outlined in FIG. 6.

RNA Isolation
1. 10 cm dish containing hPSCs was washed with 10 ml PBS, and cells were treated with 4 ml trypsin (0.25%); incubated at 37° C. for 2 minutes.
2. Trypsin was inactivated, and cells were transferred to a 15 ml tube and centrifuged.
3. The pellet was resuspended in 3 ml of PBS.
4. RNA isolation was performed with RNeasy Mini Kit (Qiagen) according to manufacturer's protocol. Concentration was measured by Qubit RNA HS Assay Kit, RNA integrity was determined by Agilent RNA 6000 Pico kit. RNA was stored at −80° C.

Template Preparation by Reverse Transcription of hPSC RNA and Control (Spike-in) RNAs
1. A matrix of 96 samples derived from bulk hPSC RNA and spiked-in RNAs was prepared according the sample map outlined in Table 14, hPSC RNA was aliquoted evenly in all wells at an amount of 128 pg. Unless indicated otherwise, the wells contained 4 spike-in molecules; T stands for thousands. Wells aliquoted with individual spiked-ins, e.g. RNA1, RNA2, etc, are indicated in the table; each containing 10T molecules. The spiked-in molecules contained a Poly A tract, enabling to reverse transcribe these molecules using Oligo(dT)$_{18}$ primers targeting cellular mRNA (step 2).
2. cDNA synthesis: preparation of reverse transcription master mix, consisting of 25 µl Oligo(dT)$_{18}$ (100 µM), 50 µl dNTPs (10 mM), 200 µl RT Buffer (5×), 100 µl DTT (0.1M), 50 µl RNaseOUT (40U/µl), 12.5 µl Superscript III RT (200 U/µl) and 62.5 µl nuclease-free water. Next, 5 µl master mix was combined with 5 µl hPSC spike-in RNA mixture. The content of the entire well plate was then reverse transcribed according to manufacturer's protocol, and stored at −20° C.

Barcode Assembly

1. Bar-code-adapter and rcAdapter-rcPrimer oligonucleotides were obtained from a manufacturer, and reconstituted in water to 100 µM. 37.5 µM working solutions of bar-code-adapter and rcAdapter-rcPrimer oligonucleotides were prepared by diluting stock solutions in water, and stored at −20° C. DNase and RNase-free water was used for all steps of this protocol.
2. All forward and reverse rcAdapter-rcPrimers were combined separately in two tubes (i.e. all forward in one tube and all reverse in the second tube) at a final concentration of 37.5 µM; equimolar amounts of all rcAdapter-rcPrimers. 2×36 µl pools of forward and reverse rcAdapter-rcPrimers were prepared by combining 8 forward rcAdapter-rcPrimers, 4.5 µl of 37.5 µM each, and 12 reverse rcAdapter-rcPrimers, 3 µl of 37.5 µM each, respectively.
3. Equal volumes of forward and reverse bar-code-adapter and forward and reverse rcAdapter-rcPrimer were combined, respectively (all 37.5 µM). The experimental outline consisted of a matrix of 8 forward barcodes and 12 reverse barcodes, the forward rcAdapter-rcPrimer pool was aliquoted into 8 tubes by pipetting 3 µl into each tub, and the reverse rcAdapter-rcPrimer pool was aliquoted into 12 tubes by pipetting 3 µl into each tube (total of 20 tubes, 8 containing forward rcAdapter-rcPrimer mix, and 12 containing reverse rcAdapter-rcPrimer mix). 3 µl aliquots of individual forward bar-code-adapters were added to each forward 3 µl rcAdapter-rcPrimer mix, and 3 µl aliquots of individual reverse bar-code-adapters were added to each reverse 3 µl rcAdapter-rcPrimer mix.
4. A 480 µl master mix for 20 bar-coding reactions each consisting of 30 µl total volume was prepared by combining 60 µl Klenow fragment reaction buffer (10×REact 2 Buffer), 16 µl 10 mM dNTP mix (to a final concentration of 267 µM), 1.67 µl (6 units/µl, 0.5 units/reaction) *E. coli* DNA Polymerase I Klenow fragment (diluted in 18.37 µl Klenow Dilution Buffer to 0.5 units/µl) and 384 µl water to a final volume of 480 µl. 24 µl aliquots of the master mix were combined with each of the bar-code-adapter and rcAdapter-rcPrimer (6 µl) mix to reach a final volume of 30 µl (total of 20 reactions, 8 forward and 12 reverse). The 8 forward bar-codes were labelled by L01 to L06, L08 and L09, and the 12 reverse bar-codes were labelled by R01 to R12 as outlined in Table 16.
5. Samples were incubated at 25° C. for 120 minutes for the fill-in reaction, and subsequently at 80° C. for 10 mins for denaturating (inactivating) the Klenow fragment polymerase.
6. A master mix for 20 lambda exonuclease reactions, each consisting of 15 µl total volume reactions, was prepared by combining 30 µl lambda exonuclease reaction buffer, 20 µl (5 units/µl) lambda exonuclease (NEB) and 50 µl of water to a final volume of 100 µl. 5 µl aliquots were transferred into new PCR tubes, and combined with 10 µl Klenow product (obtained in step 5) to reach a final volume of 15 µl per reaction.
7. For lambda exonuclease digestion of reverse complement primer-adapter-bar-code strands that harbour 5' phosphate and lack CCA sequence (that is present 5' to primer-adapter-bar-code sequence), samples were incubated at 37° C. for 60 mins, and subsequently at 80° C. for 10 mins to inactivate the enzyme.
8. Next, the matrix of 96 bar-code combinations was generated employing the products of 20 barcode assembly reactions, 8 forward and 12 reverse, as outlined in Table 14 and Table 16. For each of the 96 reactions, equal volumes of forward and reverse bar-coded primer solutions were combined. In this case, 6 µl of forward and reverse primer solutions (3 µl each) were combined with 5 µl of Platinum Multiplex PCR Master Mix (Life Technologies), 3.6 µl of 25 µM magnesium chloride, 4 µl of cDNA (from undifferentiated hPSCs as described above; at an amount of 128 µg) and 1.4 µl of nuclease-free water to a total volume of 20 µl. Table 14 illustrates the amount of spike-ins control molecules in each well.

PCR stripes were placed in a thermocycler and incubated in the following cycling conditions:
i) 5 minutes at 95° C.: HotStart DNA Polymerase Activation
ii) 20 cycles: 30 seconds at 95° C.; 3 minutes at 60° C.; 1 minute at 72° C.
iii) 10 minutes at 68° C.

Library Preparation for Next Generation Sequencing
1. All samples were pooled following PCR, to a total volume of 1920 µl for the given example.
2. Amplicons were precipitated by adding 192 µl NaAc pH 5.3 and 2 volumes of 100% EtOH, 4000 µl. The sample was incubated at −20° C. over night, and subsequently centrifuged for 30 min at 4700g and 4° C. The supernatant was then removed, pellet washed with 70% EtOH, air-dried for 5 min and re-suspended in 200 µl nuclease-free water.
3. Amplicon (100-250 bps) size selection was performed using double-sided bead approach employing two different ratios of AMPure beads (Beckman Coulter). Negative selection: incubation with 0.5×AMPure beads, fragments longer than 300 bp were removed by discarding the beads. Positive selection: incubation with 1×AMPure beads, fragments longer than 100 bp were retained. After washing and drying the beads according to the AMPure manufacturer's protocol, the amplicons were eluted from the beads in 40 µl of nuclease-free water.
4. Amplicon library was prepared using NEBNext ChIP-Seq Library Prep kit according to manufacturer's protocol by ligating purified amplicons to sequencing adapters (for Illumina Inc instruments) and utilizing PCR enrichment for 15 cycles.
5. Amplicons were sequenced using next generation sequencing (NGS) instrument, Illumina MiSeq instrument, employing 2×150 bp paired-end kit.
6. Bioinformatics was used to align paired-end reads (analysed from the forward and reverse direction) filtering out opposing sequences that do not align from the two ends (<5%). Additionally, reads with an alignment score below a certain threshold at the 5' end of bar-codes were discarded in order to guarantee an unambiguous identification of bar-codes. Read sequences were identified using BLAST, and sorted according to the bar-code combinations linked to the amplicons.
7. Finally, the sorted map of barcodes and amplicons was compared to the map of spike in amounts (Table 14 and Table 16), resulting in the plots outlined below, demonstrating quantitative detection of the transcripts using the method of invention.

EXAMPLE 4-CONTINUED; TRANSCRIPTIONAL ANALYSIS OF SINGLE HPSCS WITH RESPECT TO A PANEL OF PLURIPOTENCY TRANSCRIPTS AND SPIKED-IN RNAS

Single and bulk hPSCs and fibroblasts (negative control) were sorted into individual wells of a 384 well plate aliquoted with reverse transcription master mix and spiked-in controls. Transcript assays and barcodes were identical to the abovementioned. Transcript levels in single cells were analysed by counting the number of amplicons with the respective barcodes.

RNA Isolation
1. 10 cm dish containing hPSCs was washed with 10 ml PBS, and cells were treated with 4 ml trypsin (0.25%); incubated at 37° C. for 2 minutes.
2. Trypsin was inactivated, and cells were transferred to a 15 ml tube and centrifuged.
3. The pellet was resuspended in 3 ml of PBS.
4. RNA isolation was performed with RNeasy Mini Kit (Qiagen) according to manufacturers protocol. Concentration was measured by Qubit RNA HS Assay Kit, RNA integrity was determined by Agilent RNA 6000 Pico kit. RNA was stored at −80° C.

Reverse Transcription Master Mix
1. A master mix of 20 µl Oligo(dT)$_{18}$ (100 µM), 40 µl dNTPs (10 mM), 160 µl RT Buffer (5×), 80 µl DTT (0.1M), 40 µl RNaseOUT (40U/µl), 10 µl Superscript III RT (200 U/µl) and 50 µl nuclease-free water to a total volume of 400 µl was prepared. Additionally, isolated RNA (described above) was diluted to 512, 128, 32, and 8 pg/µl to give final RNA amounts of 256, 64, 16, and 4 pg RNA per well for bulk RNA reverse transcription. For each well of a 384 well plate, 1 µl of master mix was combined with 0.5 µl of a spike-in master mix containing 5,000 molecules of RNA Spike 1, 2, 6, and 8. To each well containing bulk RNA (shown in Table 17), 0.5 µl of the respective diluted RNA was added. To each of the remaining wells, 0.5 µl nuclease-free water was added.

FACS-Mediated Purification of Individual Cells
1. 10 cm dishes of hPSCs and of fibroblasts were washed with 10 ml PBS, and treated with 4 ml trypsin (0.25%), and incubated at 37° C. for 2 minutes.
2. Trypsin was inactivated DMEM/F-12 medium with serum, and centrifuged for 2 minutes at 100g.
3. Pellet was washed in 3 ml PBS and resuspended in 800 µl Flow Cytometry Staining Buffer. 3.5 µl propidium iodide (PI) was added for live/dead discrimination of cells and cells kept on ice until cell sorting.
4. Size gated and PI− cells where sorted into a 384 well plate according to the scheme depicted in FIG. 16.
5. The plate was shortly spun down and immediately put on dry ice for 5 min to lyse cell membranes.

Reverse Transcription
1. The content of the 384 well plate was reverse transcribed according to manufacturers protocol of SuperScript III First-Strand Synthesis System (Life Technologies), and stored at −20° C. until further use.

Barcode Assembly
1. Bar-code-adapter and rcAdapter-rcPrimer oligonucleotides were obtained from a manufacturer, and reconstituted in water to 100 µM concentration. 37.5 µM working solutions of bar-code-adapter and rcAdapter-rcPrimer oligonucleotides were prepared by diluting stock solutions in water, and stored at −20° C. DNase and RNase-free water were used for all steps of this protocol.
2. All forward and reverse rcAdapter-rcPrimers were combined separately in two tubes (i.e. all forward in one tube and all reverse in the second tube) at a final concentration of 37.5 µM; equimolar amounts of all rcAdapter-rcPrimers. 2×48 µl pools of forward and reverse rcAdapter-rcPrimers were prepared by combining 16 forward rcAdapter-rcPrimers, 3 µl of 37.5 µM each, and 24 reverse rcAdapter-rcPrimers, 2 µl of 37.5 µM each, respectively.
3. Equal volumes of forward and reverse bar-code-adapter and forward and reverse rcAdapter-rcPrimer were combined, respectively (all 37.5 µM). For the experimental outline below, consisting of a matrix of 16 forward barcodes and 24 reverse barcodes, the forward rcAdapter-rcPrimer pool was aliquoted into 16 tubes by pipetting 3 µl into each tub, and the reverse rcAdapter-rcPrimer pool was aliquoted into 24 tubes by pipetting 3 µl into each tube (total of 40 tubes, 16 containing forward rcAdapter-rcPrimer mix, and 24 containing reverse rcAdapter-rcPrimer mix). 3 µl aliquots of individual forward bar-code-adapters were added to each forward 3 µl rcAdapter-rcPrimer mix, and 3 µl aliquots of individual reverse bar-code-adapters were added to each reverse 3 µl rcAdapter-rcPrimer mix.
4. A 1008 µl master mix for 40 bar-coding reactions each consisting of 30 µl total volume was prepared, by combining 126 µl Klenow fragment reaction buffer (10×REact 2 Buffer), 33.6 µl 10 mM dNTP mix (to a final concentration of 267 µM), 3.5 µl (6 units/µl, 0.5 units/reaction) E. coli DNA Polymerase I Klenow fragment (diluted in 38.5 µl Klenow Dilution Buffer to 0.5 units/µl) and 806.4 µl water to a final volume of 1008 µl. 24 µl aliquots of the master mix were combined with each of the bar-code-adapter and rcAdapter-rcPrimer (6 µl) mix to reach a final volume of 30 µl (total of 40 reactions, 16 forward and 24 reverse). The 16 forward bar-codes were labelled by L01 to L06, and L08 to L17, and the 24 reverse bar-codes were labelled by R01 to R19, and R21 to R24 as outlined in Table 15 and Table 17.
5. Samples were incubated at 25° C. for 120 minutes for the fill-in reaction, and subsequently at 80° C. for 10 mins for denaturating (inactivating) the Klenow fragment polymerase.
6. A master mix for 40 lambda exonuclease reactions, each consisting of 15 µl total volume reactions, was prepared by combining 67.5 µl lambda exonuclease reaction buffer, 45 µl (5 units/µl) lambda exonuclease (NEB) and 113 µl of water to a final volume of 225 µl. 5 µl aliquots were transferred into new PCR tubes, and combined with 10 µl Klenow product (obtained in step 5) to reach a final volume of 15 µl per reaction.
7. For lambda exonuclease digestion of reverse complement primer-adapter-bar-code strands that harbour 5′ phosphate and lack CCA sequence (that is present 5′ to primer-adapter-bar-code sequence), samples were incubated at 37° C. for 60 mins, and subsequently at 80° C. for 10 mins to inactivate the enzyme.
8. Next, the matrix of 384 bar-code combinations was generated employing the products of 40 barcode assembly reactions, 16 forward and 24 reverse, as outlined in Table 17 and FIG. 16. For each of the 384 reactions, equal volumes of forward and reverse bar-coded primer solutions were combined. In this case, 3 µl of forward and reverse primer solutions (1.5 µl each) were combined with 2.5 µl of Platinum Multiplex PCR Master Mix (Life Technologies), 1.8 µl of 25 µM magnesium chloride and 0.7 µl of nuclease-free water were added to the respective well of the 384 well plate containing 2 µl cDNA which has been produced as described above to a total volume of 10 µl. Table 17 illustrates the amount of bulk RNA and cells in each well, respectively.

PCR stripes were placed in a thermocycler and incubated in the following cycling conditions:
i) 5 minutes at 95° C.: HotStart DNA Polymerase Activation
ii) 20 cycles: 30 seconds at 95° C.; 3 minutes at 60° C.; 1 minute at 72° C.

iii) 10 minutes at 68° C.

Library Preparation for Next Generation Sequencing
1. All samples were pooled into one tube following PCR, a total volume of 3840 µl for the given example.
2. Amplicons were precipitated by adding 384 µl NaAc pH 5.3 and 2 volumes of 100% EtOH, 8000 µl. The sample was incubated at −20° C. over night, and subsequently centrifuged for 30 min at 4700g and 4° C. The supernatant was then removed, pellet was washed with 70% EtOH, air-dried for 5 min and re-suspended in 200 µl nuclease-free water.
3. Amplicon (100-250 bps) size selection was performed using double-sided bead approach employing two different ratios of AMPure beads (Beckman Coulter). Negative selection: incubation with 0.5×AMPure beads, fragments longer than 300 bp were removed by discarding the beads. Positive selection: incubation with 1×AMPure beads, fragments longer than 100 bp were retained. After washing and drying the beads according to the AMPure manufacturer's protocol, the amplicons were eluted from the beads in 40 µl of nuclease-free water.
4. Amplicon library was prepared using NEBNext ChIP-Seq Library Prep kit according to manufacturer's protocol by ligating purified amplicons to sequencing adapters (for Illumina Inc instruments) and utilizing 15 cycles of PCR enrichment.
5. Amplicons were sequenced using next generation sequencing (NGS) instrument, Illumina MiSeq instrument, employing 2×150 bp paired-end kit.
6. Bioinformatics was used to align paired-end reads (analysed from the forward and reverse direction) filtering out sequences that do not align from the two ends (<5%). Additionally, reads with an alignment score below a certain threshold at the 5' end of bar-codes were discarded in order to guarantee an unambiguous identification of bar-codes. Read sequences were identified using BLAST, and sorted according to the barcode combinations linked to the amplicons.
7. Finally, the sorted map of barcodes and amplicons was compared to the map of bulk RNA and single/bulk cell distribution plan (FIG. 16), resulting in the plots outlined below, demonstrating quantitative detection of the transcripts using the method of invention.

Tables:

TABLE 1

Barcodes-Adapters and rcPrimers-rcAdapters:

| description | sequence |
|---|---|
| Barcode L01 - F Adapter | CCATCCTCAGGTAGCGACGAG (SEQ ID NO: 1) |
| Barcode L02 - F Adapter | CCACCGAACACTAGCGACGAG (SEQ ID NO: 2) |
| Barcode L03 - F Adapter | CCAACTGAGGCTAGCGACGAG (SEQ ID NO: 3) |
| Barcode L04 - F Adapter | CCACACCTAGGTAGCGACGAG (SEQ ID NO: 4) |
| Barcode L05 - F Adapter | CCACACACCTCTAGCGACGAG (SEQ ID NO: 5) |
| Barcode L06 - F Adapter | CCATACGGCACTAGCGACGAG (SEQ ID NO: 6) |
| Barcode L07 - F Adapter | CCAGATCCAGGTAGCGACGAG (SEQ ID NO: 7) |
| Barcode L08 - F Adapter | CCACCAGACGATAGCGACGAG (SEQ ID NO: 8) |
| Barcode R01 - R Adapter | CCAACGCGCTACCATACGACG (SEQ ID NO: 9) |
| Barcode R02 - R Adapter | CCAACGCTAGCCCATACGACG (SEQ ID NO: 10) |
| Barcode R03 - R Adapter | CCAACTCCTCCCCATACGACG (SEQ ID NO: 11) |
| Barcode R04 - R Adapter | CCAGCGCATCTCCATACGACG (SEQ ID NO: 12) |
| Barcode R05 - R Adapter | CCACGGACAAGCCATACGACG (SEQ ID NO: 13) |
| Barcode R06 - R Adapter | CCACGGTCCAACCATACGACG (SEQ ID NO: 14) |
| Barcode R07 - R Adapter | CCAGGACGCAACCATACGACG (SEQ ID NO: 15) |
| Barcode R08 - R Adapter | CCAGACCTTCCCCATACGACG (SEQ ID NO: 16) |
| Barcode R09 - R Adapter | CCAAGGAGAGCCCATACGACG (SEQ ID NO: 17) |
| Barcode R10 - R Adapter | CCACCATCACGCCATACGACG (SEQ ID NO: 18) |
| Barcode R11 - R Adapter | CCACGGCAACACCATACGACG (SEQ ID NO: 19) |
| Barcode R12 - R Adapter | CCACGGAATGCCCATACGACG (SEQ ID NO: 20) |
| rcF Primer 185delAG - rcF Adapter | GACATTTTGTACTTCTTCAACGCCTCGTCGCTA (SEQ ID NO: 21) |
| rcR Primer 185delAG - rcR Adapter | CTCCTATGCAAATGAACAGAACGTCGTATGG (SEQ ID NO: 22) |

TABLE 1-continued

Barcodes-Adapters and rcPrimers-rcAdapters:

| description | sequence |
|---|---|
| rcF Primer 5382insC - rcF Adapter | CTTGCTCGCTTTGGACCTTCTCGTCGCTA (SEQ ID NO: 23) |
| rcR Primer 5382insC - rcR Adapter | CACTCTTCCATCCCAACCACGTCGTATGG (SEQ ID NO: 24) |
| rcF Primer p.Y978* - rcF Adapter | ATTTGGAGTAATGAGTCCAGTTTCGCTCGTCGCTA (SEQ ID NO: 25) |
| rcR Primer p.Y978*-rcR Adapter | GAGAACATTCCAAGTACAGTGAGCGTCGTATGG (SEQ ID NO: 26) |
| rcF Primer p.A1708E-rcF Adapter | GTCCGTTCACACACAAACTCCTCGTCGCTA (SEQ ID NO: 27) |
| rcR Primer p.A1708E - rcR Adapter | CCCCTCCTCCCTTTAACACCGTCGTATGG (SEQ ID NO: 28) |
| rcF Primer 981delAT - rcF Adapter | CCTTACTTCCAGCCCATCTCTCGTCGCTA (SEQ ID NO: 29) |
| rcR Primer 981delAT - rcR Adapter | GCCATGCTCAGAGAATCCTCGTCGTATGG (SEQ ID NO: 30) |
| rcF Primer c.6174delT - rcF Adapter | GACTTATGAAGCTTCCCTATACTCTCGTCGCTA (SEQ ID NO: 31) |
| rcR Primer c.6174delT - rcR Adapter | CCAGGTATCAGATGCTTCACGTCGTATGG (SEQ ID NO: 32) |
| rcF Primer 8765delAG - rcF Adapter | CATTGCGAAATATGTATAATCCAGACTCGTCGCTA (SEQ ID NO: 33) |
| rcR Primer 8765delAG - rcR Adapter | GGTACACATTGTTATTTCTAATATGACGTCGTATGG (SEQ ID NO: 34) |
| rcF Primer IVS2 + 1G > A - rcF Adapter | ACGATATTCCTCCAATGCTTGCTCGTCGCTA (SEQ ID NO: 35) |
| rcR Primer IVS2 + 1G > A - rcR Adapter | CCAGTTAACAACATAATCATCGTCGTCGTATGG (SEQ ID NO: 36) |
| rcF Primer p.R2336P - rcF Adapter | ACACAGGTAATCGGCTCTACTCGTCGCTA (SEQ ID NO: 37) |
| rcR Primer p.R2336P - rcR Adapter | GGTAGTATTTTATAGTGCTGTTCACGTCGTATGG (SEQ ID NO: 38) |
| rcF Primer p.P1812A - rcF Adapter | AGGACTACTGGAACTGTCACTCTCGTCGCTA (SEQ ID NO: 39) |
| rcR Primer p.P1812A - rcR Adapter | GGTAAGGTGCCTGCATGTACGTCGTATGG (SEQ ID NO: 40) |

TABLE 2

Barcode map:

| | 1 | 2 | 3 | 4 | 5 | 6 | 7 | 8 | 9 | 10 | 11 | 12 |
|---|---|---|---|---|---|---|---|---|---|---|---|---|
| A | L01-R01 | L01-R02 | L01-R03 | L01-R04 | L01-R05 | L01-R06 | L01-R07 | L01-R08 | L01-R09 | L01-R10 | L01-R11 | L01-R12 |
| B | L02-R01 | L02-R02 | L02-R03 | L02-R04 | L02-R05 | L02-R06 | L02-R07 | L02-R08 | L02-R09 | L02-R10 | L02-R11 | L02-R12 |
| C | L03-R01 | L03-R02 | L03-R03 | L03-R04 | L03-R05 | L03-R06 | L03-R07 | L03-R08 | L03-R09 | L03-R10 | L03-R11 | L03-R12 |
| D | L04-R01 | L04-R02 | L04-R03 | L04-R04 | L04-R05 | L04-R06 | L04-R07 | L04-R08 | L04-R09 | L04-R10 | L04-R11 | L04-R12 |
| E | L05-R01 | L05-R02 | L05-R03 | L05-R04 | L05-R05 | L05-R06 | L05-R07 | L05-R08 | L05-R09 | L05-R10 | L05-R11 | L05-R12 |
| F | L06-R01 | L06-R02 | L06-R03 | L06-R04 | L06-R05 | L06-R06 | L06-R07 | L06-R08 | L06-R09 | L06-R10 | L06-R11 | L06-R12 |
| G | L07-R01 | L07-R02 | L07-R03 | L07-R04 | L07-R05 | L07-R06 | L07-R07 | L07-R08 | L07-R09 | L07-R10 | L07-R11 | L07-R12 |
| H | L08-R01 | L08-R02 | L08-R03 | L08-R04 | L08-R05 | L08-R06 | L08-R07 | L08-R08 | L08-R09 | L08-R10 | L08-R11 | L08-R12 |

TABLE 3

Wild-type and mutation bearing amplicon read numbers of patient samples:

| patient sample | 185delAG wt | 5382insC wt | p.Y978* wt | p.A1708E wt | 981delAT wt | c.6174delT wt | 8765delAG wt | IVS2 + 1G > A wt | p.R2336P wt | p.P1812A wt |
|---|---|---|---|---|---|---|---|---|---|---|
| A1 | 2040 | 6579 | 4056 | 3387 | 3753 | 1366 | 1812 | 3814 | 1096 | 6637 |
| A2 | 1189 | 4521 | 2542 | 1731 | 2754 | 447 | 1134 | 2380 | 655 | 3987 |
| A3 | 2133 | 4139 | 3004 | 845 | 3535 | 1029 | 1522 | 2643 | 892 | 4679 |
| A4 | 705 | 2840 | 1513 | 1079 | 1744 | 423 | 648 | 1314 | 184 | 2314 |
| A5 | 637 | 3878 | 2113 | 1080 | 1702 | 373 | 796 | 1544 | 260 | 2572 |
| A6 | 1385 | 3958 | 2503 | 1743 | 3273 | 834 | 1321 | 1498 | 712 | 3934 |
| A7 | 908 | 3180 | 1864 | 1221 | 2063 | 560 | 952 | 1581 | 440 | 2728 |
| A8 | 1044 | 3360 | 2139 | 855 | 2381 | 567 | 1033 | 1418 | 529 | 1786 |
| A9 | 988 | 3543 | 2023 | 1291 | 1793 | 549 | 486 | 1727 | 642 | 3049 |
| A10 | 1777 | 6481 | 3581 | 2788 | 2733 | 1045 | 1245 | 2814 | 550 | 6117 |
| A11 | 391 | 1883 | 896 | 696 | 1004 | 226 | 291 | 673 | 213 | 1376 |
| A12 | 966 | 4568 | 2229 | 1811 | 2303 | 381 | 950 | 2066 | 671 | 3767 |
| B1 | 274 | 1249 | 590 | 279 | 521 | 74 | 241 | 498 | 138 | 808 |
| B2 | 668 | 2719 | 1563 | 600 | 1596 | 444 | 676 | 1107 | 581 | 2384 |
| B3 | 930 | 2345 | 1680 | 441 | 1920 | 289 | 807 | 1212 | 628 | 2729 |
| B4 | 302 | 1276 | 616 | 413 | 723 | 185 | 194 | 558 | 198 | 1019 |
| B5 | 1029 | 3868 | 2189 | 926 | 2074 | 619 | 983 | 2004 | 873 | 3474 |
| B6 | 996 | 2724 | 1801 | 1208 | 2364 | 356 | 798 | 1845 | 795 | 2976 |
| B7 | 886 | 3573 | 2279 | 1523 | 2777 | 689 | 927 | 2115 | 960 | 3728 |
| B8 | 897 | 2260 | 1228 | 488 | 1625 | 352 | 541 | 737 | 355 | 2109 |
| B9 | 850 | 2804 | 1789 | 1049 | 1430 | 262 | 621 | 1602 | 844 | 2621 |
| B10 | 536 | 2631 | 1368 | 893 | 942 | 196 | 445 | 908 | 418 | 2235 |
| B11 | 200 | 836 | 502 | 335 | 571 | 95 | 155 | 365 | 134 | 837 |
| B12 | 287 | 1645 | 797 | 404 | 748 | 177 | 270 | 454 | 276 | 1193 |
| C1 | 2059 | 5803 | 3666 | 2689 | 3500 | 1237 | 1732 | 3075 | 1384 | 6555 |
| C2 | 2172 | 6822 | 4406 | 3017 | 4670 | 1541 | 1991 | 4365 | 1045 | 7418 |
| C3 | 796 | 3271 | 2514 | 595 | 2659 | 713 | 1101 | 1706 | 903 | 4039 |
| C4 | 488 | 1958 | 789 | 722 | 1237 | 273 | 408 | 564 | 284 | 1615 |
| C5 | 765 | 3833 | 1578 | 1174 | 1731 | 478 | 777 | 1327 | 526 | 2954 |
| C6 | 938 | 3060 | 1881 | 1258 | 2375 | 537 | 536 | 1461 | 689 | 3007 |
| C7 | 1227 | 2632 | 2371 | 1501 | 2784 | 662 | 1016 | 1632 | 871 | 3812 |
| C8 | 925 | 2893 | 1879 | 689 | 2181 | 504 | 490 | 1452 | 649 | 2739 |
| C9 | 565 | 1553 | 955 | 507 | 671 | 219 | 337 | 478 | 249 | 1245 |
| C10 | 2083 | 6279 | 3818 | 2934 | 2994 | 1120 | 1351 | 2136 | 1282 | 6774 |
| C11 | 190 | 1320 | 595 | 403 | 664 | 123 | 171 | 306 | 158 | 677 |
| C12 | 741 | 2089 | 1432 | 914 | 1438 | 342 | 550 | 1085 | 451 | 2368 |
| D1 | 2004 | 7143 | 4287 | 2972 | 4066 | 1313 | 1988 | 3488 | 567 | 6608 |
| D2 | 1254 | 5807 | 2402 | 2160 | 3452 | 934 | 1297 | 2444 | 761 | 4724 |
| D3 | 1179 | 3650 | 2277 | 572 | 1945 | 553 | 885 | 1761 | 389 | 3382 |
| D4 | 1765 | 6932 | 3813 | 2967 | 4983 | 633 | 1417 | 3312 | 994 | 5923 |
| D5 | 3464 | 11934 | 10536 | 7772 | 10017 | 3224 | 4736 | 7269 | 3049 | 15782 |
| D6 | 869 | 4020 | 2263 | 1329 | 2688 | 308 | 925 | 1763 | 428 | 3064 |
| D7 | 1734 | 7162 | 4396 | 3036 | 5242 | 1266 | 1946 | 2811 | 1144 | 6111 |
| D8 | 1435 | 7569 | 4642 | 1908 | 5705 | 1313 | 2022 | 2949 | 1198 | 6199 |
| D9 | 998 | 4224 | 2532 | 972 | 2047 | 553 | 860 | 2043 | 573 | 3338 |
| D10 | 3768 | 17615 | 10035 | 9335 | 8457 | 3256 | 3454 | 3767 | 2754 | 18572 |
| D11 | 1216 | 7475 | 3457 | 3434 | 4384 | 1047 | 648 | 2704 | 992 | 5881 |
| D12 | 2931 | 11194 | 6328 | 5119 | 6960 | 2054 | 3046 | 4089 | 1045 | 11072 |
| E1 | 886 | 3769 | 1404 | 1271 | 1842 | 495 | 726 | 1594 | 621 | 3189 |
| E2 | 1048 | 4125 | 2283 | 1450 | 2434 | 629 | 860 | 1996 | 450 | 3687 |
| E3 | 471 | 2454 | 1635 | 370 | 1623 | 385 | 655 | 1204 | 463 | 2221 |
| E4 | 1715 | 5168 | 2763 | 2219 | 3541 | 948 | 1021 | 1474 | 1005 | 5090 |
| E5 | 5925 | 18751 | 11261 | 7909 | 11018 | 4083 | 4988 | 8724 | 5533 | 20524 |
| E6 | 482 | 2272 | 1205 | 587 | 1423 | 176 | 444 | 961 | 302 | 1729 |
| E7 | 909 | 3356 | 1811 | 1072 | 2108 | 431 | 690 | 968 | 610 | 2735 |
| E8 | 2883 | 6771 | 4237 | 1759 | 5371 | 733 | 1798 | 3788 | 1658 | 7168 |
| E9 | 762 | 2586 | 1442 | 791 | 1125 | 387 | 325 | 1102 | 524 | 2232 |
| E10 | 789 | 4346 | 2174 | 1316 | 1530 | 514 | 474 | 1396 | 572 | 3529 |
| E11 | 365 | 2150 | 988 | 698 | 1110 | 225 | 307 | 715 | 315 | 1068 |
| E12 | 564 | 2995 | 1397 | 847 | 1443 | 329 | 517 | 859 | 431 | 2293 |
| F1 | 402 | 2002 | 1184 | 613 | 1041 | 260 | 350 | 951 | 264 | 1583 |
| F2 | 444 | 1702 | 1216 | 694 | 1202 | 274 | 451 | 968 | 281 | 1727 |
| F3 | 1612 | 3273 | 2572 | 696 | 2825 | 795 | 1156 | 2084 | 406 | 4107 |
| F4 | 541 | 2217 | 1262 | 888 | 1502 | 291 | 269 | 1010 | 328 | 2058 |
| F5 | 3370 | 5039 | 4692 | 3687 | 4454 | 1625 | 2009 | 3823 | 1789 | 7674 |
| F6 | 3950 | 4520 | 5311 | 4148 | 7092 | 1888 | 2365 | 4962 | 2144 | 9150 |
| F7 | 2373 | 6800 | 4565 | 3306 | 5555 | 1446 | 1079 | 3586 | 1695 | 7669 |
| F8 | 891 | 2061 | 1792 | 694 | 2219 | 472 | 756 | 1520 | 487 | 2649 |
| F9 | 1630 | 5073 | 3163 | 2163 | 2725 | 938 | 1199 | 2495 | 1327 | 5164 |
| F10 | 433 | 2595 | 1466 | 800 | 971 | 162 | 340 | 719 | 214 | 2026 |
| F11 | 334 | 1911 | 1010 | 825 | 1129 | 223 | 179 | 746 | 295 | 1615 |
| F12 | 1302 | 5452 | 3019 | 2305 | 3111 | 1002 | 1389 | 1093 | 1294 | 5570 |
| G1 | 840 | 3070 | 1371 | 688 | 1638 | 525 | 770 | 1543 | 594 | 2843 |
| G2 | 1594 | 3897 | 1973 | 1666 | 2667 | 892 | 1082 | 1251 | 905 | 3801 |
| G3 | 1234 | 2924 | 1572 | 543 | 2401 | 361 | 973 | 2016 | 676 | 3522 |

TABLE 3-continued

Wild-type and mutation bearing amplicon read numbers of patient samples:

| | | | | | | | | | | |
|---|---|---|---|---|---|---|---|---|---|---|
| G4 | 980 | 2192 | 1481 | 1516 | 2349 | 601 | 775 | 1751 | 662 | 3370 |
| G5 | 938 | 3746 | 1624 | 1188 | 1276 | 493 | 855 | 1365 | 599 | 3120 |
| G6 | 1299 | 3452 | 1795 | 1588 | 2967 | 692 | 1085 | 2116 | 838 | 3597 |
| G7 | 421 | 2064 | 988 | 625 | 1221 | 229 | 467 | 616 | 281 | 1489 |
| G8 | 2093 | 5216 | 2873 | 1451 | 4667 | 1161 | 1644 | 3123 | 1258 | 5358 |
| G9 | 485 | 1761 | 852 | 605 | 774 | 238 | 245 | 889 | 343 | 1479 |
| G10 | 949 | 4050 | 1760 | 1601 | 1628 | 560 | 775 | 909 | 641 | 3786 |
| G11 | 729 | 2983 | 1254 | 1326 | 1775 | 470 | 542 | 728 | 546 | 2681 |
| G12 | 461 | 2432 | 1044 | 756 | 1279 | 294 | 501 | 791 | 312 | 1296 |
| H1 | 1536 | 6733 | 3389 | 2618 | 3159 | 1188 | 1495 | 1582 | 1296 | 6330 |
| H2 | 1021 | 4951 | 2639 | 1620 | 2615 | 794 | 1099 | 1403 | 913 | 4070 |
| H3 | 1606 | 5406 | 3914 | 531 | 4221 | 1291 | 1987 | 1827 | 1655 | 6173 |
| H4 | 950 | 3901 | 2117 | 1344 | 2432 | 554 | 749 | 702 | 738 | 3240 |
| H5 | 654 | 4595 | 2417 | 1178 | 1945 | 422 | 766 | 940 | 514 | 3062 |
| H6 | 1747 | 5990 | 3583 | 2335 | 4492 | 1101 | 1737 | 2048 | 786 | 6086 |
| H7 | 2086 | 7991 | 4924 | 3048 | 5498 | 1592 | 1217 | 2770 | 1996 | 7563 |
| H8 | 830 | 3834 | 1927 | 650 | 2316 | 483 | 761 | 1025 | 587 | 2870 |
| H9 | 373 | 2115 | 1079 | 515 | 772 | 216 | 320 | 568 | 280 | 997 |
| H10 | 1954 | 12567 | 6757 | 5367 | 5151 | 2053 | 1353 | 3458 | 2776 | 12305 |
| H11 | 1284 | 4721 | 1479 | 1902 | 2634 | 667 | 821 | 1132 | 897 | 4238 |
| H12 | 1578 | 8519 | 4067 | 3332 | 4191 | 1277 | 901 | 2412 | 1780 | 7586 |

| patient sample | 185delAG mut | 5382insC mut | p.Y978* mut | p.A1708E mut | 981delAT mut | c.6174delT mut | 8765delAG mut | IVS2 + 1G > A mut | p.R2336P mut | p.P1812A mut |
|---|---|---|---|---|---|---|---|---|---|---|
| A1 | 1247 | 9 | 15 | 6 | 1 | 9 | 16 | 15 | 19 | 12 |
| A2 | 14 | 12 | 21 | 4 | 3 | 331 | 18 | 12 | 11 | 10 |
| A3 | 20 | 6 | 4 | 0 | 9 | 2 | 19 | 5 | 11 | 10 |
| A4 | 3 | 16 | 10 | 2 | 2 | 11 | 4 | 3 | 163 | 9 |
| A5 | 7 | 48 | 14 | 2 | 3 | 3 | 18 | 12 | 139 | 14 |
| A6 | 12 | 18 | 8 | 1 | 6 | 8 | 19 | 481 | 14 | 9 |
| A7 | 25 | 14 | 3 | 4 | 1 | 3 | 28 | 17 | 7 | 13 |
| A8 | 12 | 13 | 7 | 4 | 6 | 8 | 20 | 9 | 9 | 1175 |
| A9 | 5 | 10 | 3 | 6 | 5 | 1 | 365 | 4 | 3 | 4 |
| A10 | 40 | 18 | 4 | 7 | 2 | 4 | 28 | 18 | 416 | 21 |
| A11 | 5 | 4 | 14 | 0 | 0 | 1 | 17 | 4 | 6 | 10 |
| A12 | 6 | 12 | 0 | 3 | 2 | 298 | 30 | 5 | 13 | 23 |
| B1 | 16 | 36 | 7 | 7 | 1 | 44 | 8 | 4 | 2 | 2 |
| B2 | 3 | 57 | 3 | 405 | 2 | 5 | 5 | 8 | 3 | 2 |
| B3 | 8 | 21 | 2 | 6 | 1 | 244 | 8 | 9 | 34 | 2 |
| B4 | 1 | 35 | 3 | 3 | 2 | 3 | 10 | 1 | 1 | 0 |
| B5 | 4 | 270 | 10 | 488 | 1 | 9 | 13 | 6 | 6 | 3 |
| B6 | 2 | 226 | 4 | 13 | 2 | 211 | 9 | 3 | 1 | 2 |
| B7 | 416 | 51 | 10 | 8 | 3 | 6 | 49 | 5 | 2 | 1 |
| B8 | 5 | 91 | 5 | 8 | 1 | 6 | 5 | 192 | 3 | 14 |
| B9 | 3 | 27 | 8 | 6 | 1 | 230 | 5 | 2 | 4 | 3 |
| B10 | 9 | 63 | 0 | 15 | 0 | 128 | 12 | 5 | 0 | 1 |
| B11 | 1 | 261 | 5 | 5 | 0 | 5 | 15 | 2 | 2 | 10 |
| B12 | 2 | 31 | 1 | 21 | 0 | 6 | 0 | 31 | 1 | 4 |
| C1 | 18 | 86 | 33 | 9 | 1 | 5 | 28 | 4 | 9 | 5 |
| C2 | 2 | 89 | 36 | 4 | 3 | 6 | 32 | 7 | 954 | 6 |
| C3 | 394 | 70 | 14 | 6 | 3 | 0 | 19 | 5 | 11 | 6 |
| C4 | 5 | 79 | 345 | 0 | 0 | 0 | 9 | 2 | 5 | 3 |
| C5 | 7 | 176 | 516 | 5 | 2 | 2 | 18 | 8 | 17 | 8 |
| C6 | 2 | 102 | 29 | 0 | 1 | 7 | 333 | 11 | 12 | 5 |
| C7 | 9 | 1175 | 26 | 0 | 1 | 1 | 31 | 6 | 7 | 8 |
| C8 | 10 | 83 | 23 | 1 | 0 | 6 | 270 | 7 | 11 | 28 |
| C9 | 2 | 70 | 9 | 4 | 1 | 3 | 9 | 105 | 15 | 7 |
| C10 | 23 | 128 | 32 | 1 | 4 | 6 | 27 | 9 | 14 | 7 |
| C11 | 2 | 59 | 22 | 1 | 1 | 1 | 8 | 52 | 3 | 233 |
| C12 | 2 | 640 | 29 | 0 | 2 | 5 | 19 | 11 | 8 | 13 |
| D1 | 52 | 287 | 36 | 18 | 16 | 7 | 30 | 12 | 516 | 3 |
| D2 | 27 | 307 | 968 | 23 | 25 | 7 | 23 | 8 | 18 | 7 |
| D3 | 32 | 219 | 19 | 7 | 621 | 12 | 16 | 2 | 20 | 0 |
| D4 | 23 | 225 | 18 | 4 | 24 | 502 | 27 | 7 | 13 | 6 |
| D5 | 57 | 6514 | 86 | 26 | 33 | 15 | 71 | 9 | 52 | 6 |
| D6 | 28 | 302 | 37 | 7 | 13 | 179 | 25 | 6 | 16 | 0 |
| D7 | 1057 | 353 | 39 | 15 | 32 | 2 | 53 | 7 | 14 | 3 |
| D8 | 755 | 285 | 30 | 5 | 14 | 15 | 25 | 6 | 18 | 43 |
| D9 | 20 | 185 | 18 | 607 | 11 | 13 | 18 | 3 | 18 | 14 |
| D10 | 2316 | 483 | 64 | 17 | 23 | 23 | 51 | 8 | 30 | 13 |
| D11 | 12 | 199 | 31 | 3 | 11 | 4 | 506 | 5 | 12 | 35 |
| D12 | 22 | 331 | 37 | 11 | 23 | 7 | 44 | 14 | 980 | 18 |
| E1 | 19 | 16 | 594 | 2 | 0 | 1 | 14 | 7 | 5 | 6 |
| E2 | 3 | 12 | 28 | 2 | 4 | 0 | 13 | 9 | 372 | 7 |
| E3 | 152 | 6 | 10 | 0 | 2 | 7 | 6 | 6 | 6 | 2 |
| E4 | 1 | 9 | 18 | 0 | 4 | 16 | 9 | 5 | 10 | 4 |
| E5 | 1 | 59 | 69 | 10 | 12 | 10 | 48 | 11 | 33 | 14 |

TABLE 3-continued

Wild-type and mutation bearing amplicon read numbers of patient samples:

| | | | | | | | | | | |
|---|---|---|---|---|---|---|---|---|---|---|
| E6 | 2 | 21 | 25 | 1 | 2 | 81 | 14 | 6 | 11 | 6 |
| E7 | 11 | 20 | 30 | 4 | 6 | 5 | 28 | 252 | 11 | 6 |
| E8 | 4 | 10 | 20 | 0 | 10 | 678 | 25 | 10 | 3 | 34 |
| E9 | 0 | 5 | 18 | 5 | 0 | 7 | 176 | 5 | 6 | 9 |
| E10 | 24 | 17 | 31 | 1 | 3 | 4 | 199 | 10 | 6 | 4 |
| E11 | 2 | 13 | 15 | 0 | 3 | 1 | 6 | 7 | 0 | 482 |
| E12 | 4 | 13 | 23 | 0 | 0 | 3 | 14 | 9 | 6 | 15 |
| F1 | 15 | 327 | 9 | 3 | 1 | 0 | 131 | 7 | 3 | 3 |
| F2 | 0 | 602 | 16 | 2 | 2 | 3 | 29 | 11 | 8 | 1 |
| F3 | 5 | 254 | 5 | 3 | 3 | 10 | 32 | 10 | 408 | 3 |
| F4 | 1 | 227 | 6 | 1 | 1 | 8 | 145 | 7 | 3 | 6 |
| F5 | 3 | 2961 | 17 | 10 | 2 | 10 | 51 | 14 | 12 | 8 |
| F6 | 0 | 3274 | 11 | 3 | 8 | 5 | 38 | 31 | 13 | 5 |
| F7 | 19 | 346 | 12 | 3 | 4 | 3 | 789 | 13 | 8 | 3 |
| F8 | 6 | 1024 | 4 | 1 | 1 | 7 | 32 | 9 | 6 | 22 |
| F9 | 0 | 208 | 11 | 10 | 3 | 3 | 24 | 11 | 6 | 14 |
| F10 | 21 | 501 | 6 | 1 | 3 | 46 | 49 | 9 | 3 | 2 |
| F11 | 0 | 220 | 11 | 0 | 1 | 0 | 117 | 8 | 6 | 22 |
| F12 | 0 | 340 | 6 | 5 | 3 | 5 | 31 | 736 | 8 | 27 |
| G1 | 14 | 70 | 5 | 490 | 10 | 1 | 7 | 15 | 7 | 4 |
| G2 | 0 | 55 | 10 | 3 | 9 | 6 | 9 | 476 | 13 | 5 |
| G3 | 5 | 49 | 2 | 4 | 13 | 271 | 5 | 18 | 3 | 6 |
| G4 | 0 | 1225 | 9 | 6 | 13 | 4 | 14 | 21 | 2 | 8 |
| G5 | 0 | 139 | 4 | 17 | 556 | 1 | 12 | 33 | 3 | 17 |
| G6 | 0 | 60 | 5 | 8 | 15 | 6 | 18 | 25 | 6 | 6 |
| G7 | 11 | 70 | 5 | 6 | 21 | 1 | 15 | 150 | 0 | 4 |
| G8 | 1 | 57 | 5 | 8 | 29 | 9 | 13 | 15 | 6 | 19 |
| G9 | 0 | 30 | 2 | 5 | 13 | 3 | 124 | 12 | 1 | 13 |
| G10 | 21 | 81 | 7 | 7 | 22 | 8 | 9 | 255 | 5 | 12 |
| G11 | 2 | 30 | 8 | 1 | 11 | 2 | 8 | 241 | 0 | 12 |
| G12 | 1 | 73 | 3 | 4 | 15 | 2 | 10 | 18 | 3 | 575 |
| H1 | 845 | 42 | 44 | 13 | 6 | 5 | 62 | 9 | 17 | 4 |
| H2 | 5 | 43 | 48 | 5 | 5 | 3 | 57 | 6 | 14 | 7 |
| H3 | 8 | 22 | 26 | 392 | 5 | 7 | 75 | 5 | 16 | 8 |
| H4 | 5 | 32 | 24 | 6 | 2 | 4 | 42 | 188 | 6 | 6 |
| H5 | 11 | 552 | 65 | 13 | 5 | 3 | 113 | 3 | 18 | 9 |
| H6 | 11 | 42 | 49 | 9 | 3 | 12 | 69 | 7 | 679 | 6 |
| H7 | 16 | 42 | 32 | 9 | 2 | 5 | 929 | 5 | 21 | 7 |
| H8 | 18 | 38 | 28 | 0 | 4 | 8 | 55 | 7 | 8 | 39 |
| H9 | 3 | 23 | 21 | 2 | 1 | 3 | 30 | 7 | 7 | 388 |
| H10 | 42 | 41 | 61 | 3 | 2 | 10 | 1142 | 12 | 18 | 14 |
| H11 | 2 | 28 | 1023 | 2 | 1 | 1 | 34 | 2 | 6 | 20 |
| H12 | 8 | 34 | 27 | 11 | 3 | 2 | 672 | 1 | 16 | 17 |

TABLE 4

Comparison of genotyping results performed with and without exonuclease digestion step of reverse complementary strand of the barcoded primers . . . This demonstrates that exonuclease digestion of rcprimer-adapter-bar-code strands is advantageous for genotyping purposes.

| patient sample | Sanger | NGS w/ lambda | NGS w/o lambda |
|---|---|---|---|
| A1 | 185delAG | 185delAG | 185delAG |
| A2 | c.6174delT | c.6174delT | c.6174delT |
| A3 | n | wt | wt |
| A4 | p.R2336P | p.R2336P | p.R2336P |
| A5 | p.R2336P | p.R2336P | p.R2336P |
| A6 | IVS2 + 1G < A | IVS2 + 1G > A | wt |
| A7 | n | wt | wt |
| A8 | p.P1812A | p.P1812A | p.P1812A |
| A9 | 8765delAG | 8765delAG | 8765delAG |
| A10 | p.R2336P | p.R2336P | p.R2336P |
| A11 | n | wt | wt |
| A12 | c.6174delT | c.6174delT | c.6174delT |
| B1 | c.6174delT | c.6174delT | wt |
| B2 | p.A1708E | p.A1708E | p.A1708E |
| B3 | c.6174delT | c.6174delT | c.6174delT |
| B4 | n | wt | wt |
| B5 | p.A1708E | p.A1708E | p.A1708E |
| B6 | c.6174delT | c.6174delT | c.6174delT |
| B7 | 185delAG | 185delAG | 185delAG |
| B8 | IVS2 + 1G < A | IVS2 + 1G > A | wt |
| B9 | c.6174delT | c.6174delT | c.6174delT |
| B10 | c.6174delT | c.6174delT | c.6174delT |
| B11 | 5382insC | 5382insC | 5382insC |
| B12 | n | wt | wt |
| C1 | n | wt | wt |
| C2 | p.R2336P | p.R2336P | p.R2336P |
| C3 | 185delAG | 185delAG | 185delAG |
| C4 | p.Y978* | p.Y978* | p.Y978* |
| C5 | p.Y978* | p.Y978* | p.Y978* |
| C6 | 8765delAG | 8765delAG | 8765delAG |
| C7 | 5382insC | 5382insC | 5382insC |
| C8 | 8765delAG | 8765delAG | 8765delAG |
| C9 | IVS2 + 1G > A | IVS2 + 1G > A | wt |
| C10 | n | wt | wt |
| C11 | p.P1812A | p.P1812A | p.P1812A |
| C12 | 5382insC | 5382insC | 5382insC |
| D1 | p.R2336P | p.R2336P | p.R2336P |
| D2 | p.Y978* | p.Y978* | p.Y978* |
| D3 | 981delAT | 981delAT | 981delAT |
| D4 | c.6174delT | c.6174delT | c.6174delT |

TABLE 4-continued

Comparison of genotyping results performed with and without exonuclease digestion step of reverse complementary strand of the barcoded primers . . . This demonstrates that exonuclease digestion of rcprimer-adapter-bar-code strands is advantageous for genotyping purposes.

| patient sample | Sanger | NGS w/ lambda | NGS w/o lambda |
|---|---|---|---|
| D5 | 5382insC | 5382insC | 5382insC |
| D6 | c.6174delT | c.6174delT | c.6174delT |
| D7 | 185delAG | 185delAG | 185delAG |
| D8 | 185delAG | 185delAG | 185delAG |
| D9 | p.A1708E | p.A1708E | p.A1708E |
| D10 | 185delAG | 185delAG | 185delAG |
| D11 | 8765delAG | 8765delAG | 8765delAG |
| D12 | p.R2336P | p.R2336P | p.R2336P |
| E1 | p.Y978* | p.Y978* | p.Y978* |
| E2 | p.R2336P | p.R2336P | p.R2336P |
| E3 | 185delAG | 185delAG | 185delAG |
| E4 | n | wt | wt |
| E5 | n | wt | wt |
| E6 | c.6174delT | c.6174delT | wt |
| E7 | IVS2 + 1G < A | IVS2 + 1G > A | wt |
| E8 | c.6174delT | c.6174delT | c.6174delT |
| E9 | 8765delAG | 8765delAG | 8765delAG |
| E10 | 8765delAG | 8765delAG | 8765delAG |
| E11 | p.P1812A | p.P1812A | p.P1812A |
| E12 | n | wt | wt |
| F1 | 8765delAG | 8765delAG | 8765delAG |
| F2 | 5382insC | 5382insC | 5382insC |
| F3 | p.R2336P | p.R2336P | p.R2336P |
| F4 | 8765delAG | 8765delAG | 8765delAG |
| F5 | 5382insC | 5382insC | 5382insC |
| F6 | 5382insC | 5382insC | 5382insC |
| F7 | 8765delAG | 8765delAG | 8765delAG |
| F8 | 5382insC | 5382insC | 5382insC |
| F9 | ? | wt | wt |
| F10 | c.6174delT | c.6174delT | wt |
| F11 | 8765delAG | 8765delAG | 8765delAG |
| F12 | IVS2 + 1G < A | IVS2 + 1G > A | IVS2 + 1G > A |
| G1 | p.A1708E | p.A1708E | p.A1708E |
| G2 | IVS2 + 1G > A | IVS2 + 1G > A | wt |
| G3 | c.6174delT | c.6174delT | c.6174delT |
| G4 | 5382insC | 5382insC | 5382insC |
| G5 | 981delAT | 981delAT | 981delAT |
| G6 | n | wt | wt |
| G7 | IVS2 + 1G < A | IVS2 + 1G > A | wt |
| G8 | n | wt | wt |
| G9 | 8765delAG | 8765delAG | 8765delAG |
| G10 | IVS2 + 1G < A | IVS2 + 1G > A | wt |
| G11 | IVS2 + 1G < A | IVS2 + 1G > A | wt |
| G12 | p.P1812A | p.P1812A | p.P1812A |
| H1 | 185delAG | 185delAG | 185delAG |
| H2 | n | wt | wt |
| H3 | p.A1708E | p.A1708E | p.A1708E |
| H4 | IVS2 + 1G < A | IVS2 + 1G > A | wt |
| H5 | 5382insC | wt | 5382insC |
| H6 | p.R2336P | p.R2336P | p.R2336P |
| H7 | 8765delAG | 8765delAG | 8765delAG |
| H8 | n | wt | wt |
| H9 | p.P1812A | p.P1812A | p.P1812A |
| H10 | 8765delAG | 8765delAG | 8765delAG |
| H11 | p.Y978* | p.Y978* | p.Y978* |
| H12 | 8765delAG | 8765delAG | 8765delAG |

TABLE 5

Comparison of genotyping results with (lib1, upper left) and without (lib2, upper right) digestion of reverse complement strand by lamda exonuclease after Klenow fill-in reaction during bar-code assembly (performed with CCA protected bar-codes). Digestion leads to 98.9% correct genotype identification, while left-out digestion results in only 87.4% correct identification. A detailed analysis (lower left) reveals that higher percentages in identified right barcodes (Fraction bcright), left barcodes (Fraction bcleft), inserts (Fraction insert), and complete amplicons (Fraction bc left + right + insert) is achieved upon removal of the reverse complement strand. This demonstrates that exonuclease digestion of rcprimer-adapter-bar-code strands according to the invention is advantageous for genotyping purposes

| lib1 (CCA) | | % | lib2 (CCA-λ) | | % |
|---|---|---|---|---|---|
| 95 | samples included in analysis | | 95 | samples included in analysis | |
| 94 | true positive/negative | 98.9 | 83 | true positive/negative | 87.4 |
| 1 | false negative | 1.1 | 12 | false negative | 12.6 |
| 0 | false positive | 0.0 | 0 | false positive | 0.0 |

| | lib1 (CCA) | lib2 (CCA-λ) |
|---|---|---|
| Fraction bc left + right + insert | 0.9561 | 0.8708 |
| Fraction insert | 0.9885 | 0.9308 |
| Fraction bcleft | 0.9662 | 0.8894 |
| Fraction bcright | 0.9756 | 0.9075 |

TABLE 6

Map of spike-in amounts.

| | 1 | 2 | 3 | 4 | 5 | 6 | 7 | 8 | 9 | 10 | 11 | 12 |
|---|---|---|---|---|---|---|---|---|---|---|---|---|
| A | 100T | 100T | 100T | 100T | 10T | 10T | 10T | 10T | 1T | 1T | 1T | 1T |
| B | 100T | 100T | 100T | 100T | 10T | 10T | 10T | 10T | 1T | 1T | 1T | 1T |
| C | 100T | 100T | 100T | 100T | 10T | 10T | 10T | 10T | 1T | 1T | 1T | 1T |
| D | 100 | 100 | 100 | 100 | RNA1 | RNA1 | RNA2 | RNA2 | RNA6 | RNA6 | RNA8 | RNA8 |
| E | 100 | 100 | 100 | 100 | RNA1 | RNA1 | RNA2 | RNA2 | RNA6 | RNA6 | RNA8 | RNA8 |
| F | 100 | 100 | 100 | 100 | RNA1 | RNA1 | RNA2 | RNA2 | RNA6 | RNA6 | RNA8 | RNA8 |
| G | 10 | 10 | 10 | 10 | 1 | 1 | 1 | 1 | — | — | — | — |
| H | 10 | 10 | 10 | 10 | 1 | 1 | 1 | 1 | — | — | — | — |

TABLE 7

| Barcodes-Adapters and rcPrimers-rcAdapters: | | |
|---|---|---|
| description | sequence | |
| Barcode R01 - R Adapter | CCAGCCACCTTAGCGTAACCT | (SEQ ID NO: 41) |
| Barcode R02 - R Adapter | CCAGAACCACGAGCGTAACCT | (SEQ ID NO: 42) |
| Barcode R03 - R Adapter | CCACTCAGGCAAGCGTAACCT | (SEQ ID NO: 43) |
| Barcode R04 - R Adapter | CCAGTACAGCGAGCGTAACCT | (SEQ ID NO: 44) |
| Barcode R05 - R Adapter | CCACTCGAGCTAGCGTAACCT | (SEQ ID NO: 45) |
| Barcode R06 - R Adapter | CCAGCGACACAAGCGTAACCT | (SEQ ID NO: 46) |
| Barcode R07 - R Adapter | CCAGTCATCGGAGCGTAACCT | (SEQ ID NO: 47) |
| Barcode R08 - R Adapter | CCATGCCTCCAAGCGTAACCT | (SEQ ID NO: 48) |
| Barcode R09 - R Adapter | CCACCGATTCCAGCGTAACCT | (SEQ ID NO: 49) |
| Barcode R10 - R Adapter | CCAGCATAGGCAGCGTAACCT | (SEQ ID NO: 50) |
| Barcode R11 - R Adapter | CCAGACAGAGGAGCGTAACCT | (SEQ ID NO: 51) |
| Barcode R12 - R Adapter | CCACACCGGTAAGCGTAACCT | (SEQ ID NO: 52) |
| Barcode R13 - R Adapter | CCAGTGGAAGGAGCGTAACCT | (SEQ ID NO: 53) |
| Barcode R14 - R Adapter | CCAGGATCCTCAGCGTAACCT | (SEQ ID NO: 54) |
| Barcode R15 - R Adapter | CCAGGACAGTGAGCGTAACCT | (SEQ ID NO: 55) |
| Barcode R16 - R Adapter | CCATGTGGCGTAGCGTAACCT | (SEQ ID NO: 56) |
| Barcode R17 - R Adapter | CCAGCGATCAGAGCGTAACCT | (SEQ ID NO: 57) |
| Barcode R18 - R Adapter | CCAACAAGGCCAGCGTAACCT | (SEQ ID NO: 58) |
| Barcode R19 - R Adapter | CCACTCGGAGAAGCGTAACCT | (SEQ ID NO: 59) |
| Barcode R20 - R Adapter | CCACAAGCTGCAGCGTAACCT | (SEQ ID NO: 60) |
| Barcode R21 - R Adapter | CCAGTCCACCAAGCGTAACCT | (SEQ ID NO: 61) |
| Barcode R22 - R Adapter | CCATCGAGGACAGCGTAACCT | (SEQ ID NO: 62) |
| Barcode R23 - R Adapter | CCATCCGGCAAAGCGTAACCT | (SEQ ID NO: 63) |
| Barcode R24 - R Adapter | CCAGTCTCACGAGCGTAACCT | (SEQ ID NO: 64) |
| Barcode L01 - F Adapter | CCACCTTCTCGATGCGCATTC | (SEQ ID NO: 65) |
| Barcode L02 - F Adapter | CCACCAGTAGCATGCGCATTC | (SEQ ID NO: 66) |
| Barcode L03 - F Adapter | CCACCTAACGCATGCGCATTC | (SEQ ID NO: 67) |
| Barcode L04 - F Adapter | CCAGGCCGATTATGCGCATTC | (SEQ ID NO: 68) |
| Barcode L05 - F Adapter | CCACGTTCGTCATGCGCATTC | (SEQ ID NO: 69) |
| Barcode L06 - F Adapter | CCAGCCTGGTAATGCGCATTC | (SEQ ID NO: 70) |
| Barcode L07 - F Adapter | CCACCAGACGAATGCGCATTC | (SEQ ID NO: 71) |
| Barcode L08 - F Adapter | CCAACGACACCATGCGCATTC | (SEQ ID NO: 72) |
| Barcode L09 - F Adapter | CCAGCCTCTTGATGCGCATTC | (SEQ ID NO: 73) |
| Barcode L10 - F Adapter | CCATACGGCACATGCGCATTC | (SEQ ID NO: 74) |
| Barcode L11 - F Adapter | CCACTCCAGTCATGCGCATTC | (SEQ ID NO: 75) |
| Barcode L12 - F Adapter | CCAAACGTCGGATGCGCATTC | (SEQ ID NO: 76) |
| Barcode L13 - F Adapter | CCAGTTGGAGCATGCGCATTC | (SEQ ID NO: 77) |
| Barcode L14 - F Adapter | CCAACGAGCCTATGCGCATTC | (SEQ ID NO: 78) |

TABLE 7-continued

Barcodes-Adapters and rcPrimers-rcAdapters:

| description | sequence | |
|---|---|---|
| Barcode L15 - F Adapter | CCAGATCCAGGATGCGCATTC | (SEQ ID NO: 79) |
| Barcode L16 - F Adapter | CCATCCTGGCTATGCGCATTC | (SEQ ID NO: 80) |
| rcF Primer GAPDH - rcF Adapter | GATGGCATGGACTGTGGTGAATGCGCAT | (SEQ ID NO: 81) |
| rcR Primer GAPDH - rcR Adapter | GAACGGGAAGCTCACTGGAGGTTACGCT | (SEQ ID NO: 82) |
| rcF Primer B2M - rcF Adapter | AAGGCCACGGAGCGAGAGAATGCGCAT | (SEQ ID NO: 83) |
| rcR Primer B2M - rcR Adapter | CACGTCATCCAGCAGAGAAAGGTTACGCT | (SEQ ID NO: 84) |
| rcF Primer POU5F1 - rcF Adapter | GAGAAAGGAGACCCAGCAGGAATGCGCAT | (SEQ ID NO: 85) |
| rcR Primer POU5F1 - rcR Adapter | CACTGCACTGTACTCCTCGAGGTTACGCT | (SEQ ID NO: 86) |
| rcF Primer NANOG - rcF Adapter | GGTGGAAGAATCAGGGCTGGAATGCGCAT | (SEQ ID NO: 87) |
| rcR Primer NANOG - rcR Adapter | CCCGGTCAAGAAACAGAAGAAGGTTACGCT | (SEQ ID NO: 88) |
| rcF Primer SOX2 - rcF Adapter | GGAGTGGGAGGAAGAGGTAGAATGCGCAT | (SEQ ID NO: 89) |
| rcR Primer SOX2 - rcR Adapter | GTCCCAGCACTACCAGAGAGGTTACGCT | (SEQ ID NO: 90) |
| rcF Primer LIN28A - rcF Adapter | CATGGACAGGAAGCCGAACGAATGCGCAT | (SEQ ID NO: 91) |
| rcR Primer LIN28A - rcR Adapter | AAGCTGCACATGGAAGGGTAGGTTACGCT | (SEQ ID NO: 92) |
| rcF Primer RNA 1 (EC2) - rcF Adapter | TGCATGGCCTTTGGTGATGGAATGCGCAT | (SEQ ID NO: 93) |
| rcR Primer RNA 1 (EC2) - rcR Adapter | GCAAGCGTGTAAGATCGTCAGGTTACGCT | (SEQ ID NO: 94) |
| rcF Primer RNA 2 (EC12) - rcF Adapter | ACGGCGATAGAGGCGATCGAATGCGCAT | (SEQ ID NO: 95) |
| rcR Primer RNA 2 (EC12) -rcR Adapter | TGAACAGGCAGCGGAAAAGAGGTTACGCT | (SEQ ID NO: 96) |
| rcF Primer RNA 6 (EC13) - rcF Adapter | CGATGTGTTAGATGCGCTGGAATGCGCAT | (SEQ ID NO: 97) |
| rcR Primer RNA 6 (EC13) - rcR Adapter | GTTGCGGATGATATTGGCGAGGTTACGCT | (SEQ ID NO: 98) |
| rcF Primer RNA 8 (EC5) - rcF Adapter | GTCGGCAGGTAACTTCAACGAATGCGCAT | (SEQ ID NO: 99) |
| rcR Primer RNA 8 (EC5) - rcR Adapter | GCGTAGTCATAAGCGTCCTAGGTTACGCT | (SEQ ID NO: 100) |

TABLE 8

Barcode map

| | 1 | 2 | 3 | 4 | 5 | 6 | 7 | 8 | 9 | 10 | 11 | 12 |
|---|---|---|---|---|---|---|---|---|---|---|---|---|
| A | L01-R01 | L01-R02 | L01-R03 | L01-R04 | L01-R05 | L01-R06 | L01-R07 | L01-R08 | L01-R09 | L01-R10 | L01-R11 | L01-R12 |
| B | L02-R01 | L02-R02 | L02-R03 | L02-R04 | L02-R05 | L02-R06 | L02-R07 | L02-R08 | L02-R09 | L02-R10 | L02-R11 | L02-R12 |
| C | L03-R01 | L03-R02 | L03-R03 | L03-R04 | L03-R05 | L03-R06 | L03-R07 | L03-R08 | L03-R09 | L03-R10 | L03-R11 | L03-R12 |
| D | L04-R01 | L04-R02 | L04-R03 | L04-R04 | L04-R05 | L04-R06 | L04-R07 | L04-R08 | L04-R09 | L04-R10 | L04-R11 | L04-R12 |
| E | L05-R01 | L05-R02 | L05-R03 | L05-R04 | L05-R05 | L05-R06 | L05-R07 | L05-R08 | L05-R09 | L05-R10 | L05-R11 | L05-R12 |
| F | L06-R01 | L06-R02 | L06-R03 | L06-R04 | L06-R05 | L06-R06 | L06-R07 | L06-R08 | L06-R09 | L06-R10 | L06-R11 | L06-R12 |
| G | L07-R01 | L07-R02 | L07-R03 | L07-R04 | L07-R05 | L07-R06 | L07-R07 | L07-R08 | L07-R09 | L07-R10 | L07-R11 | L07-R12 |
| H | L08-R01 | L08-R02 | L08-R03 | L08-R04 | L08-R05 | L08-R06 | L08-R07 | L08-R08 | L08-R09 | L08-R10 | L08-R11 | L08-R12 |

TABLE 9

Barcode map of 384 well plate sorted with single cells

|   | 1 | 2 | 3 | 4 | 5 | 6 | 7 | 8 | 9 | 10 | 11 | 12 |
|---|---|---|---|---|---|---|---|---|---|----|----|----|
| A | L01-R01 | L01-R13 | L01-R02 | L01-R14 | L01-R03 | L01-R15 | L01-R04 | L01-R16 | L01-R05 | L01-R17 | L01-R06 | L01-R18 |
| B | L09-R01 | L09-R13 | L09-R02 | L09-R14 | L09-R03 | L09-R15 | L09-R04 | L09-R16 | L09-R05 | L09-R17 | L09-R06 | L09-R18 |
| C | L02-R01 | L02-R13 | L02-R02 | L02-R14 | L02-R03 | L02-R15 | L02-R04 | L02-R16 | L02-R05 | L02-R17 | L02-R06 | L02-R18 |
| D | L10-R01 | L10-R13 | L10-R02 | L10-R14 | L10-R03 | L10-R15 | L10-R04 | L10-R16 | L10-R05 | L10-R17 | L10-R06 | L10-R18 |
| E | L03-R01 | L03-R13 | L03-R02 | L03-R14 | L03-R03 | L03-R15 | L03-R04 | L03-R16 | L03-R05 | L03-R17 | L03-R06 | L03-R18 |
| F | L11-R01 | L11-R13 | L11-R02 | L11-R14 | L11-R03 | L11-R15 | L11-R04 | L11-R16 | L11-R05 | L11-R17 | L11-R06 | L11-R18 |
| G | L04-R01 | L04-R13 | L04-R02 | L04-R14 | L04-R03 | L04-R15 | L04-R04 | L04-R16 | L04-R05 | L04-R17 | L04-R06 | L04-R18 |
| H | L12-R01 | L12-R13 | L12-R02 | L12-R14 | L12-R03 | L12-R15 | L12-R04 | L12-R16 | L12-R05 | L12-R17 | L12-R06 | L12-R18 |
| I | L05-R01 | L05-R13 | L05-R02 | L05-R14 | L05-R03 | L05-R15 | L05-R04 | L05-R16 | L05-R05 | L05-R17 | L05-R06 | L05-R18 |
| J | L13-R01 | L13-R13 | L13-R02 | L13-R14 | L13-R03 | L13-R15 | L13-R04 | L13-R16 | L13-R05 | L13-R17 | L13-R06 | L13-R18 |
| K | L06-R01 | L06-R13 | L06-R02 | L06-R14 | L06-R03 | L06-R15 | L06-R04 | L06-R16 | L06-R05 | L06-R17 | L06-R06 | L06-R18 |
| L | L14-R01 | L14-R13 | L14-R02 | L14-R14 | L14-R03 | L14-R15 | L14-R04 | L14-R16 | L14-R05 | L14-R17 | L14-R06 | L14-R18 |
| M | L07-R01 | L07-R13 | L07-R02 | L07-R14 | L07-R03 | L07-R15 | L07-R04 | L07-R16 | L07-R05 | L07-R17 | L07-R06 | L07-R18 |
| N | L15-R01 | L15-R13 | L15-R02 | L15-R14 | L15-R03 | L15-R15 | L15-R04 | L15-R16 | L15-R05 | L15-R17 | L15-R06 | L15-R18 |
| O | L08-R01 | L08-R13 | L08-R02 | L08-R14 | L08-R03 | L08-R15 | L08-R04 | L08-R16 | L08-R05 | L08-R17 | L08-R06 | L08-R18 |
| P | L16-R01 | L16-R13 | L16-R02 | L16-R14 | L16-R03 | L16-R15 | L16-R04 | L16-R16 | L16-R05 | L16-R17 | L16-R06 | L16-R18 |

|   | 13 | 14 | 15 | 16 | 17 | 18 | 19 | 20 | 21 | 22 | 23 | 24 |
|---|----|----|----|----|----|----|----|----|----|----|----|----|
| A | L01-R07 | L01-R19 | L01-R08 | L01-R20 | L01-R09 | L01-R21 | L01-R10 | L01-R22 | L01-R11 | L01-R23 | L01-R12 | L01-R24 |
| B | L09-R07 | L09-R19 | L09-R08 | L09-R20 | L09-R09 | L09-R21 | L09-R10 | L09-R22 | L09-R11 | L09-R23 | L09-R12 | L09-R24 |
| C | L02-R07 | L02-R19 | L02-R08 | L02-R20 | L02-R09 | L02-R21 | L02-R10 | L02-R22 | L02-R11 | L02-R23 | L02-R12 | L02-R24 |
| D | L10-R07 | L10-R19 | L10-R08 | L10-R20 | L10-R09 | L10-R21 | L10-R10 | L10-R22 | L10-R11 | L10-R23 | L10-R12 | L10-R24 |
| E | L03-R07 | L03-R19 | L03-R08 | L03-R20 | L03-R09 | L03-R21 | L03-R10 | L03-R22 | L03-R11 | L03-R23 | L03-R12 | L03-R24 |
| F | L11-R07 | L11-R19 | L11-R08 | L11-R20 | L11-R09 | L11-R21 | L11-R10 | L11-R22 | L11-R11 | L11-R23 | L11-R12 | L11-R24 |
| G | L04-R07 | L04-R19 | L04-R08 | L04-R20 | L04-R09 | L04-R21 | L04-R10 | L04-R22 | L04-R11 | L04-R23 | L04-R12 | L04-R24 |
| H | L12-R07 | L12-R19 | L12-R08 | L12-R20 | L12-R09 | L12-R21 | L12-R10 | L12-R22 | L12-R11 | L12-R23 | L12-R12 | L12-R24 |
| I | L05-R07 | L05-R19 | L05-R08 | L05-R20 | L05-R09 | L05-R21 | L05-R10 | L05-R22 | L05-R11 | L05-R23 | L05-R12 | L05-R24 |
| J | L13-R07 | L13-R19 | L13-R08 | L13-R20 | L13-R09 | L13-R21 | L13-R10 | L13-R22 | L13-R11 | L13-R23 | L13-R12 | L13-R24 |
| K | L06-R07 | L06-R19 | L06-R08 | L06-R20 | L06-R09 | L06-R21 | L06-R10 | L06-R22 | L06-R11 | L06-R23 | L06-R12 | L06-R24 |
| L | L14-R07 | L14-R19 | L14-R08 | L14-R20 | L14-R09 | L14-R21 | L14-R10 | L14-R22 | L14-R11 | L14-R23 | L14-R12 | L14-R24 |
| M | L07-R07 | L07-R19 | L07-R08 | L07-R20 | L07-R09 | L07-R21 | L07-R10 | L07-R22 | L07-R11 | L07-R23 | L07-R12 | L07-R24 |
| N | L15-R07 | L15-R19 | L15-R08 | L15-R20 | L15-R09 | L15-R21 | L15-R10 | L15-R22 | L15-R11 | L15-R23 | L15-R12 | L15-R24 |
| O | L08-R07 | L08-R19 | L08-R08 | L08-R20 | L08-R09 | L08-R21 | L08-R10 | L08-R22 | L08-R11 | L08-R23 | L08-R12 | L08-R24 |
| P | L16-R07 | L16-R19 | L16-R08 | L16-R20 | L16-R09 | L16-R21 | L16-R10 | L16-R22 | L16-R11 | L16-R23 | L16-R12 | L16-R24 |

TABLE 10

Barcodes-Adapters and rcPrimers-rcAdapters:

| description | sequence |
|---|---|
| Barcode L01 - F Adapter (SEQ ID NO: 101) | CCACCTTCTCGATGCGCATTC |
| Barcode L02 - F Adapter (SEQ ID NO: 102) | CCACCAGTAGCATGCGCATTC |
| Barcode L03 - F Adapter (SEQ ID NO: 103) | CCACCTAACGCATGCGCATTC |
| Barcode L04 - F Adapter (SEQ ID NO: 104) | CCAGGCCGATTATGCGCATTC |
| Barcode L05 - F Adapter (SEQ ID NO: 105) | CCACGTTCGTCATGCGCATTC |
| Barcode L06 - F Adapter (SEQ ID NO: 106) | CCAGCCTGGTAATGCGCATTC |
| Barcode L08 - F Adapter (SEQ ID NO: 107) | CCAACGACACCATGCGCATTC |
| Barcode L09 - F Adapter (SEQ ID NO: 108) | CCAGCCTCTTGATGCGCATTC |
| Barcode R01 - R Adapter (SEQ ID NO: 109) | CCAGCCACCTTAGCGTAACCT |
| Barcode R02 - R Adapter (SEQ ID NO: 110) | CCAGAACCACGAGCGTAACCT |

TABLE 10 -continued

Barcodes-Adapters and rcPrimers-rcAdapters:

| description | sequence |
| --- | --- |
| Barcode R03 - R Adapter (SEQ ID NO: 111) | CCACTCAGGCAAGCGTAACCT |
| Barcode R04 - R Adapter (SEQ ID NO: 112) | CCAGTACAGCGAGCGTAACCT |
| Barcode R05 - R Adapter (SEQ ID NO: 113) | CCACTCGAGCTAGCGTAACCT |
| Barcode R06 - R Adapter (SEQ ID NO: 114) | CCAGCGACACAAGCGTAACCT |
| Barcode R07 - R Adapter (SEQ ID NO: 115) | CCAGTCATCGGAGCGTAACCT |
| Barcode R08 - R Adapter (SEQ ID NO: 116) | CCATGCCTCCAAGCGTAACCT |
| Barcode R09 - R Adapter (SEQ ID NO: 117) | CCACCGATTCCAGCGTAACCT |
| Barcode R11 - R Adapter (SEQ ID NO: 118) | CCAGACAGAGGAGCGTAACCT |
| rcF Primer EGFR_1 - rcF Adapter (SEQ ID NO: 119) | TCGCATGAAGAGGCCGATCCGAATGCGCAT |
| rcR Primer EGFR_1 - rcR Adapter (SEQ ID NO: 120) | CTGCCTCACCTCCACCGTAGGTTACGCT |
| rcF Primer EGFR_2 - rcF Adapter (SEQ ID NO: 121) | GATGAGCTGCACGGTGGAGGAATGCGCAT |
| rcR Primer EGFR_2 - rcR Adapter (SEQ ID NO: 122) | GATGTCTGGAGCTACGGGGTAGGTTACGCT |
| rcF Primer KRAS - rcF Adapter (SEQ ID NO: 123) | CTCTCCCGCACCTGGGAGAATGCGCAT |
| rcR Primer KRAS - rcR Adapter (SEQ ID NO: 124) | GGGGAGGGCTTTCTTTGTGTAGGTTACGCT |
| rcF Primer RNA 2 (EC12) - rcF Adapter (SEQ ID NO: 125) | AAGCGGCTGAAACGGTGAGTGAATGCGCAT |
| rcR Primer RNA 2 (EC12) - rcR Adapter (SEQ ID NO: 126) | TGAACAGGCAGCGGAAAAGCAGGTTACGCT |
| rcF Primer RNA 8 (EC5) - rcF Adapter (SEQ ID NO: 127) | CGATGAAGTGATGGACGCGTGAATGCGCAT |
| rcR Primer RNA 8 (EC5) - rcR Adapter (SEQ ID NO: 128) | GGTAACGCACGCTGAGGTTAAGGTTACGCT |

TABLE 11

Barcode map:

| | 1 | 2 | 3 | 4 | 5 | 6 | 7 | 8 | 9 | 10 |
| --- | --- | --- | --- | --- | --- | --- | --- | --- | --- | --- |
| A | L01-R01 | L01-R02 | L01-R03 | L01-R04 | L01-R05 | L01-R06 | L01-R07 | L01-R08 | L01-R09 | L01-R11 |
| B | L02-R01 | L02-R02 | L02-R03 | L02-R04 | L02-R05 | L02-R06 | L02-R07 | L02-R08 | L02-R09 | L02-R11 |
| C | L03-R01 | L03-R02 | L03-R03 | L03-R04 | L03-R05 | L03-R06 | L03-R07 | L03-R08 | L03-R09 | L03-R11 |
| D | L04-R01 | L04-R02 | L04-R03 | L04-R04 | L04-R05 | L04-R06 | L04-R07 | L04-R08 | L04-R09 | L04-R11 |
| E | L05-R01 | L05-R02 | L05-R03 | L05-R04 | L05-R05 | L05-R06 | L05-R07 | L05-R08 | L05-R09 | L05-R11 |
| F | L06-R01 | L06-R02 | L06-R03 | L06-R04 | L06-R05 | L06-R06 | L06-R07 | L06-R08 | L06-R09 | L06-R11 |
| G | L08-R01 | L08-R02 | L08-R03 | L08-R04 | L08-R05 | L08-R06 | L08-R07 | L08-R08 | L08-R09 | L08-R11 |
| H | L09-R01 | L09-R02 | L09-R03 | L09-R04 | L09-R05 | L09-R06 | L09-R07 | L09-R08 | L09-R09 | L09-R11 |

TABLE 12

List of mutations covered by BART-seq lung cancer assays:

| mutation name | exon | frequency of mutation in . . . |
|---|---|---|
| KRAS | | KRAS-mutated lung adenocarcinoma |
| KRAS c.34G > T (G12C) | exon 2 | 42% |
| KRAS c.34G > C (G12R) | exon 2 | 2% |
| KRAS c.34G > A (G12S) | exon 2 | 5% |
| KRAS c.35G > C (G12A) | exon 2 | 7% |
| KRAS c.35G > A (G12D) | exon 2 | 17% |
| KRAS c.35G > T (G12V) | exon 2 | 20% |
| KRAS c.37G > T (G13C) | exon 2 | 3% |
| KRAS c.37G > C (G13R) | exon 2 | <1% |
| KRAS c.37G > A (G13S) | exon 2 | <1% |
| KRAS c.38G > C (G13A) | exon 2 | <1% |
| KRAS c.38G > A (G13D) | exon 2 | 2% |
| KRAS c.181C > A (Q61K) | exon 3 | <1% |
| KRAS c.182A > T (Q61L) | exon 3 | <1% |
| KRAS c.182A > G (Q61R) | exon 3 | <1% |
| KRAS c.183A > C (Q61H) | exon 3 | <1% |
| KRAS c.183A > T (Q61H) | exon 3 | <1% |
| EGFR | | EGFR-mutated NSCLC |
| EGFR c.2156G > C (G719A) | exon 18 | 3% |
| EGFR c.2155G > T (G719C) | exon 18 | |
| EGFR c.2155G > A (G719S) | exon 18 | |
| EGFR Exon 19 Deletion | exon 19 | 48% |
| EGFR Exon 19 Insertions | exon 19 | 1% |
| EGFR Exon 20 Insertions | exon 20 | 4-9.2% |
| EGFR c.2290_2291ins (A763_Y764insFQEA) | exon 20 | <1% |
| EGFR c.2369C > T (T790M) | exon 20 | <5% of untreated EGFR mutant tumors 50% of EGFR mutant tumors with acquired resistance to erlotinib/gefitinib |
| EGFR c.2573T > G (L858R) | exon 21 | 43% |
| EGFR c.2582T > A (L861Q) | exon 21 | 2% |

TABLE 13

Comparison of genotyping results obtained by BART-seq to expected mutations:

| sample name | cDNA amount [ng] | expected mutation | called mutation |
|---|---|---|---|
| A549-1 | 2048 | KRAS c.34G > A (hom) | KRAS c.34G > A (hom) |
| A549-1 | 1024 | KRAS c.34G > A (hom) | KRAS c.34G > A (hom) |
| A549-1 | 512 | KRAS c.34G > A (hom) | KRAS c.34G > A (hom) |
| A549-1 | 256 | KRAS c.34G > A (hom) | KRAS c.34G > A (hom) |
| A549-1 | 128 | KRAS c.34G > A (hom) | KRAS c.34G > A (hom) |
| A549-1 | 64 | KRAS c.34G > A (hom) | KRAS c.34G > A (hom) |
| A549-2 | 2048 | KRAS c.34G > A (hom) | KRAS c.34G > A (hom) |
| A549-2 | 1024 | KRAS c.34G > A (hom) | KRAS c.34G > A (hom) |
| A549-2 | 512 | KRAS c.34G > A (hom) | KRAS c.34G > A (hom) |
| A549-2 | 256 | KRAS c.34G > A (hom) | KRAS c.34G > A (hom) |
| A549-2 | 128 | KRAS c.34G > A (hom) | KRAS c.34G > A (hom) |
| A549-2 | 64 | KRAS c.34G > A (hom) | KRAS c.34G > A (hom) |
| HEK293 | 2048 | — | non |
| HEK293 | 512 | — | non |
| HEK293 | 128 | — | non |
| HEK293 | 32 | — | non |
| H1299 | 5 | — | non |
| H2030 | 5 | KRAS c.34G > T (hom) | KRAS c.34G > T (hom) |
| H441 | 5 | KRAS c.35G > T (het) | KRAS c.35G > A (het) |
| H520 | 5 | — | non |
| AdCa 127 | 5 | tumor tissue | non |
| AdCa 140 | 5 | tumor tissue | KRAS c.34G > T |
| AdCa 145 | 5 | tumor tissue | non |
| AdCa 155 | 5 | tumor tissue | non |
| AdCa 242 | 5 | tumor tissue | KRAS c.37G > T |
| AdCa 243 | 5 | tumor tissue | non |
| AdCa 256 | 5 | tumor tissue | KRAS c.34G > T |
| AdCa 85 | 5 | tumor tissue | KRAS c.34G > T |
| KL637.1 | 5 | tumor tissue | KRAS c.34G > T |
| KL637.3 | 5 | tumor tissue | KRAS c.34G > T |
| KL638.2 | 5 | normal tissue | non |
| KL638.3 | 5 | normal tissue | non |
| PlCa 111 | 5 | tumor tissue | non |
| PlCa 163 | 5 | tumor tissue | non |
| PlCa 204 | 5 | tumor tissue | non |
| PlCa 274 | 5 | tumor tissue | non |
| PlCa 94 | 5 | tumor tissue | non |
| PlCa 99 | 5 | tumor tissue | non |
| water #1 | 0 | — | non |
| water #2 | 0 | — | non |

TABLE 14

Map of spike-in amounts.

| | 1 | 2 | 3 | 4 | 5 | 6 | 7 | 8 | 9 | 10 | 11 | 12 |
|---|---|---|---|---|---|---|---|---|---|---|---|---|
| A | RNA1 | RNA1 | RNA1 | 100 | 100 | 100 | 100T | 100T | 100T | RNA2 | RNA2 | RNA2 |
| B | RNA1 | RNA1 | RNA1 | 100 | 100 | 100 | 100T | 100T | 100T | RNA2 | RNA2 | RNA2 |
| C | — | 1 | 1 | 1T | 1T | 1T | 10T | 10T | 10T | 10 | 10 | — |
| D | — | 1 | 1 | 1T | 1T | 1T | 10T | 10T | 10T | 10 | 10 | — |
| E | — | 1 | 1 | 10T | 10T | 10T | 1T | 1T | 1T | 10 | 10 | — |
| F | — | 1 | 1 | 10T | 10T | 10T | 1T | 1T | 1T | 10 | 10 | — |
| G | RNA6 | RNA6 | RNA6 | 100T | 100T | 100T | 100 | 100 | 100 | RNA8 | RNA8 | RNA8 |
| H | RNA6 | RNA6 | RNA6 | 100T | 100T | 100T | 100 | 100 | 100 | RNA8 | RNA8 | RNA8 |

TABLE 15

Barcodes-Adapters and rcPrimers-rcAdapters:

| description | sequence |
|---|---|
| Barcode R01 - R Adapter (SEQ ID NO: 129) | CCAGCCACCTTAGCGTAACCT |
| Barcode R02 - R Adapter (SEQ ID NO: 130) | CCAGAACCACGAGCGTAACCT |

TABLE 15 -continued

Barcodes-Adapters and rcPrimers-rcAdapters:

| description | sequence |
|---|---|
| Barcode R03 - R Adapter (SEQ ID NO: 131) | CCACTCAGGCAAGCGTAACCT |
| Barcode R04 - R Adapter (SEQ ID NO: 132) | CCAGTACAGCGAGCGTAACCT |
| Barcode R05 - R Adapter (SEQ ID NO: 133) | CCACTCGAGCTAGCGTAACCT |
| Barcode R06 - R Adapter (SEQ ID NO: 134) | CCAGCGACACAAGCGTAACCT |
| Barcode R07 - R Adapter (SEQ ID NO: 135) | CCAGTCATCGGAGCGTAACCT |
| Barcode R08 - R Adapter (SEQ ID NO: 136) | CCATGCCTCCAAGCGTAACCT |
| Barcode R09 - R Adapter (SEQ ID NO: 137) | CCACCGATTCCAGCGTAACCT |
| Barcode R10 - R Adapter (SEQ ID NO: 138) | CCAGCATAGGCAGCGTAACCT |
| Barcode R11 - R Adapter (SEQ ID NO: 139) | CCAGACAGAGGAGCGTAACCT |
| Barcode R12 - R Adapter (SEQ ID NO: 140) | CCACACCGGTAAGCGTAACCT |
| Barcode R13 - R Adapter (SEQ ID NO: 141) | CCAGTGGAAGGAGCGTAACCT |
| Barcode R14 - R Adapter (SEQ ID NO: 142) | CCAGGATCCTCAGCGTAACCT |
| Barcode R15 - R Adapter (SEQ ID NO: 143) | CCAGGACAGTGAGCGTAACCT |
| Barcode R16 - R Adapter (SEQ ID NO: 144) | CCATGTGGCGTAGCGTAACCT |
| Barcode R17 - R Adapter (SEQ ID NO: 145) | CCAGCGATCAGAGCGTAACCT |
| Barcode R18 - R Adapter (SEQ ID NO: 146) | CCAACAAGGCCAGCGTAACCT |
| Barcode R19 - R Adapter (SEQ ID NO: 147) | CCACTCGGAGAAGCGTAACCT |
| Barcode R21 - R Adapter (SEQ ID NO: 148) | CCAGTCCACCAAGCGTAACCT |
| Barcode R22 - R Adapter (SEQ ID NO: 149) | CCATCGAGGACAGCGTAACCT |
| Barcode R23 - R Adapter (SEQ ID NO: 150) | CCATCCGGCAAAGCGTAACCT |
| Barcode R24 - R Adapter (SEQ ID NO: 151) | CCAGTCTCACGAGCGTAACCT |
| Barcode R25 - R Adapter (SEQ ID NO: 152) | CCAGATCGGCTAGCGTAACCT |
| Barcode L01 - F Adapter (SEQ ID NO: 153) | CCACCTTCTCGATGCGCATTC |
| Barcode L02 - F Adapter (SEQ ID NO: 154) | CCACCAGTAGCATGCGCATTC |
| Barcode L03 - F Adapter (SEQ ID NO: 155) | CCACCTAACGCATGCGCATTC |

TABLE 15 -continued

Barcodes-Adapters and rcPrimers-rcAdapters:

| description | sequence |
|---|---|
| Barcode L04 - F Adapter (SEQ ID NO: 156) | CCAGGCCGATTATGCGCATTC |
| Barcode L05 - F Adapter (SEQ ID NO: 157) | CCACGTTCGTCATGCGCATTC |
| Barcode L06 - F Adapter (SEQ ID NO: 158) | CCAGCCTGGTAATGCGCATTC |
| Barcode L08-F Adapter (SEQ ID NO: 159) | CCAACGACACCATGCGCATTC |
| Barcode L09 - F Adapter (SEQ ID NO: 160) | CCAGCCTCTTGATGCGCATTC |
| Barcode L10 - F Adapter (SEQ ID NO: 161) | CCATACGGCACATGCGCATTC |
| Barcode L11 - F Adapter (SEQ ID NO: 162) | CCACTCCAGTCATGCGCATTC |
| Barcode L12 - F Adapter (SEQ ID NO: 163) | CCAAACGTCGGATGCGCATTC |
| Barcode L13 - F Adapter (SEQ ID NO: 164) | CCAGTTGGAGCATGCGCATTC |
| Barcode L14 - F Adapter (SEQ ID NO: 165) | CCAACGAGCCTATGCGCATTC |
| Barcode L15 - F Adapter (SEQ ID NO: 166) | CCAGATCCAGGATGCGCATTC |
| Barcode L16 - F Adapter (SEQ ID NO: 167) | CCATCCTGGCTATGCGCATTC |
| Barcode L17 - F Adapter (SEQ ID NO: 168) | CCAGGTCCATGATGCGCATTC |
| rcF Primer GAPDH - rcF Adapter (SEQ ID NO: 169) | CCGACCTTCACCTTCCCCAGAATGCGCAT |
| rcR Primer GAPDH - rcR Adapter (SEQ ID NO: 170) | CAAGGCTGAGAACGGGAAGCAGGTTACGCT |
| rcF Primer B2M - rcF Adapter (SEQ ID NO: 171) | CACATGGTTCACACGGCAGGAATGCGCAT |
| rcR Primer B2M - rcR Adapter (SEQ ID NO: 172) | CATGGAGGTTTGAAGATGCCGAGGTTACGCT |
| rcF Primer POU5F1 - rcF Adapter (SEQ ID NO: 173) | GGGTGGAGGAAGCTGACAAGAATGCGCAT |
| rcR Primer POU5F1 - rcR Adapter (SEQ ID NO: 174) | CAAAGCGGCAGATGGTCGTAGGTTACGCT |
| rcF Primer NANOG - rcF Adapter (SEQ ID NO: 175) | GTCTTTTCTAGGCAGGGCGGAATGCGCAT |
| rcR Primer NANOG - rcR Adapter (SEQ ID NO: 176) | GTTTGGGATTGGGAGGCTTTGAGGTTACGCT |
| rcF Primer SOX2 - rcF Adapter (SEQ ID NO: 177) | CCTGCAAAGCTCCTACCGTGAATGCGCAT |
| rcR Primer SOX2 - rcR Adapter (SEQ ID NO: 178) | CGAGATAAACATGGCAATCAAAATGTAGGTTACGCT |
| rcF Primer LIN28A - rcF Adapter (SEQ ID NO: 179) | CCCTTTCTTGGCCTCCTGACGAATGCGCAT |
| rcR Primer LIN28A - rcR Adapter (SEQ ID NO: 180) | TATGTCAAAGTGGCCACAAGATTGAGGTTACGCT |

TABLE 15 -continued

Barcodes-Adapters and rcPrimers-rcAdapters:

| description | sequence |
| --- | --- |
| rcF Primer COND1 - rcF Adapter (SEQ ID NO: 181) | GAACCTGGACGTGAGCTGGGAATGCGCAT |
| rcR Primer COND1 - rcR Adapter (SEQ ID NO: 182) | GTTGTGTGTGCAGGGAGGGAGGTTACGCT |
| rcF Primer CCNE1 - rcF Adapter (SEQ ID NO: 183) | TGGCTGCAGAAGAGGGTGTGAATGCGCAT |
| rcR Primer CONE1 - rcR Adapter (SEQ ID NO: 184) | GACCGGTATATGGCGACACAAGGTTACGCT |
| rcF Primer CER1 - rcF Adapter (SEQ ID NO: 185) | AGTCTGGCTGAAGGGCACTGGAATGCGCAT |
| rcR Primer CER1 - rcR Adapter (SEQ ID NO: 186) | TGCCTGCCAAGTTCACCACAGGTTACGCT |
| rcF Primer DNMT3B - rcF Adapter (SEQ ID NO: 187) | CCCGGCATGTCTGACAGAGGAATGCGCAT |
| rcR Primer DNMT3B - rcR Adapter (SEQ ID NO: 188) | GCCGGTGTTTCTGTGTGGAAGGTTACGCT |
| rcF Primer ZFP42 - rcF Adapter (SEQ ID NO: 189) | AGCTAAGTTTAAACATGTTGTGGGGAATGCGCAT |
| rcR Primer ZFP42 - rcR Adapter (SEQ ID NO: 190) | GAAGCAGGAGGATAGCTTGAGAGGTTACGCT |
| rcF Primer RNA 1 (EC2) - rcF Adapter (SEQ ID NO: 191) | GCAGCATATTCTCGGGGCGGAATGCGCAT |
| rcR Primer RNA 1 (EC2) - rcR Adapter (SEQ ID NO: 192) | CGCGCCAAAGTAGAGAGGGAGGTTACGCT |
| rcF Primer RNA 2 (EC12) - rcF Adapter (SEQ ID NO: 193) | ATCATCGGAGGGGCTACGGGAATGCGCAT |
| rcR Primer RNA 2 (EC12) - rcR Adapter (SEQ ID NO: 194) | GATGCAATGGTGGTACGCGAGGTTACGCT |
| rcF Primer RNA 6 (EC13) - rcF Adapter (SEQ ID NO: 195) | GGCCGAAATCATCCCCTGGGAATGCGCAT |
| rcR Primer RNA 6 (EC13) - rcR Adapter (SEQ ID NO: 196) | GATCGTGGCACCAGAGCGAGGTTACGCT |
| rcF Primer RNA 8 (ECS) - rcF Adapter (SEQ ID NO: 197) | GCTGGCTGAAACTGCTGGAGAATGCGCAT |
| rcR Primer RNA 8 (ECS) - rcR Adapter (SEQ ID NO: 198) | AACACAGTTGCAGCGCCTGAGGTTACGCT |

TABLE 16

Barcode map

|   | 1 | 2 | 3 | 4 | 5 | 6 | 7 | 8 | 9 | 10 | 11 | 12 |
| --- | --- | --- | --- | --- | --- | --- | --- | --- | --- | --- | --- | --- |
| A | L01-R01 | L01-R02 | L01-R03 | L01-R04 | L01-R05 | L01-R06 | L01-R07 | L01-R08 | L01-R09 | L01-R10 | L01-R11 | L01-R12 |
| B | L02-R01 | L02-R02 | L02-R03 | L02-R04 | L02-R05 | L02-R06 | L02-R07 | L02-R08 | L02-R09 | L02-R10 | L02-R11 | L02-R12 |
| C | L03-R01 | L03-R02 | L03-R03 | L03-R04 | L03-R05 | L03-R06 | L03-R07 | L03-R08 | L03-R09 | L03-R10 | L03-R11 | L03-R12 |
| D | L04-R01 | L04-R02 | L04-R03 | L04-R04 | L04-R05 | L04-R06 | L04-R07 | L04-R08 | L04-R09 | L04-R10 | L04-R11 | L04-R12 |
| E | L05-R01 | L05-R02 | L05-R03 | L05-R04 | L05-R05 | L05-R06 | L05-R07 | L05-R08 | L05-R09 | L05-R10 | L05-R11 | L05-R12 |
| F | L06-R01 | L06-R02 | L06-R03 | L06-R04 | L06-R05 | L06-R06 | L06-R07 | L06-R08 | L06-R09 | L06-R10 | L06-R11 | L06-R12 |
| G | L08-R01 | L08-R02 | L08-R03 | L08-R04 | L08-R05 | L08-R06 | L08-R07 | L08-R08 | L08-R09 | L08-R10 | L08-R11 | L08-R12 |
| H | L09-R01 | L09-R02 | L09-R03 | L09-R04 | L09-R05 | L09-R06 | L09-R07 | L09-R08 | L09-R09 | L09-R10 | L09-R11 | L09-R12 |

TABLE 17

Barcode map of 384 well plate sorted with single cells

|   | 1 | 2 | 3 | 4 | 5 | 6 | 7 | 8 | 9 | 10 | 11 | 12 |
|---|---|---|---|---|---|---|---|---|---|----|----|----|
| A | L01-R01 | L01-R13 | L01-R02 | L01-R14 | L01-R03 | L01-R15 | L01-R04 | L01-R16 | L01-R05 | L01-R17 | L01-R06 | L01-R18 |
| B | L10-R01 | L10-R13 | L10-R02 | L10-R14 | L10-R03 | L10-R15 | L10-R04 | L10-R16 | L10-R05 | L10-R17 | L10-R06 | L10-R18 |
| C | L02-R01 | L02-R13 | L02-R02 | L02-R14 | L02-R03 | L02-R15 | L02-R04 | L02-R16 | L02-R05 | L02-R17 | L02-R06 | L02-R18 |
| D | L11-R01 | L11-R13 | L11-R02 | L11-R14 | L11-R03 | L11-R15 | L11-R04 | L11-R16 | L11-R05 | L11-R17 | L11-R06 | L11-R18 |
| E | L03-R01 | L03-R13 | L03-R02 | L03-R14 | L03-R03 | L03-R15 | L03-R04 | L03-R16 | L03-R05 | L03-R17 | L03-R06 | L03-R18 |
| F | L12-R01 | L12-R13 | L12-R02 | L12-R14 | L12-R03 | L12-R15 | L12-R04 | L12-R16 | L12-R05 | L12-R17 | L12-R06 | L12-R18 |
| G | L04-R01 | L04-R13 | L04-R02 | L04-R14 | L04-R03 | L04-R15 | L04-R04 | L04-R16 | L04-R05 | L04-R17 | L04-R06 | L04-R18 |
| H | L13-R01 | L13-R13 | L13-R02 | L13-R14 | L13-R03 | L13-R15 | L13-R04 | L13-R16 | L13-R05 | L13-R17 | L13-R06 | L13-R18 |
| I | L05-R01 | L05-R13 | L05-R02 | L05-R14 | L05-R03 | L05-R15 | L05-R04 | L05-R16 | L05-R05 | L05-R17 | L05-R06 | L05-R18 |
| J | L14-R01 | L14-R13 | L14-R02 | L14-R14 | L14-R03 | L14-R15 | L14-R04 | L14-R16 | L14-R05 | L14-R17 | L14-R06 | L14-R18 |
| K | L06-R01 | L06-R13 | L06-R02 | L06-R14 | L06-R03 | L06-R15 | L06-R04 | L06-R16 | L06-R05 | L06-R17 | L06-R06 | L06-R18 |
| L | L15-R01 | L15-R13 | L15-R02 | L15-R14 | L15-R03 | L15-R15 | L15-R04 | L15-R16 | L15-R05 | L15-R17 | L15-R06 | L15-R18 |
| M | L08-R01 | L08-R13 | L08-R02 | L08-R14 | L08-R03 | L08-R15 | L08-R04 | L08-R16 | L08-R05 | L08-R17 | L08-R06 | L08-R18 |
| N | L16-R01 | L16-R13 | L16-R02 | L16-R14 | L16-R03 | L16-R15 | L16-R04 | L16-R16 | L16-R05 | L16-R17 | L16-R06 | L16-R18 |
| O | L09-R01 | L09-R13 | L09-R02 | L09-R14 | L09-R03 | L09-R15 | L09-R04 | L09-R16 | L09-R05 | L09-R17 | L09-R06 | L09-R18 |
| P | L17-R01 | L17-R13 | L17-R02 | L17-R14 | L17-R03 | L17-R15 | L17-R04 | L17-R16 | L17-R05 | L17-R17 | L17-R06 | L17-R18 |

|   | 13 | 14 | 15 | 16 | 17 | 18 | 19 | 20 | 21 | 22 | 23 | 24 |
|---|----|----|----|----|----|----|----|----|----|----|----|----|
| A | L01-R07 | L01-R19 | L01-R08 | L01-R21 | L01-R09 | L01-R22 | L01-R10 | L01-R23 | L01-R11 | L01-R24 | L01-R12 | L01-R25 |
| B | L10-R07 | L10-R19 | L10-R08 | L10-R21 | L10-R09 | L10-R22 | L10-R10 | L10-R23 | L10-R11 | L10-R24 | L10-R12 | L10-R25 |
| C | L02-R07 | L02-R19 | L02-R08 | L02-R21 | L02-R09 | L02-R22 | L02-R10 | L02-R23 | L02-R11 | L02-R24 | L02-R12 | L02-R25 |
| D | L11-R07 | L11-R19 | L11-R08 | L11-R21 | L11-R09 | L11-R22 | L11-R10 | L11-R23 | L11-R11 | L11-R24 | L11-R12 | L11-R25 |
| E | L03-R07 | L03-R19 | L03-R08 | L03-R21 | L03-R09 | L03-R22 | L03-R10 | L03-R23 | L03-R11 | L03-R24 | L03-R12 | L03-R25 |
| F | L12-R07 | L12-R19 | L12-R08 | L12-R21 | L12-R09 | L12-R22 | L12-R10 | L12-R23 | L12-R11 | L12-R24 | L12-R12 | L12-R25 |
| G | L04-R07 | L04-R19 | L04-R08 | L04-R21 | L04-R09 | L04-R22 | L04-R10 | L04-R23 | L04-R11 | L04-R24 | L04-R12 | L04-R25 |
| H | L13-R07 | L13-R19 | L13-R08 | L13-R21 | L13-R09 | L13-R22 | L13-R10 | L13-R23 | L13-R11 | L13-R24 | L13-R12 | L13-R25 |
| I | L05-R07 | L05-R19 | L05-R08 | L05-R21 | L05-R09 | L05-R22 | L05-R10 | L05-R23 | L05-R11 | L05-R24 | L05-R12 | L05-R25 |
| J | L14-R07 | L14-R19 | L14-R08 | L14-R21 | L14-R09 | L14-R22 | L14-R10 | L14-R23 | L14-R11 | L14-R24 | L14-R12 | L14-R25 |
| K | L06-R07 | L06-R19 | L06-R08 | L06-R21 | L06-R09 | L06-R22 | L06-R10 | L06-R23 | L06-R11 | L06-R24 | L06-R12 | L06-R25 |
| L | L15-R07 | L15-R19 | L15-R08 | L15-R21 | L15-R09 | L15-R22 | L15-R10 | L15-R23 | L15-R11 | L15-R24 | L15-R12 | L15-R25 |
| M | L08-R07 | L08-R19 | L08-R08 | L08-R21 | L08-R09 | L08-R22 | L08-R10 | L08-R23 | L08-R11 | L08-R24 | L08-R12 | L08-R25 |
| N | L16-R07 | L16-R19 | L16-R08 | L16-R21 | L16-R09 | L16-R22 | L16-R10 | L16-R23 | L16-R11 | L16-R24 | L16-R12 | L16-R25 |
| O | L09-R07 | L09-R19 | L09-R08 | L09-R21 | L09-R09 | L09-R22 | L09-R10 | L09-R23 | L09-R11 | L09-R24 | L09-R12 | L09-R25 |
| P | L17-R07 | L17-R19 | L17-R08 | L17-R21 | L17-R09 | L17-R22 | L17-R10 | L17-R23 | L17-R11 | L17-R24 | L17-R12 | L17-R25 |

The invention claimed is:

1. A method of producing a plurality (M) of nucleic acid amplification products and/or reverse transcription products of interest carrying at least one sample-specific bar-code, the method comprising
  (i) producing a set of primers suitable for the reverse transcription and/or amplification of a plurality (N) of nucleic acid molecules of interest, wherein for each nucleic acid molecule of interest at least one primer is produced and wherein the primers carry a bar-code, the method comprising the steps of:
    (a)(i') combining
      (1) a first oligonucleotide, wherein said first oligonucleotide comprises a first bar-code nucleic acid sequence linked at its 3' end to a first adapter nucleic acid sequence with
      (2) a plurality (N) of second oligonucleotides, wherein each second oligonucleotide comprises the reverse complementary sequence of a forward primer specific for a nucleic acid molecule of interest, wherein said reverse complementary sequence of the forward primer is linked at its 3' end to the reverse complementary sequence of the first adapter nucleic acid sequence; and/or
    (a)(ii') combining
      (1) a third oligonucleotide, wherein said third oligonucleotide comprises a second bar-code nucleic acid sequence linked at its 3' end to a second adapter nucleic acid sequence with
      (2) a plurality (N) of fourth oligonucleotides, wherein each fourth oligonucleotide comprises the reverse complementary sequence of a reverse primer specific for said nucleic acid molecule of interest, wherein said reverse complementary sequence of the reverse primer is linked at its 3' end to the reverse complementary sequence of the second adapter nucleic acid sequence;
    wherein the bar-code nucleic acid sequences are at least 3 nucleotides in length, wherein the adapter nucleic acid sequences are at least 4 nucleotides in length, wherein the primer is at least 10 nucleotides in length, wherein steps (a)(i') and (a)(ii') are carried out under conditions that enable the annealing of the first and second adapter nucleic acid sequences to the respective reverse complementary sequences thereof;
    (b) extending the oligonucleotides of (a)(i') and (a)(ii') by polymerase-mediated oligonucleotide synthesis, wherein the polymerase is a DNA polymerase selected from the group consisting of Klenow DNA polymerase and T4 polymerase; and
    (c) removing the second and fourth oligonucleotides, wherein said removing is effected by exonuclease digestion; and
  (ii) amplifying and/or reverse transcribing a plurality (M) of nucleic acid molecules of interest from a sample using the set of primers produced in (i).

2. The method of claim 1, further comprising:
  (iii) producing at least a second set of primers suitable for the reverse transcription and/or amplification of a plurality (M) of nucleic acid molecules of interest, wherein for each nucleic acid molecule of interest at least one primer is produced and wherein the primers carry a bar-code, wherein said at least one second set of primers differs in its bar-code nucleic acid sequence from the first set of primers of (i); and
  (iv) amplifying and/or reverse transcribing said plurality (M) of nucleic acid molecules of interest from a second sample using the second set of primers produced in (iii).

3. The method of claim 2, wherein steps (iii) and (iv) are repeated for a plurality (X) of samples, wherein each set of primers produced in (iii) differs in their bar-code nucleic acid sequences from each of the other sets of primers; thereby producing from each sample a plurality (M) of nucleic acid amplification products and/or reverse transcription products of interest carrying at least one sample-specific bar-code.

4. A method for multiplex sequencing of a plurality (M) of nucleic acid amplification products and/or reverse transcription products of interest from different samples and identifying the individual sample from which each nucleic acid amplification product and/or reverse transcription product is derived, the method comprising:
  (a') producing a plurality (M) of nucleic acid amplification products and/or reverse transcription products of interest for each individual sample in accordance with the method of producing a plurality (M) of nucleic acid amplification products and/or reverse transcription products of interest carrying at least one sample-specific bar-code, the method comprising
    (i) producing a set of primers suitable for the reverse transcription and/or amplification of a plurality (N) of nucleic acid molecules of interest, wherein for each nucleic acid molecule of interest at least one primer is produced and wherein the primers carry a bar-code, the method comprising the steps of:

(a)(i') combining
- (1) a first oligonucleotide, wherein said first oligonucleotide comprises a first bar-code nucleic acid sequence linked at its 3' end to a first adapter nucleic acid sequence with
- (2) a plurality (N) of second oligonucleotides, wherein each second oligonucleotide comprises the reverse complementary sequence of a forward primer specific for a nucleic acid molecule of interest, wherein said reverse complementary sequence of the forward primer is linked at its 3' end to the reverse complementary sequence of the first adapter nucleic acid sequence; and/or (a)(ii') combining
- (1) a third oligonucleotide, wherein said third oligonucleotide comprises a second bar-code nucleic acid sequence linked at its 3' end to a second adapter nucleic acid sequence with
- (2) a plurality (N) of fourth oligonucleotides, wherein each fourth oligonucleotide comprises the reverse complementary sequence of a reverse primer specific for said nucleic acid molecule of interest, wherein said reverse complementary sequence of the reverse primer is linked at its 3' end to the reverse complementary sequence of the second adapter nucleic acid sequence;

wherein the bar-code nucleic acid sequences are at least 3 nucleotides in length, wherein the adapter nucleic acid sequences are at least 4 nucleotides in length, wherein the primer is at least 10 nucleotides in length, wherein steps (a)(i') and (a)(ii') are carried out under conditions that enable the annealing of the first and second adapter nucleic acid sequences to the respective reverse complementary sequences thereof;

(b) extending the oligonucleotides of (a)(i') and (a)(ii') by polymerase-mediated oligonucleotide synthesis, wherein the polymerase is a DNA polymerase selected from the group consisting of Klenow DNA polymerase and T4 polymerase; and (c) removing the second and fourth oligonucleotides, wherein said removing is effected by exonuclease digestion; and (ii) amplifying and/or reverse transcribing a plurality (M) of nucleic acid molecules of interest from a sample using the set of primers produced in (i);

(iii) producing at least a second set of primers suitable for the reverse transcription and/or amplification of a plurality (M) of nucleic acid molecules of interest, wherein for each nucleic acid molecule of interest at least one primer is produced and wherein the primers carry a bar-code, wherein said at least one second set of primers differs in its bar-code nucleic acid sequence from the first set of primers of (i); and (iv) amplifying and/or reverse transcribing said plurality (M) of nucleic acid molecules of interest from a second sample using the second set of primers produced in (iii);

(b') combining the nucleic acid amplification products and/or reverse transcription products produced in (a') from all samples;

(c') sequencing the combined nucleic acid amplification products and/or reverse transcription products of (b'); and (d') identifying the individual sample from which each nucleic acid amplification product and/or reverse transcription product is derived based on the sample-specific bar-code associated with the nucleic acid amplification product and/or reverse transcription product.

5. The method of claim 1, wherein N represents an integral number of at least 2.

6. The method of claim 1, wherein in step (i) the first and/or third oligonucleotide further comprise a 5' protecting group.

* * * * *